(12) United States Patent
Pan et al.

(10) Patent No.: US 10,836,813 B2
(45) Date of Patent: Nov. 17, 2020

(54) FC CONTAINING POLYPEPTIDES WITH ALTERED GLYCOSYLATION AND REDUCED EFFECTOR FUNCTION

(71) Applicant: Genzyme Corporation, Cambridge, MA (US)

(72) Inventors: Clark Pan, Sutton, MA (US); Huawei Qiu, Westborough, MA (US)

(73) Assignee: GENZYME CORPORATION, Cambridge, MA (US)

( * ) Notice: Subject to any disclaimer, the term of this patent is extended or adjusted under 35 U.S.C. 154(b) by 290 days.

(21) Appl. No.: 15/702,368

(22) Filed: Sep. 12, 2017

(65) Prior Publication Data

US 2018/0100010 A1    Apr. 12, 2018

Related U.S. Application Data

(60) Division of application No. 14/205,264, filed on Mar. 11, 2014, now Pat. No. 9,790,268, which is a continuation of application No. 14/241,099, filed as application No. PCT/EP2012/003819 on Sep. 12, 2012, now Pat. No. 10,017,573, said application No. 14/205,264 is a continuation of application No. PCT/US2013/059481, filed on Sep. 12, 2013.

(60) Provisional application No. 61/776,724, filed on Mar. 11, 2013, provisional application No. 61/776,715, filed on Mar. 11, 2013, provisional application No. 61/776,710, filed on Mar. 11, 2013.

(51) Int. Cl.

| | |
|---|---|
| *C07H 21/02* | (2006.01) |
| *C07H 21/04* | (2006.01) |
| *C12N 5/02* | (2006.01) |
| *C12N 5/16* | (2006.01) |
| *C12N 1/20* | (2006.01) |
| *C12N 15/00* | (2006.01) |
| *C12P 21/06* | (2006.01) |
| *C12P 21/04* | (2006.01) |
| *C07K 16/00* | (2006.01) |
| *C07K 16/18* | (2006.01) |
| *A61K 49/00* | (2006.01) |
| *C07K 16/32* | (2006.01) |
| *C07K 16/40* | (2006.01) |
| *C07K 16/28* | (2006.01) |
| *A61K 47/68* | (2017.01) |
| *A61K 39/00* | (2006.01) |

(52) U.S. Cl.
CPC .......... *C07K 16/18* (2013.01); *A61K 47/6803* (2017.08); *A61K 47/6811* (2017.08); *A61K 47/6851* (2017.08); *A61K 47/6889* (2017.08); *A61K 49/0002* (2013.01); *A61K 49/0004* (2013.01); *C07K 16/00* (2013.01); *C07K 16/2809* (2013.01); *C07K 16/2851* (2013.01); *C07K 16/2893* (2013.01); *C07K 16/32* (2013.01); *C07K 16/40* (2013.01); *A61K 2039/505* (2013.01); *C07K 2317/41* (2013.01); *C07K 2317/52* (2013.01); *C07K 2317/522* (2013.01); *C07K 2317/71* (2013.01); *C07K 2317/73* (2013.01)

(58) Field of Classification Search
None
See application file for complete search history.

(56) References Cited

U.S. PATENT DOCUMENTS

| | | |
|---|---|---|
| 5,606,017 A | 2/1997 | Willner et al. |
| 5,648,260 A | 7/1997 | Winter et al. |
| 5,739,277 A | 4/1998 | Presta et al. |
| 5,834,250 A | 11/1998 | Wells et al. |
| 5,837,821 A | 11/1998 | Wu |
| 5,869,046 A | 2/1999 | Presta et al. |
| 5,880,270 A | 3/1999 | Berninger et al. |
| 5,989,830 A | 11/1999 | Davis et al. |
| 6,096,871 A | 8/2000 | Presta et al. |
| 6,121,022 A | 9/2000 | Presta et al. |
| 6,193,980 B1 | 2/2001 | Efstathiou et al. |
| 6,194,551 B1 | 2/2001 | Idusogie et al. |
| 6,218,149 B1 | 4/2001 | Morrison et al. |

(Continued)

FOREIGN PATENT DOCUMENTS

| | | |
|---|---|---|
| EP | 0 403 156 A1 | 12/1990 |
| EP | 0 706 799 A2 | 4/1996 |

(Continued)

OTHER PUBLICATIONS

Bause et al. (1979) "Primary structural requirements for N-glycosylation of peptides in rat liver," FEBS Letters. 108(2):341-344.

(Continued)

*Primary Examiner* — Chun W Dahle
(74) *Attorney, Agent, or Firm* — Lathrop GPM LLP; James H. Velema, Esq.; Judith Stone-Hulslander, Esq.

(57) ABSTRACT

Provided are binding polypeptides (e.g., antibodies), and drug conjugates thereof, comprising an Fc domain with an altered glycosylation profile and reduced effector function. In particular embodiment, the Fc domain comprises: an asparagine residue at amino acid position 298, according to EU numbering; and a serine or threonine residue at amino acid position 300, according to EU numbering. Also provided are nucleic acids encoding the antigen-binding polypeptides, recombinant expression vectors and host cells for making such antigen-binding polypeptides. Methods of using the antigen-binding polypeptides disclosed herein to treat disease are also provided.

23 Claims, 42 Drawing Sheets

Specification includes a Sequence Listing.

(56) References Cited

U.S. PATENT DOCUMENTS

| | | |
|---|---|---|
| 6,242,195 B1 | 6/2001 | Idusogie et al. |
| 6,277,375 B1 | 8/2001 | Ward |
| 6,465,612 B1 | 10/2002 | Bertozzi et al. |
| 6,514,498 B1 | 2/2003 | Antonsson et al. |
| 6,528,624 B1 | 3/2003 | Idusogie et al. |
| 6,538,124 B1 | 3/2003 | Idusogie et al. |
| 6,737,056 B1 | 5/2004 | Presta |
| 6,821,505 B2 | 11/2004 | Ward |
| 6,998,253 B1 | 2/2006 | Presta et al. |
| 7,083,784 B2 | 8/2006 | Dall'Acqua et al. |
| 7,183,387 B1 | 2/2007 | Presta |
| 7,317,091 B2 | 1/2008 | Lazar et al. |
| 7,332,581 B2 | 2/2008 | Presta |
| 7,335,742 B2 | 2/2008 | Presta |
| 7,355,008 B2 | 4/2008 | Stavenhagen et al. |
| 7,371,826 B2 | 5/2008 | Presta |
| 7,612,181 B2 | 11/2009 | Wu et al. |
| 7,785,791 B2 | 8/2010 | Presta |
| 7,790,858 B2 | 9/2010 | Presta |
| 8,163,881 B2 | 4/2012 | Ober |
| 9,580,511 B2 | 2/2017 | Pan et al. |
| 9,701,753 B2 | 7/2017 | Pan et al. |
| 9,790,268 B2 * | 10/2017 | Pan .................. A61K 49/0004 |
| 2002/0102208 A1 | 8/2002 | Chinn et al. |
| 2002/0193572 A1 | 12/2002 | Leung et al. |
| 2003/0082749 A1 | 5/2003 | Sun et al. |
| 2004/0002587 A1 | 1/2004 | Watkins et al. |
| 2005/0107595 A1 | 5/2005 | Cairns et al. |
| 2005/0238649 A1 | 10/2005 | Doronina et al. |
| 2007/0092940 A1 | 4/2007 | Eigenbrot et al. |
| 2007/0248600 A1 | 10/2007 | Hansen et al. |
| 2008/0038260 A1 | 2/2008 | Ponath et al. |
| 2008/0311134 A1 | 12/2008 | Junutula et al. |
| 2010/0190247 A1 | 7/2010 | Lazar et al. |
| 2010/0226923 A1 | 9/2010 | Rao et al. |
| 2010/0260751 A1 | 10/2010 | Raju et al. |
| 2011/0191867 A1 | 8/2011 | Natunen et al. |
| 2012/0251541 A1 | 10/2012 | Baurin et al. |
| 2014/0271676 A1 | 9/2014 | Pan et al. |
| 2014/0294867 A1 | 10/2014 | Pan et al. |
| 2015/0079070 A1 | 3/2015 | Pan et al. |
| 2015/0099861 A1 | 4/2015 | Snell et al. |
| 2016/0060354 A1 | 3/2016 | Avila et al. |
| 2016/0136299 A1 | 5/2016 | Avila et al. |
| 2017/0267774 A1 | 9/2017 | Pan et al. |

FOREIGN PATENT DOCUMENTS

| | | |
|---|---|---|
| JP | 2001-521909 A | 11/2001 |
| JP | 2008-537941 A | 10/2008 |
| JP | 2012-522008 A | 9/2012 |
| JP | 2012-254996 A | 12/2012 |
| RU | 2006138181 A | 6/2008 |
| UA | 40611 C2 | 8/2001 |
| WO | 1988/007089 A1 | 9/1988 |
| WO | 1994/009817 A1 | 5/1994 |
| WO | 1996/014339 A1 | 5/1996 |
| WO | 1998/005787 A1 | 2/1998 |
| WO | 1998/023289 A1 | 6/1998 |
| WO | 1999/022764 A1 | 5/1999 |
| WO | 1999/051642 A1 | 10/1999 |
| WO | 1999/058572 A1 | 11/1999 |
| WO | 2000/009560 A2 | 2/2000 |
| WO | 2000/032767 A1 | 6/2000 |
| WO | 2000/042072 A2 | 7/2000 |
| WO | 2002/002781 A1 | 1/2002 |
| WO | 2002/044215 A2 | 6/2002 |
| WO | 2002/060919 A2 | 8/2002 |
| WO | 2003/074569 A2 | 9/2003 |
| WO | 2004/016750 A2 | 2/2004 |
| WO | 2004/029207 A2 | 4/2004 |
| WO | 2004/035752 A2 | 4/2004 |
| WO | 2004/063351 A2 | 7/2004 |
| WO | 2004/074455 A2 | 9/2004 |
| WO | 2004/099249 A2 | 11/2004 |
| WO | 2005/018572 A2 | 3/2005 |
| WO | 2005/040217 A2 | 5/2005 |
| WO | 2005/047327 A2 | 5/2005 |
| WO | 2005/000892 A2 | 6/2005 |
| WO | 2005/070963 A1 | 8/2005 |
| WO | 2005/077981 A2 | 8/2005 |
| WO | 2005/092925 A2 | 10/2005 |
| WO | 2005/111225 A1 | 11/2005 |
| WO | 2005/123780 A2 | 12/2005 |
| WO | 2006/019447 A1 | 2/2006 |
| WO | 2006/036922 A2 | 4/2006 |
| WO | 2006/047350 A2 | 5/2006 |
| WO | 2006/085967 A2 | 8/2006 |
| WO | 2006/105021 A2 | 10/2006 |
| WO | 2006/105338 A2 | 10/2006 |
| WO | 2007/005786 A2 | 1/2007 |
| WO | 2007/115813 A1 | 10/2007 |
| WO | 2008/086006 A2 | 7/2008 |
| WO | 2008/091954 A2 | 7/2008 |
| WO | 2009/052249 A1 | 4/2009 |
| WO | 2009/099728 A1 | 8/2009 |
| WO | 2010/027797 A1 | 3/2010 |
| WO | 2010/111633 A2 | 9/2010 |
| WO | 2011/109400 A2 | 9/2011 |
| WO | 2012/020065 A1 | 2/2012 |
| WO | 2013/037484 A2 | 3/2013 |
| WO | 2014/043361 A1 | 3/2014 |
| WO | 2014/164503 A1 | 10/2014 |
| WO | 2014/164534 A2 | 10/2014 |
| WO | 2015/143091 A1 | 9/2015 |

OTHER PUBLICATIONS

Hodoniczky et al. (2005) "Control of Recombinant Monoclonal Antibody Effector Functions by Fc N-Glycan Remodeling in Vitro," Biotechnol. Prog. 21:1644-1652.

Junutula et al. (2008) "Rapid identification of reactive cysteine residues for site-specific labeling of antibody-Fabs," Journal of Immunological Methods. 332:41-52.

Nippon Nogeikagaku Kaishi., 1998, vol. 72, No. 10, pp. 9-18.

Al-Lazikani et al. (1997) "Standard conformations for the canonical structures of immunoglobulins," J. Mol. Biol. 273:927-948.

Axup et al. (Sep. 17, 2012) "Synthesis of site-specific antibody-drug conjugates using unnatural amino acids," Proc. Natl. Acad. Sci. USA. 109(40)16101-16106.

Boeggeman et al. (2009) "Site Specific Conjugation of Fluoroprobes to the Remodeled Fc N-Glycans of Monoclonal Antibodies Using Mutant Glycosyltransferases: Application for Cell Surface Antigen Detection," Bioconjugate Chemistry. 20:1228-1236.

Carrasquillo et al. (1985) "Improved imaging of metastatic melanoma with high dose 9.2.27 In-11 1 monoclonal antibody," J. Nuc. Med. 26:67. Abstract No. 276.

Carter et al. (2008) "Antibody-drug conjugates for cancer therapy," Caner Journal. 14:154-169.

Cervigni et al. (1996) "Synthesis of Glycopeptides and Lipopeptides by Chemoselective Ligation," Angew. Chem., Int. Ed. 35(11):1230-1232.

Chan et al. (2010) "Therapeutic antibodies for autoimmunity and inflammation," The Journal of Immunology. 10:301-316.

Chari (2008) "Targeted Cancer Therapy: Conferring Specificity to Cytotoxic Drugs," Accounts of Chemical Research. 41:98-107.

Cobos-Correa et al. (2009) "Membrane-bound FRET probe visualizes MMP12 activity in pulmonary inflammation," Nature Chemical Biology. 5(9):628-663.

Doronina et al. (2003) "Development of potent monoclonal antibody auristatin conjugates for cancer therapy," Nat. Biotech. 21(7):778-784.

Ebersbach et al. (2007) "Affilin-novel binding molecules based on human gamma-B-crystallin, an all beta-sheet protein," Journal of Molecular Biology. 372(1):172-185.

Gehrig et.al. (May 3, 2012) "Spatially resolved monitoring of neutrophil elastase activity with ratiometric fluorescent reporters," Angewandte Chemie International Edition. 51(25):6258-6261.

(56) References Cited

OTHER PUBLICATIONS

Giudicelli et al. (Jun. 1, 2011) "IMGTN-QUEST: IMGT Standardized Analysis of the Immunoglobulin (IG) and T Cell Receptor (TR) Nucleotide Sequences," Cold Springs Harbor Protocols. pp. 58-78.
Grabulovski et al. (2007) "A Novel, Non-immunogenic Fyn SH3-derived Binding Protein with Tumor Vascular Targeting Proteins," The Journal of Biological Chemistry. 282(5):3196-3204.
Guan et al. (1998) "Homogeneous Immunoconjugates for Boron Neutron-capture Therapy: Design, Synthesis, and Preliminary Characterization," Proc. Natl. Acad. Sci. USA. 95(22):13206-13210.
Heidecke et al. (1996) "Alpha-Beta T Cell Receptor-Directed Therapy in Rat Allograft Recipients," Transplantation. 61:948-956.
Heidecke et al. (1996) "Induction of Long-Term Rat Renal Allograft Survival by Pretransplant T Cell Receptor-NB-Targeted Therapy," Transplantation 61:336-339.
Jassal et al. (2001) "Sialylation of Human IgG-Fc Carbohydrate by Transfected Rat a2,6-Sialyltransferase," Biochemical and Biophysical Research Communications. 286:243-249.
Jones (1977) "Proteinase Mutants of *Saccharomyces cerevisiae*," Genetics. 85:23-33.
Jung et al. (1992) "Prevention and therapy of experimental autoimmune neuritis by an antibody against T cell receptors-alpha/beta," Journal of Immunology. 148:3768-3775.
Junutula et al. (2008) "Site-specific conjugation of a cytotoxic drug to an antibody improves the therapeutic index," Nat. Biotechnol. 26:925-932.
Junutula et al. (2010) "Engineered Thio-Trastuzumab-DM1 Conjugate with an Improved Therapeutic Index to Target Human Epidermal Growth Factor Receptor 2—Positive Breast Cancer," Clin. Cancer Res. 16:4769-4778.
Kaneko et al. (2006) "Anti-inflammatory activity of immunoglobulin G resulting from Fc sialylation," Science. 313 (5787):670-673.
Khidekel et al. (2003) "A Chemoenzymatic Approach toward the Rapid and Sensitive Detection of O-GlcNAc Posttranslational Modifications," J. Am. Chem. Soc. 125:16162-16163.
Kingsman et al. (1979) "Replication in *Saccharomyces cerevisiae* of Plasmid pBR313 Carrying DNA from the Yeast trpl Region," Gene. 7:141-152.
Koide et al. (2007) "Monobodies: Antibody Mimics Based on the Scaffold of the Fibronectin Type III Domain," Methods in Molecular Biology. 352:95-109.
Krehenbrink et al. (2008) "Artificial Binding Proteins (Affitins) as Probes for Conformational Changes in Secretin PulD," Journal of Molecular Biology. 383(5):1058-1068.
Labrijn et al. (2008) "When binding is enough: nonactivating antibody formats," Curr. Opin. Immunol. 20:479-485.
Leung et al. (1999) "The effects of domain deletion, glycosylation, and long IgG3 hinge on the biodistribution and serum stability properties of a humanized IgG1 immunoglobulin, hLL2, and its fragments," Clin. Cancer Res. 5:3106s-3117s.
Martin (2010) "Protein Sequencing and Structure Analysis of Antibody Variable Domains," Ch. 3 In; Antibody Engineering. vol. 2. Eds: Kontermann et al. Springer-Verlag Berlin. Heidelberg, Germany. pp. 33-51.
Nixon et al. (2006) "Engineered Protein Inhibitors of Proteases," Current Opinion in Drug Discovery & Development. 9(2):261-268.
North et al. (Oct. 28, 2010) "A new clustering of antibody CDR loop conformations," J. Mol. Biol. 406:228-256.
Nygren et al. (2008) "Alternative Binding Proteins: Affibody Binding Proteins Devloped from a Small Three-helix Bundle Scaffold," The FEBS Journal. 275(11):2668-2676.
Page et al. (2012) "Biologics in Organ Transplant," Transplant International. 25:707-719.
Piatesi et al. (2004) "Immunological optimization of a generic hydrophobic pocket for high affinity hapten binding and Diels-Alder activity," ChemBio Chem 5:460-466.
Polakis (2005) "Arming antibodies for cancer therapy," Current Opinion in Pharmacology. 5:382-387.
Qu et al. (1998) "Carbohydrates engineered at antibody constant domains can be used for site-specific conjugation of drugs and chelates," Journal of Immunological Methods. 213:131-144.
Renaudet et al. (2006) "On-bead synthesis and binding assay of chemoselectively template-assembled multivalent neoglycopeptides," Org. Biomol. Chem. 4:2628-2636.
Roche Diagnostics (May 2013) "Alpha-2,6, Sialyltransferase Cat. No. 07 012 250 103 (Data Sheet)," XP002727803. Retrieved from Internet: URL: hftps://cssportal.roche.com/LFR_PublicDocs/ras/07012250103_en_02.pdf. [retrieved on Jul. 25, 2014].
Roux et al. (1998) "Comparisons of the Ability of Human IgG3 Hinge Mutants, IgM, 19E, and IgA2, to Form Small Immune Complexes: A Role for Flexibility and Geometry," Journal of Immunology. 161(8):4083-4090.
Sazinsky et al. (2008) "Aglycosylated immunoglobulin G1 variants productively engage activating Fc receptors," Proc. Natl. Acad. Sci. USA. 105(51):20167-20172.—with supplementary information.
Scharpf et al. (2006) "Immunomodulation with anti-anti-a[3T-cell receptor monoclonal antibodies in combination with cyclosporine a improves regeneration in nerve allografts," Microsurgery. 26:599-607.
Schorlemmer et al. (1995) "Synergistic effects of 15-deoxyspergualin with cyclosporine and the TCR-targeted monoclonal antibody R73 to induce specific unresponsiveness to skin allografts in rats," Transplantation Proceedings. 27:414-416.
Shao et al. (1995) "Unprotected Peptides as Building Blocks for the Synthesis of Peptide Dendrimers with Oxime, Hydrazone, and Thiazolidine Linkages," Journal of the American Chemical Society. 117(14):3893-3899.
Shearman et al. (1991) "Construction, expression and characterization of humanized antibodies directed against the human alpha/beta T cell receptor," The Journal of Immunology. 147:4366-4373.
Shields et al. (2001) "High Resolution Mapping of the Binding Site on Human IgG1 for FcγRI, FcγRII, FcγRIII, and FcRn and Design of IgG1 Variants with Improved Binding to the FcγR," J. Biol. Chem. 276:6591-6604.
Silverman et al. (2005) "Multivalent Avimer Proteins Evolved by Exon Shuffling of a Family of Human Receptor Domains," Nature Biotechnology. 23(12):1556-1561.
Skerra et al. (2008) "Alternative Binding Proteins: Anticalins—Harnessing the Structural Plasticity of the Lipocalin Ligand Pocket to Engineer Novel Binding Activites," The FEBS Journal. 275(11):2677-2683.
Stinchcomb et al. (1979) "Isolation and Characterization of a Yeast Chromosomal Replicator," Nature. 282:39-43.
Stumpp et al. (2008) "DARPins: A New Generation of Protein Therpeutics," Drug Discovery Today. 13(15-16):695-670.
Schroeder et al. (2010) "Structure and Function of Immunoglobulins," The Journal of Allergy and Clinical Immunology, vol. 125, No. 2, supplement 2, pp. S41-S52.
Teicher (2009) "Antibody-drug conjugate targets," Current Cancer Drug Targets. 9(8):982-1004.
Tschumper et al. (1980) "Sequence of a Yeast DNA Fragment Containing a Chromosomal Replicator and the TRP1 Gene," Gene. 10:157-166.
Wang et al. (1998) "Single-chain Fv with manifold N-glycans as bifunctional scaffolds for immunomolecules," Protein Engineering. 11:1277-1283.
Wang et al. (2011) "Impact of methionine oxidation in human IgG1 Fc on serum half-life of monoclonal antibodies," Molecular Immunology. 48(6):860-866.
Williams et al. (2010) "Humanising Antibodies by CDR Grafting," Ch. 21 In; Antibody Engineering. vol. 1. Eds: Kontermann et al. Springer-Verlag Berlin. Heidelberg, Germany. pp. 319-339.
Winkler et al. (2000) "Changing the antigen binding specificity by single point mutations of an anti-p24 (HIV-1) antibody," J. Immunol. 265:4505-4514.
Wright et al. (1992) "Genetically Engineered Antibodies: Progress and Prospects," Critical Reviews in Immunology. 12:125-168.
Wu et al. (1999) "Humanization of a murine monoclonal antibody by simultaneous optimization of framework and CDR residues," J. Mol. Biol. 294:151-162.

(56) References Cited

OTHER PUBLICATIONS

Yamagami et al. (1999) "Suppression of Allograft Rejection with Anti-A8 T Cell Receptor Antibody in Rat Corneal Transplantation," Transplantation. 67:600-604.
Yoshino et al. (1992) "Depletion of alpha/beta T cells by a monoclonal antibody against the alpha/beta T cell receptor suppresses established adjuvant arthritis, but not established collagen-induced arthritis in rats.," J. Exp. Med. 175:907-915.
Yu et al. (2008) "Interaction between bevacizumab and murine VEGF-A: a reassessment," Investigative Ophthalmology & Visual Science. 49(2):522-527.
Zhou et al. (2008) "Development of a simple and rapid method for producing non-fucosylated oligomannose containing antibodies with increased effector function," Biotechnol. Bioeng. 99:652-665.
Zhou et al. (2011) "Strategies for Neoglycan Conjugation to Human Acid a-Glucosidase," Bioconjugate Chemistry. 22:741-751.
Zhou et al. (2014) "Site-Specific Antibody—Drug Conjugation through Glycoengineering," Bioconjugate Chemistry. 25:510-520.
International Search Report with Written Opinion corresponding to International Patent Application No. PCT/EP2012/003819, dated Jul. 17, 2013.
International Search Report with Written Opinion corresponding to International Patent Application No. PCT/US2013/059481, dated Feb. 7, 2014.
International Search Report with Written Opinion corresponding to International Patent Application No. PCT/US2014/022623, dated Jul. 31, 2014.
International Search Report with Written Opinion corresponding to International Patent Application No. PCT/US2014/022728, dated Oct. 9, 2014.
International Search Report with Written Opinion corresponding to International Patent Application No. PCT/US2015/021342, dated Jun. 8, 2015.
Anthony et al. (2008) "Identification of a receptor required for the anti-inflammatory activity of IVIG," Proc. Natl. Acad. Sci. USA. 105:19571-19578.
Anthony et al. (2008) "Recapitulation of IVIG anti-inflammatory activity with a recombinant IgG Fc," Science. 320:373-376.
Anwer et al. (2000) "Synthetic Glycopeptide-Based Delivery Systems for Systemic Gene Targeting to Hepatocytes," Pharm. Res. 17:451-459.
Boeggeman et al. (2007) "Direct Identification of Nonreducing GlcNAc Residues on N-Glycans of Glycoproteins Using a Novel Chemoenzymatic Method," Bioconjugate Chemistry. 18(3):806-814.
Chen et al. (2010) "In vivo targeting of B-cell lymphoma with glycan ligands of CD22," Blood. 115:4778-4786.
Chen et al. (2012) "Targeting B lymphoma with nanoparticles bearing glycan ligands of CD22," Leukemia and Lymphoma. 53:208-210.
Feige et al. (2009) "Structure of the murine unglycosylated IgG1 Fc fragment," J. Mol Biol. 391:599-608.
Ganesan et al. (2011) "Rapid and Efficient Clearance of Bloodborne Virus by Liver Sinusoidal Endothelium," PLoS Pathogens. 7(9):e1002281. pp. 1-11.
Hatekeyama et al. (2011) "Targeted Drug Delivery to Tumor Vasculature by a Carbohydrate Mimetic Peptide," Proc. Natl. Acad. Sci. USA. 108:19587-19592.
Hong et al. (2003) "Beta-glucan functions as an adjuvant for monoclonal antibody immunotherapy by recruiting tumoricidal granulocytes as killer cells," Cancer Res. 23:9023-9031.
Hosoguchi (2010) "An efficient approach to the discovery of potent inhibitors against glycosyltransferases," J. Med. Chem. 53:5607-5619.
Kawasaki et al. (2013) "Targeted delivery of lipid antigen to macrophages via the CD169/sialoadhesin endocytic pathway induces robust invariant natural killer T cell activation," Proc. Natl. Acad. Sci. USA. 110:7826-7831.
Krapp et al. (2003) "Structural analysis of human IgG-Fc glycoforms reveals a correlation between glycosylation and structural integrity," J. Mol. Biol. 325:979-898.
Lepenies et al. (2013) "Targeting C-type lectin receptors with multivalent carbohydrate ligands," Adv. Drug Delivery Rev. 65:1271-1281.
Li et al. (May 23, 2014) "The Preparation of Well-Defined Antibody-Drug Conjugates Through Glycan Remodeling and Strain Promoted Azide-Alkyne Cycloadditions," Angew. Chem., Int. Ed. 53(28):7179-7182.
Mattner et al. (2005) "Exogenous and endogenous glycolipid antigens activate NKT cells during microbial infections," Nature. 434:525-529.
McCarthy (Aug. 16, 2013) "Chemoenzymatic synthesis of immunogenic meningococcal group C polysialic acid-tetanus Hc fragment glycoconjugates," Glycoconj. J. 30:857-870.
Medina et al. (2011) "N-acetylgalactosamine-functionalized dendrimers as hepatic cancer cell-targeted carriers," Biomaterials. 32:4118-4129.
Monnier et al. (2014) "Glucosepane: a poorly understood advanced glycation end product of growing importance for diabetes and its complications," Clin. Chem. Lab. Med. 52:21-32.
Murray (1985) "Imaging Findings and Pharmacaokinetics of 111-Indium ZME-018 Monoclonal Antibodies," J. Nuc. Med. 26:P16. Abstract No. 55.
Raju et al. (2011) "Glycoengineering of therapeutic glycoproteins: in vitro galactosylation and sialylation of glycoproteins with terminal N-acetylglucosamine and galactose residues," Biochem. 40(30):8868-8876.
Wei et al. (2008) "Glyco-engineering of human IgG1-Fc through combined yeast expression and in vitro chemoenzymatic glycosylation," Biochem. 47(39):10294-10304.
Zhou (Aug. 22, 2013) "Bioconjugation by native chemical tagging of C-H bonds.," J. Am. Chem. Soc. 135:12994-12997.
Zhu et al. (2009) "Glycoengineered acid alpha-glucosidase with improved efficacy at correcting the metabolic aberrations and motor function deficits in a mouse model of Pompe disease," Mol. Ther. 17(6):954-963.
International Search Report with Written Opinion corresponding to International Patent Application No. PCT/US2015/054651, dated Apr. 20, 2016.

* cited by examiner

| Sample | $k_a(\times 10^6/Ms)$ | $k_d(\times 10^{-2}/s)$ | $R_{max}(RU)$ | $K_D(nM)$ |
|---|---|---|---|---|
| GLD52 | 7.0 | 1.7 | 67.0 | 2.44 |
| WT2C3 | 6.0 | 1.1 | 64.2 | 1.75 |
| A114N | 4.7 | 1.1 | 59.5 | 2.45 |
| Y436S | 5.9 | 1.0 | 66.9 | 1.73 |
| S298N?Y300S | 5.7 | 1.0 | 63.3 | 1.80 |
| Y436T | 4.8 | 0.9 | 65.7 | 1.95 |
| S440N | 5.8 | 1.1 | 66.8 | 1.84 |
| S442N | 5.7 | 1.1 | 66.2 | 1.85 |
| NGT | 7.9 | 1.1 | 70.2 | 1.35 |

*Fig. 16*

| Sample | K on (x$10^6$M$^{-1}$s$^{-1}$) | K off (x$10^{-2}$s$^{-1}$) | KD (nM) |
|---|---|---|---|
| WT 2C3 | 5.2 | 1.1 | 2.1 |
| A114N | 5.3 | 1.3 | 2.4 |

| Sample | lot # | Octet Conc (µg/mL) |
|---|---|---|
| Mock media | 11/23/2009 | too low |
| wt 2C3 | 11/23/2009 | 2.54 |
| A114N | 11/23/2009 | 2.83 |
| S298N/Y300S | 11/23/2009 | 1.36 |
| S440N | 11/23/2009 | 1.32 |
| S442N | 11/23/2009 | 1.21 |
| Y436S | 11/23/2009 | 1.92 |
| Y436T | 11/23/2009 | 0.34 |
| NGT | 11/23/2009 | 1.90 |

B

A

A

FC CONTAINING POLYPEPTIDES WITH ALTERED GLYCOSYLATION AND REDUCED EFFECTOR FUNCTION

RELATED APPLICATIONS

This application is a divisional U.S. patent application Ser. No. 14/205,264, filed Mar. 11, 2014, now U.S. Pat. No. 9,790,268, which is a continuation of U.S. patent application Ser. No. 14/241,099, filed Nov. 18, 2014, now U.S. Pat. No. 10,017,573, which is a National Stage of International Patent Application No. PCT/EP2012/003819, filed Sep. 12, 2012. U.S. patent application Serial No. 14/205,264 is a continuation of International Patent Application No. PCT/US2013/059481, filed Sep. 12, 2013, and also claims priority to U.S. Provisional Patent Application Ser. Nos. 61/776,724, 61/776,715, and 61/776,710, all filed Mar. 11, 2013. The contents of the aforementioned applications are hereby incorporated by reference herein in their entireties.

BACKGROUND

Antibodies with reduced or abolished Fc glycosylation have been employed for the treatment of inflammatory and autoimmune diseases or disorders in order to reduce side effects or toxicity associated with unwanted effector function (see e.g., Chan and Carter, Nat. Reviews Immunology, 2010). However, antibody Fc domain glycosylation is important for antibody structure, stability, and function and aglycosylation can result in antibodies with poor biophysical properties. Accordingly, there is a need in the art for engineered binding proteins with reduced effector function but which also retain the desirable properties of a glycosylated Fc domain.

SUMMARY

The current disclosure improves upon the prior art by providing binding polypeptides (e.g., antibodies or fusion), and optionally drug conjugates thereof, comprising an Fc domain with altered glycosylation and reduced effector function. In exemplary embodiments, the Fc domain comprises: an asparagine residue at amino acid position 298, according to EU numbering; and a serine or threonine residue at amino acid position 300, according to EU numbering. The current disclosure also provides nucleic acids encoding the antigen-binding polypeptides, recombinant expression vectors and host cells for making such antigen-binding polypeptides. Methods of using the antigen-binding polypeptides disclosed herein to treat disease are also provided.

The inventors have surprisingly found that the binding polypeptides (e.g., antibodies) of the current disclosure exhibit altered glycosylation profiles which are advantageous in that they abolish binding of the binding polypeptide to Fcγ receptors, thereby altering effector function of the binding polypeptide while retaining the desirable biophysical properties that are afforded by glycosylation. Moreover, the engineered N-linked glycosylation site at amino acid position 298 can also be used as a site for conjugation of effector moieties, such as cytotoxic drugs.

Accordingly, in one aspect the invention provides an isolated binding polypeptide comprising an Fc domain with altered glycosylation, wherein the Fc domain comprises: an asparagine residue at amino acid position 298, according to EU numbering; and a serine or threonine residue at amino acid position 300, according to EU numbering, and wherein the binding polypeptide exhibits reduced effector function due to said altered glycosylation. In one embodiment, the binding polypeptide further comprises an alanine residue at amino acid position 299, according to EU numbering. In another embodiment, the binding polypeptide further comprises a glutamine residue at amino acid position 297, according to EU numbering. In one embodiment, the Fc domain is an IgG1 Fc domain. In another embodiment, the Fc domain is human.

In one embodiment, the side chain of the asparagine residue is linked to a glycan though a β-glycosylamide linkage. In another embodiment, the glycan is a biantennary glycan. In another embodiment, the glycan is a naturally occurring mammalian glycoform.

In another embodiment, the binding polypeptide has a lower affinity for an Fcγ receptor than a binding polypeptide having a native Fc domain. In one embodiment, the Fcγ receptor is FcγRI and/or FcγRIIIa. In another embodiment, the binding polypeptide has a similar affinity for an FcRn receptor as a binding polypeptide having a native Fc domain.

In another embodiment, the glycan comprises a reactive aldehyde group. In another embodiment, the glycan comprises an oxidized saccharide residue comprising a reactive aldehyde group. In another embodiment, the oxidized saccharide residue is a terminal sialic acid or galactose.

In another embodiment, the glycan is linked to an effector moiety. In another embodiment, the effector moiety is a cytotoxin. In another embodiment, the cytotoxin is selected from the group of cytotoxins listed in Table 1. In another embodiment, the effector moiety is a detection agent. In another embodiment, the effector moiety is linked through an oxime or hydrazone linkage to a saccharide residue of the glycan. In another embodiment, the saccharide residue is a terminal sialic acid or galactose residue of the glycan. In another embodiment, the effector moiety comprises a pH-sensitive linker, disulfide linker, enzyme-sensitive linker or other cleavable linker moiety. In another embodiment, the effector moiety comprises a linker moiety selected from the group of linker moieties depicted in Table 2 or 14.

In certain embodiments, the binding polypeptide is an antibody or immunoadhesin.

In another aspect, the invention provides an isolated binding polypeptide comprising an Fc domain, wherein the Fc domain comprises: a free asparagine residue at amino acid position 298, according to EU numbering; and a free serine or threonine residue at amino acid position 300, according to EU numbering.

In another aspect, the invention provides isolated binding polypeptide comprising an Fc domain, wherein the Fc domain comprises: a modified asparagine residue at amino acid position 298, according to EU numbering; and a free serine or threonine residue at amino acid position 300, according to EU numbering.

In another embodiment, the effector moiety is linked through a side chain of the modified asparagine residue to a saccharide residue of a glycan. In one embodiment, the saccharide is a terminal sialic acid or galactose residue of the glycan. In one embodiment, the effector moiety is linked through an oxime or hydrazone linkage to saccharide residue of the glycan. In one embodiment, the saccharide is a terminal sialic acid or galactose residue of the glycan. In another embodiment, the modified asparagine residue is linked to a drug effector moiety to form an antibody drug conjugate (ADC).

In another aspect, a composition comprises a binding polypeptide of any one of the preceding claims and a pharmaceutically acceptable carrier or excipient.

In another aspect, the invention provides of treating a patient in thereof comprising administering an effective amount of the composition of the invention.

In another aspect, the invention provides an isolated polynucleotide encoding the binding polypeptide of the invention. In another aspect, the invention provides a vector comprising the polynucleotide or a host cell comprising the polynucleotide or vector.

In yet another aspect, the invention provides a method of making a binding polypeptide comprising expressing the polynucleotide or vector in a cell.

BRIEF DESCRIPTION OF THE DRAWINGS

FIG. 16 depicts the results of plasmon resonance experiments experiments measuring the binding kinetics of 2C3 mutants to CD-52 peptide 741.

FIG. 17 depicts the results of plasmon resonance experiments experiments comparing the antigen binding affinity of WT anti-CD-52 2C3 and the A114N hyperglycosylation mutant.

DETAILED DESCRIPTION

Figure 1:
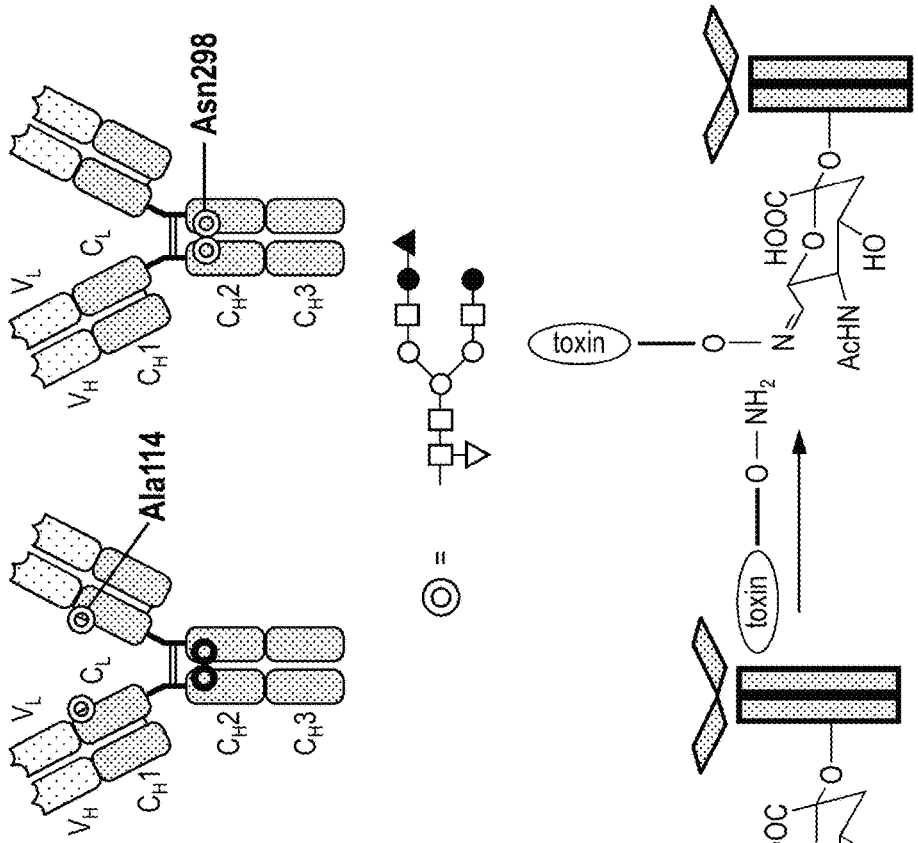
FIG. 1 is a schematic illustration of the synthesis of an antibody drug conjugate where a toxin moiety is linked to an oxidized sialic acid residue of the antibody glycan using an oxime linkage.
Figure 1:
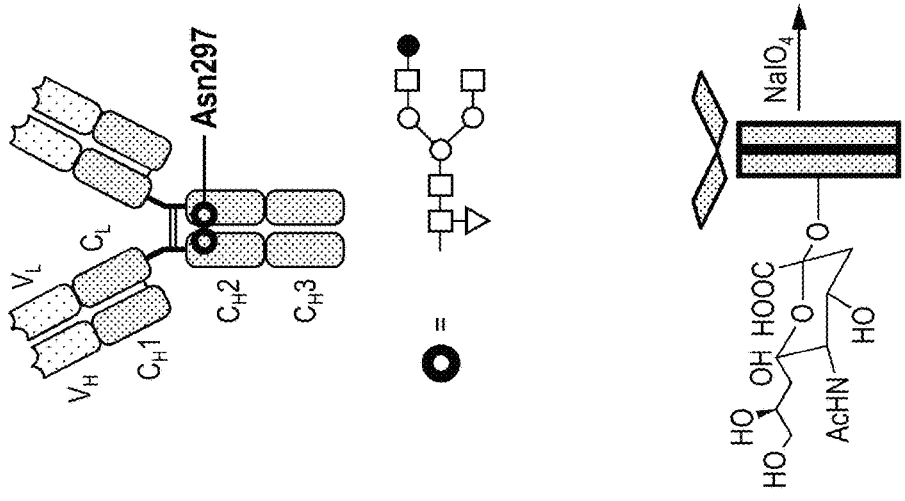

The current disclosure provides binding polypeptides (e.g., antibodies), and drug conjugates thereof, comprising an Fc domain, wherein the Fc domain comprises: an asparagine residue at amino acid position 298, according to EU numbering; and a serine or threonine residue at amino acid position 300, according to EU numbering. The current disclosure also provides nucleic acids encoding the antigen-binding polypeptides, recombinant expression vectors and host cells for making such antigen-binding polypeptides. Methods of using the antigen-binding polypeptides disclosed herein to treat disease are also provided.

I. Definitions

As used herein, the term "binding polypeptide" or "binding polypeptide" shall refer to a polypeptide (e.g., an antibody) that contains at least one binding site which is responsible for selectively binding to a target antigen of interest (e.g. a human antigen). Exemplary binding sites include an antibody variable domain, a ligand binding site of a receptor, or a receptor binding site of a ligand. In certain aspects, the binding polypeptides of the invention comprise multiple (e.g., two, three, four, or more) binding sites.

As used herein, the term "native residue" shall refer to an amino acid residue that occurs naturally at a particular amino acid position of a binding polypeptide (e.g., an antibody or fragment thereof) and which has not been modified, introduced, or altered by the hand of man. As used herein, the term "altered binding polypeptide" or "altered binding polypeptide" includes binding polypeptides (e.g., an antibody or fragment thereof) comprising at least one non-native mutated amino acid residue.

The term "specifically binds" as used herein, refers to the ability of an antibody or an antigen-binding fragment thereof to bind to an antigen with a dissociation constant (Kd) of at most about $1 \times 10^{-6}$ M, $1 \times 10^{-7}$ M, $1 \times 10^{-8}$ M, $1 \times 10^{-9}$ M, $1 \times 10^{-10}$ M, $1 \times 10^{-11}$ M, $1 \times 10^{-12}$ M, or less, and/or to bind to an antigen with an affinity that is at least two-fold greater than its affinity for a nonspecific antigen.

As used herein, the term "antibody" refers to such assemblies (e.g., intact antibody molecules, antibody fragments, or variants thereof) which have significant known specific immunoreactive activity to an antigen of interest (e.g. a tumor associated antigen). Antibodies and immunoglobulins comprise light and heavy chains, with or without an interchain covalent linkage between them. Basic immunoglobulin structures in vertebrate systems are relatively well understood.

As will be discussed in more detail below, the generic term "antibody" comprises five distinct classes of antibody that can be distinguished biochemically. All five classes of antibodies are clearly within the scope of the current disclosure, the following discussion will generally be directed to the IgG class of immunoglobulin molecules. With regard to IgG, immunoglobulins comprise two identical light chains of molecular weight approximately 23,000 Daltons, and two identical heavy chains of molecular weight 53,000-70,000. The four chains are joined by disulfide bonds in a "Y" configuration wherein the light chains bracket the heavy chains starting at the mouth of the "Y" and continuing through the variable region.

Light chains of immunoglobulin are classified as either kappa or lambda (κ, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells, or genetically engineered host cells. In the heavy chain, the amino acid sequences run from an N-terminus at the forked ends of the Y configuration to the C-terminus at the bottom of each chain. Those skilled in the art will appreciate that heavy chains are classified as gamma, mu, alpha, delta, or epsilon, (γ, μ, α, δ, ε) with some subclasses among them (e.g., γ1-γ4). It is the nature of this chain that determines the "class" of the antibody as IgG, IgM, IgA IgG, or IgE, respectively. The immunoglobulin isotype subclasses (e.g., IgG1, IgG2, IgG3, IgG4, IgA1, etc.) are well characterized and are known to confer functional specialization. Modified versions of each of these classes and isotypes are readily discernable to the skilled artisan in view of the instant disclosure and, accordingly, are within the scope of the current disclosure.

Both the light and heavy chains are divided into regions of structural and functional homology. The term "region" refers to a part or portion of an immunoglobulin or antibody chain and includes constant region or variable regions, as well as more discrete parts or portions of said regions. For example, light chain variable regions include "complementarily determining regions" or "CDRs" interspersed among "framework regions" or "FRs", as defined herein.

The regions of an immunoglobulin heavy or light chain may be defined as "constant" (C) region or "variable" (V) regions, based on the relative lack of sequence variation within the regions of various class members in the case of a "constant region", or the significant variation within the regions of various class members in the case of a "variable regions". The terms "constant region" and "variable region" may also be used functionally. In this regard, it will be appreciated that the variable regions of an immunoglobulin or antibody determine antigen recognition and specificity. Conversely, the constant regions of an immunoglobulin or antibody confer important effector functions such as secretion, transplacental mobility, Fc receptor binding, complement binding, and the like. The subunit structures and three dimensional configurations of the constant regions of the various immunoglobulin classes are well known.

The constant and variable regions of immunoglobulin heavy and light chains are folded into domains. The term "domain" refers to a globular region of a heavy or light chain comprising peptide loops (e.g., comprising 3 to 4 peptide loops) stabilized, for example, by β-pleated sheet and/or intrachain disulfide bond. Constant region domains on the light chain of an immunoglobulin are referred to interchangeably as "light chain constant region domains", "CL regions" or "CL domains". Constant domains on the heavy chain (e.g. hinge, CH1, CH2 or CH3 domains) are referred to interchangeably as "heavy chain constant region domains", "CH" region domains or "CH domains". Variable domains on the light chain are referred to interchangeably as "light chain variable region domains", "VL region domains or "VL domains" Variable domains on the heavy chain are referred to interchangeably as "heavy chain variable region domains", "VH region domains" or "VH domains".

By convention the numbering of the variable constant region domains increases as they become more distal from the antigen binding site or amino-terminus of the immunoglobulin or antibody. The N-terminus of each heavy and light immunoglobulin chain is a variable region and at the C-terminus is a constant region; the CH3 and CL domains actually comprise the carboxy-terminus of the heavy and light chain, respectively. Accordingly, the domains of a light chain immunoglobulin are arranged in a VL-CL orientation, while the domains of the heavy chain are arranged in the VH-CH1-hinge-CH2-CH3 orientation.

Amino acid positions in a heavy chain constant region, including amino acid positions in the CH1, hinge, CH2, CH3, and CL domains, may be numbered according to the Kabat index numbering system (see Kabat et al, in "Sequences of Proteins of Immunological Interest", U.S. Dept. Health and Human Services, 5th edition, 1991). Alternatively, antibody amino acid positions may be numbered according to the EU index numbering system (see Kabat et al, ibid).

As used herein, the term "VH domain" includes the amino terminal variable domain of an immunoglobulin heavy chain, and the term "VL domain" includes the amino terminal variable domain of an immunoglobulin light chain.

As used herein, the term "CH1 domain" includes the first (most amino terminal) constant region domain of an immunoglobulin heavy chain that extends, e.g., from about positions 114-223 in the Kabat numbering system (EU positions 118-215). The CH1 domain is adjacent to the VH domain and amino terminal to the hinge region of an immunoglobulin heavy chain molecule, and does not form a part of the Fc region of an immunoglobulin heavy chain.

As used herein, the term "hinge region" includes the portion of a heavy chain molecule that joins the CH1 domain to the CH2 domain. This hinge region comprises approximately 25 residues and is flexible, thus allowing the two N-terminal antigen binding regions to move independently. Hinge regions can be subdivided into three distinct domains: upper, middle, and lower hinge domains (Roux et al. J. Immunol. 1998, 161: 4083).

As used herein, the term "CH2 domain" includes the portion of a heavy chain immunoglobulin molecule that extends, e.g., from about positions 244-360 in the Kabat numbering system (EU positions 231-340). The CH2 domain is unique in that it is not closely paired with another domain. Rather, two N-linked branched carbohydrate chains are interposed between the two CH2 domains of an intact native IgG molecule. In one embodiment, a binding polypeptide of the current disclosure comprises a CH2 domain derived from an IgG1 molecule (e.g. a human IgG1 molecule).

As used herein, the term "CH3 domain" includes the portion of a heavy chain immunoglobulin molecule that extends approximately 110 residues from N-terminus of the CH2 domain, e.g., from about positions 361-476 of the Kabat numbering system (EU positions 341-445). The CH3 domain typically forms the C-terminal portion of the antibody. In some immunoglobulins, however, additional domains may extend from CH3 domain to form the C-terminal portion of the molecule (e.g. the CH4 domain in the μ chain of IgM and the e chain of IgE). In one embodiment, a binding polypeptide of the current disclosure comprises a CH3 domain derived from an IgG1 molecule (e.g. a human IgG1 molecule).

As used herein, the term "CL domain" includes the constant region domain of an immunoglobulin light chain that extends, e.g. from about Kabat position 107A-216. The CL domain is adjacent to the VL domain. In one embodiment, a binding polypeptide of the current disclosure comprises a CL domain derived from a kappa light chain (e.g., a human kappa light chain).

As used herein, the term "Fc region" is defined as the portion of a heavy chain constant region beginning in the hinge region just upstream of the papain cleavage site (i.e. residue 216 in IgG, taking the first residue of heavy chain constant region to be 114) and ending at the C-terminus of the antibody. Accordingly, a complete Fc region comprises at least a hinge domain, a CH2 domain, and a CH3 domain.

The term "native Fc" as used herein refers to a molecule comprising the sequence of a non-antigen-binding fragment resulting from digestion of an antibody or produced by other means, whether in monomeric or multimeric form, and can contain the hinge region. The original immunoglobulin source of the native Fc is preferably of human origin and can be any of the immunoglobulins, although IgG1 and IgG2 are preferred. Native Fc molecules are made up of monomeric polypeptides that can be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, and IgE) or subclass (e.g., IgG1, IgG2, IgG3, IgA1, and IgA2). One example of a native Fc is a disulfide-bonded dimer resulting from papain digestion of an IgG. The term "native Fc" as used herein is generic to the monomeric, dimeric, and multimeric forms.

The term "Fc variant" as used herein refers to a molecule or sequence that is modified from a native Fc but still comprises a binding site for the salvage receptor, FcRn (neonatal Fc receptor). Exemplary Fc variants, and their interaction with the salvage receptor, are known in the art. Thus, the term "Fc variant" can comprise a molecule or sequence that is humanized from a non-human native Fc. Furthermore, a native Fc comprises regions that can be removed because they provide structural features or biological activity that are not required for the antibody-like binding polypeptides of the invention. Thus, the term "Fc variant" comprises a molecule or sequence that lacks one or more native Fc sites or residues, or in which one or more Fc sites or residues has be modified, that affect or are involved in: (1) disulfide bond formation, (2) incompatibility with a selected host cell, (3) N-terminal heterogeneity upon expression in a selected host cell, (4) glycosylation, (5) interaction with complement, (6) binding to an Fc receptor other than a salvage receptor, or (7) antibody-dependent cellular cytotoxicity (ADCC).

The term "Fc domain" as used herein encompasses native Fc and Fc variants and sequences as defined above. As with Fc variants and native Fc molecules, the term "Fc domain" includes molecules in monomeric or multimeric form, whether digested from whole antibody or produced by other means.

As indicated above, the variable regions of an antibody allow it to selectively recognize and specifically bind epitopes on antigens. That is, the VL domain and VH domain of an antibody combine to form the variable region (Fv) that defines a three dimensional antigen binding site. This quaternary antibody structure forms the antigen binding site present at the end of each arm of the Y. More specifically, the antigen binding site is defined by three complementary determining regions (CDRs) on each of the heavy and light chain variable regions. As used herein, the term "antigen binding site" includes a site that specifically binds (immunoreacts with) an antigen (e.g., a cell surface or soluble antigen). The antigen binding site includes an immunoglobulin heavy chain and light chain variable region and the binding site formed by these variable regions determines the specificity of the antibody. An antigen binding site is formed by variable regions that vary from one antibody to another. The altered antibodies of the current disclosure comprise at least one antigen binding site.

In certain embodiments, binding polypeptides of the current disclosure comprise at least two antigen binding domains that provide for the association of the binding polypeptide with the selected antigen. The antigen binding domains need not be derived from the same immunoglobulin molecule. In this regard, the variable region may or be derived from any type of animal that can be induced to mount a humoral response and generate immunoglobulins against the desired antigen. As such, the variable region of the a binding polypeptide may be, for example, of mammalian origin e.g., may be human, murine, rat, goat, sheep, non-human primate (such as cynomolgus monkeys, macaques, etc.), lupine, or camelid (e.g., from camels, llamas and related species).

In naturally occurring antibodies, the six CDRs present on each monomeric antibody are short, non-contiguous sequences of amino acids that are specifically positioned to form the antigen binding site as the antibody assumes its three dimensional configuration in an aqueous environment. The remainder of the heavy and light variable domains show less inter-molecular variability in amino acid sequence and are termed the framework regions. The framework regions largely adopt a β-sheet conformation and the CDRs form loops which connect, and in some cases form part of, the β-sheet structure. Thus, these framework regions act to form a scaffold that provides for positioning the six CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to the immunoreactive antigen epitope.

Exemplary binding polypeptides of the invention include antibody variants. As used herein, the term "antibody variant" includes synthetic and engineered forms of antibodies which are altered such that they are not naturally occurring, e.g., antibodies that comprise at least two heavy chain portions but not two complete heavy chains (such as, domain deleted antibodies or minibodies); multispecific forms of antibodies (e.g., bispecific, trispecific, etc.) altered to bind to two or more different antigens or to different epitopes on a single antigen); heavy chain molecules joined to scFv molecules and the like. In addition, the term "antibody variant" includes multivalent forms of antibodies (e.g., trivalent, tetravalent, etc., antibodies that bind to three, four or more copies of the same antigen.

As used herein the term "valency" refers to the number of potential target binding sites in a polypeptide. Each target binding site specifically binds one target molecule or specific site on a target molecule. When a polypeptide comprises more than one target binding site, each target binding site may specifically bind the same or different molecules (e.g., may bind to different ligands or different antigens, or different epitopes on the same antigen). The subject binding polypeptides preferably have at least one binding site specific for a human antigen molecule.

The term "specificity" refers to the ability to specifically bind (e.g., immunoreact with) a given target antigen (e.g., a human target antigen). A binding polypeptide may be monospecific and contain one or more binding sites which specifically bind a target or a polypeptide may be multispecific and contain two or more binding sites which specifically bind the same or different targets. In certain embodiments, a binding polypeptide of the invention is specific for two different (e.g., non-overlapping) portions of the same target. In certain embodiments, a binding polypeptide of the invention is specific for more than one target. Exemplary binding polypeptides (e.g., antibodies) which comprise antigen binding sites that bind to antigens expressed on tumor cells are known in the art and one or more CDRs from such antibodies can be included in an antibody of the invention.

The term "linking moiety" includes moieties which are capable of linking the effector moiety to the binding polypeptides disclosed herein. The linking moiety may be selected such that it is cleavable (e.g., enzymatically cleavable or pH-sensitive) or non-cleavable. Exemplary linking moieties are set forth in Table 2 herein.

As used herein, the term "effector moiety" comprises diagnostic and therapeutic agents (e.g. proteins, nucleic acids, lipids, drug moieties, and fragments thereof) with biological or other functional activity. For example, a modified binding polypeptide comprising an effector moiety conjugated to a binding polypeptide has at least one additional function or property as compared to the unconjugated antibody. For example, the conjugation of a cytotoxic drug (e.g., an effector moiety) to binding polypeptide results in the formation of a binding polypeptide with drug cytotoxicity as second function (i.e. in addition to antigen binding). In another example, the conjugation of a second binding polypeptide to the binding polypeptide may confer additional binding properties. In certain embodiments, where the effector moiety is a genetically encoded therapeutic or diagnostic protein or nucleic acid, the effector moiety may be synthesized or expressed by either peptide synthesis or recombinant DNA methods that are well known in the art. In another aspect, where the effector is a non-genetically encoded peptide, or a drug moiety, the effector moiety may be synthesized artificially or purified from a natural source. As used herein, the term "drug moiety" includes anti-inflammatory, anticancer, anti-infective (e.g., anti-fungal, antibacterial, anti-parasitic, anti-viral, etc.), and anesthetic therapeutic agents. In a further embodiment, the drug moiety is an anticancer or cytotoxic agent. Compatible drug moieties may also comprise prodrugs. Exemplary effector moieties are set forth in Table 1 herein.

As used herein, the term "prodrug" refers to a precursor or derivative form of a pharmaceutically active agent that is less active, reactive or prone to side effects as compared to the parent drug and is capable of being enzymatically activated or otherwise converted into a more active form in vivo. Prodrugs compatible with the compositions of the current disclosure include, but are not limited to, phosphate-containing prodrugs, amino acid-containing prodrugs, thiophosphate-containing prodrugs, sulfate-containing prodrugs, peptide-containing prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs that can be converted to the more active cytotoxic free drug. One skilled in the art may make chemical modifications to the desired drug moiety or its prodrug in order to make reactions of that compound more convenient for purposes of preparing modified binding polypeptides of the current disclosure. The drug moieties also include derivatives, pharmaceutically acceptable salts, esters, amides, and ethers of the drug moieties described herein. Derivatives include modifications to drugs identified herein which may improve or not significantly reduce a particular drug's desired therapeutic activity.

As used herein, the term "anticancer agent" includes agents which are detrimental to the growth and/or proliferation of neoplastic or tumor cells and may act to reduce, inhibit or destroy malignancy. Examples of such agents include, but are not limited to, cytostatic agents, alkylating agents, antibiotics, cytotoxic nucleosides, tubulin binding agents, hormones, hormone antagonists, cytotoxic agents, and the like. Cytotoxic agents include tomaymycin derivatives, maytansine derivatives, cryptophycine derivatives, anthracycline derivatives, bisphosphonate derivatives, leptomycin derivatives, streptonigrin derivatives, auristatine derivatives, and duocarmycin derivatives. Any agent that acts to retard or slow the growth of immunoreactive cells or malignant cells is within the scope of the current disclosure.

The term "antigen" or "target antigen" as used herein refers to a molecule or a portion of a molecule that is capable of being bound by the binding site of a binding polypeptide. A target antigen may have one or more epitopes.

II. Binding Polypeptides

In one aspect, the current disclosure provides binding polypeptides (e.g., antibodies, antibody fragments, antibody variants, and fusion proteins) comprising an Fc domain, wherein the Fc domain comprises: an asparagine residue at amino acid position 298, according to EU numbering; and a serine or threonine residue at amino acid position 300, according to EU numbering.

Fc domains from any immunoglobulin class (e.g., IgM, IgG, IgD, IgA and IgE) and species can be used in the binding polypeptides disclosed herein. Chimeric Fc domains comprising portions of Fc domains from different species or Ig classes can also be employed. In certain embodiments, the Fc domain is a human IgG1 Fc domain. In the case of a human IgG1 Fc domain, mutation of the wild type amino acid at Kabat position 298 to an asparagine and Kabat position 300 to a serine or threonine results in the formation of an N-linked glycosylation consensus site (i.e, the N-X-T/S sequon, where X is any amino acid except proline). However, in the case of Fc domains of other species and/or Ig classes or isotypes, the skilled artisan will appreciate that it may be necessary to mutate Kabat position 299 of the Fc domain if a proline residue is present to recreate an N-X-T/S sequon.

The binding polypeptides disclosed herein encompass any binding polypeptide that comprises an Fc domain having an N-linked glycosylation site at position 298, according to Kabat numbering. In certain embodiments, the binding polypeptide is an antibody, or fragment or derivative thereof. Any antibody from any source or species can be employed in the binding polypeptides disclosed herein. Suitable antibodies include without limitation, human antibodies, humanized antibodies or chimeric antibodies.

In certain embodiments, the binding polypeptide of the current disclosure may comprise an antigen binding fragment of an antibody. The term "antigen-binding fragment" refers to a polypeptide fragment of an immunoglobulin or antibody which binds antigen or competes with intact antibody {i.e., with the intact antibody from which they were derived) for antigen binding {i.e., specific binding). Antigen binding fragments can be produced by recombinant or biochemical methods that are well known in the art. Exemplary antigen-binding fragments include Fv, Fab, Fab', and (Fab')2. In preferred embodiments, the antigen-binding fragment of the current disclosure is an altered antigen-binding fragment comprising at least one engineered glycosylation site. In one exemplary embodiment, an altered antigen binding fragment of the current disclosure comprises an altered VH domain described supra. In another exemplary embodiment, an altered antigen binding fragment of the current disclosure comprises an altered CH1 domain described supra.

In exemplary embodiments, the binding polypeptide comprises a single chain variable region sequence (ScFv). Single chain variable region sequences comprise a single polypeptide having one or more antigen binding sites, e.g., a VL domain linked by a flexible linker to a VH domain ScFv molecules can be constructed in a VH-linker-VL orientation or VL-linker-VH orientation. The flexible hinge that links the VL and VH domains that make up the antigen binding site preferably comprises from about 10 to about 50 amino acid residues. Connecting peptides are known in the art. Binding polypeptide of the invention may comprise at least one scFv and/or at least one constant region. In one embodiment, a binding polypeptide of the current disclosure may comprise at least one scFv linked or fused to an antibody or fragment comprising an CH1 domain (e.g. a CH1 domain comprising an asparagine residue at Kabat position 114) and/or CH2 domain (e.g. a CH2 domain comprising an asparagine residue at EU position 298, and a serine or threonine residue at EU position 300).

In certain exemplary embodiments, a binding polypeptide of the current disclosure is a multivalent (e.g., tetravalent) antibody which is produced by fusing a DNA sequence encoding an antibody with a ScFv molecule (e.g., an altered ScFv molecule). For example, in one embodiment, these sequences are combined such that the ScFv molecule (e.g., an altered ScFv molecule) is linked at its N-terminus or C-terminus to an Fc fragment of an antibody via a flexible linker (e.g., a gly/ser linker). In another embodiment a tetravalent antibody of the current disclosure can be made by fusing an ScFv molecule to a connecting peptide, which is fused to a CH1 domain (e.g. a CH1 domain comprising an asparagine residue at Kabat position 114) to construct an ScFv-Fab tetravalent molecule.

In another embodiment, a binding polypeptide of the current disclosure is an altered minibody. Altered minibodies of the current disclosure are dimeric molecules made up of two polypeptide chains each comprising an ScFv molecule (e.g., an altered ScFv molecule comprising an altered VH domain described supra) which is fused to a CH3 domain or portion thereof via a connecting peptide. Minibodies can be made by constructing an ScFv component and connecting peptide-CH3 component using methods described in the art (see, e.g., U.S. Pat. No. 5,837,821 or WO 94/09817A1). In another embodiment, a tetravalent minibody can be constructed. Tetravalent minibodies can be constructed in the same manner as minibodies, except that two ScFv molecules are linked using a flexible linker. The linked scFv-scFv construct is then joined to a CH3 domain.

In another embodiment, a binding polypeptide of the current disclosure comprises a diabody. Diabodies are dimeric, tetravalent molecules each having a polypeptide similar to scFv molecules, but usually having a short (less than 10 and preferably 1-5) amino acid residue linkers connecting both variable domains, such that the VL and VH domains on the same polypeptide chain cannot interact. Instead, the VL and VH domain of one polypeptide chain interact with the VH and VL domain (respectively) on a second polypeptide chain (see, for example, WO 02/02781). Diabodies of the current disclosure comprise an scFv molecule fused to a CH3 domain.

In other embodiments, the binding polypeptide s of the invention comprise multispecific or multivalent antibodies comprising one or more variable domain in series on the same polypeptide chain, e.g., tandem variable domain (TVD) polypeptides. Exemplary TVD polypeptides include the "double head" or "Dual-Fv" configuration described in U.S. Pat. No. 5,989,830. In the Dual-Fv configuration, the variable domains of two different antibodies are expressed in a tandem orientation on two separate chains (one heavy chain and one light chain), wherein one polypeptide chain has two times a VH in series separated by a peptide linker (VH1-linker-VH2) and the other polypeptide chain consists of complementary VL domains connected in series by a peptide linker (VL1-linker-VL2). In the cross-over double head configuration, the variable domains of two different antibodies are expressed in a tandem orientation on two separate polypeptide chains (one heavy chain and one light chain), wherein one polypeptide chain has two VH in series separated by a peptide linker (VH1-linker-VH2) and the other polypeptide chain consists of complementary VL domains connected in series by a peptide linker in the opposite orientation (VL2-linker-VL1). Additional antibody variants based on the "Dual-Fv" format include the Dual-Variable-Domain IgG (DVD-IgG) bispecific antibody (see U.S. Pat. No. 7,612,181 and the TBTI format (see US 2010/0226923 A1). The addition of constant domains to respective chains of the Dual-Fv (CH1-Fc to the heavy chain and kappa or lambda constant domain to the light chain) leads to functional bispecific antibodies without any need for additional modifications (i.e., obvious addition of constant domains to enhance stability).

In another exemplary embodiment, the binding polypeptide comprises a cross-over dual variable domain IgG (CODV-IgG) bispecific antibody based on a "double head" configuration (see US20120251541 A1, which is incorporated by reference herein in its entirety). CODV-IgG antibody variants have one polypeptide chain with VL domains connected in series to a CL domain (VL1-L1-VL2-L2-CL) and a second polypeptide chain with complementary VH domains connected in series in the opposite orientation to a CH1 domain (VH2-L3-VH1-L4-CH1), where the polypeptide chains form a cross-over light chain-heavy chain pair. In certain embodiment, the second polypeptide may be further connected to an Fc domain (VH2-L3-VH1-L4-CH1-Fc). In certain embodiments, linker L3 is at least twice the length of linker L1 and/or linker L4 is at least twice the length of linker L2. For example, L1 and L2 may be 1-3 amino acid residues in length, L3 may be 2 to 6 amino acid residues in length, and L4 may be 4 to 7 amino acid residues in length. Examples of suitable linkers include a single glycine (Gly) residue; a diglycine peptide (Gly-Gly); a tripeptide (Gly-Gly-Gly); a peptide with four glycine residues (Gly-Gly-Gly-Gly) (SEQ ID NO:39); a peptide with five glycine residues (Gly-Gly-Gly-Gly-Gly) (SEQ ID NO: 40); a peptide with six glycine residues (Gly-Gly-Gly-Gly-Gly-Gly) (SEQ ID NO: 41); a peptide with seven glycine residues (Gly-Gly-Gly-Gly-Gly-Gly-Gly) (SEQ ID NO: 42); a peptide with eight glycine residues (Gly-Gly-Gly-Gly-Gly-Gly-Gly-Gly) (SEQ ID NO: 43). Other combinations of amino acid residues may be used such as the peptide Gly-Gly-Gly-Gly-Ser (SEQ ID NO: 44) and the peptide Gly-Gly-Gly-Gly-Ser-Gly-Gly-Gly-Gly-Ser (SEQ ID NO: 45).

In certain embodiments, the binding polypeptide comprises an immunoadhesin molecule comprising a non-antibody binding region (e.g., a receptor, ligand, or cell-adhesion molecule) fused to an antibody constant region (see e.g., Ashkenazi et al., Methods, 1995 8(2), 104-115, which is incorporated by reference herein in its entirety)

In certain embodiments, the binding polypeptide comprises immunoglobulin-like domains. Suitable immunoglobulin-like domains include, without limitation, fibronectin domains (see, for example, Koide et al. (2007), *Methods Mol. Biol.* 352: 95-109, which is incorporated by reference herein in its entirety), DARPin (see, for example, Stumpp et al. (2008) *Drug Discov. Today* 13 (15-16): 695-701, which is incorporated by reference herein in its entirety), Z domains of protein A (see, Nygren et al. (2008) *FEBS J.* 275 (11): 2668-76, which is incorporated by reference herein in its entirety), Lipocalins (see, for example, Skerra et al. (2008) *FEBS J.* 275 (11): 2677-83, which is incorporated by reference herein in its entirety), Affilins (see, for example, Ebersbach et al. (2007) *J. Mol. Biol.* 372 (1): 172-85, which is incorporated by reference herein in its entirety), Affitins (see, for example, Krehenbrink et al. (2008). *J. Mol. Biol.* 383 (5): 1058-68, which is incorporated by reference herein in its entirety), Avimers (see, for example, Silverman et al. (2005) *Nat. Biotechnol.* 23 (12): 1556-61, which is incorporated by reference herein in its entirety), Fynomers, (see, for example, Grabulovski et al. (2007) *J Biol Chem* 282 (5): 3196-3204, which is incorporated by reference herein in its entirety), and Kunitz domain peptides (see, for example, Nixon et al. (2006) *Curr Opin Drug Discov Devel* 9 (2): 261-8, which is incorporated by reference herein in its entirety).

III. N-Linked Glycans

In certain embodiments, the Fc domain of the binding polypeptides disclosed herein is glycosylated at the engineered arginine at position 298 (N298), according to EU numbering. The N-linked glycan is generally linked though a β-glycosylamide linkage to the nitrogen group of the N298 side chain. However, other suitable art recognized linkages can also be employed.

Any type of naturally occurring or synthetic (i.e., non-natural) N-linked glycan can be linked to N114. For example, the glycan may be a native glycan or an engineered glycan containing non-native linkages. In certain embodiments, the glycan comprises a saccharide that can be oxidized (e.g., by periodate treatment) to produce a group suitable for conjugation to an effector moiety (e.g., a reactive aldehyde group). Suitable oxidizable saccharides included, without limitation, galactose and sialic acid (e.g., N-Acetylneuraminic acid). In certain embodiments, the glycan is a biantennary glycan. In certain embodiments, the glycan is a naturally occurring mammalian glycoform.

Glycosylation can be achieved through any means known in the art. In certain embodiments, the glycosylation is achieved by expression of the binding polypeptides in cells capable of N-linked glycosylation. Any natural or engineered cell (e.g., prokaryotic or eukaryotic) can be employed. In general, mammalian cells are employed to effect glycosylation. The N-glycans that are produced in mammalian cells are commonly referred to as complex N-glycans (see e.g., Drickamer K, Taylor M E (2006). Introduction to Glycobiology, 2nd ed., which is incorporated herein by reference in its entirety). These complex N-glycans have a structure with typically two to six outer branches with a sialyllactosamine sequence linked to an inner core structure $Man_3GlcNAc_2$. A complex N-glycan has at least one branch, and preferably at least two, of alternating GlcNAc and galactose (Gal) residues that terminate in oligosaccharides such as, for example: NeuNAc-; NeuAc α2,6 GalNAc α1-; NeuAc α2,3 Gal β1,3 GalNAc α1-; and NeuAc α2,3/6 Gal β1,4 GlcNAc β 1. In addition, sulfate esters can occur on galactose, GalNAc, and GlcNAc residues, and phosphate esters can occur on mannose residues. NeuAc can be 0-acetylated or replaced by NeuGl (N-glycolylneuraminic acid). Complex N-glycans may also have intrachain substitutions of bisecting GlcNAc and core fucose (Fuc).

Additionally or alternatively, glycosylation can be achieved or modified through enzymatic means, in vitro. For example, one or more glycosyltransferases may be employed to add specific saccharide residues to N298, and one or more glycosidases may be employed to remove unwanted saccharides from the N-linked glycan. Such enzymatic means are well known in the art (see. e.g., WO/2007/005786, which is incorporated herein by reference in its entirety).

IV. Immunological Effector Functions and Fc Modifications

In certain embodiments, binding polypeptides of the invention may comprise an antibody constant region (e.g. an IgG constant region e.g., a human IgG constant region, e.g., a human IgG1 or IgG4 constant region) which mediates one or more effector functions. For example, binding of the C1 component of complement to an antibody constant region may activate the complement system. Activation of complement is important in the opsonisation and lysis of cell pathogens. The activation of complement also stimulates the inflammatory response and may also be involved in autoimmune hypersensitivity. Further, antibodies bind to receptors on various cells via the Fc region, with a Fc receptor binding site on the antibody Fc region binding to a Fc receptor (FcR) on a cell. There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production. In preferred embodiments, the binding polypeptides (e.g., antibodies or antigen binding fragments thereof) of the invention bind to an Fc-gamma receptor. In alternative embodiments, binding polypeptides of the invention may comprise a constant region which is devoid of one or more effector functions (e.g., ADCC activity) and/or is unable to bind Fcγ receptor.

Certain embodiments of the invention include antibodies in which at least one amino acid in one or more of the constant region domains has been deleted or otherwise altered so as to provide desired biochemical characteristics such as reduced or enhanced effector functions, the ability to non-covalently dimerize, increased ability to localize at the site of a tumor, reduced serum half-life, or increased serum half-life when compared with a whole, unaltered antibody of approximately the same immunogenicity. For example, certain antibodies for use in the diagnostic and treatment methods described herein are domain deleted antibodies which comprise a polypeptide chain similar to an immunoglobulin heavy chain, but which lack at least a portion of one or more heavy chain domains. For instance, in certain antibodies, one entire domain of the constant region of the modified antibody will be deleted, for example, all or part of the CH2 domain will be deleted.

In certain other embodiments, binding polypeptides comprise constant regions derived from different antibody isotypes (e.g., constant regions from two or more of a human IgG1, IgG2, IgG3, or IgG4). In other embodiments, binding polypeptides comprises a chimeric hinge (i.e., a hinge comprising hinge portions derived from hinge domains of different antibody isotypes, e.g., an upper hinge domain from an IgG4 molecule and an IgG1 middle hinge domain). In one embodiment, binding polypeptides comprise an Fc region or portion thereof from a human IgG4 molecule and a Ser228Pro mutation (EU numbering) in the core hinge region of the molecule.

In certain embodiments, the Fc portion may be mutated to increase or decrease effector function using techniques known in the art. For example, the deletion or inactivation (through point mutations or other means) of a constant region domain may reduce Fc receptor binding of the circulating modified antibody thereby increasing tumor localization. In other cases it may be that constant region modifications consistent with the instant invention moderate complement binding and thus reduce the serum half-life and nonspecific association of a conjugated cytotoxin. Yet other modifications of the constant region may be used to modify disulfide linkages or oligosaccharide moieties that allow for enhanced localization due to increased antigen specificity or flexibility. The resulting physiological profile, bioavailability and other biochemical effects of the modifications, such as tumor localization, biodistribution and serum half-life, may easily be measured and quantified using well know immunological techniques without undue experimentation.

In certain embodiments, an Fc domain employed in an antibody of the invention is an Fc variant. As used herein, the term "Fc variant" refers to an Fc domain having at least one amino acid substitution relative to the wild-type Fc domain from which said Fc domain is derived. For example, wherein the Fc domain is derived from a human IgG1 antibody, the Fc variant of said human IgG1 Fc domain comprises at least one amino acid substitution relative to said Fc domain.

The amino acid substitution(s) of an Fc variant may be located at any position (i.e., any EU convention amino acid position) within the Fc domain. In one embodiment, the Fc variant comprises a substitution at an amino acid position located in a hinge domain or portion thereof. In another embodiment, the Fc variant comprises a substitution at an amino acid position located in a CH2 domain or portion thereof. In another embodiment, the Fc variant comprises a substitution at an amino acid position located in a CH3 domain or portion thereof. In another embodiment, the Fc variant comprises a substitution at an amino acid position located in a CH4 domain or portion thereof.

The binding polypeptides of the invention may employ any art-recognized Fc variant which is known to impart an improvement (e.g., reduction or enhancement) in effector function and/or FcR binding. Said Fc variants may include, for example, any one of the amino acid substitutions disclosed in International PCT Publications WO88/07089A1, WO96/14339A1, WO98/05787A1, WO98/23289A1, WO99/51642A1, WO99/58572A1, WO00/09560A2, WO00/32767A1, WO00/42072A2, WO02/44215A2, WO02/060919A2, WO03/074569A2, WO04/016750A2, WO04/029207A2, WO04/035752A2, WO04/063351A2, WO04/074455A2, WO04/099249A2, WO05/040217A2, WO05/070963A1, WO05/077981A2, WO05/092925A2, WO05/123780A2, WO06/019447A1, WO06/047350A2, and WO06/085967A2 or U.S. Pat. Nos. 5,648,260; 5,739,277; 5,834,250; 5,869,046; 6,096,871; 6,121,022; 6,194,551; 6,242,195; 6,277,375; 6,528,624; 6,538,124; 6,737,056; 6,821,505; 6,998,253; and 7,083,784, each of which is incorporated by reference herein. In one exemplary embodiment, a binding polypeptide of the invention may comprise an Fc variant comprising an amino acid substitution at EU position 268 (e.g., H268D or H268E). In another exemplary embodiment, a binding polypeptide of the invention may comprise an amino acid substitution at EU position 239 (e.g., S239D or S239E) and/or EU position 332 (e.g., I332D or I332Q).

In certain embodiments, a binding polypeptide of the invention may comprise an Fc variant comprising an amino acid substitution which alters the antigen-independent effector functions of the antibody, in particular the circulating half-life of the binding polypeptide. Such binding polypeptides exhibit either increased or decreased binding to FcRn when compared to binding polypeptides lacking these substitutions, therefore, have an increased or decreased half-life in serum, respectively. Fc variants with improved affinity for FcRn are anticipated to have longer serum half-lives, and such molecules have useful applications in methods of treating mammals where long half-life of the administered antibody is desired, e.g., to treat a chronic disease or disorder. In contrast, Fc variants with decreased FcRn binding affinity are expected to have shorter half-lives, and such molecules are also useful, for example, for administration to a mammal where a shortened circulation time may be advantageous, e.g. for in vivo diagnostic imaging or in situations where the starting antibody has toxic side effects when present in the circulation for prolonged periods. Fc variants with decreased FcRn binding affinity are also less likely to cross the placenta and, thus, are also useful in the treatment of diseases or disorders in pregnant women. In addition, other applications in which reduced FcRn binding affinity may be desired include those applications in which localization the brain, kidney, and/or liver is desired. In one exemplary embodiment, the altered binding polypeptides (e.g., antibodies or antigen binding fragments thereof) of the invention exhibit reduced transport across the epithelium of kidney glomeruli from the vasculature. In another embodiment, the altered binding polypeptides (e.g., antibodies or antigen binding fragments thereof) of the invention exhibit reduced transport across the blood brain barrier (BBB) from the brain, into the vascular space. In one embodiment, an antibody with altered FcRn binding comprises an Fc domain having one or more amino acid substitutions within the "FcRn binding loop" of an Fc domain. The FcRn binding loop is comprised of amino acid residues 280-299 (according to EU numbering). Exemplary amino acid substitutions which altered FcRn binding activity are disclosed in International PCT Publication No. WO05/047247 which is incorporated by reference herein. In certain exemplary embodiments, the binding polypeptides (e.g., antibodies or antigen binding fragments thereof) of the invention comprise an Fc domain having one or more of the following substitutions: V284E, H285E, N286D, K290E and S304D (EU numbering). In yet other exemplary embodiments, the biding molecules of the invention comprise a human Fc domain with the double mutation H433K/N434F (see, e.g., U.S. Pat. No. 8,163,881).

In other embodiments, binding polypeptides, for use in the diagnostic and treatment methods described herein have a constant region, e.g., an IgG1 or IgG4 heavy chain constant region, which is altered to reduce or eliminate glycosylation. For example, binding polypeptides (e.g., antibodies or antigen binding fragments thereof) of the invention may also comprise an Fc variant comprising an amino acid substitution which alters the glycosylation of the antibody Fc. For example, said Fc variant may have reduced glycosylation (e.g., N- or O-linked glycosylation). In exemplary embodiments, the Fc variant comprises reduced glycosylation of the N-linked glycan normally found at amino acid position 297 (EU numbering). In another embodiment, the antibody has an amino acid substitution near or within a glycosylation motif, for example, an N-linked glycosylation motif that contains the amino acid sequence NXT or NXS. In a particular embodiment, the antibody comprises an Fc variant with an amino acid substitution at amino acid position 228 or 299 (EU numbering). In more particular embodiments, the antibody comprises an IgG1 or IgG4 constant region comprising an S228P and a T299A mutation (EU numbering).

VIII. Effector Moieties

In certain embodiments, the binding polypeptides of the current disclosure comprise effector moieties. In general these effector moieties are conjugated (either directly or through a linker moiety) to an N-linked glycan on the binding polypeptide, (e.g., an N-linked glycan linked to N298 (EU numbering) of the CH2 domain and/or N114 (Kabat numbering) of a CH1 domain). In certain embodiments, the binding polypeptide is full length antibody comprising two CH1 domains with a glycan at Kabat position 114, wherein both of the glycans are conjugated to one or more effector moieties.

Any effector moiety can be added to the binding polypeptides disclosed herein. The effector moieties preferably add a non-natural function to an altered antibody or fragments thereof, without significantly altering the intrinsic activity of the binding polypeptide. The effector moiety may be, for example but not limited to, a therapeutic or diagnostic agent. A modified binding polypeptide (e.g., an antibody) of the current disclosure may comprise one or more effector moieties, which may by the same of different.

In one embodiment, the effector moiety can be of Formula (I):

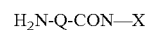 Formula (I), wherein:
A) Q is NH or O; and
B) CON is a connector moiety; and
C) X is a therapeutic agent as defined herein.

The connector moiety connects the therapeutic agent to H$_2$N-Q-. The connector moiety can include at least one of any suitable components known those skilled in the art, including, for example, an alkylenyl component, a polyethylene glycol component, a poly(glycine) component, a poly (oxazoline) component, a carbonyl component, a component derived from cysteinamide, a component derived from valine coupled with citruline, and a component derived from 4-aminobenzyl carbamate, or any combination thereof.

In another embodiment, the effector moiety of Formula (I) can be of Formula (Ia):

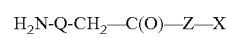 Formula (Ia), wherein:
A) Q is NH or O; and
B) Z is -Cys-(MC)$_a$-(VC)$_b$-(PABC)$_c$-(C$_{16}$H$_{32}$O$_8$C$_2$H$_4$)$_f$, wherein
  i. Cys is a component derived cysteinamide;
  ii. MC is a component derived from maleimide;
  iii. VC is a component derived from valine coupled with citruline;
  iv. PABC is a component derived from 4-aminobenzyl carbamate;
  v. X is a therapeutic agent as defined herein;
  vi. a is 0 or 1;
  vii. b is 0 or 1;
  viii. c is 0 or 1; and
  ix. f is 0 or 1

The "component derived from cysteinamide" is the point of attachment to $H_2N\text{-}Q\text{-}CH_2\text{—}C(O)\text{—}$. In one embodiment, the "component derived from cysteinamide" can refer to one or more portions of the effector moiety having the structure:

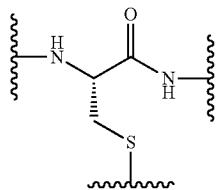 [SMILES: *NC(=O)[C@H](CS*)N*]

In one embodiment, the "Cys" component of an effector moiety may include one such portion. For example, the following structure shows an effector moiety with one such portion (wherein the "Cys" component is indicated with the dotted line box):

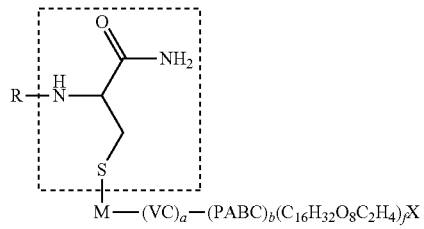

In another embodiment, the "Cys" component of an effector moiety may include two or more such portions. For example, the following moiety contains two such portions:

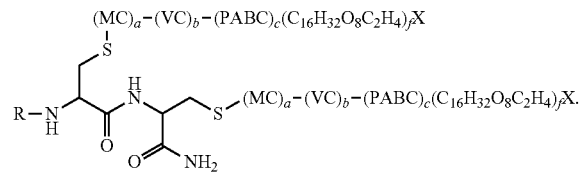

As can be seen from the structure, each "Cys" component bears an $\text{-}(MC)_a(VC)_b\text{-}(PABC)_c\text{-}(C_{16}H_{32}O_8C_2H_4)_f\text{—}X$ group.

In one embodiment, the phrase "component derived from maleimide" can refer to any portion of the effector moiety having the structure:

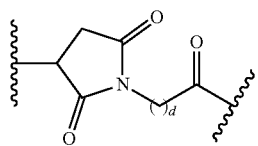

wherein d is an integer from 2 to 5. The number of MC components included in any Cys-$(MC)_a(VC)_b$-$(PABC)_c$-$(C_{16}H_{32}O_8C_2H_4)_f$—X group in the effector moiety is indicated by subscript "a," and can be 0 or 1 In one embodiment, a is 1. In another embodiment, b is 0.

In one embodiment, the "Cys" component can be connected to the "MC" component via the sulfur atom in the "Cys" component, as indicated with the dotted line box in the structure below:

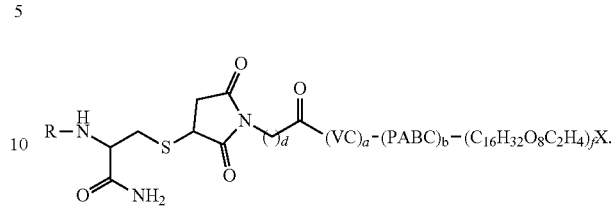

In one embodiment, the phrase "component derived from valine coupled with citruline" can refer to any portion of the effector moiety with the following structure:

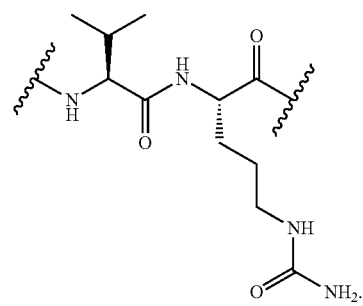 [SMILES: *N[C@H](C(=O)N[C@@H](CCCNC(N)=O)C(*)=O)C(C)C]

The number of VC components included in any Cys-$(MC)_a(VC)_b$-$(PABC)_c$-$(C_{16}H_{32}O_8C_2H_4)_f$—X group in the effector moiety is indicated by subscript "b," and can be 0 or 1. In one embodiment, b is 1. In another embodiment, b is 0.

In one embodiment, the phrase "component derived from 4-aminobenzyl carbamate" can refer to any portion of the effector moiety with the following structure:

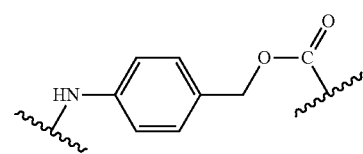 [SMILES: *Nc1ccc(COC(*)=O)cc1]

The number of PABC components included in any Cys-$(MC)_a$-$(VC)_b$-$(PABC)_c$-$(C_{16}H_{32}O_8C_2H_4)_f$—X group in the effector moiety is indicated by subscript "c," and can be 0 or 1. In one embodiment, c is 1. In another embodiment, c is 0.

In one embodiment, "$C_{16}H_{32}O_8C_2H_4$" refers to the following structure:

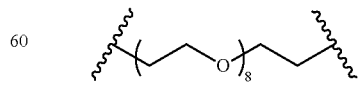

The number of $C_{16}H_{32}O_8$ units included in any Cys-$(MC)_a$-$(VC)_b$-$(PABC)_c$-$(C_{16}H_{32}O_8C_2H_4)_f$—X group in the effector moiety is indicated by subscript "f," In one embodiment, f is 1. In another embodiment, f is 0.

In one embodiment, a is 1, b is 1, c is 1, and f is 0.

a) Therapeutic Effector Moieties

In certain embodiments, the binding polypeptides of the current disclosure are conjugated to an effector moiety comprising a therapeutic agent, e.g. a drug moiety (or prodrug thereof) or radiolabeled compound. In one embodiment the therapeutic agent is a cytotoxin. Exemplary cytotoxic effector moieties are set forth in Table 1 herein.

TABLE 1

Exemplary cytotoxic effector moieties

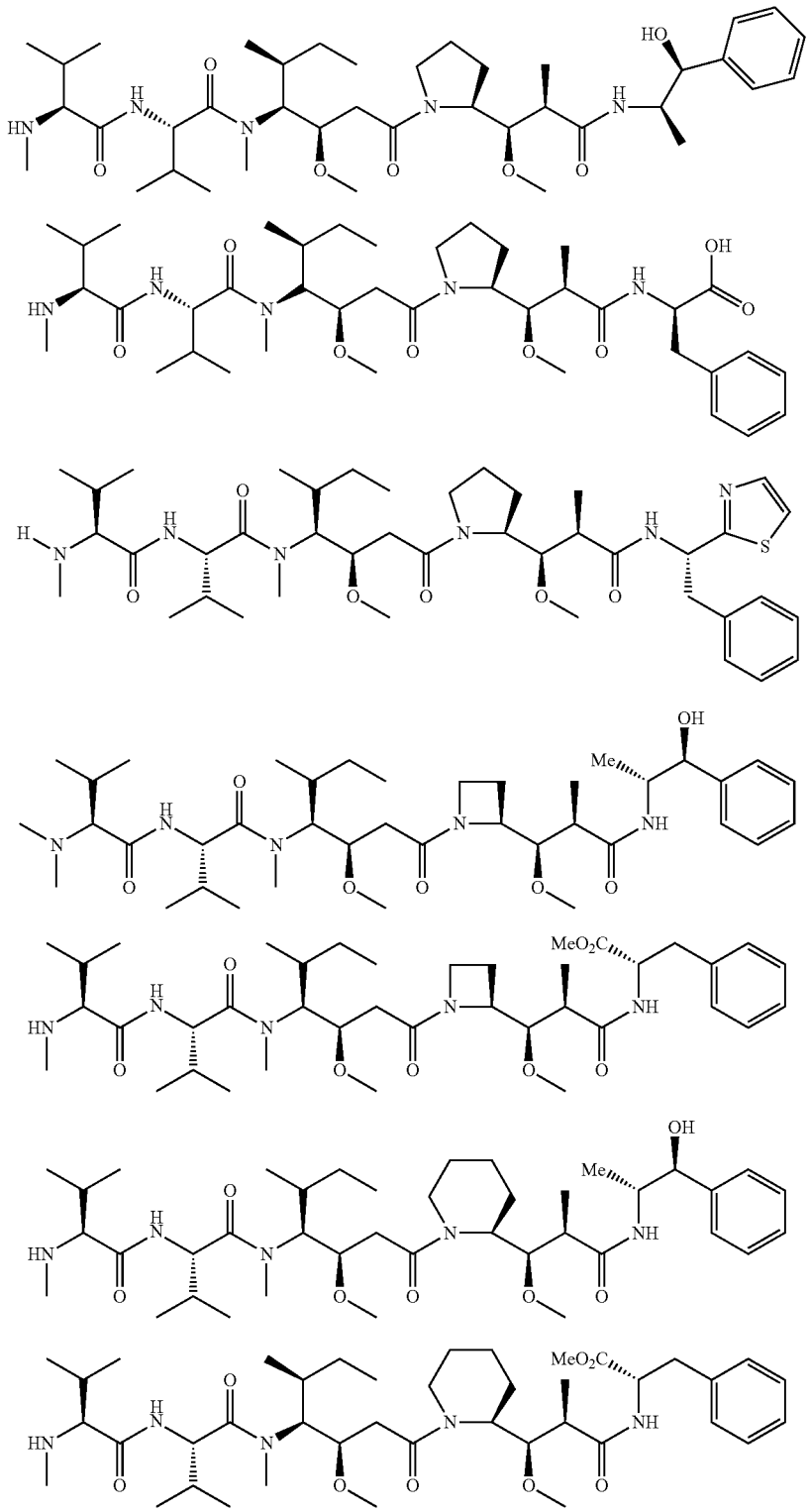

TABLE 1-continued
Exemplary cytotoxic effector moieties
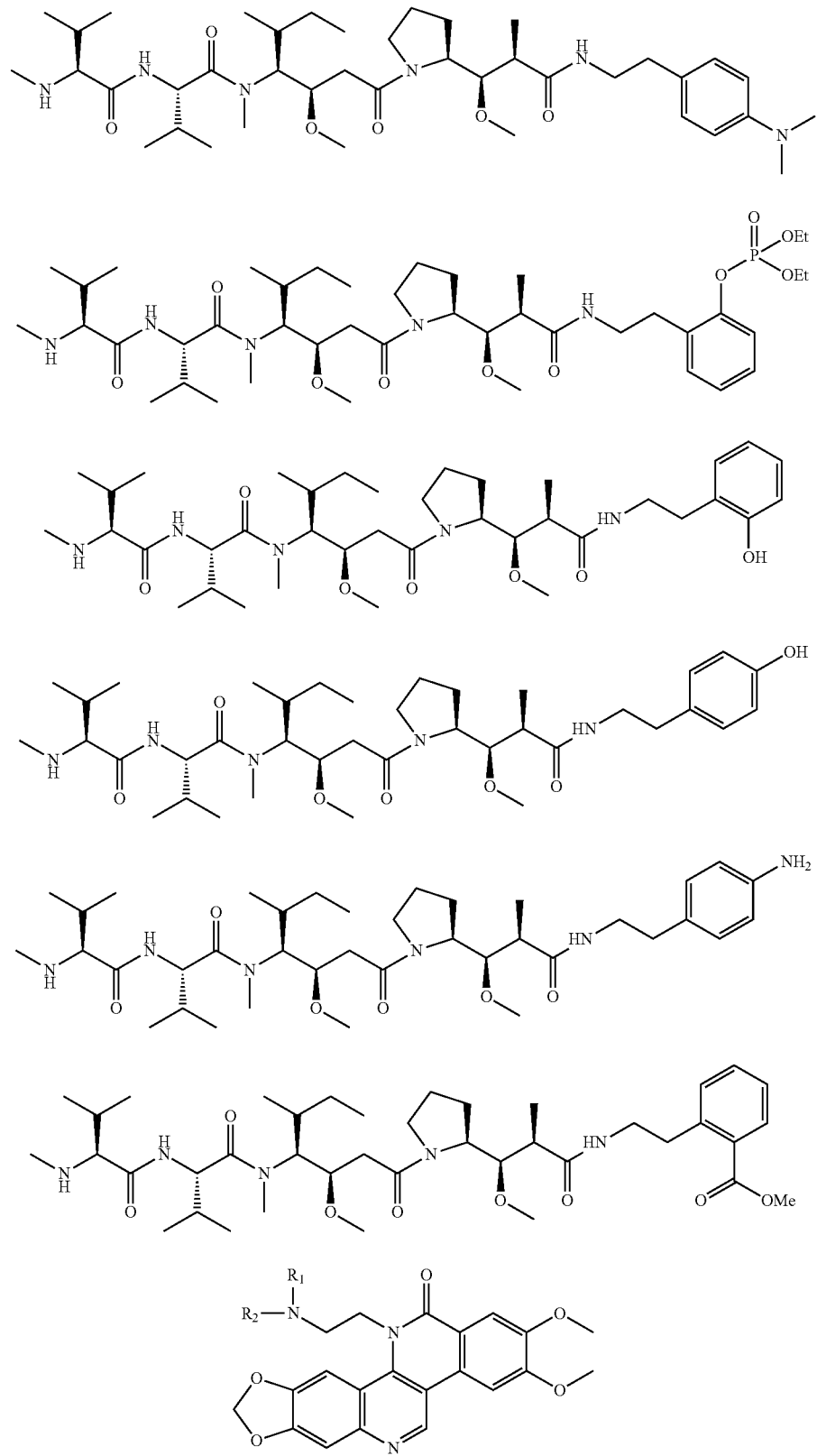

TABLE 1-continued
Exemplary cytotoxic effector moieties
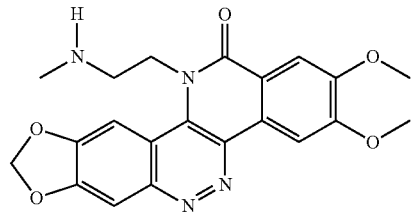 [SMILES: CNCCn1c(=O)c2cc(OC)c(OC)cc2c2nnc3cc4c(cc3c21)OCO4]
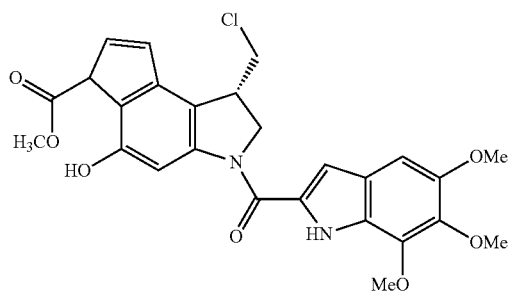 [SMILES: COC(=O)C1C=Cc2c1c(O)cc1c2[C@H](CCl)CN1C(=O)c1cc2cc(OC)c(OC)c(OC)c2[nH]1]
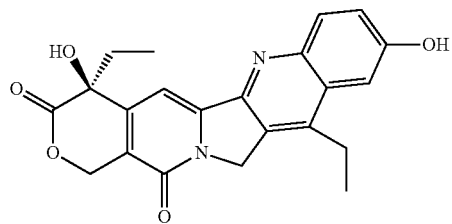 [SMILES: CCc1c2c(nc3ccc(O)cc13)-c1cc3c(c(=O)n1C2)COC(=O)[C@]3(O)CC]
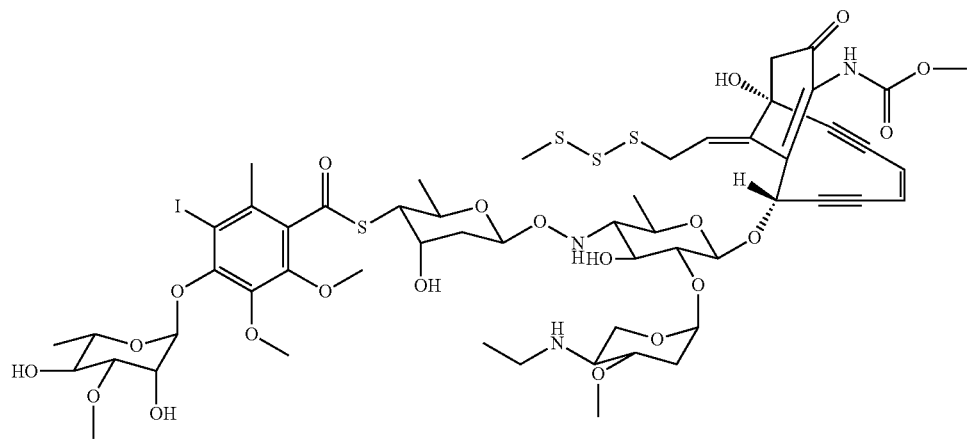 [SMILES: CCNC1COC(OC2C(O[C@H]3C#C/C=C\C#C[C@]4(O)CC(=O)C(NC(=O)OC)=C3/C4=C\CSSSC)OC(C)C(NOC3CC(O)C(SC(=O)c4c(C)c(I)c(OC5OC(C)C(O)C(OC)C5O)c(OC)c4OC)C(C)O3)C2O)CC1OC]
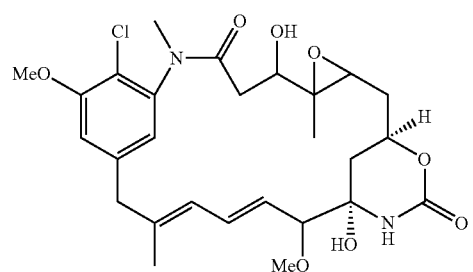 [SMILES: COc1cc2cc(c1Cl)N(C)C(=O)CC(O)C1(C)OC1C[C@@H]1C[C@@](O)(NC(=O)O1)C(OC)/C=C/C=C(\C)C2]

TABLE 1-continued

Exemplary cytotoxic effector moieties

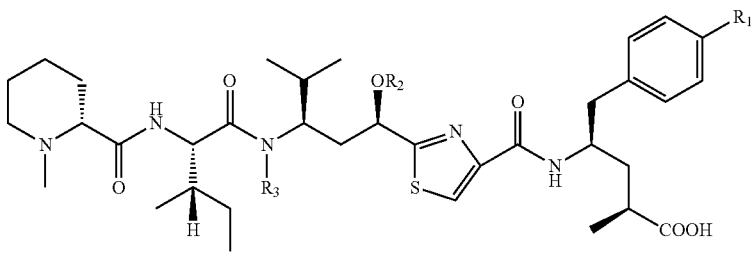

R₁ = alkyl, aryl, alkoxy, aryloxy, R₂, R₃ = alkyl, aryl

Further exemplary drug moieties include anti-inflammatory, anticancer, anti-infective (e.g., anti-fungal, antibacterial, anti-parasitic, anti-viral, etc.), and anesthetic therapeutic agents. In a further embodiment, the drug moiety is an anticancer agent. Exemplary anti-cancer agents include, but are not limited to, cytostatics, enzyme inhibitors, gene regulators, cytotoxic nucleosides, tubulin binding agents or tubulin inhibitors, proteasome inhibitors, hormones and hormone antagonists, anti-angiogenesis agents, and the like. Exemplary cytostatic anti-cancer agents include alkylating agents such as the anthracycline family of drugs (e.g. adriamycin, carminomycin, cyclosporin-A, chloroquine, methopterin, mithramycin, porfiromycin, streptonigrin, porfiromycin, anthracenediones, and aziridines). Other cytostatic anti-cancer agents include DNA synthesis inhibitors (e.g., methotrexate and dichloromethotrexate, 3-amino-1,2,4-benzotriazine 1,4-dioxide, aminopterin, cytosine β-D-arabinofuranoside, 5-fluoro-5'-deoxyuridine, 5-fluorouracil, ganciclovir, hydroxyurea, actinomycin-D, and mitomycin C), DNA-intercalators or cross-linkers (e.g., bleomycin, carboplatin, carmustine, chlorambucil, cyclophosphamide, cis-diammineplatinum(II) dichloride (cisplatin), melphalan, mitoxantrone, and oxaliplatin), and DNA-RNA transcription regulators (e.g., actinomycin D, daunorubicin, doxorubicin, homoharringtonine, and idarubicin). Other exemplary cytostatic agents that are compatible with the present disclosure include ansamycin benzoquinones, quinonoid derivatives (e.g. quinolones, genistein, bactacyclin), busulfan, ifosfamide, mechlorethamine, triaziquone, diaziquone, carbazilquinone, indoloquinone E09, diaziridinyl-benzoquinone methyl DZQ, triethylenephosphoramide, and nitrosourea compounds (e.g. carmustine, lomustine, semustine).

Exemplary cytotoxic nucleoside anti-cancer agents include, for example, adenosine arabinoside, cytarabine, cytosine arabinoside, 5-fluorouracil, fludarabine, floxuridine, ftorafur, and 6-mercaptopurine. Exemplary anti-cancer tubulin binding agents include taxoids (e.g. paclitaxel, docetaxel, taxane), nocodazole, rhizoxin, dolastatins (e.g. Dolastatin-10, -11, or -15), colchicine and colchicinoids (e.g. ZD6126), combretastatins (e.g. Combretastatin A-4, AVE-6032), and vinca alkaloids (e.g. vinblastine, vincristine, vindesine, and vinorelbine (navelbine)). Exemplary anti-cancer hormones and hormone antagonists, include corticosteroids (e.g. prednisone), progestins (e.g. hydroxyprogesterone or medroprogesterone), estrogens, (e.g. diethylstilbestrol), antiestrogens (e.g. tamoxifen), androgens (e.g. testosterone), aromatase inhibitors (e.g., aminoglutethimide), 17-(allylamino)-17-demethoxygeldanamycin, 4-amino-1,8-naphthalimide, apigenin, brefeldin A, cimetidine, dichloromethylene-diphosphonic acid, leuprolide (leuprorelin), luteinizing hormone-releasing hormone, pifithrin-a, rapamycin, sex hormone-binding globulin, and thapsigargin. Exemplary anti-cancer, anti-angiogenesis compounds included Angiostatin K1-3, DL-a-difluoromethyl-ornithine, endostatin, fumagillin, genistein, minocycline, staurosporine, and (±)-thalidomide.

Exemplary anti-cancer enzyme inhibitors include but are not limited to, S(+)-camptothecin, curcumin, (−)-deguelin, 5,6-diCH1orobenz-imidazole 1-β-D-ribofuranoside, etoposide, formestane, fostriecin, hispidin, 2-imino-1-imidazolidineacetic acid (cyclocreatine), mevinolin, trichostatin A, tyrphostin AG 34, and tyrphostin AG 879.

Exemplary anti-cancer gene regulators include 5-aza-2'-deoxycytidine, 5-azacytidine, cholecalciferol (vitamin D3), 4-hydroxytamoxifen, melatonin, mifepristone, raloxifene, trans-retinal (vitamin A aldehydes), retinoic acid, vitamin A acid, 9-cis-retinoic acid, 13-cis-retinoic acid, retinol (vitamin A), tamoxifen, and troglitazone.

Other preferred classes of anti-cancer agents include, for example, the pteridine family of drugs, diynenes, and the podophyllotoxins. Particularly useful members of those classes include, for example, methopterin, podophyllotoxin, or podophyllotoxin derivatives such as etoposide or etoposide phosphate, leurosidine, vindesine, leurosine and the like.

Still other anti-cancer agents that are compatible with the teachings herein include auristatins (e.g. auristatin E and monomethylauristan E), geldanamycin, calicheamicin, gramicidin D, maytansanoids (e.g. maytansine), neocarzinostatin, topotecan, taxanes, cytochalasin B, ethidium bromide, emetine, tenoposide, colchicin, dihydroxy anthracindione, mitoxantrone, procaine, tetracaine, lidocaine, propranolol, puromycin, and analogs or homologs thereof.

Still other anti-cancer agents that are compatible with the teachings herein include tomaymycin derivatives, maytansine derivatives, cryptophycine derivatives, anthracycline derivatives, bisphosphonate derivatives, leptomycin derivatives, streptonigrin derivatives, auristatine derivatives, and duocarmycin derivatives Another class of compatible anti-cancer agents that may be used as drug moieties are radiosensitizing drugs that may be effectively directed to tumor or immunoreactive cells. Such drug moeities enhance the sensitivity to ionizing radiation, thereby increasing the efficacy of radiotherapy. Not to be limited by theory, but an antibody modified with a radiosensitizing drug moiety and internalized by the tumor cell would deliver the radiosensitizer nearer the nucleus where radiosensitization would be maximal. Antibodies which lose the radiosensitizer moiety would be cleared quickly from the blood, localizing the remaining radiosensitization agent in the target tumor and providing minimal uptake in normal tissues. After clearance from the blood, adjunct radiotherapy could be administered by external beam radiation directed specifically to the tumor, radioactivity directly implanted in the tumor, or systemic radioimmunotherapy with the same modified antibody.

In one embodiment, the therapeutic agent comprises radionuclides or radiolabels with high-energy ionizing radiation are capable of causing multiple strand breaks in nuclear DNA, leading to cell death. Exemplary high-energy radionuclides include: 90Y, 125I, 131I, 123I, 111In, 105Rh, 153Sm, 67Cu, 67Ga, 166Ho, 177Lu, 186Re and 188Re. These isotopes typically produce high energy α- or β-particles which have a short path length. Such radionuclides kill cells to which they are in close proximity, for example neoplastic cells to which the conjugate has attached or has entered. They have little or no effect on non-localized cells and are essentially non-immunogenic. Alternatively, high-energy isotopes may be generated by thermal irradiation of an otherwise stable isotope, for example as in boron neutron-capture therapy (Guan et al., PNAS, 95: 13206-10, 1998).

In one embodiment, the therapeutic agent is selected from MMAE, MMAF, and PEGS-Do110.

Exemplary therapeutic effector moieties include the structures:

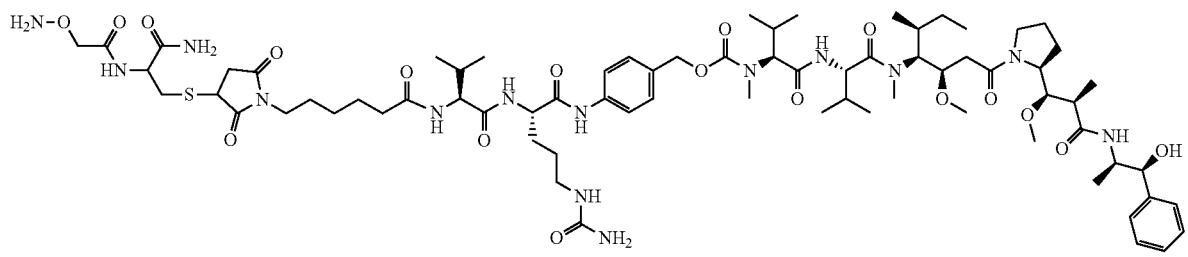

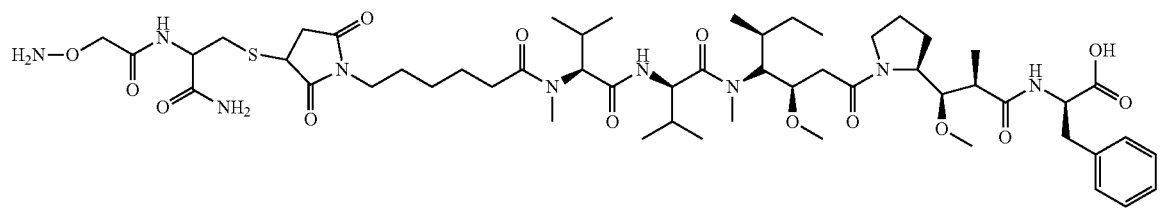

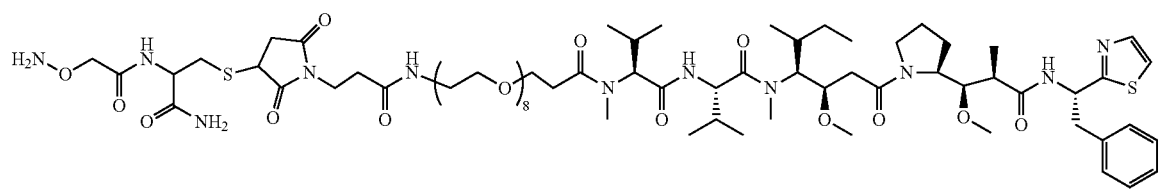

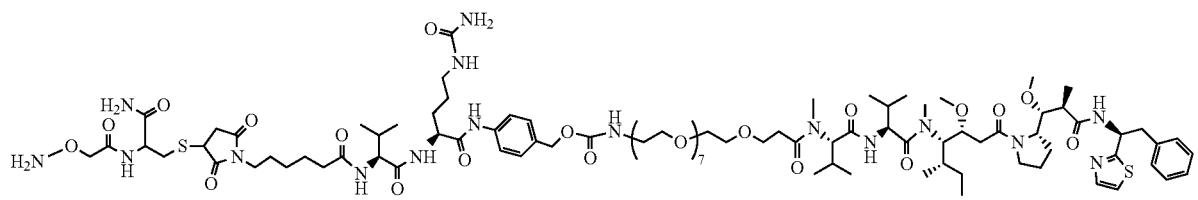

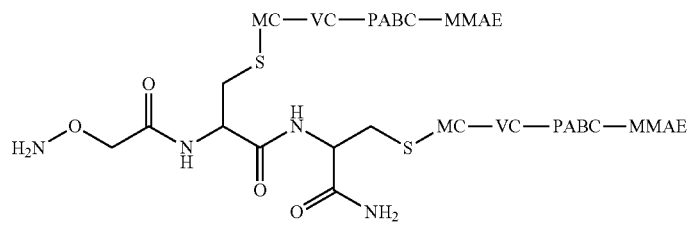

-continued
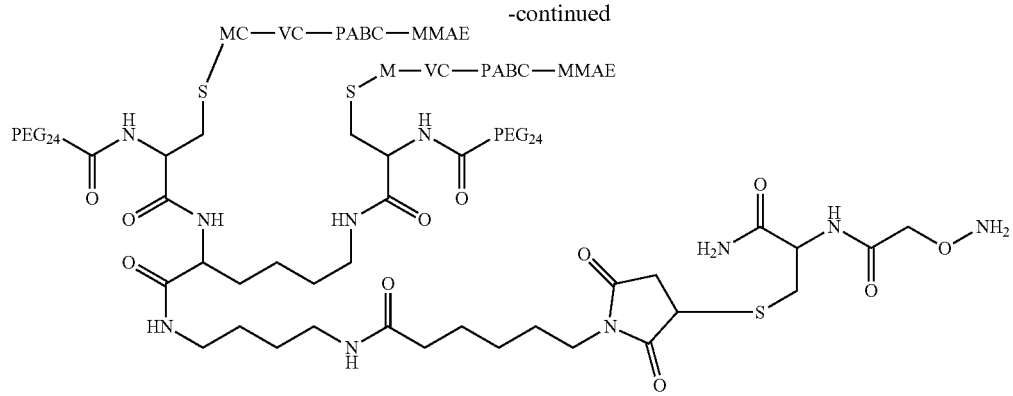
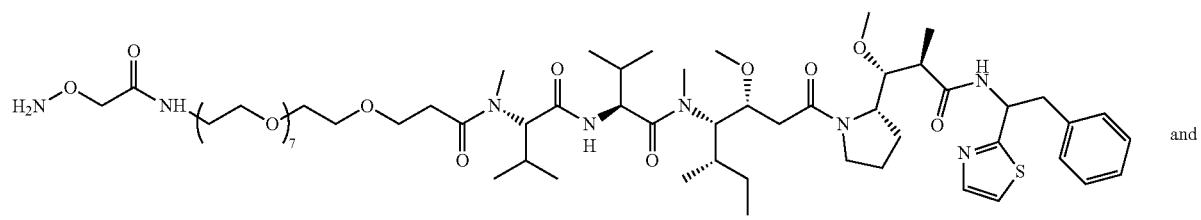
and
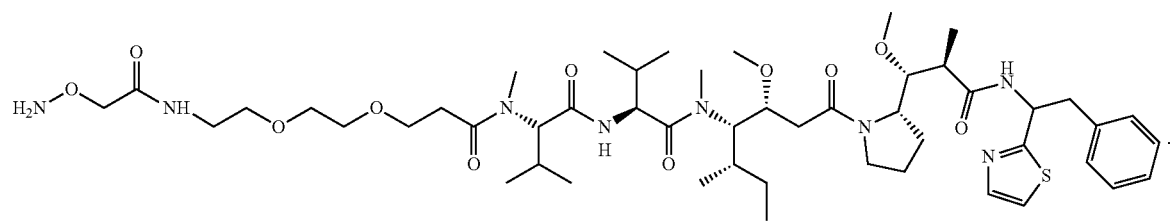
In one embodiment, the effector moiety is selected from:
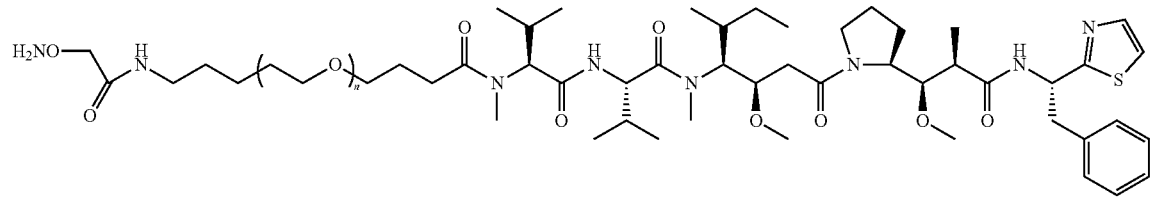
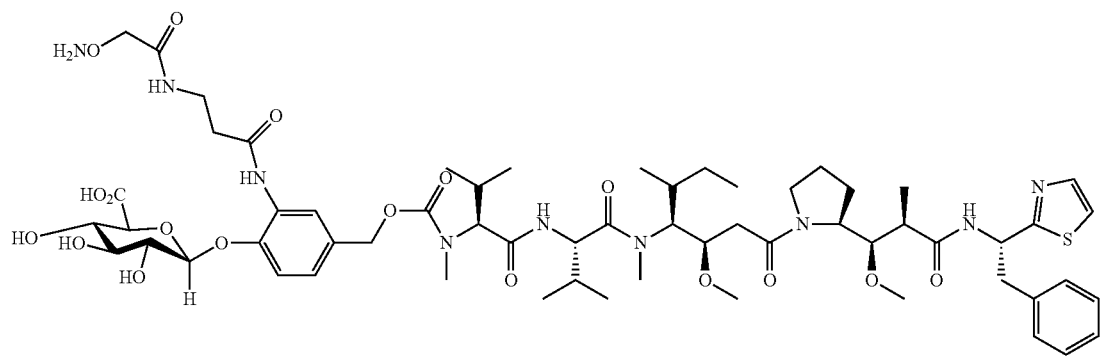

-continued

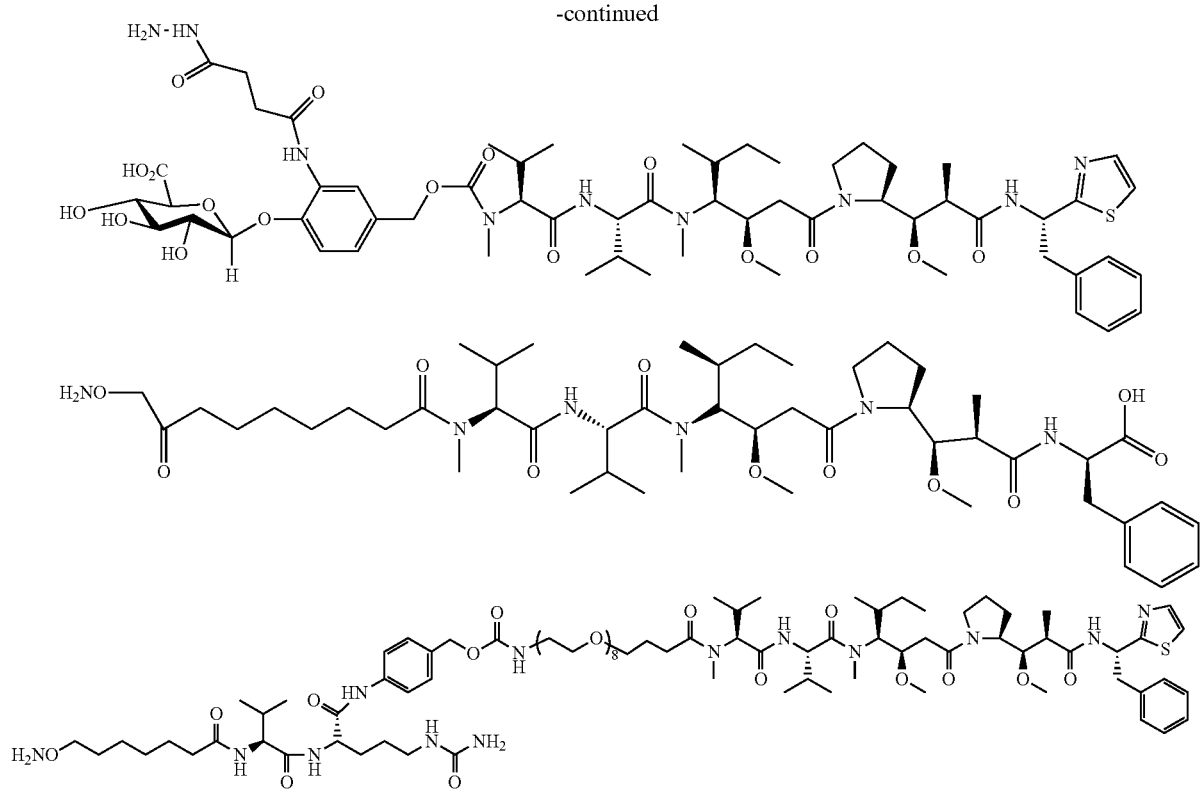

In certain embodiments, the effector moiety contains more than one therapeutic agent. These multiple therapeutic agents can be the same or different.

i. Diagnostic Effector Moieties

In certain embodiments, the binding polypeptides of the current disclosure are conjugated to an effector moiety comprising a diagnostic agent. In one embodiment, the diagnostic agent is a detectable small molecule labels e.g. biotin, fluorophores, chromophores, spin resonance probes, or radiolabels. Exemplary fluorophores include fluorescent dyes (e.g. fluorescein, rhodamine, and the like) and other luminescent molecules (e.g. luminal). A fluorophore may be environmentally-sensitive such that its fluorescence changes if it is located close to one or more residues in the modified binding polypeptide that undergo structural changes upon binding a substrate (e.g. dansyl probes). Exemplary radiolabels include small molecules containing atoms with one or more low sensitivity nuclei (13C, 15N, 2H, 125I, 124I, 123I, 99Tc, 43K, 52Fe, 64Cu, 68Ga, 111In and the like). Preferably, the radionuclide is a gamma, photon, or positron-emitting radionuclide with a half-life suitable to permit activity or detection after the elapsed time between administration and localization to the imaging site.

In one embodiment, the diagnostic agent is a polypeptide. Exemplary diagnostic polypeptides include enzymes with fluorogenic or chromogenic activity, e.g. the ability to cleave a substrate which forms a fluorophore or chromophore as a product (i.e. reporter proteins such as luciferase). Other diagnostic proteins may have intrinsic fluorogenic or chromogenic activity (e.g., green, red, and yellow fluorescent bioluminescent aequorin proteins from bioluminescent marine organisms) or they may comprise a protein containing one or more low-energy radioactive nuclei (13C, 15N, 2H, 125I, 124I, 123I, 99Tc, 43K, 52Fe, 64Cu, 68Ga, 111In and the like).

With respect to the use of radiolabeled conjugates in conjunction with the present disclosure, binding polypeptides of the current disclosure may be directly labeled (such as through iodination) or may be labeled indirectly through the use of a chelating agent. As used herein, the phrases "indirect labeling" and "indirect labeling approach" both mean that a chelating agent is covalently attached to a binding polypeptide and at least one radionuclide is associated with the chelating agent. Such chelating agents are typically referred to as bifunctional chelating agents as they bind both the polypeptide and the radioisotope. Exemplary chelating agents comprise 1-isothiocycmatobenzyl-3-methyldiothelene triaminepentaacetic acid ("MX-DTPA") and cyclohexyl diethylenetriamine pentaacetic acid ("CHX-DTPA") derivatives. Other chelating agents comprise P-DOTA and EDTA derivatives. Particularly preferred radionuclides for indirect labeling include 111In and 90Y. Most imaging studies utilize 5 mCi 111In-labeled antibody, because this dose is both safe and has increased imaging efficiency compared with lower doses, with optimal imaging occurring at three to six days after antibody administration. See, for example, Murray, (1985), J. Nuc. Med. 26: 3328 and Carraguillo et al, (1985), J. Nuc. Med. 26: 67. A particularly preferred radionuclide for direct labeling is 131I. Those skilled in the art will appreciate that non-radioactive conjugates may also be assembled depending on the selected agent to be conjugated.

In certain embodiments, the diagnostic effector moiety is a FRET (Fluorescence Resonance Energy Transfer) probe. FRET has been used for a variety of diagnostic applications including cancer diagnostics. A FRET probe may include a cleavable linker (enzyme sensitive or pH linker) connecting the donor and acceptor moieties of the FRET probe, wherein cleavage results in enhanced fluorescence (including near Infrared) (see, e.g., A. Cobos-Correa et. al. *Membrane-bound FRET probe visualizes MMP12 activity in pulmonary inflammation*, Nature Chemical Biology (2009), 5(9), 628-63; S. Gehrig et. al. *Spatially Resolved Monitoring of Neutrophil Elastase Activity with Ratiometric Fluorescent Reporters* (2012) Angew. Chem. Int. Ed., 51, 6258-6261).
In one embodiment, the effector moiety is selected from:
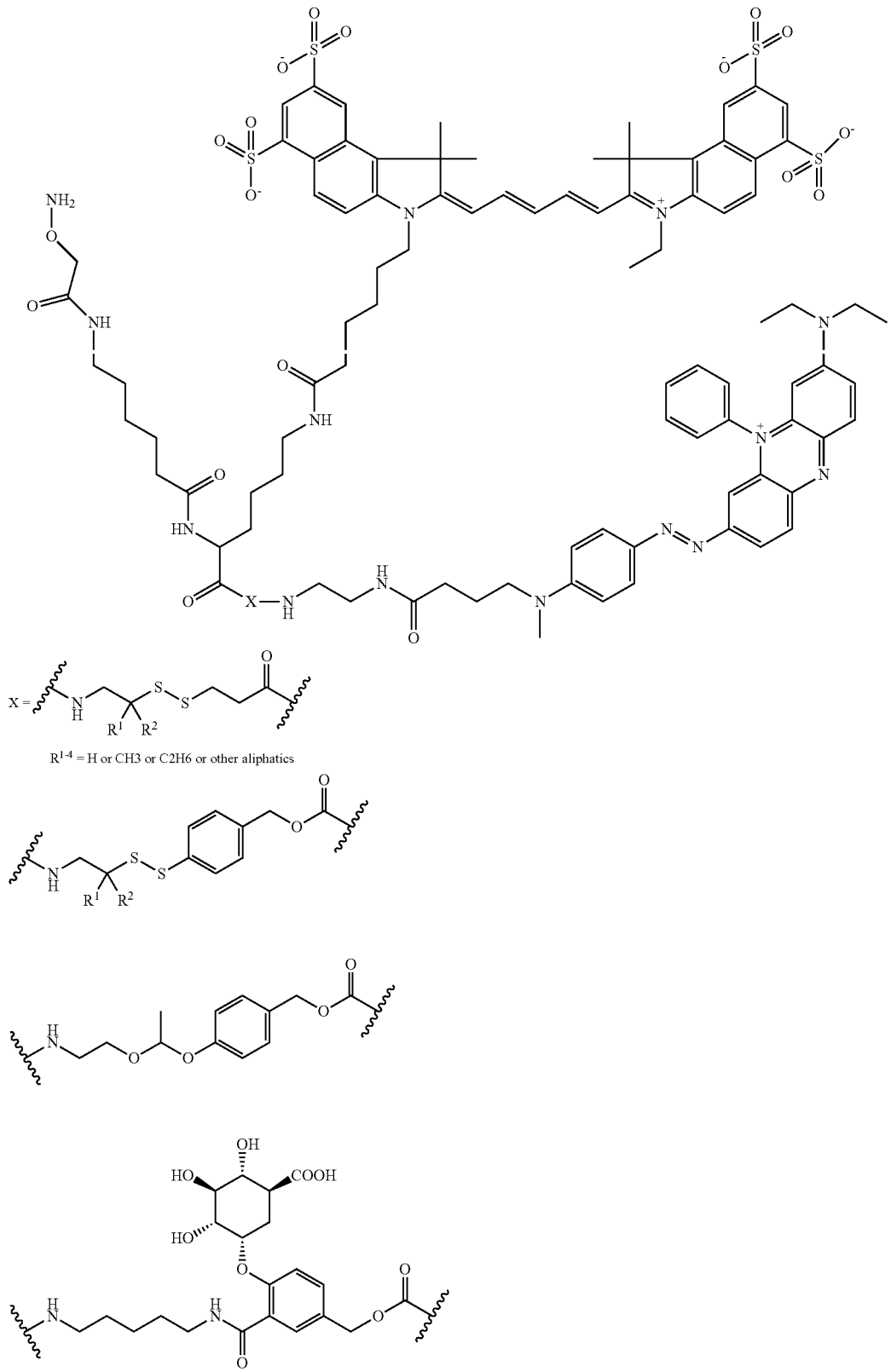

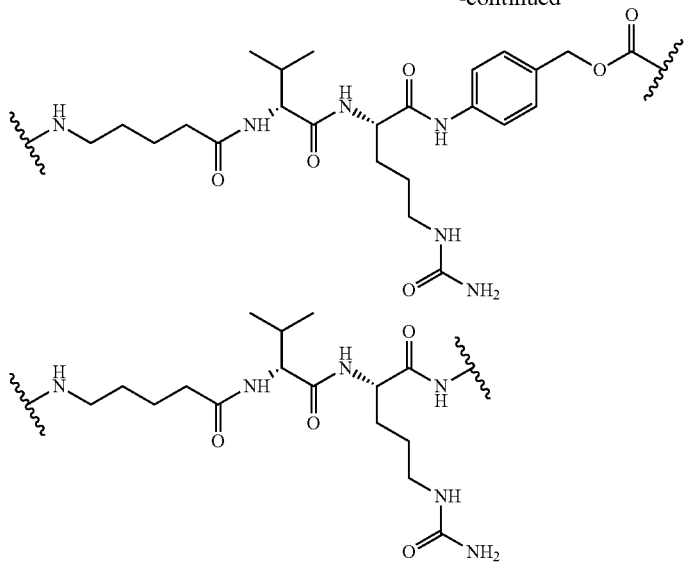

c. Functionalized Effector Moieties

In certain embodiments, the effector moieties of the invention may be functionalized to contain additional groups in addition to the effector moiety itself. For example, the effector moiety may contain cleavable linkers which release the effector moiety from the binding polypeptide under particular conditions. In exemplary embodiments, the effector moiety may include a linker that is cleavable by cellular enzymes and/or is pH sensitive. Additionally or alternatively, the effector moiety may contain a disulfide bond that cleaved by intracellular glutathione upon uptake into the cell. Exemplary disulfide and pH sensitive linkers are provided below:

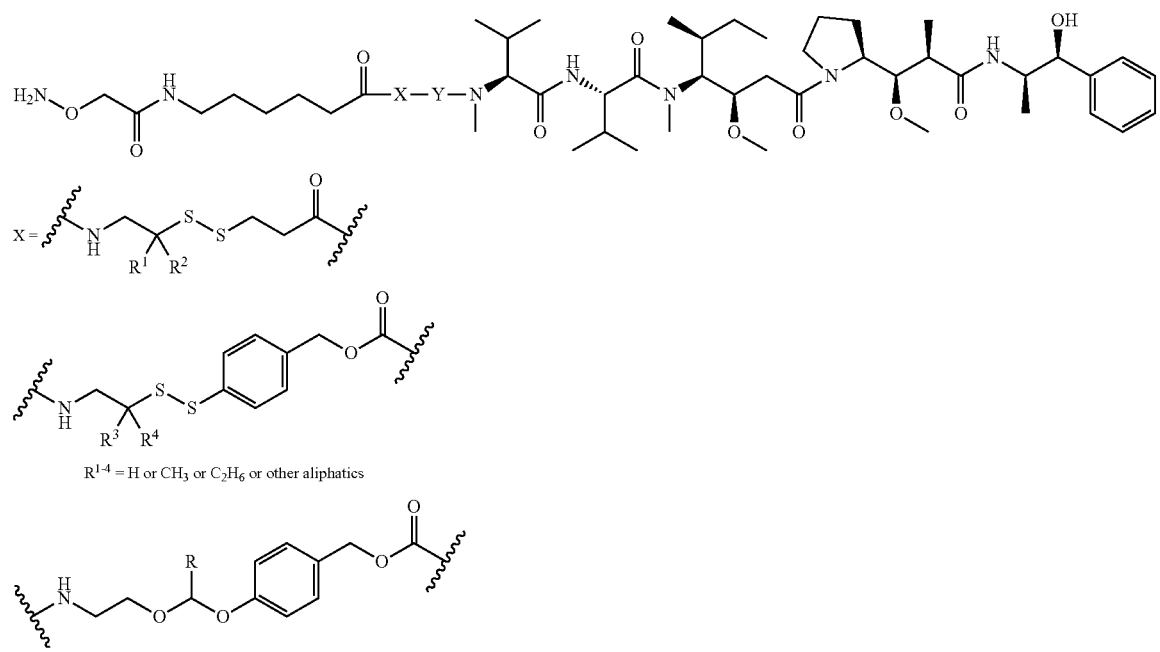

In yet other embodiments, the effector moiety may include hydrophilic and biocompatible moieties such as poly(glycine), poly(oxazoline), or PEG moieties. Exemplary structures ("Y") are provided below:

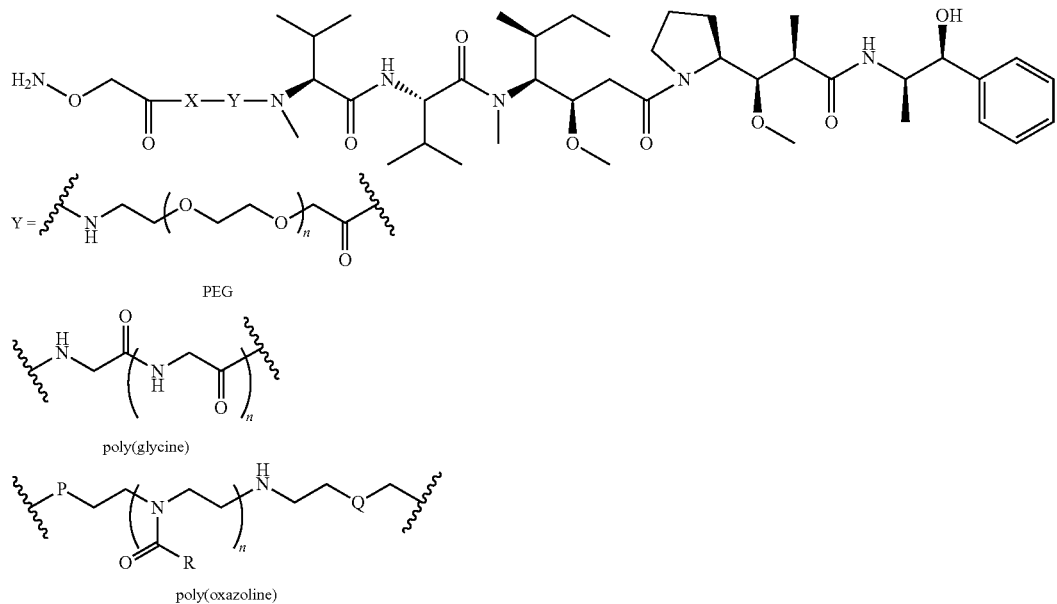

R=H, unsubstituted or functional group containing alkyl groups

P and Q=same or different functional groups for linking drugs, reporter molecules and protein In certain embodiments, the effector moiety contains an aminooxy group which facilitates conjugation to a binding polypeptide via a stable oxime linkage. Exemplary effector moieties containing aminooxy groups are set forth in Table 2 herein.

TABLE 2

Exemplary aminooxy functionalized linker moieties
Table 2. Exemplary aminoxy effector moieties (wherein X can be any linker, Y is any spacer, and wherein X and/or Y are optional)
Drug here can be any drug of the table 1 in the text. Drug1 and Drug 2 can be same or different drugs.

Z—Y—X-Drug

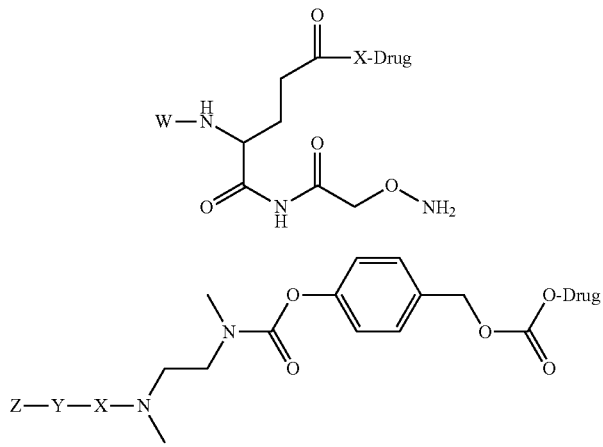

TABLE 2-continued
Exemplary aminooxy functionalized linker moieties
Table 2. Exemplary aminoxy effector moieties (wherein X can be any linker, Y is any spacer, and wherein X and/or Y are optional)
Drug here can be any drug of the table 1 in the text. Drug1 and Drug 2 can be same or different drugs.
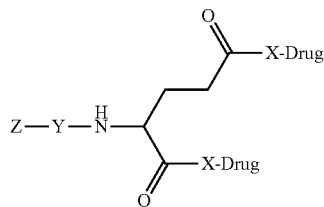
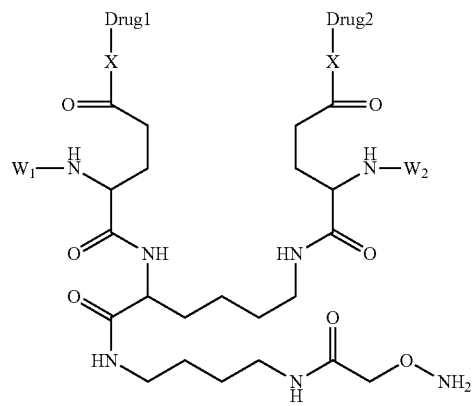
W, W1 and W2 =
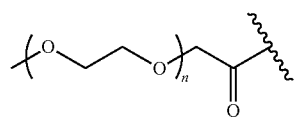
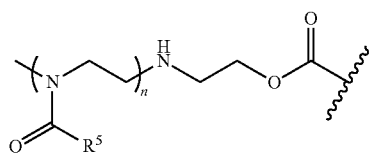
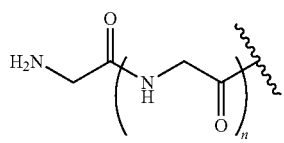
Y =
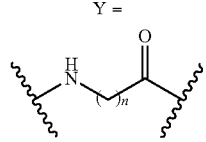
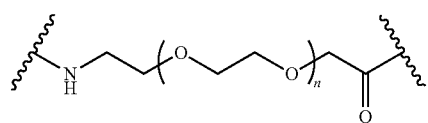

TABLE 2-continued
Exemplary aminooxy functionalized linker moieties
Table 2. Exemplary aminoxy effector moieties (wherein X can be any linker, Y is any spacer, and wherein X and/or Y are optional)
Drug here can be any drug of the table 1 in the text. Drug1 and Drug 2 can be same or different drugs.
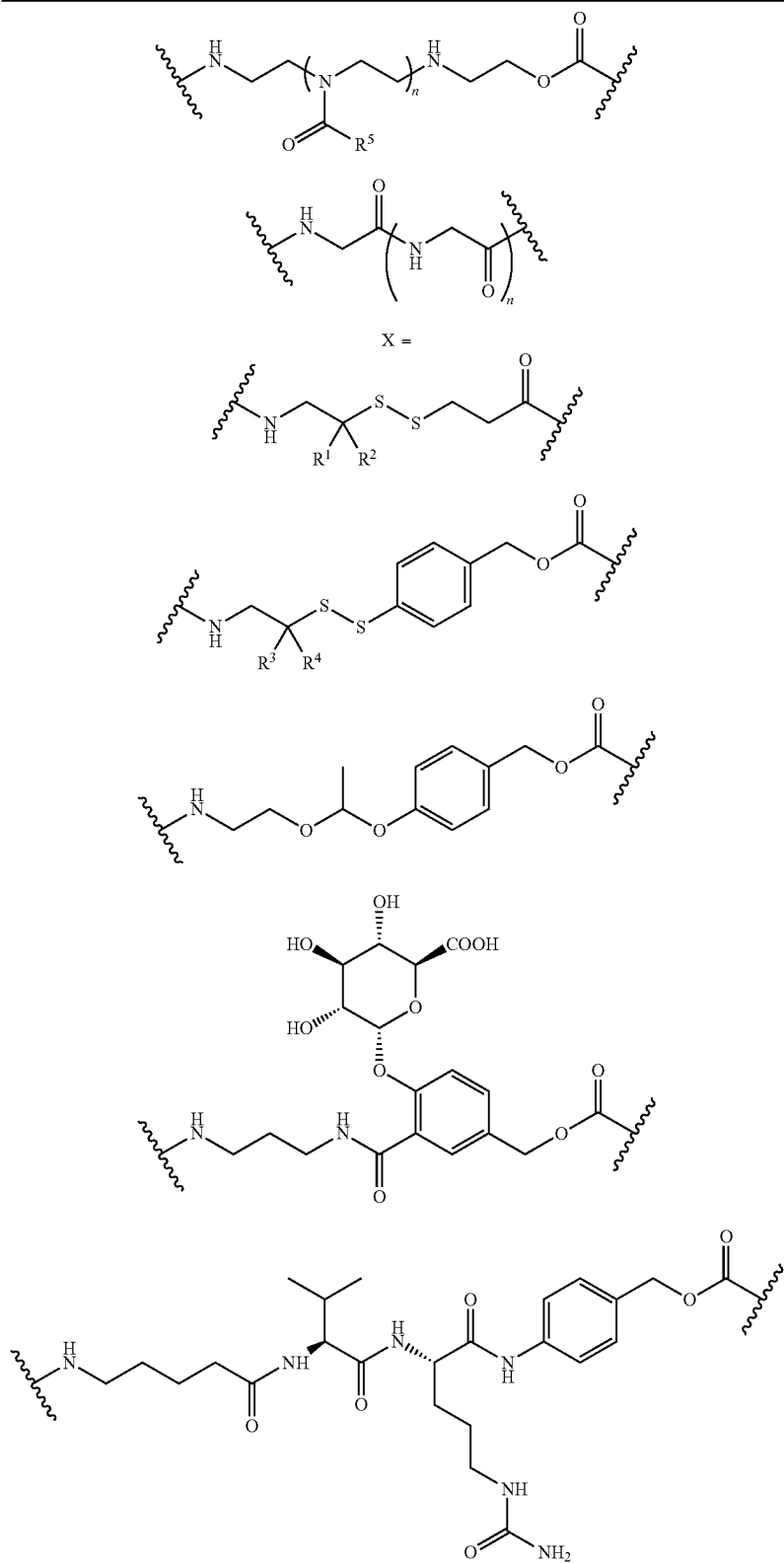

TABLE 2-continued

Exemplary aminooxy functionalized linker moieties
Table 2. Exemplary aminoxy effector moieties (wherein X can be any linker, Y is any spacer, and wherein X and/or Y are optional)
Drug here can be any drug of the table 1 in the text. Drug1 and Drug 2 can be same or different drugs.

$R^{1-5}$ = H, Alkyl or Aryl

Z =

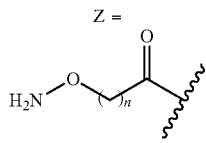

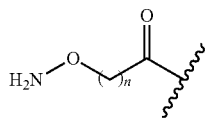

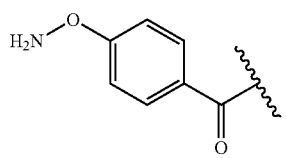 [SMILES: *C(=O)c1ccc(ON)cc1]

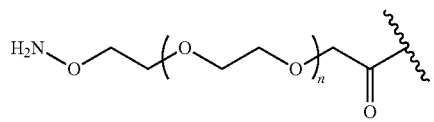

In other embodiments, the effector moiety contains a hydrazide and/or N-alkylated hydrazine group to facilitate conjugation to a binding polypeptide via a stable hydrazone linkage. Exemplary effector moieties containing aminooxy groups are set forth in Table 14 herein.

TABLE 14

Exemplary hydrazine and/or hyarzide effector moieties

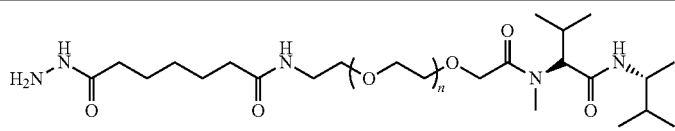

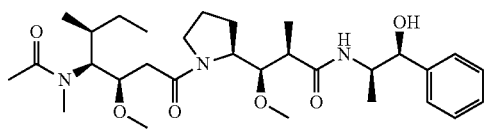

TABLE 14-continued

Exemplary hydrazine and/or hyarzide effector moieties

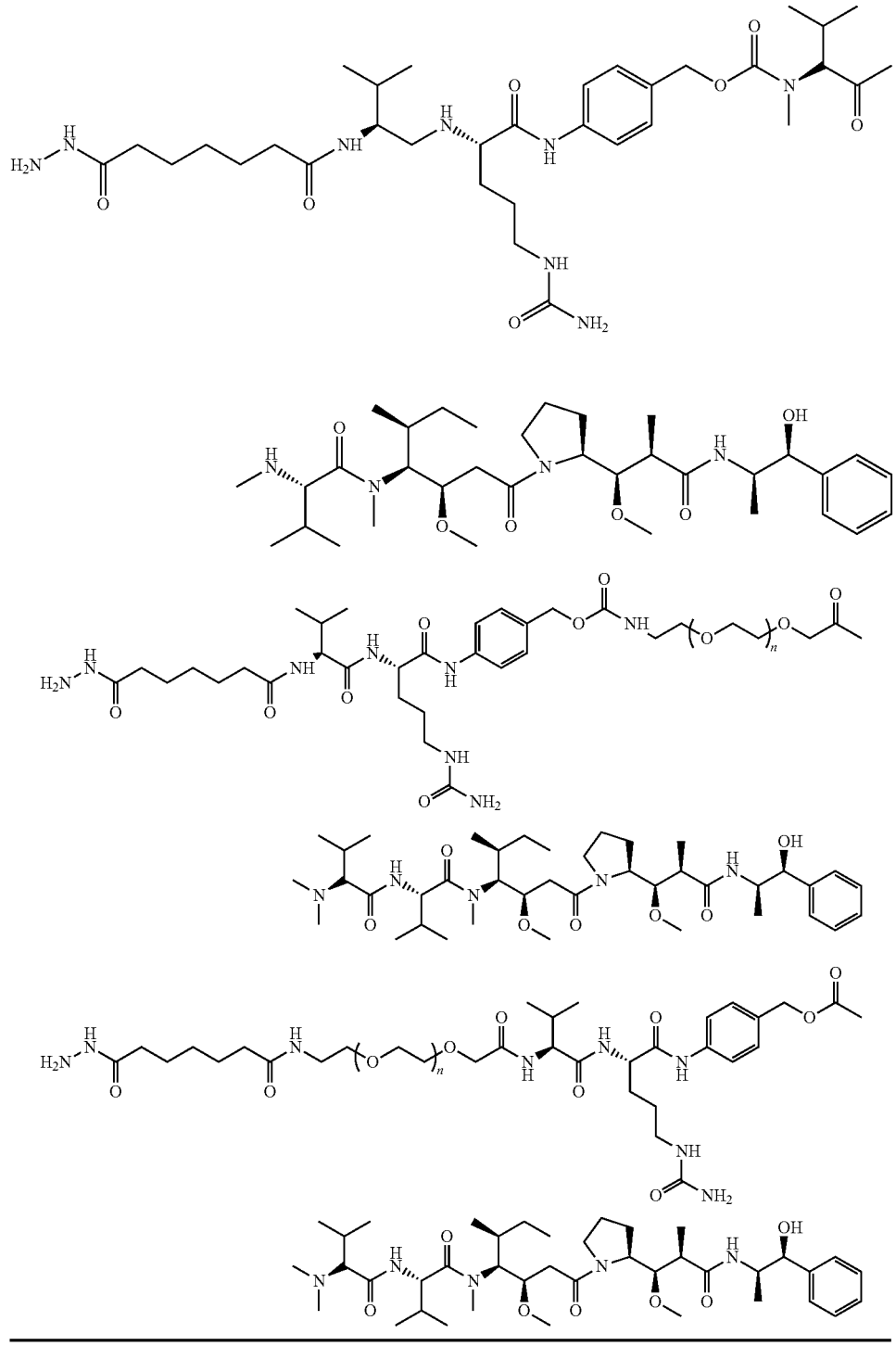

V. Conjugation of Effector Moieties to Binding Polypeptides

In certain embodiments, effector moieties are conjugated (either directly or through a linker moiety) to an oxidized glycan (e.g., an oxidized N-linked glycan) of an altered binding polypeptide, (e.g., an engineered glycan at N298 of an antibody Fc domain). The term "oxidized glycan" means that an alcohol substituent on the glycan has been oxidized, providing a carbonyl substituent. The carbonyl substituent can react with suitable nitrogen nucleophile to form a carbon-nitrogen double bond. For example, reaction of the carbonyl group with an aminooxy group or hydrazine group would form an oxime or hydrazine, respectively. In one embodiment, the carbonyl substituent is an aldehyde. Suitable oxidized glycans include oxidized galactose and oxidized sialic acid.

In one embodiment, the modified polypeptide of Formula (II) may be of Formula (II):

Ab(Gal-C(O)H)$_x$(Gal-Sia-C(O)H)$_y$  Formula (II), wherein
A) Ab is an antibody or other binding polypeptide as defined herein;
B) Gal is a component derived from galactose;
C) Sia is a component derived from sialic acid;
D) x is 0 to 5; and
E) y is 0 to 5,
wherein at least one of x and y is not 0.

Any art recognized chemistry can be employed to conjugate an effector moiety (e.g., an effector moiety comprising a linker moiety) to a glycan (see e.g., Hermanson, G. T., Bioconjugate Techniques. Academic Press (1996), which is incorporated herein ion its entirety). In certain embodiments, a saccharide residue (e.g., a sialic acid or galactose residue) of the glycan is first oxidized (e.g., using sodium periodate or galactose oxidase treatment) to generate a reactive aldehyde group. This aldehyde group is reacted with effector moiety an aminooxy group or hydrazine group to form an oxime or hydrazone linker, respectively. Exemplary methods employing this general reaction scheme are set forth in Examples 10 to 15.

In certain embodiments, the native or engineered glycans of a binding polypeptide are first pre-treated with a glycosyltransferase enzyme in vitro to provide a terminal saccharide residue that is suitably reactive. For example, sialylation may be achieved first using a combination of galactosyltransferase (Gal T) and sialyltransferase (Sial T). In certain embodiments, biantennary glycans that lack galatose (G0F or G0) or that contain only one galactose (G1F or G1) can be converted to higher-order galactosylated or sialylated structures suitable for conjugation (G1F, G1, G2F, G2, G1S1F, G1S1, G2S1F, G2S1, G2S2F, or G2S2).

Figure 25:
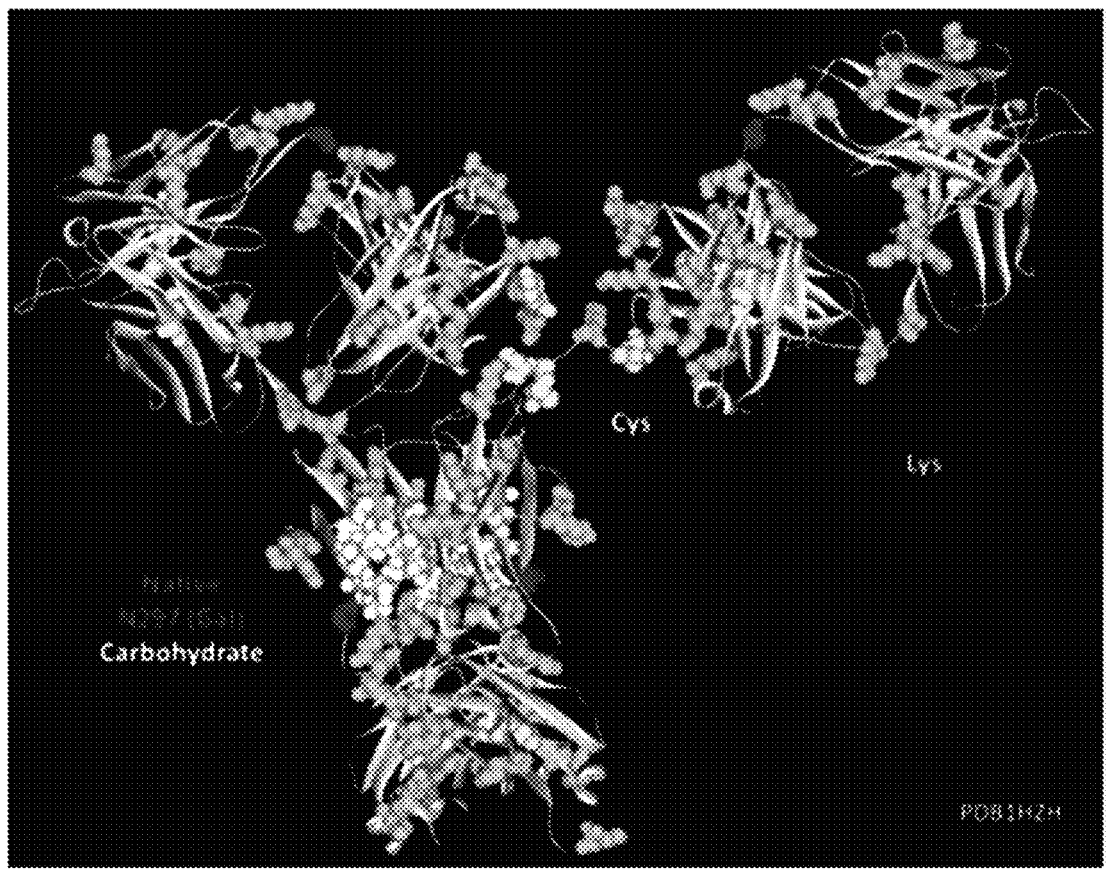
FIG. 25 depicts an exemplary method for performing site-specific conjugation of an antibody according to the methods of the invention.
Figure 25:
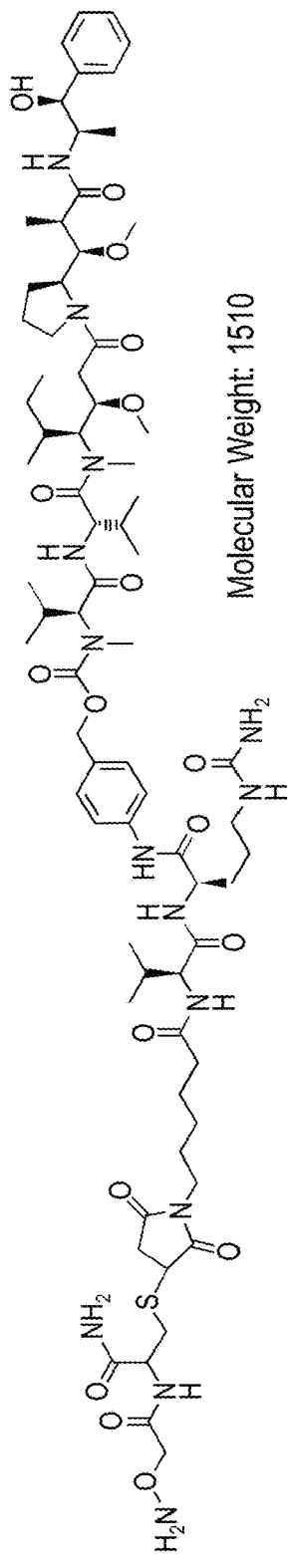
Figure 25:
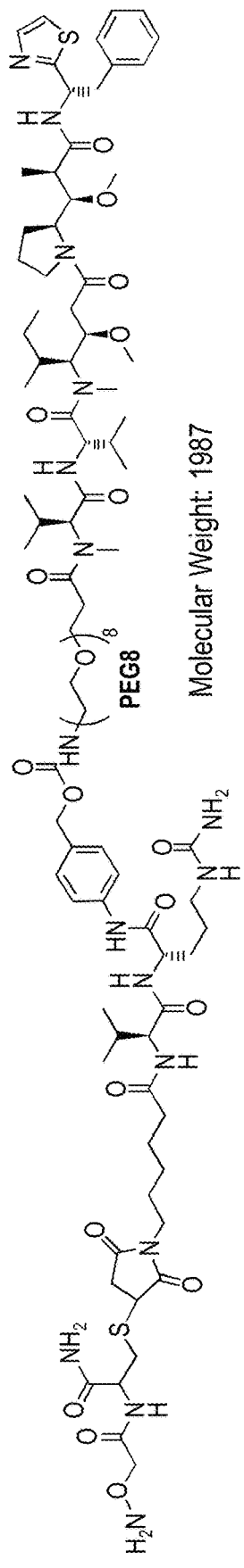
Figure 25:
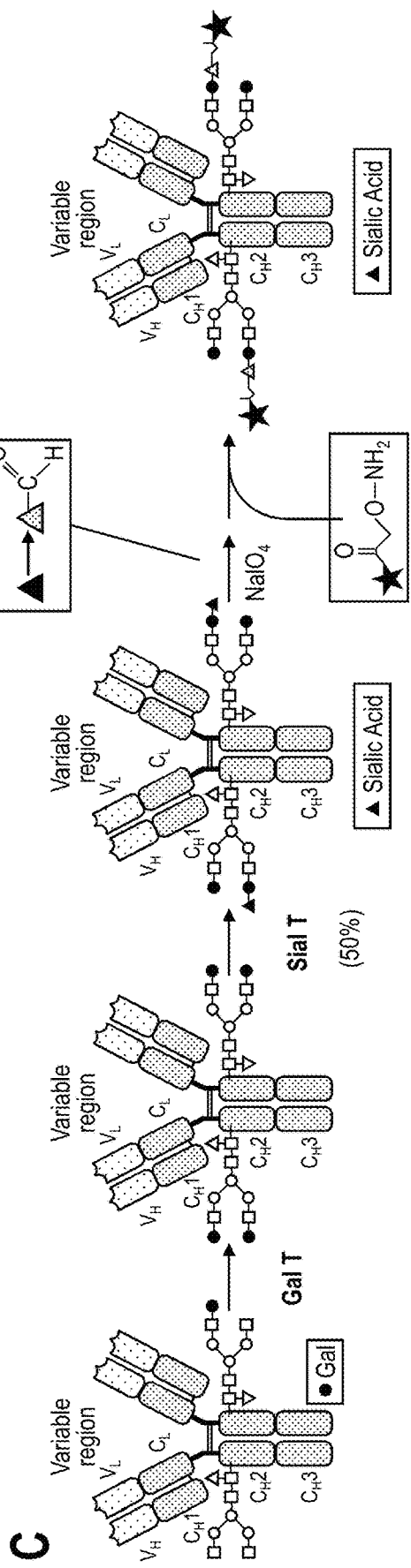
Figure 26:
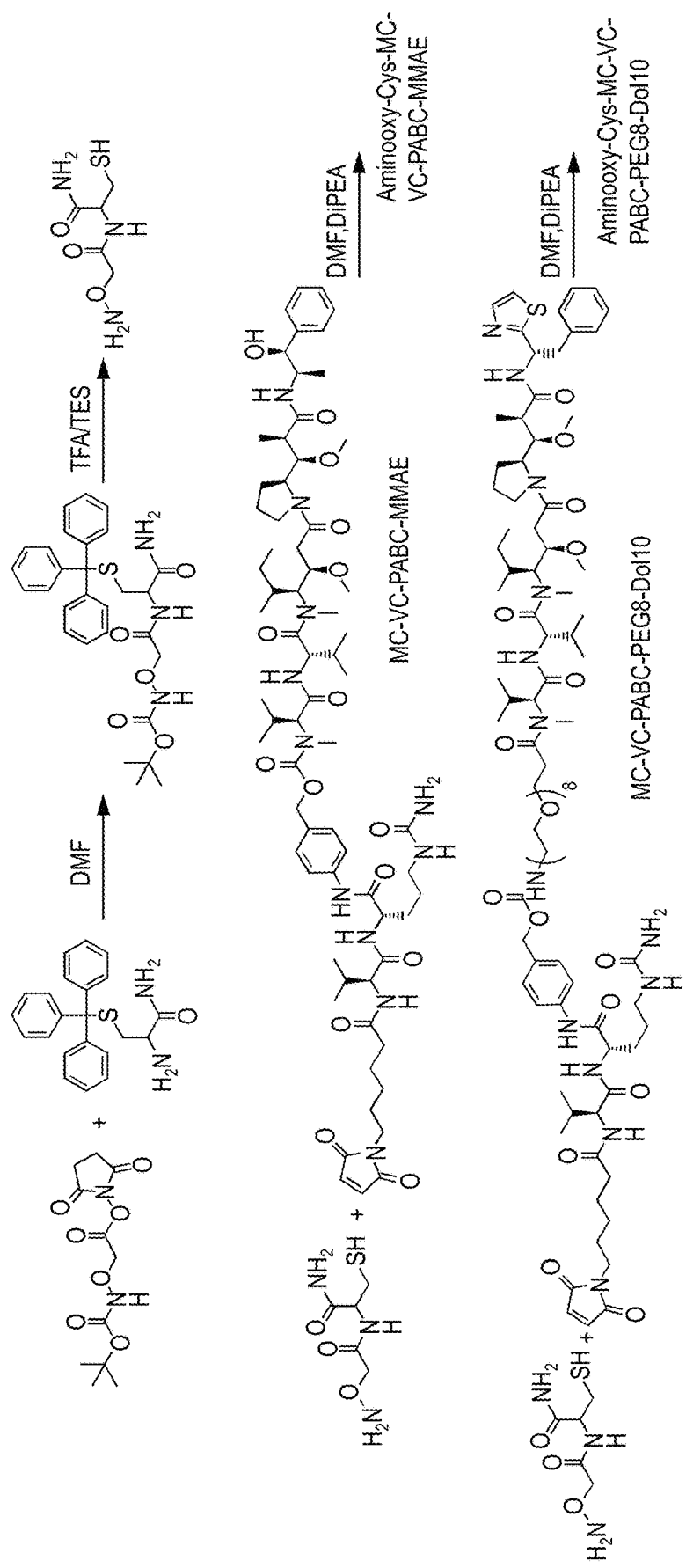
FIG. 26 depicts a synthesis of exemplary effector moieties of the invention: aminooxy-Cys-MC-VC-PABC-MMAE and aminooxy-Cys-MC-VC-PABC-PEG8-Dol10.

An exemplary conjugation scheme for producing sialylated glycoconjugates is shown in FIG. 25C. Sialic acid residues are introduced enzymatically and site specifically into the glycan of an antibody (e.g., an engineered glycan at N298 of the Fc domain) using a combination of galactosyltransferase (Gal T) and sialyltransferase (Sial T). Introduced sialic acid residues are subsequently oxidized with a low concentration of sodium periodate to yield reactive sialic acid aldehydes suitably reactive with drug-linkers (e.g., aminooxy drug linkers) to generate antibody drug conjugates (ADC) (e.g., oxime-linked ADCs). By controlling the number of glycan and the number of sialic residues with in vitro remodeling, the skilled artisan may have precise control over the drug-antibody ratio (DAR) of the ADCs. For example, if ~1 sialic acid is added onto a single biantennary glycan (A1F) in each of heavy chain, an antibody or binding polypeptide with a DAR of 2 can be homogeneously obtained.

VI. Modified Binding Polypeptides

In certain embodiments, the invention provides modified polypeptides which are the product of the conjugating effector moieties are conjugated (either directly or through a linker moiety) to an oxidized glycan (e.g., an oxidized N-linked glycan) of an altered binding polypeptide (e.g., an engineered glycan at N298 of an antibody Fc domain).

In certain embodiments,
In one embodiment, the binding polypeptide can be of Formula (III):

Ab-(Gal-C(H)=N-Q-CON—X)$_x$(Gal-Sia-C(H)=N-Q-CON—X)$_y$  Formula (III), wherein:
A) Ab is an antibody as defined herein;
B) Q is NH or O;
C) CON is a connector moiety as defined herein; and
D) X is a therapeutic or diagnostic agent as defined herein;
E) Gal is a component derived from galactose;
F) Sia is a component derived from sialic acid;
G) x is 0 to 5; and
H) y is 0 to 5,
wherein at least one of x and y is not 0.

In one embodiment, the binding polypeptide can be of Formula (III) can be of Formula (IIIa):

Ab(Gal-C(H)=N-Q-CH$_2$—C(O)—Z—X)$_x$(Gal-Sia-C(H)=N-Q-CH$_2$—C(O)—Z—X)$_y$  Formula (IIIa), wherein:
A) Ab is an antibody;
B) Q is NH or O;
C) Z is Cys-(MC)$_a$-(VC)$_b$-(PABC)$_c$-(C$_{16}$H$_{32}$O$_8$C$_2$H$_4$)$_f$, wherein
   i. Cys is a component derived cysteinamide;
   ii. MC is a component derived from maleimide;
   iii. VC is a component derived from valine coupled with citruline;
   iv. PABC is a component derived from 4-aminobenzyl carbamate;
   v. X is a therapeutic or diagnostic agent as defined herein;
   vi. a is 0 or 1;
   vii. b is 0 or 1;
   viii. c is 0 or 1; and
   ix. f is 0 or 1;
D) X is a therapeutic agent as defined herein;
E) Gal is a component derived from galactose;
F) Sia is a component derived from sialic acid;
G) x is 0 to 5; and
H) y is 0 to 5,
wherein at least one of x and y is not 0.

It is to be understood that the Formula (III) is not intended to imply that the antibody, the Gal substituent, and the Gal-Sia substituent are connected in a chain-like manner. Rather, when such substituents are present, the antibody is connected directly connected to each substituent. For example, a binding polypeptide of Formula (III) in which x is 1 and y is 2 could have the arrangement shown below:

Formula (III)

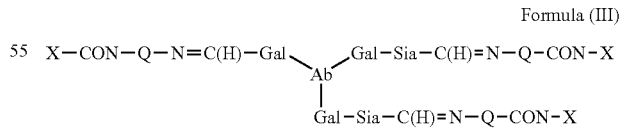

The CON substituent in Formula (III) and components therein are as described with regard to Formula (I) for effector moieties.

In one embodiment, Q is NH. In another embodiment, Q is O.

In one embodiment, x is 0.

The antibody Ab of Formula (III) may be any suitable antibody as described herein.

In one embodiment, there is provided a method for preparing the binding polypeptide of Formula (III), the method comprising reacting an effector moiety of Formula (I):

NH$_2$-Q-CON—X          Formula (I), wherein:
A) Q is NH or O;
B) CON is a connector moiety; and
C) X is a therapeutic or diagnostic agent as defined herein, with a modified antibody of Formula (II)

Ab(OXG)$_r$          Formula (II)

wherein
A) OXG is an oxidized glycan; and
B) r is selected from 0 to 4;

In one embodiment, there is provided a method for preparing the binding polypeptide of Formula (III), the method comprising reacting an effector moiety of Formula (I):

NH$_2$-Q-CON—X          Formula (I), wherein:
A) Q is NH or O;
B) CON is a connector moiety; and
C) X is a therapeutic or diagnostic agent as defined herein, with a modified antibody of Formula (IIa)

Ab(Gal-C(O)H)$_x$(Gal-Sia-C(O)H)$_y$          Formula (IIa), wherein
A) Ab is an antibody as described herein;
B) Gal is a component derived from galactose;
C) Sia is a component derived from sialic acid;
D) x is 0 to 5; and
E) y is 0 to 5,
wherein at least one of x and y is not 0.

IX. Methods of Treatment with Modified Antibodies

In one aspect, the invention provides methods of treating or diagnosing a patient in thereof comprising administering an effective amount a binding polypeptide disclosed herein. Preferred embodiments of the present disclosure provide kits and methods for the diagnosis and/or treatment of disorders, e.g., neoplastic disorders in a mammalian subject in need of such treatment. Preferably, the subject is a human.

The binding polypeptides of the current disclosure are useful in a number of different applications. For example, in one embodiment, the subject binding polypeptide s are useful for reducing or eliminating cells bearing an epitope recognized by the binding domain of the binding polypeptide. In another embodiment, the subject binding polypeptides are effective in reducing the concentration of or eliminating soluble antigen in the circulation. In one embodiment, the binding polypeptides may reduce tumor size, inhibit tumor growth and/or prolong the survival time of tumor-bearing animals. Accordingly, this disclosure also relates to a method of treating tumors in a human or other animal by administering to such human or animal an effective, non-toxic amount of modified antibody. One skilled in the art would be able, by routine experimentation, to determine what an effective, non-toxic amount of modified binding polypeptide would be for the purpose of treating malignancies. For example, a therapeutically active amount of a modified antibody or fragments thereof may vary according to factors such as the disease stage (e.g., stage I versus stage IV), age, sex, medical complications (e.g., immunosuppressed conditions or diseases) and weight of the subject, and the ability of the modified antibody to elicit a desired response in the subject. The dosage regimen may be adjusted to provide the optimum therapeutic response. For example, several divided doses may be administered daily, or the dose may be proportionally reduced as indicated by the exigencies of the therapeutic situation.

In general, the compositions provided in the current disclosure may be used to prophylactically or therapeutically treat any neoplasm comprising an antigenic marker that allows for the targeting of the cancerous cells by the modified antibody.

X. Methods of Administering Modified Antibodies or Fragments Thereof

Methods of preparing and administering binding polypeptides of the current disclosure to a subject are well known to or are readily determined by those skilled in the art. The route of administration of the binding polypeptides of the current disclosure may be oral, parenteral, by inhalation or topical. The term parenteral as used herein includes intravenous, intraarterial, intraperitoneal, intramuscular, subcutaneous, rectal or vaginal administration. The intravenous, intraarterial, subcutaneous and intramuscular forms of parenteral administration are generally preferred. While all these forms of administration are clearly contemplated as being within the scope of the current disclosure, a form for administration would be a solution for injection, in particular for intravenous or intraarterial injection or drip. Usually, a suitable pharmaceutical composition for injection may comprise a buffer (e.g. acetate, phosphate or citrate buffer), a surfactant (e.g. polysorbate), optionally a stabilizer agent (e.g. human albumin), etc. However, in other methods compatible with the teachings herein, the modified antibodies can be delivered directly to the site of the adverse cellular population thereby increasing the exposure of the diseased tissue to the therapeutic agent.

In one embodiment, the binding polypeptide that is administered is a binding polypeptide of Formula (III):

Ab(Gal-C(H)=N-Q-CON—X)$_x$(Gal-Sia-C(H)=N-Q-CON—X)$_y$          Formula (III), wherein:
A) Ab is an antibody as defined herein;
B) Q is NH or O;
C) CON is a connector moiety as defined herein; and
D) X is a therapeutic or diagnostic agent as defined herein;
E) Gal is a component derived from galactose;
F) Sia is a component derived from sialic acid;
G) x is 0 to 5; and
H) y is 0 to 5,
wherein at least one of x and y is not 0.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. In the compositions and methods of the current disclosure, pharmaceutically acceptable carriers include, but are not limited to, 0.01-0.1 M and preferably 0.05M phosphate buffer or 0.8% saline. Other common parenteral vehicles include sodium phosphate solutions, Ringer's dextrose, dextrose and sodium chloride, lactated Ringer's, or fixed oils.

Intravenous vehicles include fluid and nutrient replenishers, electrolyte replenishers, such as those based on Ringer's dextrose, and the like. Preservatives and other additives may also be present such as for example, antimicrobials, antioxidants, chelating agents, and inert gases and the like. More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., a modified binding polypeptide by itself or in combination with other active agents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit such as those described in co-pending U.S. Ser. No. 09/259,337 and U.S. Ser. No. 09/259,338 each of which is incorporated herein by reference. Such articles of manufacture will preferably have labels or package inserts indicating that the associated compositions are useful for treating a subject suffering from, or predisposed to autoimmune or neoplastic disorders.

Effective doses of the compositions of the present disclosure, for the treatment of the above described conditions vary depending upon many different factors, including means of administration, target site, physiological state of the patient, whether the patient is human or an animal, other medications administered, and whether treatment is prophylactic or therapeutic. Usually, the patient is a human but non-human mammals including transgenic mammals can also be treated. Treatment dosages may be titrated using routine methods known to those of skill in the art to optimize safety and efficacy.

For passive immunization with a binding polypeptide, the dosage can range, e.g., from about 0.0001 to 100 mg/kg, and more usually 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example dosages can be 1 mg/kg body weight or 10 mg/kg body weight or within the range of 1-10 mg/kg, preferably at least 1 mg/kg. Doses intermediate in the above ranges are also intended to be within the scope of the current disclosure. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimens entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more monoclonal antibodies with different binding specificities are administered simultaneously, in which case the dosage of each antibody administered falls within the ranges indicated.

Binding polypeptides of the current disclosure can be administered on multiple occasions. Intervals between single dosages can be weekly, monthly or yearly. Intervals can also be irregular as indicated by measuring blood levels of modified binding polypeptide or antigen in the patient. In some methods, dosage is adjusted to achieve a plasma modified binding polypeptide concentration of 1-1000 µg/ml and in some methods 25-300 µg/ml. Alternatively, binding polypeptides can be administered as a sustained release formulation, in which case less frequent administration is required. For antibodies, dosage and frequency vary depending on the half-life of the antibody in the patient. In general, humanized antibodies show the longest half-life, followed by chimeric antibodies and nonhuman antibodies.

The dosage and frequency of administration can vary depending on whether the treatment is prophylactic or therapeutic. In prophylactic applications, compositions containing the present antibodies or a cocktail thereof are administered to a patient not already in the disease state to enhance the patient's resistance. Such an amount is defined to be a "prophylactic effective dose." In this use, the precise amounts again depend upon the patient's state of health and general immunity, but generally range from 0.1 to 25 mg per dose, especially 0.5 to 2.5 mg per dose. A relatively low dosage is administered at relatively infrequent intervals over a long period of time. Some patients continue to receive treatment for the rest of their lives. In therapeutic applications, a relatively high dosage (e.g., from about 1 to 400 mg/kg of antibody per dose, with dosages of from 5 to 25 mg being more commonly used for radioimmunoconjugates and higher doses for cytotoxin-drug modified antibodies) at relatively short intervals is sometimes required until progression of the disease is reduced or terminated, and preferably until the patient shows partial or complete amelioration of symptoms of disease. Thereafter, the patient can be administered a prophylactic regime.

Binding polypeptides of the current disclosure can optionally be administered in combination with other agents that are effective in treating the disorder or condition in need of treatment (e.g., prophylactic or therapeutic). Effective single treatment dosages (i.e., therapeutically effective amounts) of 90Y-labeled modified antibodies of the current disclosure range from between about 5 and about 75 mCi, more preferably between about 10 and about 40 mCi. Effective single treatment non-marrow ablative dosages of 131I-modified antibodies range from between about 5 and about 70 mCi, more preferably between about 5 and about 40 mCi. Effective single treatment ablative dosages (i.e., may require autologous bone marrow transplantation) of 131I-labeled antibodies range from between about 30 and about 600 mCi, more preferably between about 50 and less than about 500 mCi. In conjunction with a chimeric antibody, owing to the longer circulating half-life vis-a-vis murine antibodies, an effective single treatment non-marrow ablative dosages of iodine-131 labeled chimeric antibodies range from between about 5 and about 40 mCi, more preferably less than about 30 mCi. Imaging criteria for, e.g., the 111In label, are typically less than about 5 mCi.

While the binding polypeptides may be administered as described immediately above, it must be emphasized that in other embodiments binding may be administered to otherwise healthy patients as a first line therapy. In such embodiments the binding polypeptides may be administered to patients having normal or average red marrow reserves and/or to patients that have not undergone, and are not undergoing, other therapies. As used herein, the administration of modified antibodies or fragments thereof in conjunction or combination with an adjunct therapy means the sequential, simultaneous, coextensive, concurrent, concomitant or contemporaneous administration or application of the therapy and the disclosed antibodies. Those skilled in the art will appreciate that the administration or application of the various components of the combined therapeutic regimen may be timed to enhance the overall effectiveness of the treatment. For example, chemotherapeutic agents could be administered in standard, well known courses of treatment followed within a few weeks by radioimmunoconjugates of the present disclosure. Conversely, cytotoxin associated binding polypeptides could be administered intravenously followed by tumor localized external beam radiation. In yet other embodiments, the modified binding polypeptide may be administered concurrently with one or more selected chemotherapeutic agents in a single office visit. A skilled artisan (e.g. an experienced oncologist) would be readily be able to discern effective combined therapeutic regimens without undue experimentation based on the selected adjunct therapy and the teachings of the instant specification.

In this regard it will be appreciated that the combination of the binding polypeptides and the chemotherapeutic agent may be administered in any order and within any time frame that provides a therapeutic benefit to the patient. That is, the chemotherapeutic agent and binding polypeptides may be administered in any order or concurrently. In selected embodiments the binding polypeptides of the present disclosure will be administered to patients that have previously undergone chemotherapy. In yet other embodiments, the binding polypeptides and the chemotherapeutic treatment will be administered substantially simultaneously or concurrently. For example, the patient may be given the binding polypeptides while undergoing a course of chemotherapy. In preferred embodiments the modified antibody will be administered within one year of any chemotherapeutic agent or treatment. In other preferred embodiments the binding polypeptides will be administered within 10, 8, 6, 4, or 2 months of any chemotherapeutic agent or treatment. In still other preferred embodiments the binding polypeptide will be administered within 4, 3, 2 or 1 week of any chemotherapeutic agent or treatment. In yet other embodiments the binding polypeptides will be administered within 5, 4, 3, 2 or 1 days of the selected chemotherapeutic agent or treatment. It will further be appreciated that the two agents or treatments may be administered to the patient within a matter of hours or minutes (i.e. substantially simultaneously).

It will further be appreciated that the binding polypeptides of the current disclosure may be used in conjunction or combination with any chemotherapeutic agent or agents (e.g. to provide a combined therapeutic regimen) that eliminates, reduces, inhibits or controls the growth of neoplastic cells in vivo. Exemplary chemotherapeutic agents that are compatible with the current disclosure include alkylating agents, vinca alkaloids (e.g., vincristine and vinblastine), procarbazine, methotrexate and prednisone. The four-drug combination MOPP (mechlethamine (nitrogen mustard), vincristine (Oncovin), procarbazine and prednisone) is very effective in treating various types of lymphoma and comprises a preferred embodiment of the present disclosure. In MOPP-resistant patients, ABVD (e.g., adriamycin, bleomycin, vinblastine and dacarbazine), ChIVPP (CH1orambucil, vinblastine, procarbazine and prednisone), CABS (lomustine, doxorubicin, bleomycin and streptozotocin), MOPP plus ABVD, MOPP plus ABV (doxorubicin, bleomycin and vinblastine) or BCVPP (carmustine, cyclophosphamide, vinblastine, procarbazine and prednisone) combinations can be used. Arnold S. Freedman and Lee M. Nadler, Malignant Lymphomas, in HARRISON'S PRINCIPLES OF INTERNAL MEDICINE 1774-1788 (Kurt J. Isselbacher et al, eds., 13th ed. 1994) and V. T. DeVita et al, (1997) and the references cited therein for standard dosing and scheduling. These therapies can be used unchanged, or altered as needed for a particular patient, in combination with one or more binding polypeptides of the current disclosure as described herein.

Additional regimens that are useful in the context of the present disclosure include use of single alkylating agents such as cyclophosphamide or chlorambucil, or combinations such as CVP (cyclophosphamide, vincristine and prednisone), CHOP (CVP and doxorubicin), C-MOPP (cyclophosphamide, vincristine, prednisone and procarbazine), CAP-BOP (CHOP plus procarbazine and bleomycin), m-BACOD (CHOP plus methotrexate, bleomycin and leucovorin), ProMACE-MOPP (prednisone, methotrexate, doxorubicin, cyclophosphamide, etoposide and leucovorin plus standard MOPP), ProMACE-CytaBOM (prednisone, doxorubicin, cyclophosphamide, etoposide, cytarabine, bleomycin, vincristine, methotrexate and leucovorin) and MACOP-B (methotrexate, doxorubicin, cyclophosphamide, vincristine, fixed dose prednisone, bleomycin and leucovorin). Those skilled in the art will readily be able to determine standard dosages and scheduling for each of these regimens. CHOP has also been combined with bleomycin, methotrexate, procarbazine, nitrogen mustard, cytosine arabinoside and etoposide. Other compatible chemotherapeutic agents include, but are not limited to, 2-CH1orodeoxyadenosine (2-CDA), 2'-deoxycoformycin and fludarabine.

For patients with intermediate- and high-grade NHL, who fail to achieve remission or relapse, salvage therapy is used. Salvage therapies employ drugs such as cytosine arabinoside, carboplatin, cisplatin, etoposide and ifosfamide given alone or in combination. In relapsed or aggressive forms of certain neoplastic disorders the following protocols are often used: IMVP-16 (ifosfamide, methotrexate and etoposide), MIME (methyl-gag, ifosfamide, methotrexate and etoposide), DHAP (dexamethasone, high dose cytarabine and cisplatin), ESHAP (etoposide, methylpredisolone, HD cytarabine, cisplatin), CEPP(B) (cyclophosphamide, etoposide, procarbazine, prednisone and bleomycin) and CAMP (lomustine, mitoxantrone, cytarabine and prednisone) each with well-known dosing rates and schedules.

The amount of chemotherapeutic agent to be used in combination with the modified antibodies of the current disclosure may vary by subject or may be administered according to what is known in the art. See for example, Bruce A. Chabner et al, Antineoplastic Agents, in GOODMAN & GILMAN'S THE PHARMACOLOGICAL BASIS OF THERAPEUTICS 1233-1287 (Joel G. Hardman et al., eds., 9th ed. 1996).

As previously discussed, the binding polypeptides of the present disclosure, immunoreactive fragments or recombinants thereof may be administered in a pharmaceutically effective amount for the in vivo treatment of mammalian disorders. In this regard, it will be appreciated that the disclosed binding polypeptides will be formulated to facilitate administration and promote stability of the active agent.

Preferably, pharmaceutical compositions in accordance with the present disclosure comprise a pharmaceutically acceptable, non-toxic, sterile carrier such as physiological saline, nontoxic buffers, preservatives and the like. For the purposes of the instant application, a pharmaceutically effective amount of the modified binding polypeptide, immunoreactive fragment or recombinant thereof, conjugated or unconjugated to a therapeutic agent, shall be held to mean an amount sufficient to achieve effective binding to an antigen and to achieve a benefit, e.g., to ameliorate symptoms of a disease or disorder or to detect a substance or a cell. In the case of tumor cells, the modified binding polypeptide will be preferably be capable of interacting with selected immunoreactive antigens on neoplastic or immunoreactive cells and provide for an increase in the death of those cells. Of course, the pharmaceutical compositions of the present disclosure may be administered in single or multiple doses to provide for a pharmaceutically effective amount of the modified binding polypeptide.

In keeping with the scope of the present disclosure, the binding polypeptides of the disclosure may be administered to a human or other animal in accordance with the aforementioned methods of treatment in an amount sufficient to produce a therapeutic or prophylactic effect. The binding polypeptides of the disclosure can be administered to such human or other animal in a conventional dosage form prepared by combining the antibody of the disclosure with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. Those skilled in the art will further appreciate that a cocktail comprising one or more species of binding polypeptides described in the current disclosure may prove to be particularly effective.

V. Expression of Binding Polypeptides

In one aspect, the invention provides polynucleotides encoding the binding polypeptides disclosed herein. A method of making a binding polypeptide comprising expressing these polynucleotides is also provided.

Polynucleotides encoding the binding polypeptides disclosed herein are typically inserted in an expression vector for introduction into host cells that may be used to produce the desired quantity of the claimed antibodies, or fragments thereof. Accordingly, in certain aspects, the invention provides expression vectors comprising polynucleotides disclosed herein and host cells comprising these vectors and polynucleotides.

The term "vector" or "expression vector" is used herein for the purposes of the specification and claims, to mean vectors used in accordance with the present invention as a vehicle for introducing into and expressing a desired gene in a cell. As known to those skilled in the art, such vectors may easily be selected from the group consisting of plasmids, phages, viruses and retroviruses. In general, vectors compatible with the instant invention will comprise a selection marker, appropriate restriction sites to facilitate cloning of the desired gene and the ability to enter and/or replicate in eukaryotic or prokaryotic cells.

Numerous expression vector systems may be employed for the purposes of this invention. For example, one class of vector utilizes DNA elements which are derived from animal viruses such as bovine papilloma virus, polyoma virus, adenovirus, vaccinia virus, baculovirus, retroviruses (RSV, MMTV or MOMLV) or SV40 virus. Others involve the use of polycistronic systems with internal ribosome binding sites. Additionally, cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation. Additional elements may also be needed for optimal synthesis of mRNA. These elements may include signal sequences, splice signals, as well as transcriptional promoters, enhancers, and termination signals. In particularly preferred embodiments the cloned variable region genes are inserted into an expression vector along with the heavy and light chain constant region genes (preferably human) synthetic as discussed above.

In other preferred embodiments the binding polypeptides of the invention may be expressed using polycistronic constructs. In such expression systems, multiple gene products of interest such as heavy and light chains of antibodies may be produced from a single polycistronic construct. These systems advantageously use an internal ribosome entry site (IRES) to provide relatively high levels of polypeptides of the invention in eukaryotic host cells. Compatible IRES sequences are disclosed in U.S. Pat. No. 6,193,980 which is incorporated by reference herein. Those skilled in the art will appreciate that such expression systems may be used to effectively produce the full range of polypeptides disclosed in the instant application.

More generally, once a vector or DNA sequence encoding an antibody, or fragment thereof, has been prepared, the expression vector may be introduced into an appropriate host cell. That is, the host cells may be transformed. Introduction of the plasmid into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway, A. A. G. "Mammalian Expression Vectors" Chapter 24.2, pp. 470-472 Vectors, Rodriguez and Denhardt, Eds. (Butterworths, Boston, Mass. 1988). Most preferably, plasmid introduction into the host is via electroporation. The transformed cells are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or flourescence-activated cell sorter analysis (FACS), immunohistochemistry and the like.

As used herein, the term "transformation" shall be used in a broad sense to refer to the introduction of DNA into a recipient host cell that changes the genotype and consequently results in a change in the recipient cell.

Along those same lines, "host cells" refers to cells that have been transformed with vectors constructed using recombinant DNA techniques and encoding at least one heterologous gene. In descriptions of processes for isolation of polypeptides from recombinant hosts, the terms "cell" and "cell culture" are used interchangeably to denote the source of antibody unless it is clearly specified otherwise. In other words, recovery of polypeptide from the "cells" may mean either from spun down whole cells, or from the cell culture containing both the medium and the suspended cells.

In one embodiment, the host cell line used for antibody expression is of mammalian origin; those skilled in the art can determine particular host cell lines which are best suited for the desired gene product to be expressed therein. Exemplary host cell lines include, but are not limited to, DG44 and DUXB11 (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/O (mouse myeloma), BFA-1c1BPT (bovine endothelial cells), RAJI (human lymphocyte), 293 (human kidney). In one embodiment, the cell line provides for altered glycosylation, e.g., afucosylation, of the antibodyexpressed therefrom (e.g., PER.C6® (Crucell) or FUT8-knock-out CHO cell lines (Potelligent® Cells) (Biowa, Princeton, N.J.)). In one embodiment NS0 cells may be used. CHO cells are particularly preferred. Host cell lines are typically available from commercial services, the American Tissue Culture Collection or from published literature.

In vitro production allows scale-up to give large amounts of the desired polypeptides. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose and/or (immuno-) affinity chromatography.

Genes encoding the binding polypeptides of the invention can also be expressed non-mammalian cells such as bacteria or yeast or plant cells. In this regard it will be appreciated that various unicellular non-mammalian microorganisms such as bacteria can also be transformed; i.e. those capable of being grown in cultures or fermentation. Bacteria, which are susceptible to transformation, include members of the enterobacteriaceae, such as strains of *Escherichia coli* or *Salmonella*; Bacillaceae, such as *Bacillus subtilis*; Pneumococcus; *Streptococcus*, and *Haemophilus influenzae*. It will further be appreciated that, when expressed in bacteria, the polypeptides can become part of inclusion bodies. The polypeptides must be isolated, purified and then assembled into functional molecules.

In addition to prokaryotes, eukaryotic microbes may also be used. *Saccharomyces cerevisiae*, or common baker's yeast, is the most commonly used among eukaryotic microorganisms although a number of other strains are commonly available. For expression in *Saccharomyces*, the plasmid YRp7, for example, (Stinchcomb et al., Nature, 282:39 (1979); Kingsman et al., Gene, 7:141 (1979); Tschemper et al., Gene, 10:157 (1980)) is commonly used. This plasmid already contains the TRP1 gene which provides a selection marker for a mutant strain of yeast lacking the ability to grow in tryptophan, for example ATCC No. 44076 or PEP4-1 (Jones, Genetics, 85:12 (1977)). The presence of the trpl lesion as a characteristic of the yeast host cell genome then provides an effective environment for detecting transformation by growth in the absence of tryptophan.

EXAMPLES

The present invention is further illustrated by the following examples which should not be construed as further limiting. The contents of Sequence Listing, figures and all references, patents, and published patent applications cited throughout this application are expressly incorporated herein by reference.

Example 1. Design, Preparation, and Characterization of 2C3 Anti-CD-52 Hyperglycosylation Antibody Mutants Multiple hyperglycosylation mutations were designed in the heavy chain of the anti-CD-52 antibody, 2C3, for the purpose of adding a bulky group to an interaction interface (e.g., the FcRn binding site to modulate antibody pharmacokinetics), for modulating antibody effector function by changing its interaction with FcγRs, or to introduce a novel cross-linking site subsequence chemical modification for effector moiety conjugation, including but not limited to, drugs, toxins, cytotoxic agents, and radionucleotides. The hyperglycosylated 2C3 mutants are set forth in Table 3.

TABLE 3

Hyperglycosylated 2C3 anti-CD-52 mutants

| Mutation | Desired Benefit | Applications |
|---|---|---|
| A114N | Glycosylation at Asn-Ser-Thr | 1) Control<br>2) Effector moiety conjugation |
| Y436T | Glycosylation at Asn434<br>Inhibition of FcRn binding | 1) Transplant and other indications which need short half-life |
| Y436S | Glycosylation at Asn434<br>Inhibition of FcRn binding | 1) Transplant and other indications which need short half-life |
| S440N | Glycosylation at Asn-Leu-Ser | 1) Control<br>2) Effector moiety conjugation |
| S442N | Glycosylation at Asn-Leu-Ser | 1) Control<br>2) Effector moiety conjugation |
| Add NGT to C-terminal | Glycosylation | 1) Control<br>2) Effector moiety conjugation |
| S298N/Y300S | Glycosylation at Asn298<br>Reduced effector function | 1) Reduce effector function<br>2) Effector moiety conjugation |

1A. Creation of 2C3 Anti-CD-52 Antibody Hyperglycosylation Mutants

The A114N mutation, designated based upon the Kabat numbering system, was introduced into the CH1 domain of 2C3 by mutagenic PCR. To create the full-length antibody, the VH domain plus the mutated A114N residue was inserted by ligation independent cloning (LIC) into the pENTR-LIC-IgG1 vector encoding antibody CH domains 1-3. All other mutations were introduced on pENTR-LIC-IgG1 by site-directed mutagenesis with a QuikChange site-directed mutagenesis kit (Agilent Technologies, Inc., Santa Clara, Calif., USA). The WT 2C3 VH was cloned into mutated vectors by LIC. Full-length mutants were cloned into the pCEP4(-E+I)Dest expression vector by Gateway cloning. Fc mutations were designated based on the EU numbering system. Mutations were confirmed by DNA sequencing Amino acid sequences of the WT 2C3 heavy and light chains and the mutated 2C3 heavy chains are set forth in Table 4. Mutated amino acids are highlighted in gray and the consensus glycosylation target sites created by the mutation are underlined.

TABLE 4

Amino acid sequences of 2C3 anti-CD-52 antibodies

| SEQ ID NO | Name | Amino Acid Sequence |
|---|---|---|
| 1 | Anti-CD-52 WT light chain | DIVMTQTPLSLSVTPGQPASISCKSSQSLLYSNGKTY LNWLLQKPGQSPQRLIYLVSKLDSGVPDRFSGSGSG TDFTLKISRVEAEDVGVYYCVQGTHLHTFGQGTRL EIKRTVAAPSVFIFPPSDEQLKSGTASVVCLLNNFYP REAKVQWKVDNALQSGNSQESVTEQDSKDSTYSLS STLTLSKADYEKHKVYACEVTHQGLSSPVTKSFNR GEC |
| 2 | Anti-CD-52 WT heavy chain | VQLVESGGGLVQPGGSLRLSCAASGFTFNTYWMN WVRQAPGKGLEWVGQIRLKSNNYATHYAESVKGR FTISRDDSKNSLYLQMNSLKTEDTAVYYCTPVDFW GQGTTVTVSSASTKGPSVFPLAPSSKSTSGGTAALG CLVKDYFPEPVTVSWNSGALTSGVHTFPAVLQSSG LYSLSSVVTVPSSSLGTQTYICNVNHKPSNTKVDKK VEPKSCDKTHTCPPCPAPELLGGPSVFLFPPKPKDTL MISRTPEVTCVVVDVSHEDPEVKFNWYVDGVEVH NAKTKPREEQYNSTYRVVSVLTVLHQDWLNGKEY KCKVSNKALPAPIEKTISKAKGQPREPQVYTLPPSR DELTKNQVSLTCLVKGFYPSDIAVEWESNGQPENN YKTTPPVLDSDGSFFLYSKLTVDKSRWQQGNVFSC SVMHEALHNHYTQKSLSLSPGK |
| 3 | Anti-CD-52 A114N heavy chain | EVQLVESGGGLVQPGGSLRLSCAASGFTFNTYWMN WVRQAPGKGLEWVGQIRLKSNNYATHYAESVKGR FTISRDDSKNSLYLQMNSLKTEDTAVYYCTPVDFW GQGTTVTVSS<u>NST</u>KGPSVFPLAPSSKSTSGGTAALG CLVKDYFPEPVTVSWNSGALTSGVHTFPAVLQSSG LYSLSSVVTVPSSSLGTQTYICNVNHKPSNTKVDKK VEPKSCDKTHTCPPCPAPELLGGPSVFLFPPKPKDTL MISRTPEVTCVVVDVSHEDPEVKFNWYVDGVEVH NAKTKPREEQYNSTYRVVSVLTVLHQDWLNGKEY KCKVSNKALPAPIEKTISKAKGQPREPQVYTLPPSR DELTKNQVSLTCLVKGFYPSDIAVEWESNGQPENN YKTTPPVLDSDGSFFLYSKLTVDKSRWQQGNVFSC SVMHEALHNHYTQKSLSLSPGK |
| 4 | Anti-CD-52 Y436S heavy chain | EVQLVESGGGLVQPGGSLRLSCAASGFTFNTYWMN WVRQAPGKGLEWVGQIRLKSNNYATHYAESVKGR FTISRDDSKNSLYLQMNSLKTEDTAVYYCTPVDFW GQGTTVTVSSASTKGPSVFPLAPSSKSTSGGTAALG CLVKDYFPEPVTVSWNSGALTSGVHTFPAVLQSSG LYSLSSVVTVPSSSLGTQTYICNVNHKPSNTKVDKK VEPKSCDKTHTCPPCPAPELLGGPSVFLFPPKPKDTL MISRTPEVTCVVVDVSHEDPEVKFNWYVDGVEVH NAKTKPREEQYNSTYRVVSVLTVLHQDWLNGKEY KCKVSNKALPAPIEKTISKAKGQPREPQVYTLPPSR DELTKNQVSLTCLVKGFYPSDIAVEWESNGQPENN YKTTPPVLDSDGSFFLYSKLTVDKSRWQQGNVFSC SVMHEALH<u>NHS</u>TQKSLSLSPGK |
| 5 | Anti-CD-52 S440N heavy chain | EVQLVESGGGLVQPGGSLRLSCAASGFTFNTYWMN WVRQAPGKGLEWVGQIRLKSNNYATHYAESVKGR FTISRDDSKNSLYLQMNSLKTEDTAVYYCTPVDFW GQGTTVTVSSASTKGPSVFPLAPSSKSTSGGTAALG CLVKDYFPEPVTVSWNSGALTSGVHTFPAVLQSSG LYSLSSVVTVPSSSLGTQTYICNVNHKPSNTKVDKK VEPKSCDKTHTCPPCPAPELLGGPSVFLFPPKPKDTL MISRTPEVTCVVVDVSHEDPEVKFNWYVDGVEVH NAKTKPREEQYNSTYRVVSVLTVLHQDWLNGKEY KCKVSNKALPAPIEKTISKAKGQPREPQVYTLPPSR DELTKNQVSLTCLVKGFYPSDIAVEWESNGQPENN YKTTPPVLDSDGSFFLYSKLTVDKSRWQQGNVFSC SVMHEALHNHYTQK<u>NLS</u>LSPGK |
| 6 | Anti-CD-52 S442N heavy chain | EVQLVESGGGLVQPGGSLRLSCAASGFTFNTYWMN WVRQAPGKGLEWVGQIRLKSNNYATHYAESVKGR FTISRDDSKNSLYLQMNSLKTEDTAVYYCTPVDFW GQGTTVTVSSASTKGPSVFPLAPSSKSTSGGTAALG CLVKDYFPEPVTVSWNSGALTSGVHTFPAVLQSSG LYSLSSVVTVPSSSLGTQTYICNVNHKPSNTKVDKK VEPKSCDKTHTCPPCPAPELLGGPSVFLFPPKPKDTL MISRTPEVTCVVVDVSHEDPEVKFNWYVDGVEVH NAKTKPREEQYNSTYRVVSVLTVLHQDWLNGKEY KCKVSNKALPAPIEKTISKAKGQPREPQVYTLPPSR DELTKNQVSLTCLVKGFYPSDIAVEWESNGQPENN YKTTPPVLDSDGSFFLYSKLTVDKSRWQQGNVFSC SVMHEALHNHYTQKSL<u>NLS</u>PGK |
| 7 | Anti-CD-52 NGT heavy chain | EVQLVESGGGLVQPGGSLRLSCAASGFTFNTYWMN WVRQAPGKGLEWVGQIRLKSNNYATHYAESVKGR FTISRDDSKNSLYLQMNSLKTEDTAVYYCTPVDFW GQGTTVTVSSASTKGPSVFPLAPSSKSTSGGTAALG CLVKDYFPEPVTVSWNSGALTSGVHTFPAVLQSSG LYSLSSVVTVPSSSLGTQTYICNVNHKPSNTKVDKK VEPKSCDKTHTCPPCPAPELLGGPSVFLFPPKPKDTL MISRTPEVTCVVVDVSHEDPEVKFNWYVDGVEVH NAKTKPREEQYNSTYRVVSVLTVLHQDWLNGKEY KCKVSNKALPAPIEKTISKAKGQPREPQVYTLPPSR DELTKNQVSLTCLVKGFYPSDIAVEWESNGQPENN YKTTPPVLDSDGSFFLYSKLTVDKSRWQQGNVFSC SVMHEALHNHYTQKSLSLSPGK<u>NGT</u> |
| 8 | Anti-CD-52 S298N/Y300S heavy chain | EVQLVESGGGLVQPGGSLRLSCAASGFTFNTYWMN WVRQAPGKGLEWVGQIRLKSNNYATHYAESVKGR FTISRDDSKNSLYLQMNSLKTEDTAVYYCTPVDFW GQGTTVTVSSASTKGPSVFPLAPSSKSTSGGTAALG CLVKDYFPEPVTVSWNSGALTSGVHTFPAVLQSSG LYSLSSVVTVPSSSLGTQTYICNVNHKPSNTKVDKK VEPKSCDKTHTCPPCPAPELLGGPSVFLFPPKPKDTL MISRTPEVTCVVVDVSHEDPEVKFNWYVDGVEVH NAKTKPREEQY<u>NNT</u>SRVVSVLTVLHQDWLNGKEY KCKVSNKALPAPIEKTISKAKGQPREPQVYTLPPSR DELTKNQVSLTCLVKGFYPSDIAVEWESNGQPENN YKTTPPVLDSDGSFFLYSKLTVDKSRWQQGNVFSC SVMHEALHNHYTQKSLSLSPGK |

Figure 9:
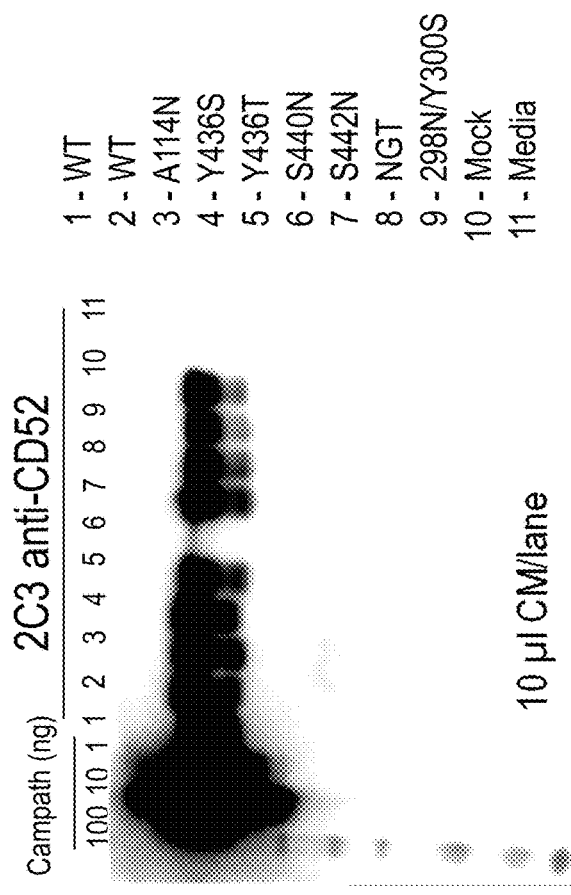
FIG. 9 depicts the results of experiments investigating the expression level of 2C3 mutants by Western blotting and surface plasmon resonance.

The mutants and WT control were transfected into HEK293-EBNA cells in a 6-well plate format. As shown in FIG. 9, the expression level was found to be ~0.1 µg/ml, as analyzed by SDS-PAGE and Western blot. Expression of mutants in conditioned media was also measured by protein A capture on Biacore. Concentration was determined using the dissociation response 6 minutes after injection into immobilized Protein A. CHO-produced WT 2C3 serially diluted in media from 90 µg/mL to 1.5 ng/mL was used as a standard curve. Concentrations were calculated down to ~0.2 µg/mL by a calibration curve using a 4-parameter fit. As shown in FIG. 9, relative expressions levels were low and generally corresponded with the Western blot results.

1B. Verification of Hyperglycosylation

Figure 10:
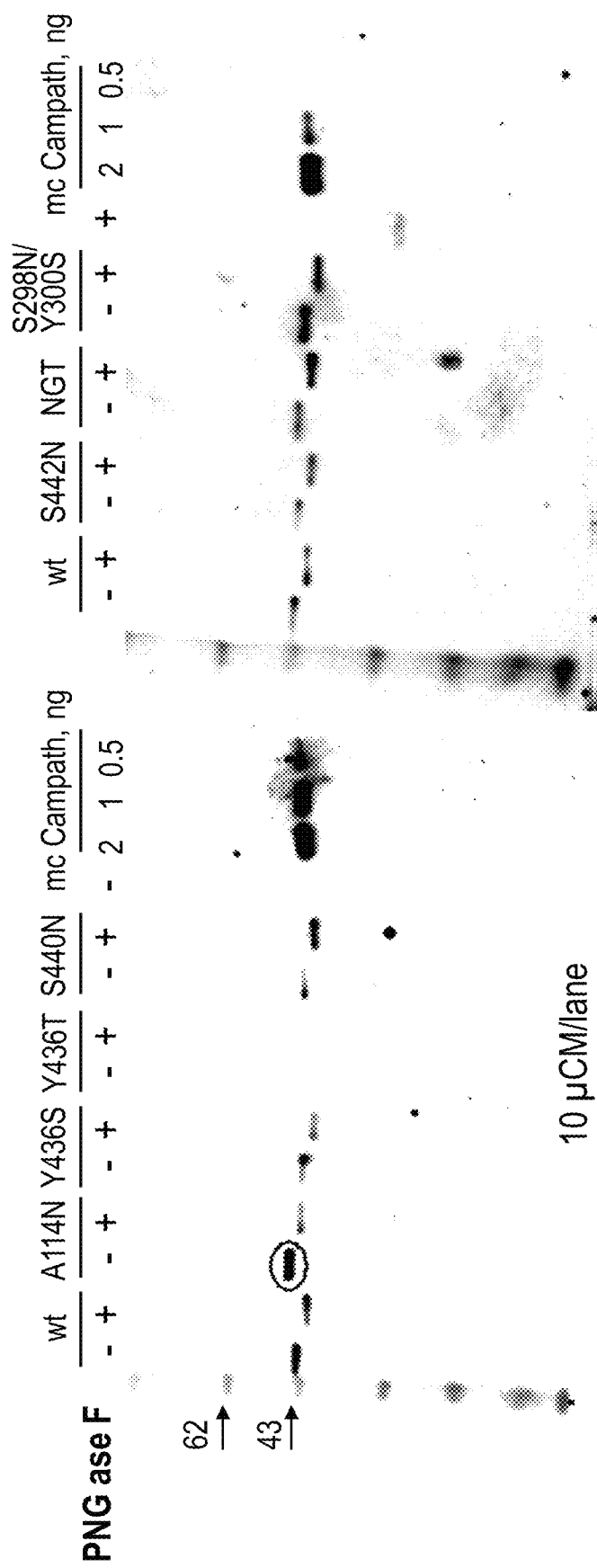
FIG. 10 depicts the results of experiments investigating glycosylation of 2C3 mutants pre- and post-PNGase F treatment.

To determine whether additional glycosylation sites were introduced by mutation, 2C3 mutant and wild type proteins were treated with the universal deglycosylating enzyme PNGase F and protein samples were analyzed by SDS-PAGE and Western blot. As shown in FIG. 10, only the A114N mutant had an increased apparent molecular weight, indicating the presence of an additional N-linked carbohydrate.

Figure 11:
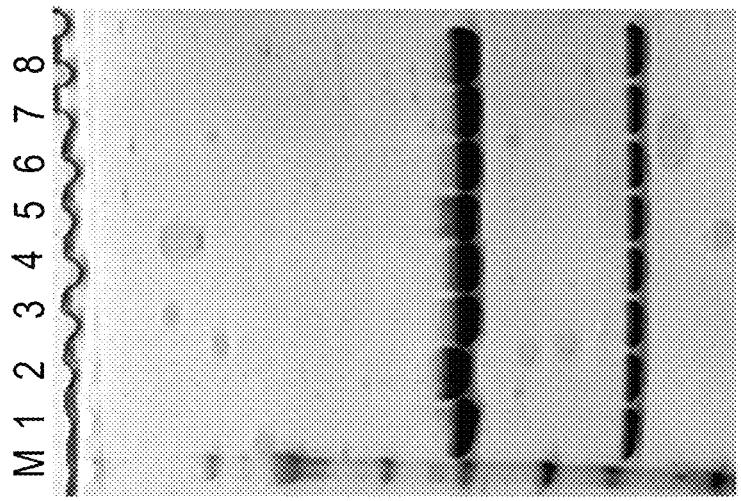
FIG. 11 depicts the results of SDS-PAGE experiments investigating glycosylation sites on 2C3 mutants isolated from cell culture.

Small scale antibody preparations were produced to purify the 2C3 mutants for further verification of glycosylation site introduction. As shown in FIG. 11, it was confirmed by SDS-PAGE that only the A114N mutant had additional glycosylation sites introduced.

1C. Binding Properties of 2C3 Anti-CD-52 Mutants

Figure 13:
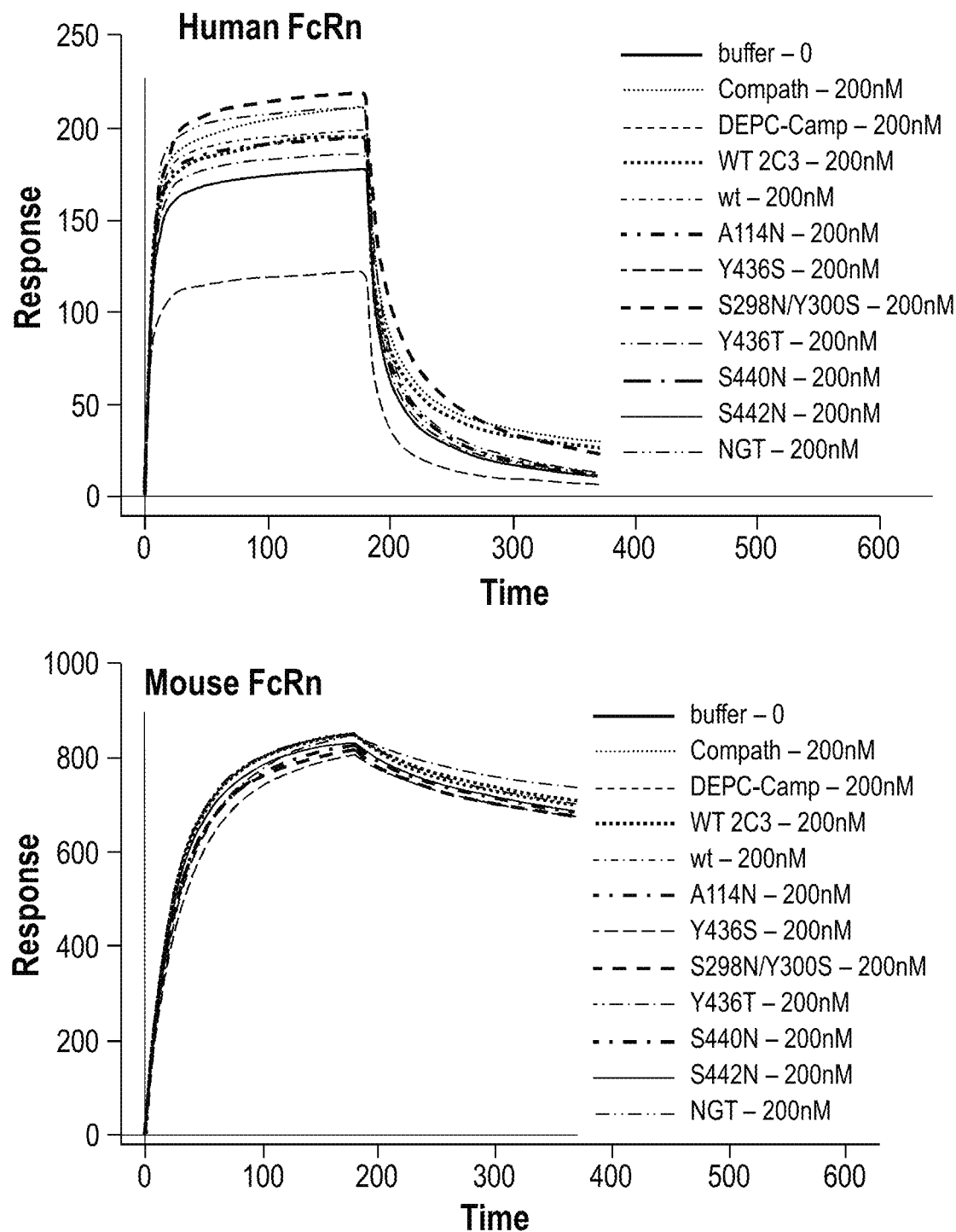
FIG. 13 depicts the results of surface plasmon resonance experiments investigating the Fc binding properties of 2C3 mutants.

Biacore was used to compare the binding properties of the purified proteins. Mouse and SEC-purified human FcRn-HPC4 were immobilized on a CM5 chip via amine coupling. Each antibody was diluted to 200, 50, and 10 nM and injected over the immobilized Fc receptors. Campath, CHO-produced WT 2C3, and DEPC-treated Campath were included as positive and negative controls. As shown in FIG. 13, the Y436S mutant displayed about a 2-fold decrease in binding to human FcRn. Interestingly, binding of this mutant to mouse FcRn was not affected. None of the other 2C3 mutations had any considerable effect on human or mouse FcRn binding.

Biacore was used to compare the antigen binding properties of the purified proteins using the CD-52 peptide 741 Biacore binding assay. CD-52 peptide 741 and control peptide 777 were immobilized to a CM5 chip. Antibodies were serially diluted 2-fold from 60 to 0.2 nM in HBS-EP and injected in duplicate for 3 min followed by a 5 min dissociation in buffer at a50 µL/min flow-rate. GLD52 lot 17200-084 was included as a control. The surface was regenerated with 1 pulse of 40 mM HCl. A 1:1 binding model was used to fit the 7.5 to 0.2 nM curves. As shown in FIG. 16, the A114N mutant had a slightly lower CD-52 binding affinity while the NGT mutant had a slightly higher affinity than the rest of the mutants in this assay. The CD-52 peptide 741 Biacore binding assay was repeated with protein purified from larger scale prep. As shown in FIG. 17, the A114N mutant exhibited CD-52 peptide binding that was comparable to WT 2C3.

1D. Charge Characterization of the A114N Mutant

Isoelectric focusing (IEF) was performed to characterize the charge of the 2C3 mutants. Purified protein was run on immobilized pH gradient (pH3-10) acrylamide (IPG) gels. As shown in FIG. 18A, A114N was found to have more negative charges, likely due to sialic acid residues. Intact MS data confirmed the complex structure with sialic acids on A114N mutant. In contrast, the WT 2C3 was shown to have G0F and G1F as the dominant glycosylation species (FIGS. 18C and 18D, respectively).

Example 2. Preparation of Hyperglycosylation Mutants in Several Antibody Backbones In addition to the 2C3 anti-CD-52 antibody, the A114N mutation was engineered in several other antibody backbones to confirm that the unique hyperglycosylation site could be introduced into unrelated heavy chain variable domain sequences. The hyperglycosylated anti-TEM1, anti-FAP, and anti-Her2 mutants are set forth in Table 5.

TABLE 5

A114N and/or S298N mutants designed in several unrelated antibody backbones

| Mutation | Antibody | Desired benefits | Applications |
|---|---|---|---|
| A114N | anti-TEM1 anti-FAP anti-Her2 | Additional glycosylation site at the elbow hinge of heavy chain for site-specific carbohydrate-mediated conjugation | 1) Control 2) Aminooxy toxin conjugation via exposed sialic acid or galactose group (SAM or GAM) |
| S298N/ T299A/ Y300S (NNAS) | anti-Her2 | Switch the glycosylation from Asn297 to an engineered Asn298. Expect solvent exposed and complex carbohydrates at S298N, offering conjugation site and means to remove effector function | 1) Aminooxy toxin conjugation via exposed sialic acid or galactose group (SAM or GAM) 2) Reduced effector function |
| A114N/ NNAS | anti-Her2 | Potential for increased conjugation yield with two conjugation sites | 1) Control 2) Aminooxy toxin conjugation via exposed sialic acid or galactose group (SAM or GAM) |

2A. Creation of Anti-TEM1 and Anti-FAP Antibody Hyperglycosylation Mutants

The A114N mutation, designated based upon the Kabat numbering system, was introduced into the CH1 domain of anti-TEM1 and anti-FAP by mutagenic PCR. To create the full-length antibody, the mutated VH plus residue 114 was inserted by ligation independent cloning (LIC) into the pENTR-LIC-IgG1 vector encoding antibody CH domains 1-3. Full-length mutants were then cloned into the pCEP4 (−E+I)Dest expression vector by Gateway cloning. Mutations were confirmed by DNA sequencing Amino acid sequences of the anti-TEM1 wild type and mutated heavy and light chains are set forth in Table 6. Mutated amino acids are highlighted in gray and the consensus glycosylation target sites created by the mutation are underlined.

TABLE 6

Amino acid sequences of anti-TEM1 and anti-FAP antibodies

| SEQ ID NO | Name | Amino Acid Sequence |
|---|---|---|
| 9 | Anti-TEM1 WT light chain (clone #187) | EIVLTQSPGTLSLSPGERATLSCRASQSVSSSYLAWY QQKPGQAPRLLIYGASSRATGIPDRFSGSGSGTDFTL TISRLEPEDFAVYYCQQYGSSPWTFGQGTKVEIKRT VAAPSVFIFPPSDEQLKSGTASVVCLLNNFYPREAK VQWKVDNALQSGNSQESVTEQDSKDSTYSLSSTLT LSKADYEKHKVYACEVTHQGLSSPVTKSFNRGEC |
| 10 | Anti-TEM1 WT heavy chain (clone #187) | QVQLQESAPGLVKPSETLSLTCTVSGGSIRSYYWSW IRQPPGKGLEYIGYIYYTGSAIYNPSLQSRVTISVDTS KNQFSLKLNSVTAADTAVYYCAREGVRGASGYYY YGMDVWGQGTTVTVSSASTKGPSVFPLAPSSKSTS GGTAALGCLVKDYFPEPVTVSWNSGALTSGVHTFP AVLQSSGLYSLSSVVTVPSSSLGTQTYICNVNHKPS NTKVDKKVEPKSCDKTHTCPPCPAPELLGGPSVFLF PPKPKDTLMISRTPEVTCVVVDVSHEDPEVKFNWY VDGVEVHNAKTKPREEQYNSTYRVVSVLTVLHQD WLNGKEYKCKVSNKALPAPIEKTISKAKGQPREPQ |

TABLE 6-continued

Amino acid sequences of anti-TEM1 and anti-FAP antibodies

| SEQ ID NO | Name | Amino Acid Sequence |
|---|---|---|
| | | VYTLPPSRDELTKNQVSLTCLVKGFYPSDIAVEWES NGQPENNYKTTPPVLDSDGSFFLYSKLTVDKSRWQ QGNVFSCSVMHEALHNHYTQKSLSLSPGK |
| 11 | Anti-TEM1 A114N | QVQLQESAPGLVKPSETLSLTCTVSGGSIRSYYWSW IRQPPGKGLEYIGYIYYTGSAIYNPSLQSRVTISVDTS KNQFSLKLNSVTAADTAVYYCAREGVRGASGYYY YGMDVWGQGTTVTVSS<u>NST</u>KGPSVFPLAPSSKSTS GGTAALGCLVKDYFPEPVTVSWNSGALTSGVHTFP AVLQSSGLYSLSSVVTVPSSSLGTQTYICNVNHKPS NTKVDKKVEPKSCDKTHTCPPCPAPELLGGPSVFLF PPKPKDTLMISRTPEVTCVVVDVSHEDPEVKFNWY VDGVEVHNAKTKPREEQYNSTYRVVSVLTVLHQD WLNGKEYKCKVSNKALPAPIEKTISKAKGQPREPQ VYTLPPSRDELTKNQVSLTCLVKGFYPSDIAVEWES NGQPENNYKTTPPVLDSDGSFFLYSKLTVDKSRWQ QGNVFSCSVMHEALHNHYTQKSLSLSPGK* |

The mutants and wild type control were transfected into HEK293-EBNA cells in a triple flask format and purified on HiTrap protein A columns (GE Healthcare Biosciences, Pittsburgh, Pa., USA). As analyzed by A280 on a NanoDrop spectrophotometer, the expression of anti-FAP A114N and anti-FAP A114C was about 3 µg/ml and about 1 µg/ml, respectively. The expression of anti-TEM1 A114N was about 0.04 µg/ml.

2B. Verification of Hyperglycosylation

Figure 20:
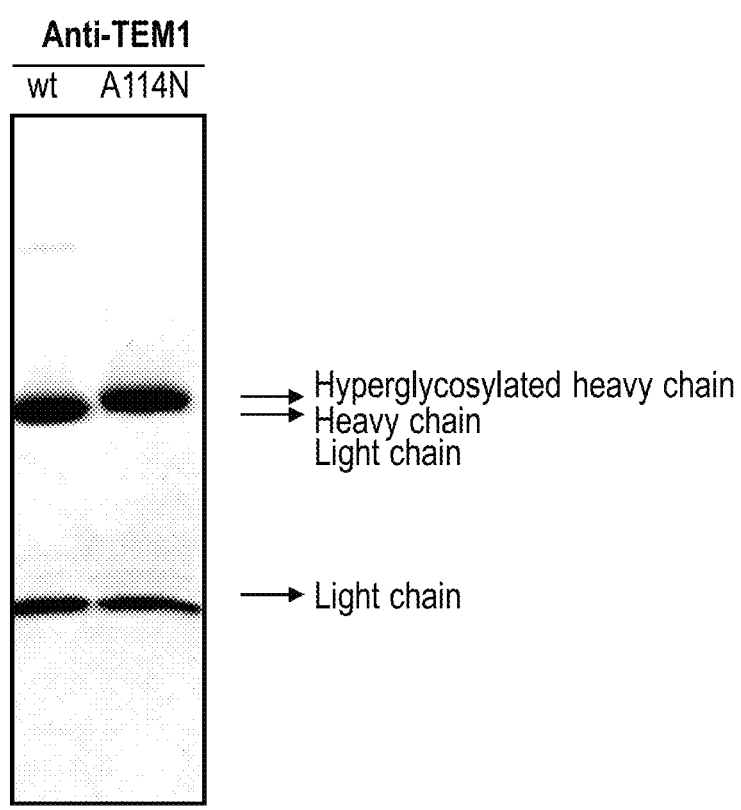
FIG. 20 depicts the results of SDS-PAGE experiments to determine the glycan content of the anti-TME1 A114N mutant.

To confirm that the additional glycosylation site was introduced into the A114N mutants, purified protein from the A114N mutants was analyzed on reducing SDS-PAGE along with wild-type control protein. One additional glycosylation site would add 2000-3000 Daltons to the molecular weight of the heavy chain. As shown in FIG. 20, SDS-PAGE indicated that the anti-FAP and anti-TEM1 A114N mutant's heavy chain bands had increased apparent molecular weight, consistent with successful introduction of an additional glycosylation site to both antibodies.

2C. Creation of Anti-Her2 Antibody Hyperglycosylation Mutants

The Her-2 A114N, Her-2 A114N/NNAS, and WT Her-2 antibodies were created by ligation independent cloning. The VH domain of Herceptin was synthesized and PCR-amplified with two LIC-compatible sets of primers, either WT or bearing the A114N mutation. To obtain a full-length antibody, amplified VH inserts (WT or A114N) were cloned into two pENTR vectors encoding CH 1-3 domains, pENTR-LIC-IgG1 WT and pENTR-LIC-IgG1 NNAS, resulting in three full-length mutants (A114N, NNAS, A114N/NNAS) and WT control as entry clones on pENTR. These mutants were cloned into the pCEP4(-E+I)Dest expression vector, by Gateway cloning. Mutations were confirmed by DNA sequencing. Amino acid sequences of the anti-Her-2 wild type and mutated heavy and light chains are set forth in Table 7. Mutated amino acids are highlighted in gray and the consensus glycosylation target sites created by the mutation are underlined.

TABLE 7

Amino acid sequences of anti-Her-2 antibodies

| SEQ ID NO | Name | Amino Acid Sequence |
|---|---|---|
| 12 | Anti-Her-2 WT light chain | DIQMTQSPSSLSASVGDRVTITCRASQDVNTAVAW YQQKPGKAPKLLIYSASFLYSGVPSRFSGSRSGTDFT LTISSLQPEDFATYYCQQHYTTPPTFGQGTKVEIKRT VAAPSVFIFPPSDEQLKSGTASVVCLLNNFYPREAK VQWKVDNALQSGNSQESVTEQDSKDSTYSLSSTLT LSKADYEKHKVYACEVTHQGLSSPVTKSFNRGEC |
| 13 | Anti-Her-2 WT heavy chain | EVQLVESGGGLVQPGGSLRLSCAASGFNIKDTYIHW VRQAPGKGLEWVARIYPTNGYTRYADSVKGRFTIS ADTSKNTAYLQMNSLRAEDTAVYYCSRWGGDGFY AMDYWGQGTLVTVSSASTKGPSVFPLAPSSKSTSG GTAALGCLVKDYFPEPVTVSWNSGALTSGVHTFPA VLQSSGLYSLSSVVTVPSSSLGTQTYICNVNHKPSNT KVDKKVEPKSCDKTHTCPPCPAPELLGGPSVFLFPP KPKDTLMISRTPEVTCVVVDVSHEDPEVKFNWYVD GVEVHNAKTKPREEQYNSTYRVVSVLTVLHQDWL NGKEYKCKVSNKALPAPIEKTISKAKGQPREPQVYT LPPSRDELTKNQVSLTCLVKGFYPSDIAVEWESNGQ PENNYKTTPPVLDSDGSFFLYSKLTVDKSRWQQGN VFSCSVMHEALHNHYTQKSLSLSPGK |
| 14 | Anti-Her-2 A114N heavy chain | EVQLVESGGGLVQPGGSLRLSCAASGFNIKDTYIHW VRQAPGKGLEWVARIYPTNGYTRYADSVKGRFTIS ADTSKNTAYLQMNSLRAEDTAVYYCSRWGGDGFY AMDYWGQGTLVTVSS<u>NST</u>KGPSVFPLAPSSKSTSG GTAALGCLVKDYFPEPVTVSWNSGALTSGVHTFPA VLQSSGLYSLSSVVTVPSSSLGTQTYICNVNHKPSNT KVDKKVEPKSCDKTHTCPPCPAPELLGGPSVFLFPP KPKDTLMISRTPEVTCVVVDVSHEDPEVKFNWYVD GVEVHNAKTKPREEQYNSTYRVVSVLTVLHQDWL NGKEYKCKVSNKALPAPIEKTISKAKGQPREPQVYT LPPSRDELTKNQVSLTCLVKGFYPSDIAVEWESNGQ PENNYKTTPPVLDSDGSFFLYSKLTVDKSRWQQGN VFSCSVMHEALHNHYTQKSLSLSPGK |
| 15 | Anti-Her2 NNAS heavy chain | EVQLVESGGGLVQPGGSLRLSCAASGFNIKDTYIHW VRQAPGKGLEWVARIYPTNGYTRYADSVKGRFTIS ADTSKNTAYLQMNSLRAEDTAVYYCSRWGGDGFY AMDYWGQGTLVTVSSASTKGPSVFPLAPSSKSTSG GTAALGCLVKDYFPEPVTVSWNSGALTSGVHTFPA VLQSSGLYSLSSVVTVPSSSLGTQTYICNVNHKPSNT KVDKKVEPKSCDKTHTCPPCPAPELLGGPSVFLFPP KPKDTLMISRTPEVTCVVVDVSHEDPEVKFNWYVD GVEVHNAKTKPREEQYN<u>NAS</u>RVVSVLTVLHQDWL NGKEYKCKVSNKALPAPIEKTISKAKGQPREPQVYT LPPSRDELTKNQVSLTCLVKGFYPSDIAVEWESNGQ PENNYKTTPPVLDSDGSFFLYSKLTVDKSRWQQGN VFSCSVMHEALHNHYTQKSLSLSPGK |
| 16 | Anti-Her2 A114N/ NNAS heavy chain | EVQLVESGGGLVQPGGSLRLSCAASGFNIKDTYIHW VRQAPGKGLEWVARIYPTNGYTRYADSVKGRFTIS ADTSKNTAYLQMNSLRAEDTAVYYCSRWGGDGFY AMDYWGQGTLVTVSS<u>NST</u>KGPSVFPLAPSSKSTSG GTAALGCLVKDYFPEPVTVSWNSGALTSGVHTFPA VLQSSGLYSLSSVVTVPSSSLGTQTYICNVNHKPSNT KVDKKVEPKSCDKTHTCPPCPAPELLGGPSVFLFPP KPKDTLMISRTPEVTCVVVDVSHEDPEVKFNWYVD GVEVHNAKTKPREEQYN<u>NAS</u>RVVSVLTVLHQDWL NGKEYKCKVSNKALPAPIEKTISKAKGQPREPQVYT LPPSRDELTKNQVSLTCLVKGFYPSDIAVEWESNGQ PENNYKTTPPVLDSDGSFFLYSKLTVDKSRWQQGN VFSCSVMHEALHNHYTQKSLSLSPGK |

2D. Expression of the A114N Anti-Her2 Antibody Hyperglycosylation Mutant

The A114N anti-Her2 and wild type constructs were transfected with Lipofectamine-2000 (2.5:1 ratio of reagent to DNA) and XtremeGene HP (3:1 ratio r of reagent to DNA) into HEK293-EBNA cells in 12 triple flasks. Octet measurement of aliquots from day 3 conditioned media (CM) showed that protein expression was consistent across 6 flasks for both Lipofectamine-2000 and XtremeGene HP.

As shown in Table 8, the overall transfection efficiency was about 30% higher with XtremeGene HP. Conditioned media collected on day 3 was pooled together for both transfection conditions and purified by protein A column. Octet measurement showed 1.8 ug/ml antibody in the serum-containing mock media versus 0 ug/ml in no serum mock media.

TABLE 8

A114N anti-Her2 hyperglycosylation mutant expression

|  |  | Lipofectamine-2000 | XtremeGene HP |
|---|---|---|---|
| Purified protein from protein A column | Concentration (mg/ml) | 1.72 | 3.18 |
|  | Volume (ml) | 3.5 | 3.5 |
|  | Total protein (mg) | 6.02 | 11.13 |
| Buffer-exchanged protein | Concentration (mg/ml) | 15.59 | 16.86 |
|  | Volume (ml) | 0.2 | 0.36 |
|  | Total protein (mg) | 3.1 | 6.07 |
|  | % Recovery | 51.8 | 54.5 |

Conditioned media from Day 6 was collected and purified separately for each transfection condition. Both eluates were buffer-exchanged separately into PBS, pH 7.2, and concentrated ~15-fold using Amicon-4 (50 kD cut-off) columns. Day 6 CM showed higher expression level compared to Day 3 CM. As shown in Table 8, a total of 3 mg of Herceptin A114N 15.59 mg/ml (from Lipofectamine transfection) and 6 mg of Herceptin A114N 16.86 mg/ml (from XtremeGene HP transfection) was produced from day 6 conditioned media for additional downstream applications, such as antibody-drug conjugation.

2E. SDS-PAGE and HIC Analysis of the A114N Anti-Her2 Mutant

Figure 21:
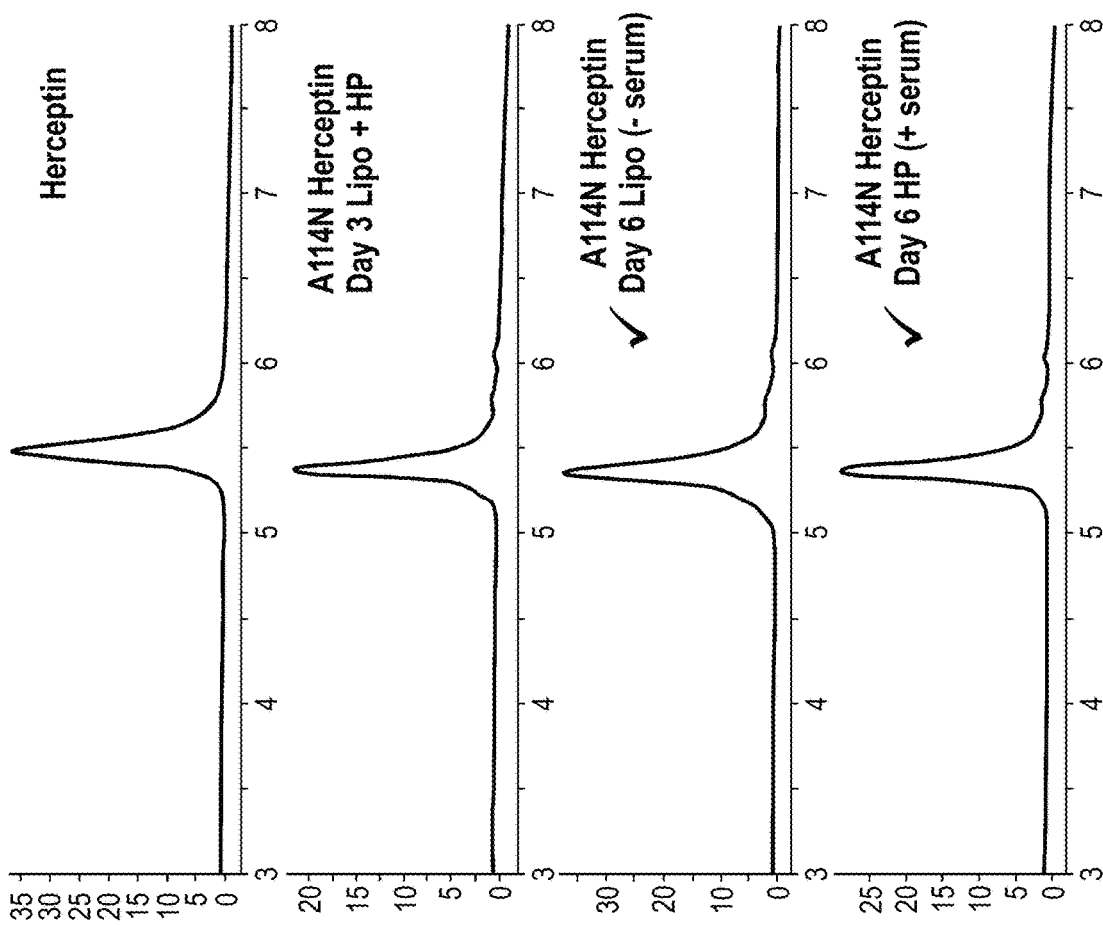
FIG. 21 depicts the results of SDS-PAGE and hydrophobic interaction chromatography analysis of the A114N anti-Her2 mutant.
Figure 21:
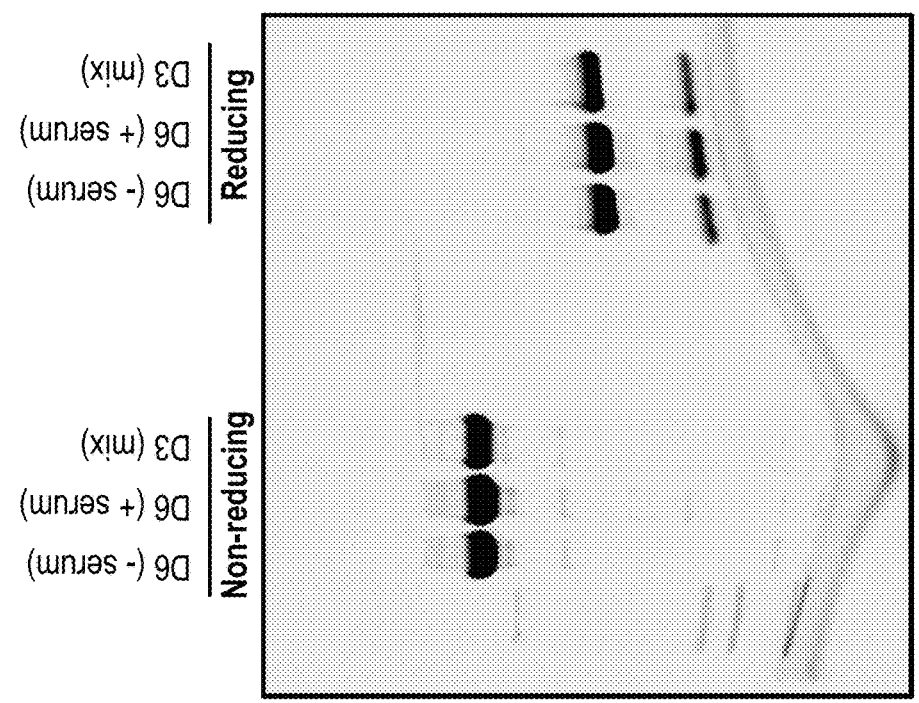

Prior to conjugation, purified A114N Herceptin was characterized by SDS-PAGE and HIC (hydrophobic interaction chromatography). As shown in FIG. 21, the quality of purified A114N Herceptin was determined to be suitable for further downstream applications.

2F. Conjugation to Engineered Glycosylation

Figure 22:
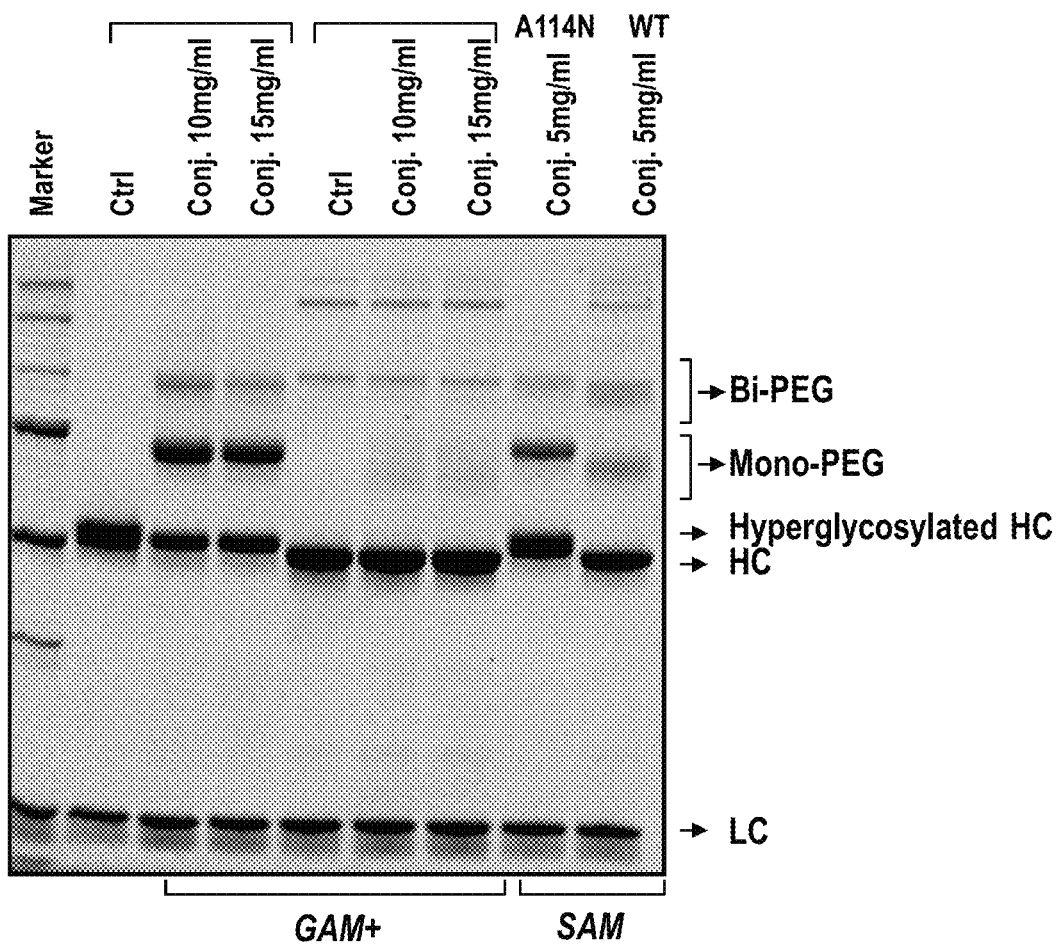
FIG. 22 depicts the results of SDS-PAGE experiments to demonstrate the conjugation of PEG to the 2C3 A114N mutant through an aminooxy linkage.
Figure 23:
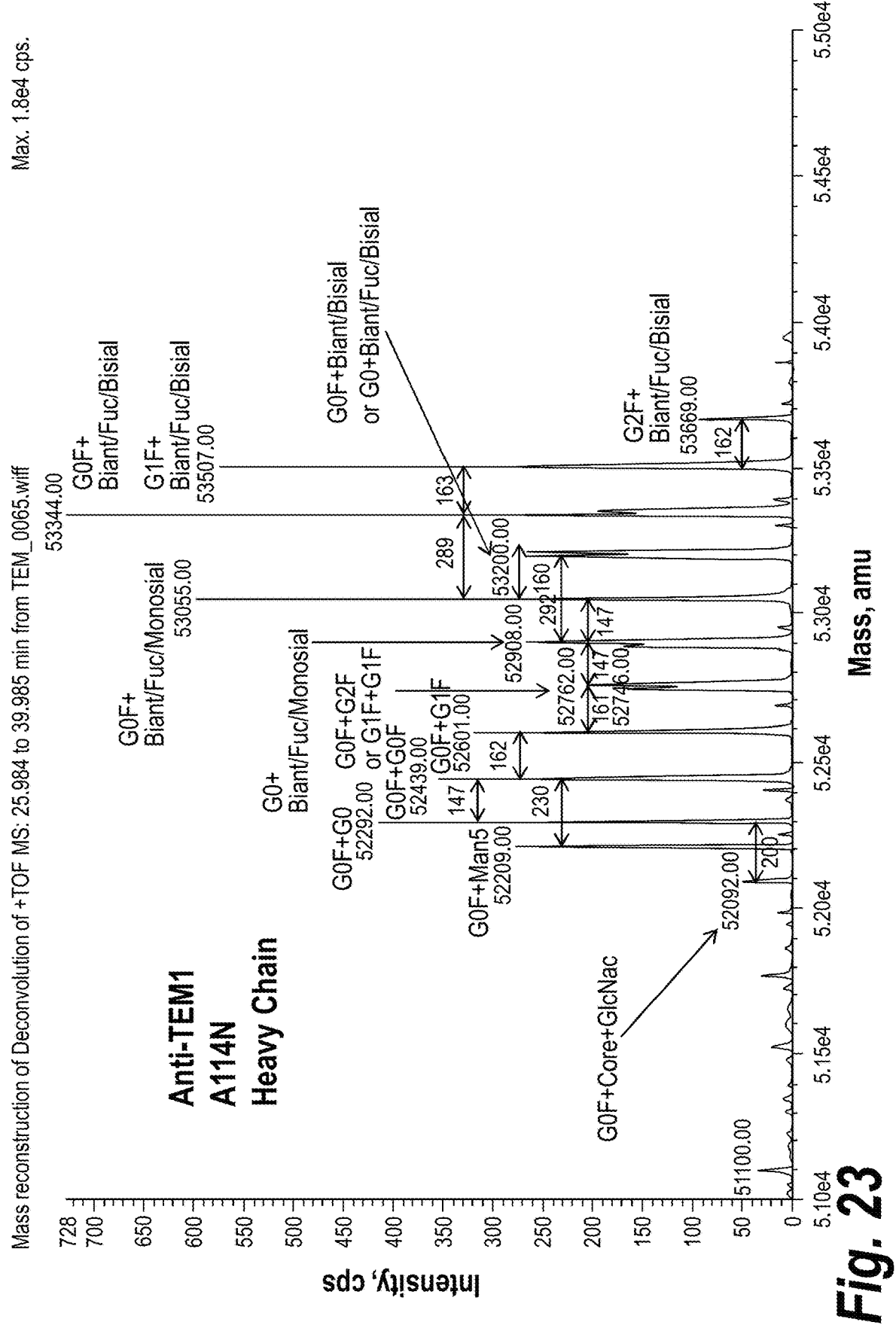
FIG. 23 depicts the results of LC-MS experiments to determine the glycan contents of anti-TEM1 A114N hyperglycosylation mutant.
Figure 24:
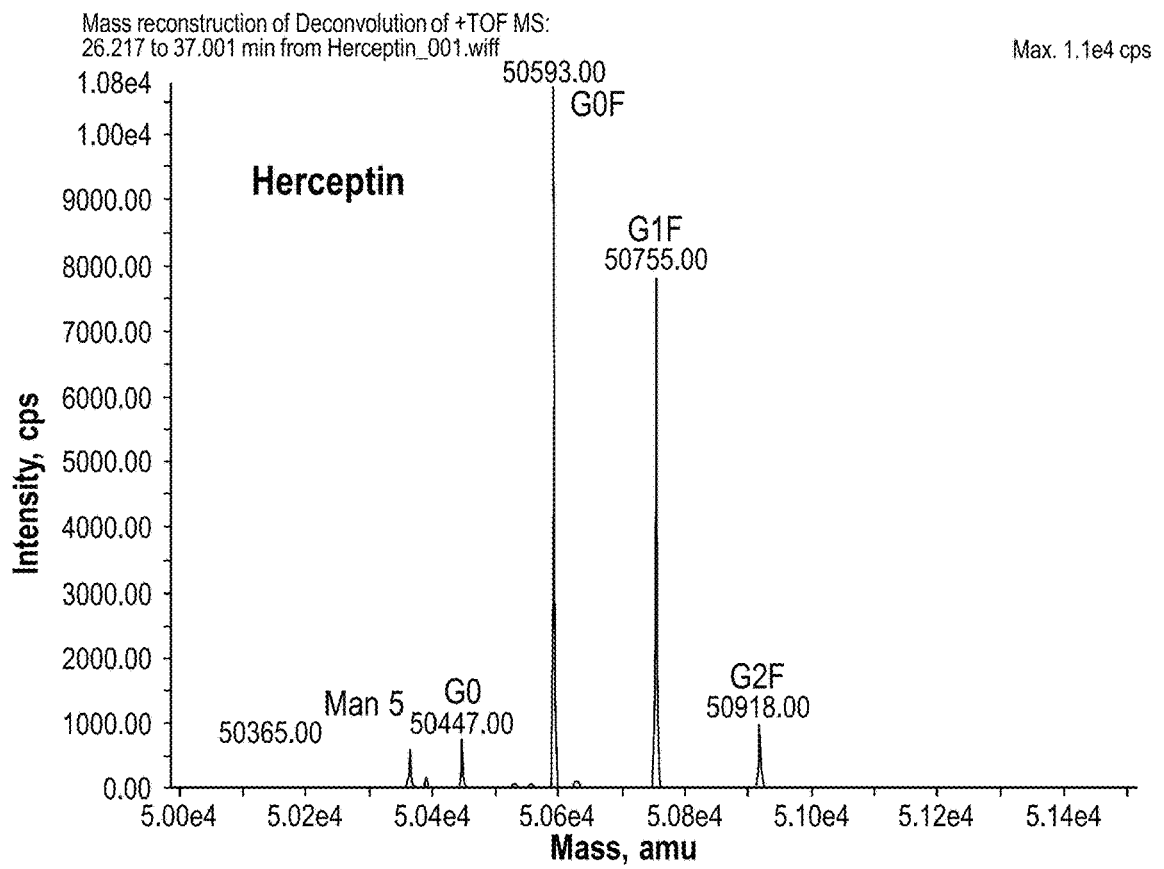
FIG. 24 depicts the results of LC-MS experiments to determine the glycan contents of a wild-type HER2 antibody and an A114N anti-Her2 hyperglycosylation mutant.
Figure 24:
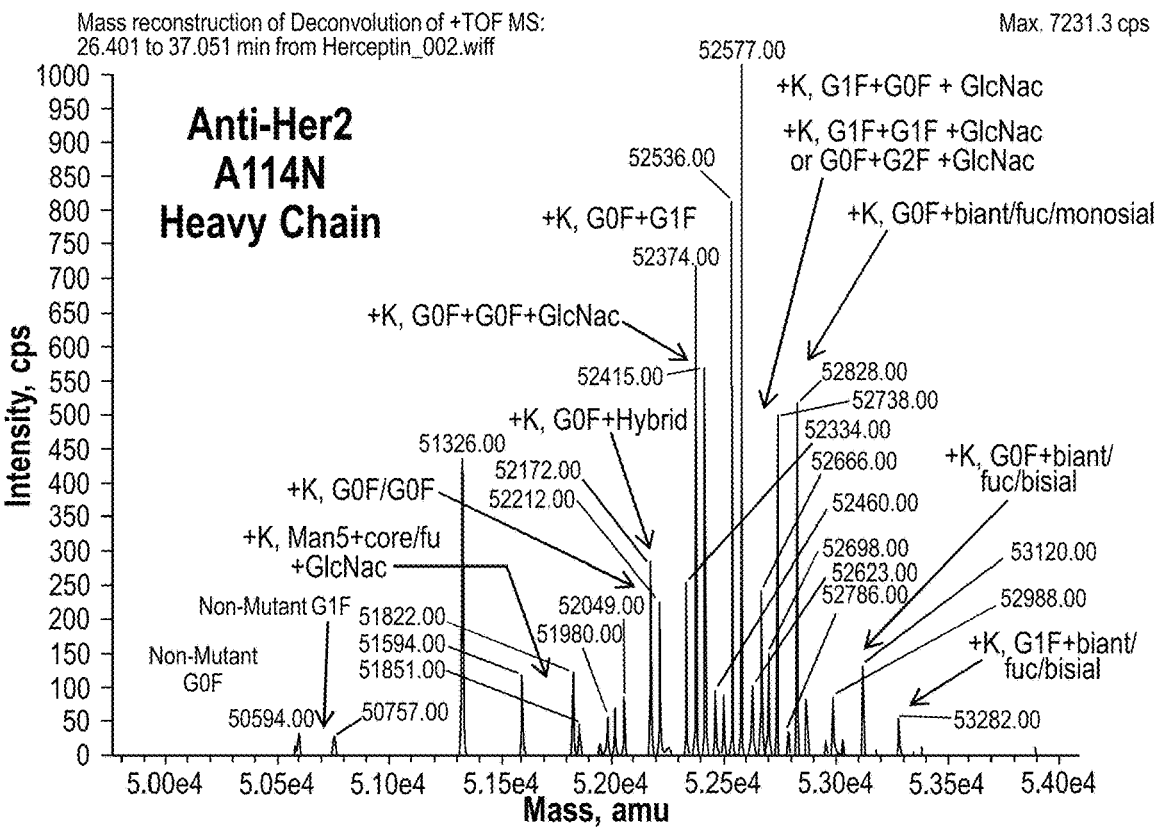

It was demonstrated that: a) a glycosylation site was introduced at Kabat position 114 site on anti-TEM1; b) the A114N mutant had hyperglycosylation on the heavy chain by reducing SDS-PAGE; and c) the A114N hyperglycosylated mutant had complex carbohydrate structure by intact LC/MS, including terminal sialic acids and galactose, which are ideal for SAM and GAM conjugation. To confirm that the engineered glycosylation site was suitable for conjugation, anti-TEM1 A114N was conjugated with a 5 kDa PEG via aminooxy chemistry. As shown in FIG. 22, PEG was successfully conjugated to anti-TEM1 A114N through an aminooxy linkage. This mutant was also successfully prepared on the anti-FAP and anti-CD-52 2C3 backbones (not shown). These data demonstrate that the glycosylation site at N114 is useful for conjugation of effector moieties.

Example 3: Generation of S298N/Y300S Fc Mutants

Engineered Fc variants were designed and generated in which a new glycosylation site was introduced at EU position Ser 298, next to the naturally-occurring Asn297 site. The glycosylation at Asn297 was either maintained or ablated by mutation. Mutations and desired glycosylation results are set forth in Table 9.

TABLE 9

Glycosylation states of various antibody variants

| # | Mutation | Desired Glycosylation State | Applications |
|---|---|---|---|
| 17 | N297Q | No glycosylation (agly) | Agly Control |
| 18 | T299A | No glycosylation (agly) | Agly Control, unknown effector function |
| 19 | N297Q/ S298N/ Y300S (NSY) | No glycosylation at 297 but engineered glycosylation site at 298 | Reduced effector function; Conjugation via exposed sialic acid or galactose groups. |
| 20 | S298N/ T299A/ Y300S (STY) | No glycosylation at 297 but engineered glycosylation site at 298 | Reduced effector function; Conjugation via exposed sialic acid or galactose groups. |
| 21 | S298N/ Y300S (SY) | Two potential glycosylation sites at 297 & 298; Alterations in glycosylation pattern. | Reduced effector function; Conjugation via exposed sialic acid or galactose groups. |
| 22 | Wild-type | 297 | control |

3A. Creation of H66 αβ-TCR Antibody Altered Glycosylation Variants

Mutations were made on the heavy chain of αβ T-cell receptor antibody clone #66 by Quikchange using a pENTR_LIC_IgG1 template. The VH domain of HEBE1 Δab IgG1 #66 was amplified with LIC primers before being cloned into mutated or wild type pENTR_LIC_IgG1 by LIC to create full-length mutant or wild-type antibodies. The subcloning was verified with DraIII/XhoI double digest, producing an approximately 1250 bp-sized insert in the successful clones. Those full-length mutants were then cloned into an expression vector, pCEP4(–E+I)Dest, via Gateway cloning. The mutations were confirmed by DNA sequencing Amino acid sequences of the WT H66 anti-αβTCR heavy and light chains and the mutated H66 heavy chains are set forth in Table 10. Mutated amino acids are highlighted in gray and the consensus glycosylation target sites created by the mutation are underlined.

TABLE 10

Amino acid sequences of H66 anti-αβTCR antibodies

| SEQ ID NO | Name | Amino Acid Sequence |
|---|---|---|
| 23 | Anti-αβTCR clone H66 light chain | EIVLTQSPATLSLSPGERATLSCSATSSVSYMHWYQQ KPGQAPRRLIYDTSKLASGVPARFSGSGSGTSYTLTIS SLEPEDFAVYYCQQWSSNPLTFGGGTKVEIKRTVAAP SVFIFPPSDEQLKSGTASVVCLLNNFYPREAKVQWKV DNALQSGNSQESVTEQDSKDSTYSLSSTLTLSKADYE KHKVYACEVTHQGLSSPVTKSFNRGEC* |
| 24 | Anti-αβTCR clone H66 heavy chain | EVQLLQSGGGLVQPGGSLRLSCAASGYKFTSYVMHW VRQAPGKGLEWVGYINPYNDVTKYNEKFKGRFTLSR DNSKNTLYLQMNSLRAEDTAVYYCARGSYYDYDGF VYWGQGTLVTVSSASTKGPSVFPLAPSSKSTSGGTAA LGCLVKDYFPEPVTVSWNSGALTSGVHTFPAVLQSSG LYSLSSVVTVPSSSLGTQTYICNVNHKPSNTKVDKKV EPKSCDKTHTCPPCPAPELLGGPSVFLFPPKPKDTLMI SRTPEVTCVVVDVSHEDPEVKFNWYVDGVEVHNAK TKPREEQYNSTYRVVSVLTVLHQDWLNGKEYKCKV SNKALPAPIEKTISKAKGQPREPQVYTLPPSRDELTKN QVSLTCLVKGFYPSDIAVEWESNGQPENNYKTTPPVL DSDGSFFLYSKLTVDKSRWQQGNVFSCSVMHEALHN HYTQKSLSLSPGK* |

TABLE 10-continued

Amino acid sequences of H66 anti-αβTCR antibodies

| SEQ ID NO | Name | Amino Acid Sequence |
|---|---|---|
| 25 | Anti-αβTCR clone H66 S298N/ Y300S heavy chain | EVQLLQSGGGLVQPGGSLRLSCAASGYKFTSYVMHW VRQAPGKGLEWVGYINPYNDVTKYNEKFKGRFTLSR DNSKNTLYLQMNSLRAEDTAVYYCARGSYYDYDGF VYWGQGTLVTVSSASTKGPSVFPLAPSSKSTSGGTAA LGCLVKDYFPEPVTVSWNSGALTSGVHTFPAVLQSSG LYSLSSVVTVPSSSLGTQTYICNVNHKPSNTKVDKKV EPKSCDKTHTCPPCPAPELLGGPSVFLFPPKPKDTLMI SRTPEVTCVVVDVSHEDPEVKFNWYVDGVEVHNAK TKPREEQY<u>NNTS</u>RVVSVLTVLHQDWLNGKEYKCKV SNKALPAPIEKTISKAKGQPREPQVYTLPPSRDELTKN QVSLTCLVKGFYPSDIAVEWESNGQPENNYKTTPPVL DSDGSFFLYSKLTVDKSRWQQGNVFSCSVMHEALHN HYTQKSLSLSPGK* |
| 26 | Anti-αβTCR clone H66 S298N/ T299A/ Y300S heavy chain | EVQLLQSGGGLVQPGGSLRLSCAASGYKFTSYVMHW VRQAPGKGLEWVGYINPYNDVTKYNEKFKGRFTLSR DNSKNTLYLQMNSLRAEDTAVYYCARGSYYDYDGF VYWGQGTLVTVSSASTKGPSVFPLAPSSKSTSGGTAA LGCLVKDYFPEPVTVSWNSGALTSGVHTFPAVLQSSG LYSLSSVVTVPSSSLGTQTYICNVNHKPSNTKVDKKV EPKSCDKTHTCPPCPAPELLGGPSVFLFPPKPKDTLMI SRTPEVTCVVVDVSHEDPEVKFNWYVDGVEVHNAK TKPREEQYN<u>NAS</u>RVVSVLTVLHQDWLNGKEYKCKV SNKALPAPIEKTISKAKGQPREPQVYTLPPSRDELTKN QVSLTCLVKGFYPSDIAVEWESNGQPENNYKTTPPVL DSDGSFFLYSKLTVDKSRWQQGNVFSCSVMHEALHN HYTQKSLSLSPGK* |
| 27 | Anti-αβTCR clone H66 N297Q/ S298N/ Y300S heavy chain | EVQLLQSGGGLVQPGGSLRLSCAASGYKFTSYVMHW VRQAPGKGLEWVGYINPYNDVTKYNEKFKGRFTLSR DNSKNTLYLQMNSLRAEDTAVYYCARGSYYDYDGF VYWGQGTLVTVSSASTKGPSVFPLAPSSKSTSGGTAA LGCLVKDYFPEPVTVSWNSGALTSGVHTFPAVLQSSG LYSLSSVVTVPSSSLGTQTYICNVNHKPSNTKVDKKV EPKSCDKTHTCPPCPAPELLGGPSVFLFPPKPKDTLMI SRTPEVTCVVVDVSHEDPEVKFNWYVDGVEVHNAK TKPREEQYQ<u>NTS</u>RVVSVLTVLHQDWLNGKEYKCKV SNKALPAPIEKTISKAKGQPREPQVYTLPPSRDELTKN QVSLTCLVKGFYPSDIAVEWESNGQPENNYKTTPPVL DSDGSFFLYSKLTVDKSRWQQGNVFSCSVMHEALHN HYTQKSLSLSPGK* |

Figure 2:
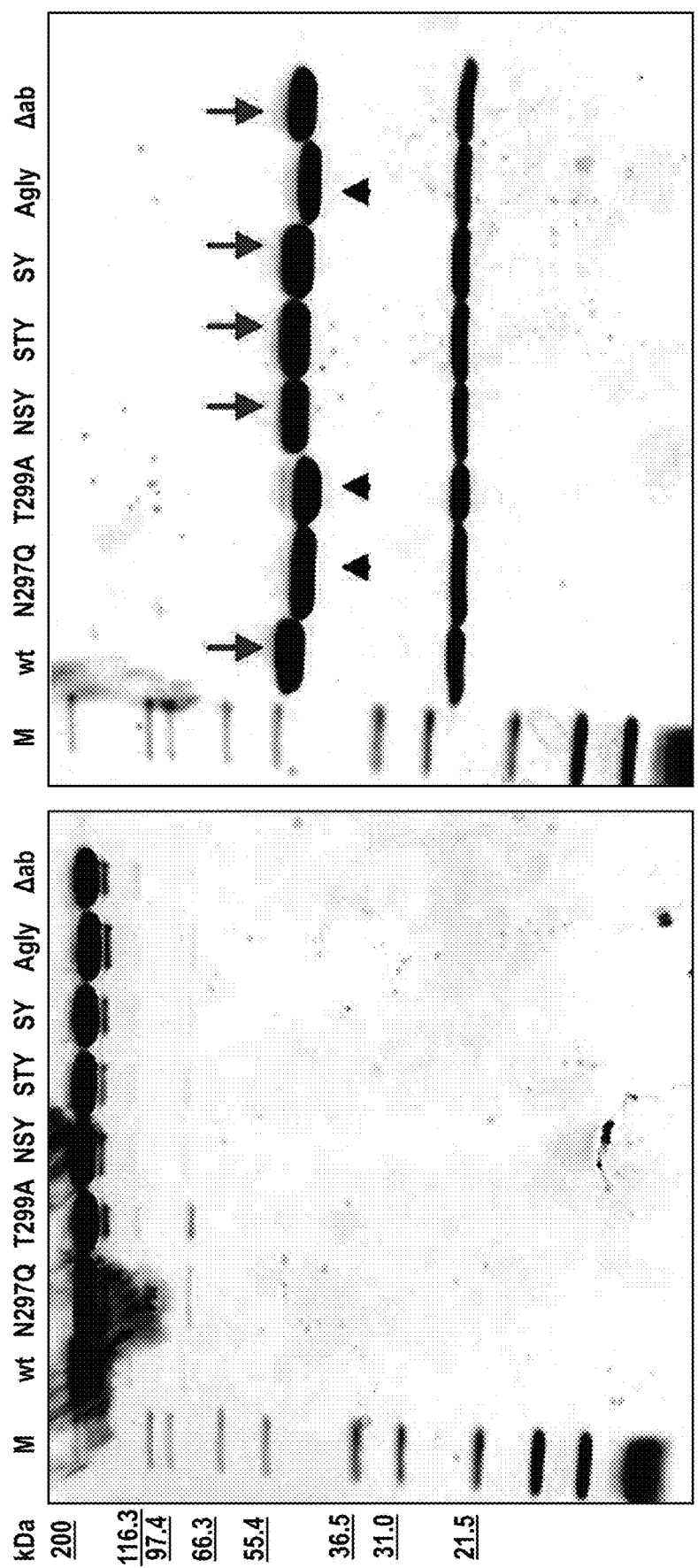
FIG. 2 is a Coomassie-blue stained gel showing the expression and purification of glycosylation mutants.

The mutant, wild-type, and two aglycosylated control (HEBE1 Agly IgG4 and HEBE1 Δab IgG1 in pCEP4) constructs were transfected into HEK293-EBNA cells in triple-flasks for expression. Proteins were purified from 160 ml of conditioned media (CM) with 1 ml HiTrap protein A columns (GE) using a multi-channel peristaltic pump. Five micrograms of each resulting supernatant were analyzed on 4-20% Tris-Glycine reducing and non-reducing SDS-PAGE gels (see FIG. 2). The heavy chains of the aglycosylated mutants (N297Q, T299A, and Agly controls), have migrated further (arrowhead), consistent with the loss of the glycans in these antibodies. The heavy chains of the engineered glycosylated antibodies (NSY, STY, SY, Δab, and wt control, arrows), however, migrate similarly to the wild-type control. This result is consistent with the existence of an engineered glycosylation site at EU position 298. SEC-HPLC analysis indicated that all mutants are expressed as monomers.

3B. Glycosylation Analysis by LC-MS

Figure 34:
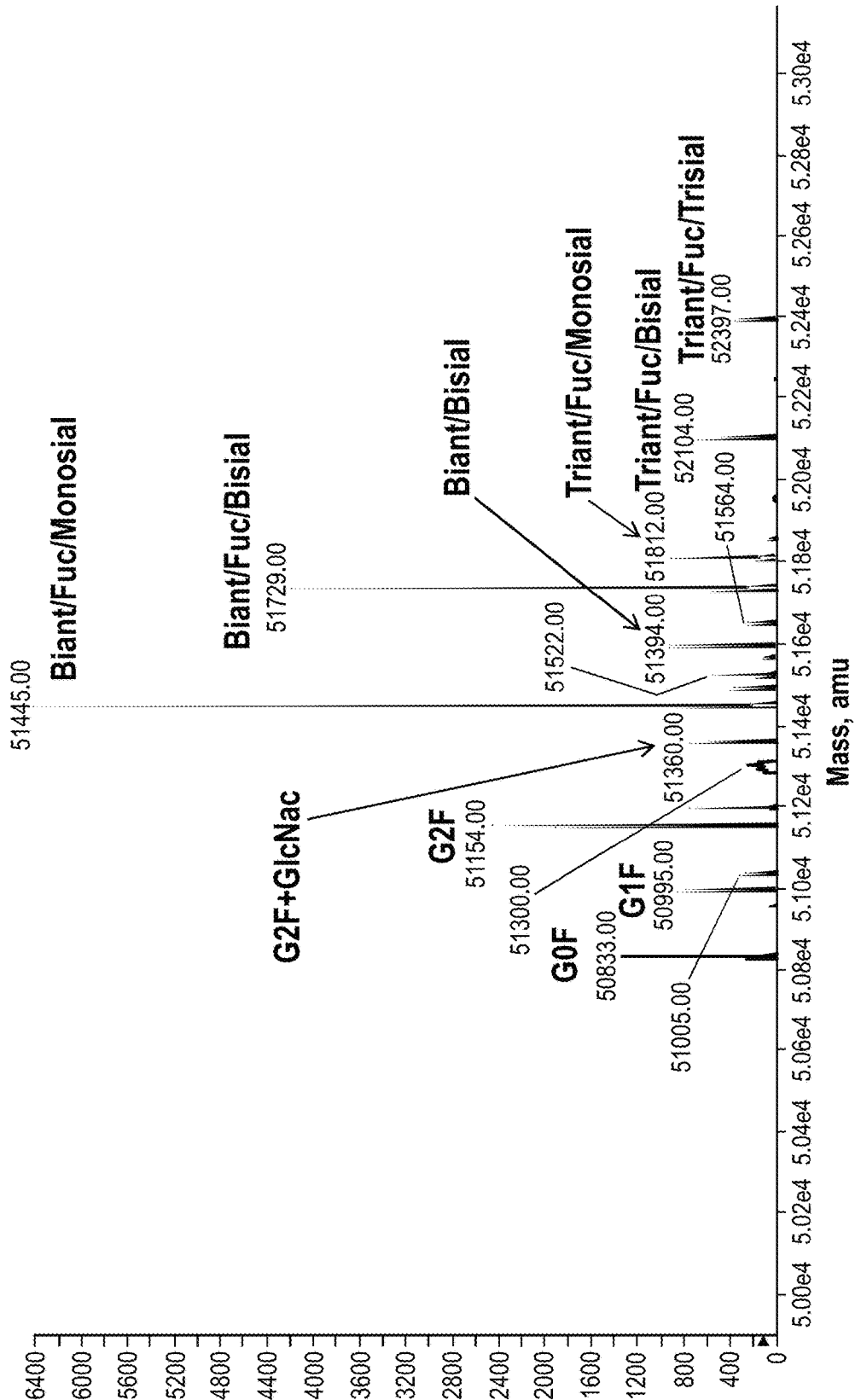
FIG. 34 depicts the results of LC-MS experiments to determine the glycan content of a mutant anti-αβTCR antibody containing the S298N/Y300S mutation.

The engineered H66 IgG1 Fc variants were partially reduced with 20 mM DTT at 37° C. for 30 min. The samples were then analyzed by capillary LC/MS on an Agilent 1100 capillary HPLC system coupled with a QSTAR qq TOF hybrid system (Applied Biosystems). A Bayesian protein reconstruction with baseline correction and computer modeling in Analyst QS 1.1 (Applied Bisoystem) was used for data analysis. In the S298N/T299A/Y300S H66 antibody mutant, one glycosylation site was observed at amino acid 298 with bi-antennary and tri-antennary complex-type glycans detected as the major species alongside G0F, G1F and G2F (see FIG. 34). This altered glycosylation profile is consistent which shifted glycosylation at N298 instead of the wild-type glycosylation site at N297.

Figure 3:
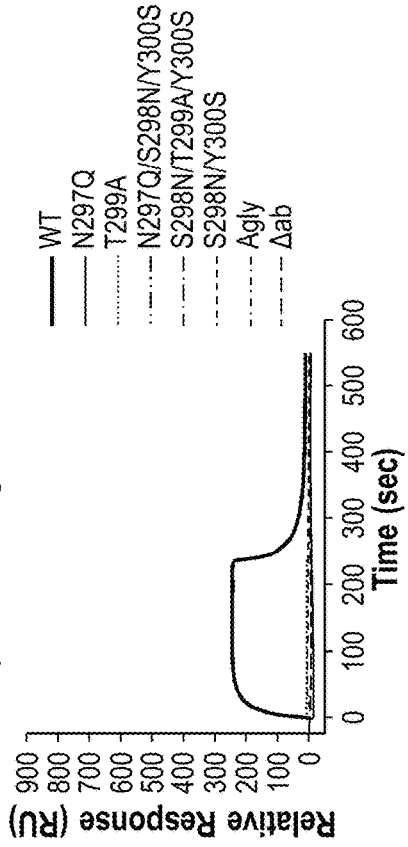
FIG. 3 depicts the results of surface plasmon resonance experiments used to assess the binding of αβTCR HEBE1 IgG antibody mutants to recombinant human FcγRIIIa (V158 & F158).
Figure 3:
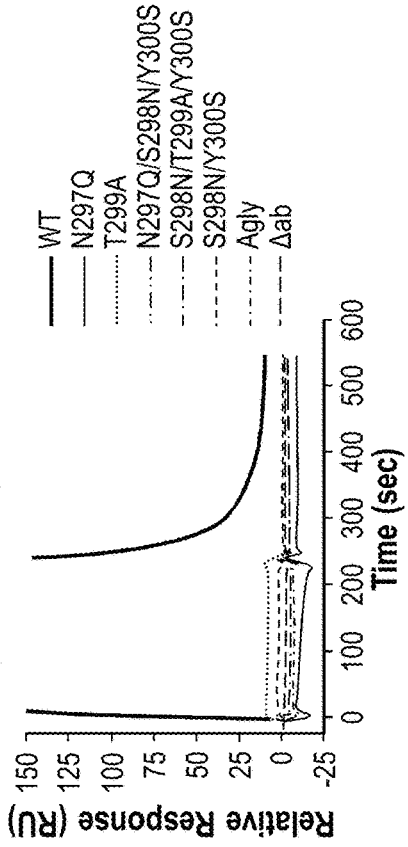
Figure 3:
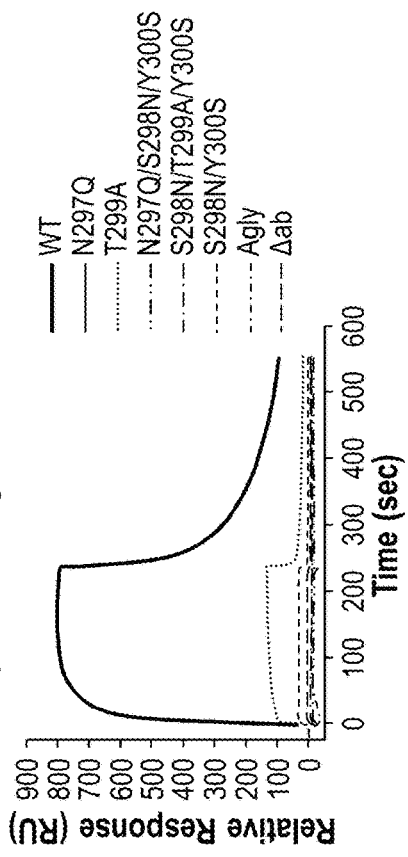
Figure 3:
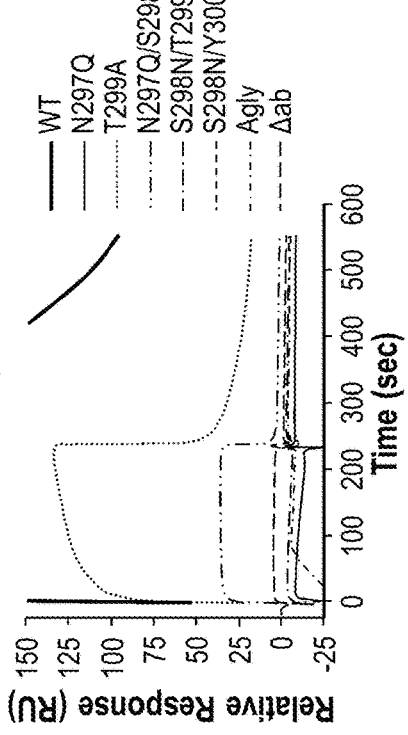

3C. Binding Properties of αβTCR Antibody Mutants to Human FcγRIIIa and FcγRI Using Biacore Biacore was used to assess binding to recombinant human FcγRIIIa (V158 & F158) and FcγRI. All four flowcells of a CMS chip were immobilized with anti-HPC4 antibody via the standard amine coupling procedure provided by Biacore. The anti-HPC4 antibody was diluted to 50 µg/mL in 10 mM sodium acetate pH 5.0 for the coupling reaction and injected for 25 min at 5 µL/min. Approximately 12,000 RU of antibody was immobilized to the chip surface. Recombinant human FcγRIIIa-V158 and FcγRIIIa-F158 were diluted to 0.6 µg/mL in binding buffer (HBS-P with 1 mM $CaCl_2$) and injected to flowcells 2 and 4, respectively, for 3 min at 5 µL/min to capture 300-400 RU receptor on the anti-HPC4 chip. In order to distinguish between the low binders, three times more rhFcγRIIIa was captured on the anti-HPC4 surface than usually used in this assay. Flowcells 1 and 3 were used as reference controls. Each antibody was diluted to 200 nM in binding buffer and injected over all four flowcells for 4 min, followed by 5 min dissociation in buffer. The surfaces were regenerated with 10 mM EDTA in HBS-EP buffer for 3 min at 20 µL/min. The results of these experiments are shown in FIG. 3.

Figure 4:
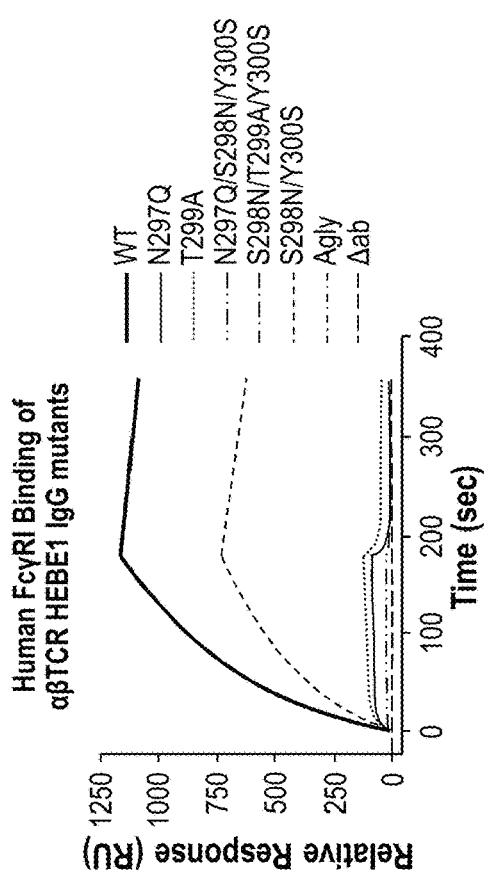
FIG. 4 depicts the results of surface plasmon resonance experiments used to assess the binding of αβTCR HEBE1 IgG antibody mutants to recombinant human FcγRI.
Figure 5:
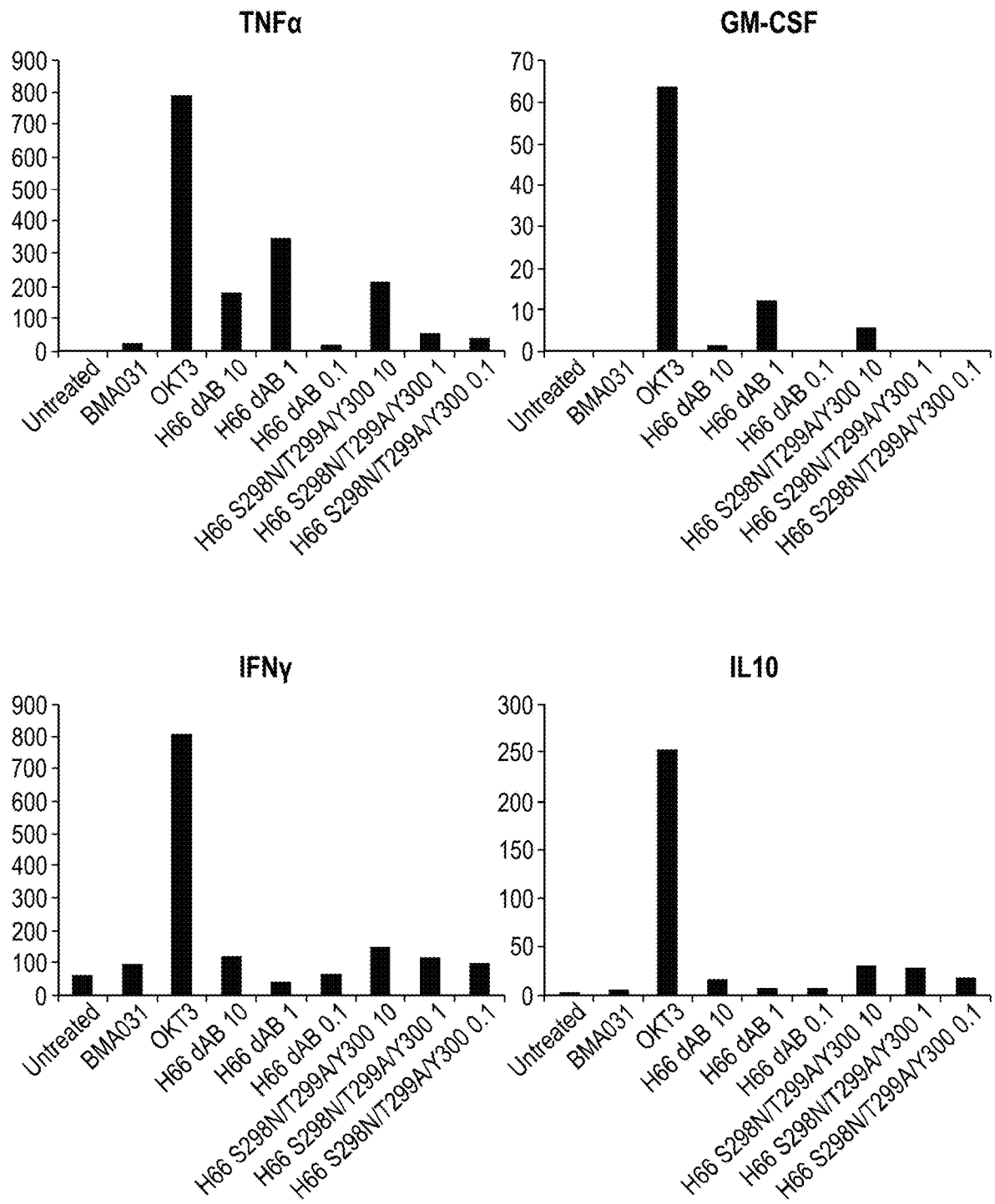
FIG. 5 depicts the cytokine release profile from PBMCs for TNFa, GM-CSF, IFNy and IL10 in the presence of mutant anti-αβTCR antibodies (day 2).
Figure 6:
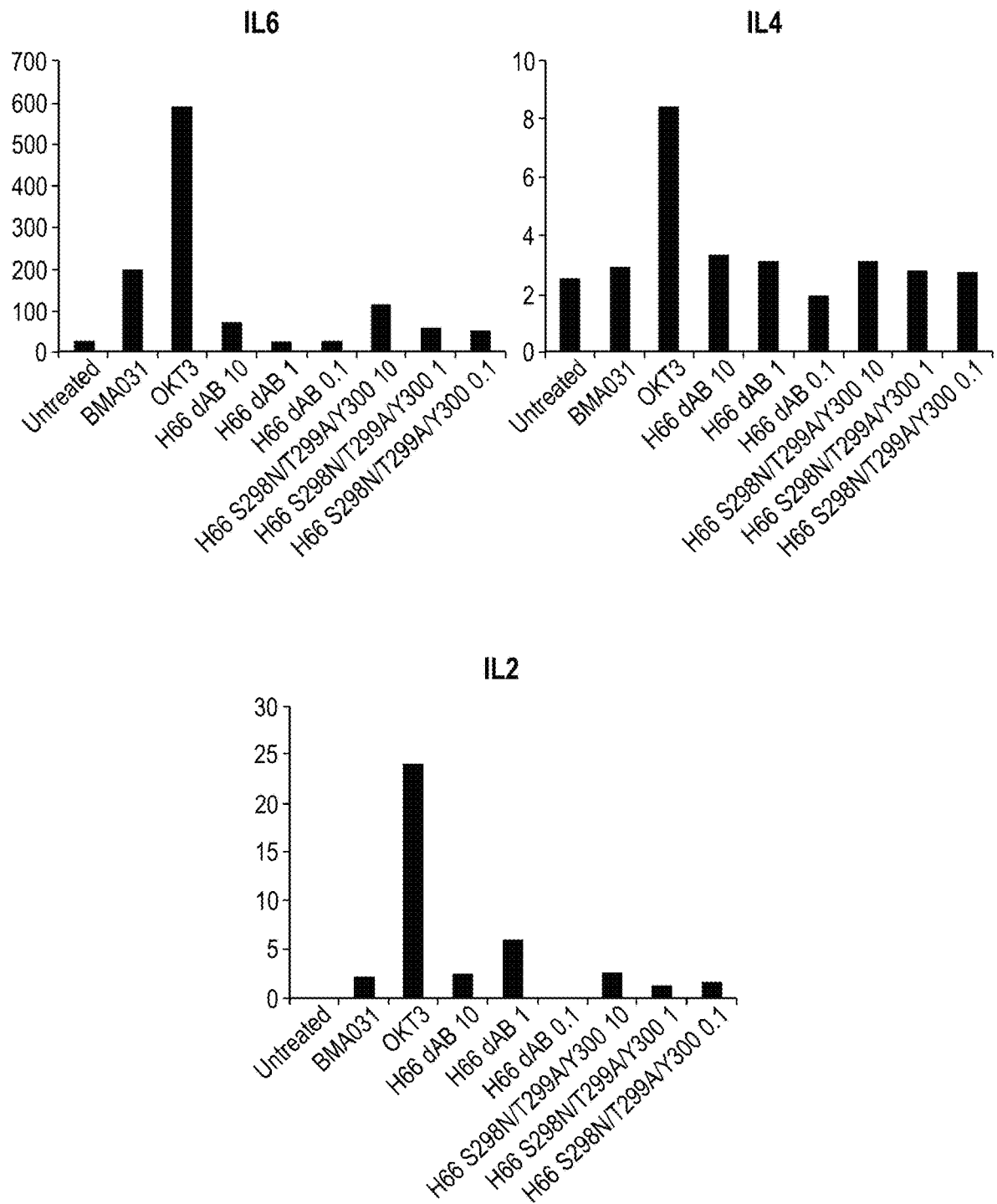
FIG. 6 depicts the cytokine release profile from PBMCs for IL6, IL4 and IL2 in the presence of mutant anti-αβTCR antibodies (day 2).
Figure 7:
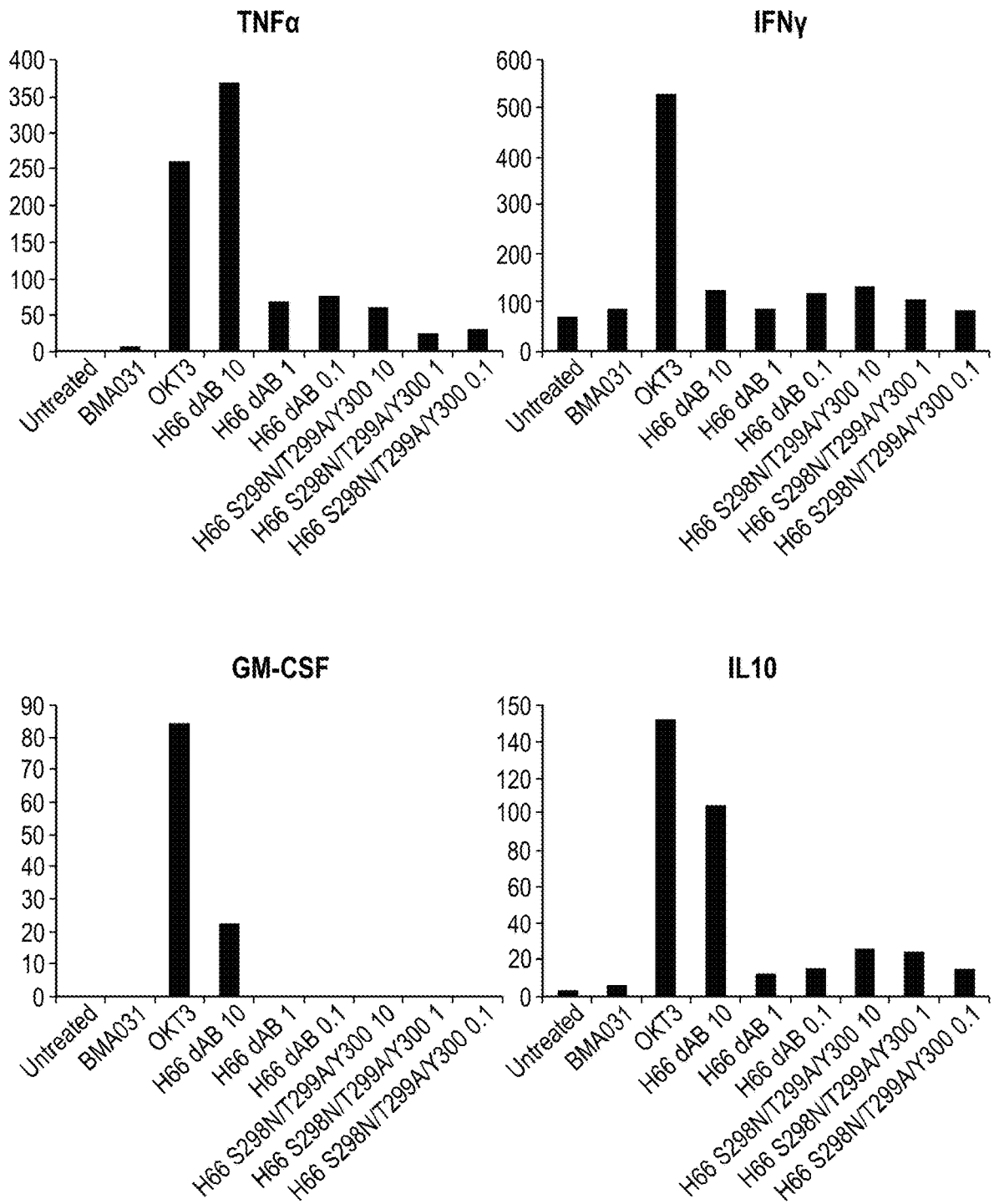
FIG. 7 depicts the cytokine release profile from PBMCs for TNFa, GM-CSF, IFNy and IL10 in the presence of mutant anti-αβTCR antibodies (day 4).
Figure 8:
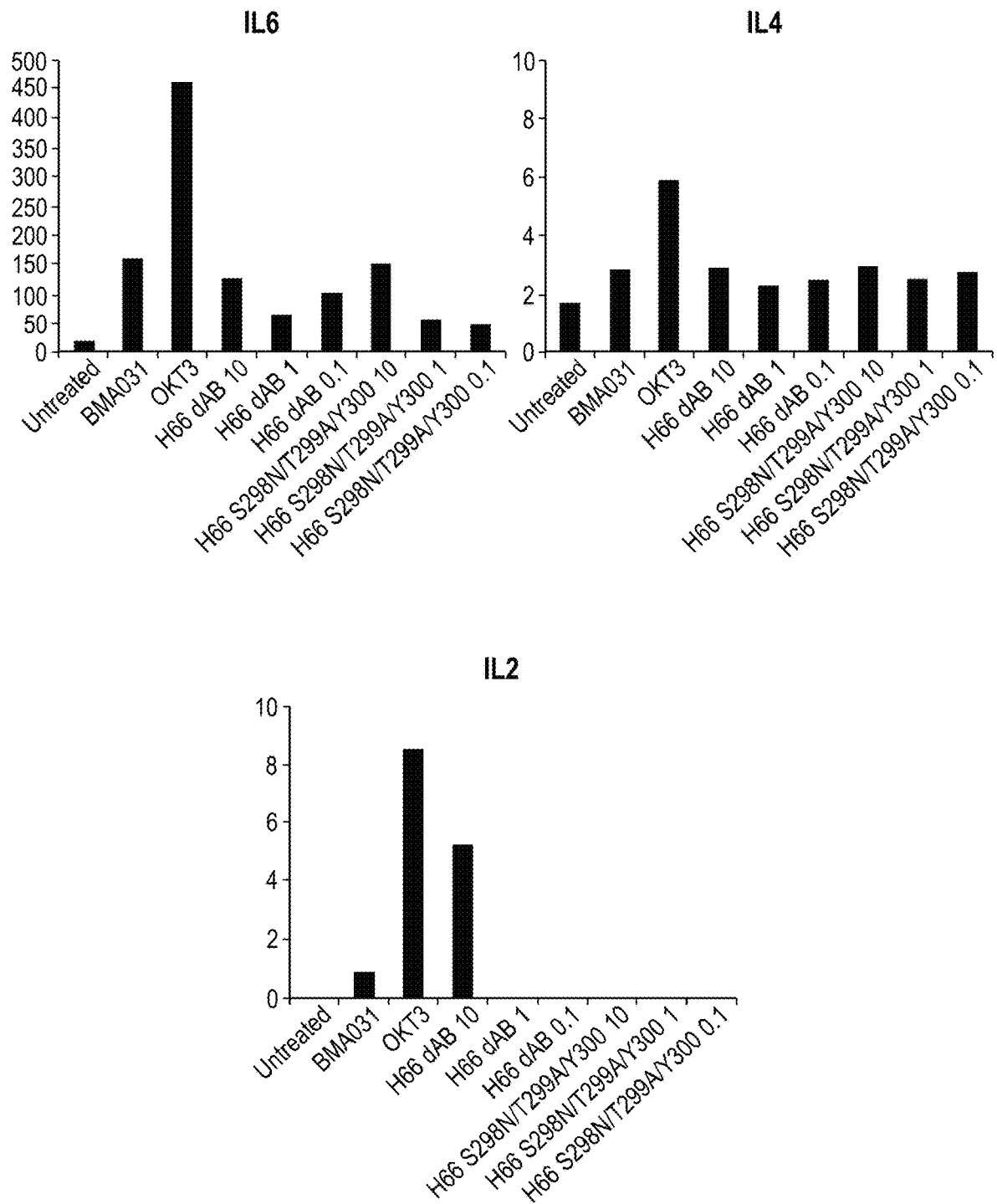
FIG. 8 depicts the cytokine release profile from PBMCs for IL6, IL4 and IL2 in the presence of mutant anti-αβTCR antibodies (day 4).

Biacore was also used to compare the FcγRI binding. Anti-tetra His antibody was buffer exchanged into 10 mM sodium acetate pH 4.0 using a Zeba Desalting column and diluted to 25 µg/mL in the acetate buffer for amine coupling. Two flowcells of a CMS chip were immobilized with ~9000 RU of the anti-Tetra-His antibody after 20 min injection at 5 µL/min. As in the previous experiment, ten times more FcγRI was captured to the anti-tetra-His surface in order to compare samples with weak binding. Recombinant human FcγRI was diluted 10 µg/mL in HBS-EP binding buffer and injected to flowcell 2 for 1 min at 5 µL/min to capture ~1000 RU receptor to the anti-tetra-His chip. A single concentration of antibody, 100 nM, was injected for 3 min at 30 µL/min over the captured receptor and control surface. Subsequently, dissociation was monitored for three minutes. The surface was then regenerated with two 30 second injections of 10 mM glycine pH 2.5 at 20 µL/min. The results of these experiments are shown in FIG. 4.

These results demonstrate a striking decrease in binding of the glycoengineered mutants to FcγRIIIa or FcγRI. H66 S298N/T299A/Y300S in particular has almost completely abolished binding to both receptors. This mutant was chosen for more detailed analysis.

3D. Stability Characterization Using Circular Dichroism (CD)

The stability of the S298N/T299A/Y300S antibody mutant was monitored by a Far-UV CD thermo melting experiment in which the CD signal at 216 nm and 222 nm was monitored as increasing temperature lead to the unfolding of the antibody (denaturation).

Figure 35:
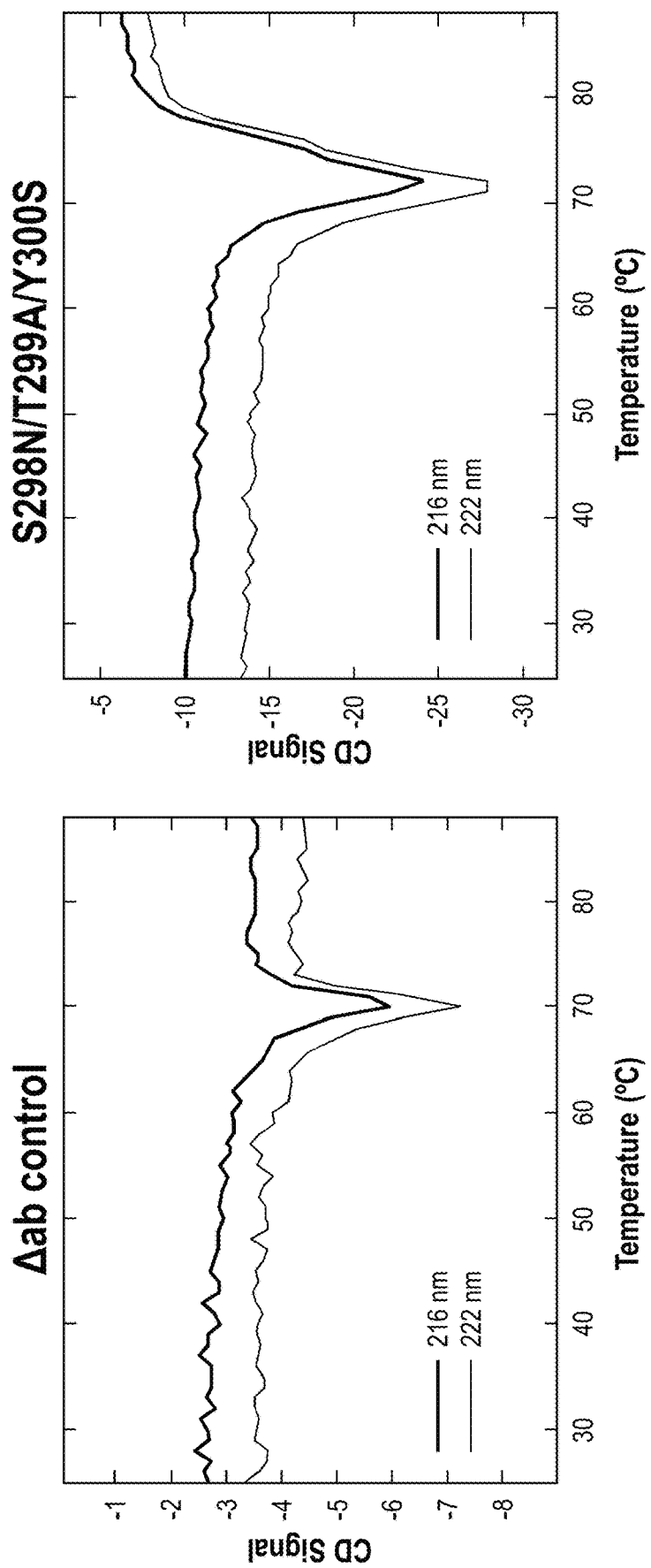
FIG. 35 depicts the results of circular dichroism experiments to determine the relative thermal stability of a wild-type anti-αβTCR antibody and mutant anti-αβTCR antibody containing the S298N/Y300S mutation.

Temperature was controlled by a thermoelectric peltier (Jasco model AWC100) and was increased at a rate of 1° C./min from 25-89° C. The CD spectra were collected on a Jasco 815 spectrophotometer at a protein concentration of approximately 0.5 mg/mL in PBS buffer in a quartz cuvette (Hellma, Inc) with a path length of 10 mm. The scanning speed was 50 nm/min and a data pitch of 0.5 nm. A bandwidth of 2.5 nm was used with a sensitivity setting of medium. The CD signal and HT voltage were collected from 210-260 nm with data intervals of 0.5 nm and at temperature intervals of 1° C. and four replicate scans were performed for each sample. The results demonstrate that both delta AB H66 and the S298N/T299A/Y300S H66 mutant exhibit similar thermal behaviors and have approximately the same onset temperature for degradation (around 63° C.) (FIG. 35), further suggesting that they have comparable stability.

Example 4: Functional Analysis of Fc-Engineered Mutants

Fc-engineered mutants were assessed through a PBMC proliferation assay and a cytokine release assay. In the PBMC proliferation assay, human PBMC were cultured with increasing concentrations of therapeutic antibody for 72 hours, $^3$H-thymidine was added and cells were harvested 18 hours later. For the T cell depletion/Cytokine Release assay, human PBMC were cultured with increasing concentrations of therapeutic antibody and were analyzed daily for cell counts and viability (Vi-Cell, Beckman Coulter) out to day 7. Cell supernatants were also harvested, stored at −20° C. and analyzed on an 8-plex cytokine panel (Bio-Rad).

Normal donor PBMC were thawed and treated under the following conditions (all in media containing complement): Untreated; BMA031, moIgG2b 10 ug/ml; OKT3, moIgG2a 10 ug/ml; H66, huIgG1 deltaAB 10 ug/ml, 1 ug/ml and 0.1 ug/ml; H66, huIgG1 S298N/T299A/Y300S 10 ug/ml, 1 ug/ml and 0.1 ug/ml.

Cytokines were harvested at day 2 (D2) and day 4 (D4) for Bioplex Analysis (IL2, IL4, IL6, IL8, IL10, GM-CSF, IFNg, TNFa). Cells were stained at D4 for CD4, CD8, CD25 and abTCR expression.

The results, shown in FIGS. 5-8, demonstrate that H66 S298N/T299A/Y300S behaved similarly to the H66 deltaAB in all the cell based assays performed, showing minimal T-cell activation by CD25 expression, binding to abTCR (with slightly different kinetics to deltaAB), and minimal cytokine release at both D2 and D4 time points. The S298N/T299A/Y300S mutant thus eliminated effector function as effectively as the deltaAB mutation.

Example 5: Preparation and Characterization of an Engineered Fc Variant in the Anti-CD52 Antibody Backbone In addition to the H66 anti-αβ TCR antibody, the S298N/Y300S mutation was also engineered in an anti-CD52 antibody backbone (clone 2C3). This mutant was then examined in order to determine whether the observed effector function modulation seen in the S298N/Y300S H66 anti-αTCR antibody was consistent in another antibody backbone.

5A. Creation of 2C3 Anti-CD52 Antibody Altered Glycosylation Variants

First, S298N/Y300S 2C3 variant DNA was prepared by quick change mutagenesis using pENTR_LIC_IgG1, and WT 2C3 VH was cloned into the mutated vector by LIC. Full-length mutants were cloned into the pCEP4 (−E+I)Dest expression vector using Gateway technology. Mutations were subsequently confirmed by DNA sequencing and the sequences are set forth in Table 11. The mutants were then transfected into HEK293-EBNA cells in a 6-well plate format and the protein was purified from conditioned media. Anti-CD52 2C3 wild-type antibody was produced in parallel as a control. The expression level was found to be 0.1 μg/mL using SD-PAGE and Western blot analyses (FIG. 9A). Expression of mutants in neat conditioned media was also measured by protein A capture on Biacore. Concentration was determined using the dissociation response after a six-minute injection to immobilized protein A. CHO-produced WT 2C3 serially diluted in media from 90 μg/mL to 1.5 ng/mL was used as a standard curve. Concentrations were calculated within approximately 0.2 μg/mL by a calibration curve using a 4-parameter fit. Relative expression levels were low and generally agree with the Western blot data (FIG. 9B).

TABLE 11

Anti-CD52 clone 2C3 antibody sequences

| SEQ ID NO | Name | Amino Acid Sequence |
|---|---|---|
| 28 | Anti-CD-52 2C3 WT light chain | DIVMTQTPLSLSVTPGQPASISCKSSQSLLYSNGKTYLNWL LQKPGQSPQRLIYLVSKLDSGVPDRFSGSGSGTDFTLKISR VEAEDVGVYYCVQGTHLHTFGQGTRLEIKRTVAAPSVFIF PPSDEQLKSGTASVVCLLNNFYPREAKVQWKVDNALQSG NSQESVTEQDSKDSTYSLSSTLTLSKADYEKHKVYACEVT HQGLSSPVTKSFNRGEC* |
| 29 | Anti-CD-52 2C3 WT heavy chain | EVQLVESGGGLVQPGGSLRLSCAASGFTFNTYWMNWVR QAPGKGLEWVGQIRLKSNNYATHYAESVKGRFTISRDDS KNSLYLQMNSLKTEDTAVYYCTPVDFWGQGTTVTVSSAS TKGPSVFPLAPSSKSTSGGTAALGCLVKDYFPEPVTVSWN SGALTSGVHTFPAVLQSSGLYSLSSVVTVPSSSLGTQTYIC NVNHKPSNTKVDKKVEPKSCDKTHTCPPCPAPELLGGPSV FLFPPKPKDTLMISRTPEVTCVVVDVSHEDPEVKFNWYVD GVEVHNAKTKPREEQYNSTYRVVSVLTVLHQDWLNGKE YKCKVSNKALPAPIEKTISKAKGQPREPQVYTLPPSRDELT KNQVSLTCLVKGFYPSDIAVEWESNGQPENNYKTTPPVLD SDGSFFLYSKLTVDKSRWQQGNVFSCSVMHEALHNHYTQ KSLSLSPGK* |
| 30 | Anti-CD-52 2C3 S298N/Y300S heavy chain | EVQLVESGGGLVQPGGSLRLSCAASGFTFNTYWMNWVR QAPGKGLEWVGQIRLKSNNYATHYAESVKGRFTISRDDS KNSLYLQMNSLKTEDTAVYYCTPVDFWGQGTTVTVSSAS TKGPSVFPLAPSSKSTSGGTAALGCLVKDYFPEPVTVSWN SGALTSGVHTFPAVLQSSGLYSLSSVVTVPSSSLGTQTYIC NVNHKPSNTKVDKKVEPKSCDKTHTCPPCPAPELLGGPSV FLFPPKPKDTLMISRTPEVTCVVVDVSHEDPEVKFNWYVD GVEVHNAKTKPREEQY<u>NNT</u>SRVVSVLTVLHQDWLNGKE YKCKVSNKALPAP<u>IEKTIS</u>KAKGQPREPQVYTLPPSRDELT KNQVSLTCLVKGFYPSDIAVEWESNGQPENNYKTTPPVLD SDGSFFLYSKLTVDKSRWQQGNVFSCSVMHEALHNHYTQ KSLSLSPGK* |

5B. Glycosylation Analysis Using PNGaseF

To evaluate the additional glycosylation sites introduced by the mutation, the enriched S298N/Y300S mutant was de-glycosylated with PNGase F. It did not demonstrate any apparent change in molecular weight, which indicates that no additional carbohydrate was present (FIG. 10). Small scale preparations were performed in order to purify these mutants for further characterization and the results reconfirmed that there was not an additional carbohydrate present on the S298N/Y300S mutant (FIG. 11).

Figure 12:
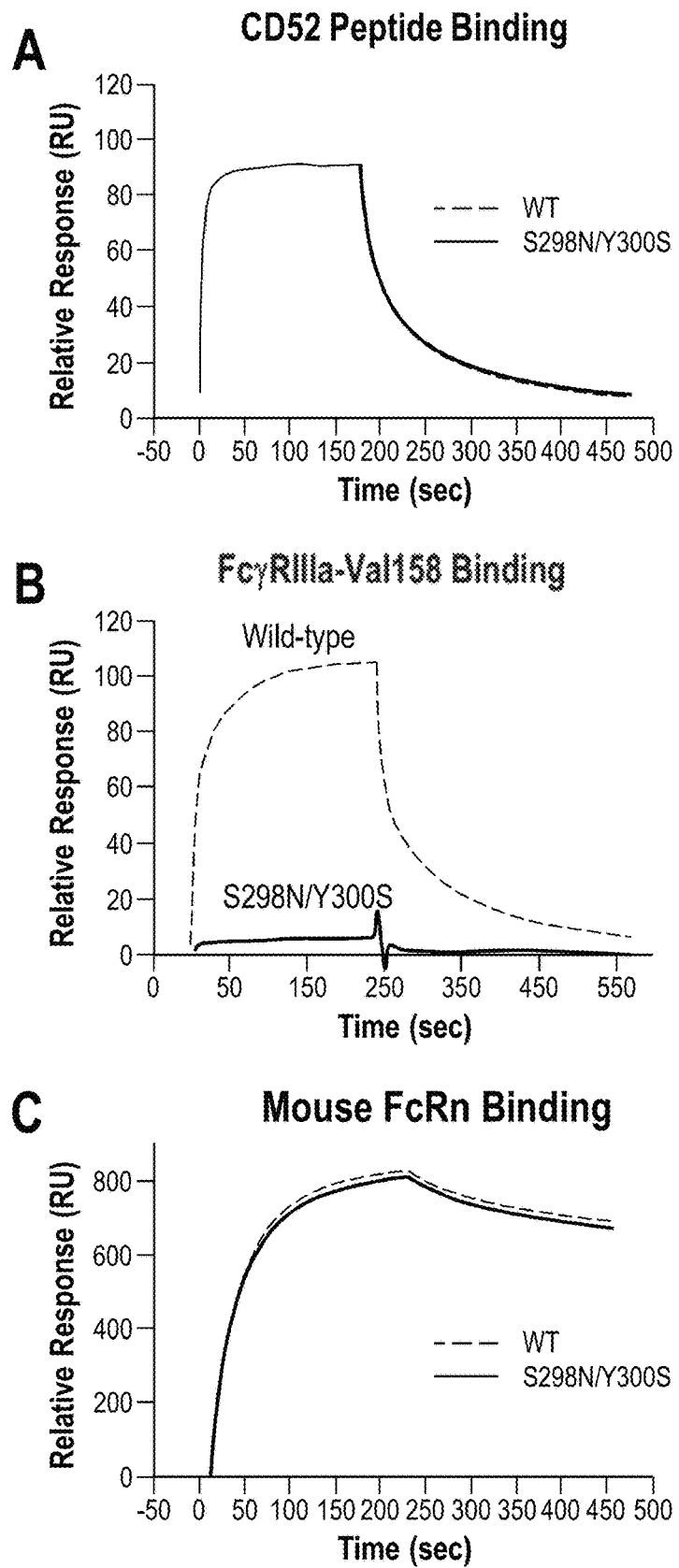
FIG. 12 depicts the results of surface plasmon resonance experiments used to assess the binding of modified anti-CD52 to recombinant human FcγRIIIa (V158). Anti-CD52 comprising S298N/Y300S mutations in the Fc domain were used to assess the effector function of the modified molecule. binding to CD52 peptide (A), binding to FcγRIIIa (V158, B), and control binding to mouse FcRn (C).
Figure 14:
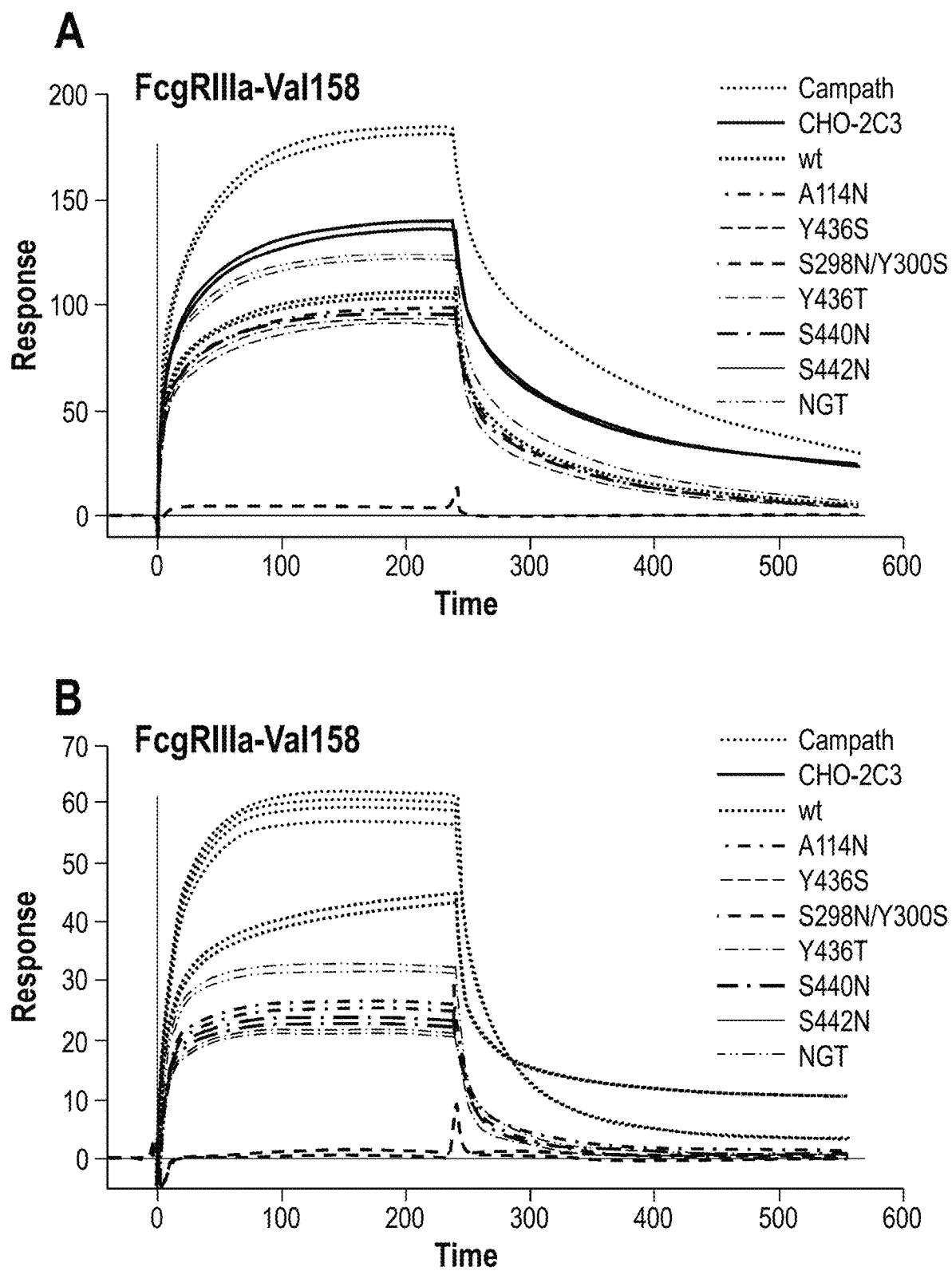
FIG. 14 depicts the results of surface plasmon resonance experiments investigating the binding of modified anti-CD52 to both FcγRIIIa (Val158) (as above) and FcγRIIIa (Phe158). Anti-CD52 antibodies comprising S298N/Y300S mutations in the Fc domain were used to assess the effector function of the modified molecule binding to FcγRIIIa (Val158, FIG. 14A) and FcγRIIIa (Phe58, FIG. 14B).

5C. Binding Properties of 2C3 Anti-CD52 Antibody Mutants to Human FcγRIIIa Using Biacore Biacore was also used to characterize the antigen-binding, FcγRIII, and binding properties of the purified antibodies (see FIGS. 12, 13, and 14). The S298N/Y300S 2C3 variant bound to the CD52 peptide tightly and the binding sensorgram was undistinguishable from the wild-type control, demonstrating that this mutation does not affect its antigen binding (FIG. 12A).

To assay for Fc effector function, FcγRIII receptor (Val158) was used in binding studies. The mutant and wild-type control antibody were diluted to 200 nM and injected to HPC4-tag captured FcγRIIIa. FcγRIII binding was almost undetectable for the S298N/Y300S mutant, which indicated a loss of effector function by this variant (FIG. 12B and FIG. 14A). To further assay for Fc effector function, the FcγRIII receptor (Phe158) was also used in binding studies. The mutant and wild-type control antibodies were diluted to 200 nM and injected to HPC4-tag captured FcγRIIIa. FcγRIII binding was almost undetectable for the S298N/Y300S mutant, which indicates a loss of effector function with the Phe158 variant (FIG. 14B). Finally, Biacore was used to compare the FcRn binding properties of the purified proteins. Mouse and SEC-purified human FcRn-HPC4 were immobilized to a CM5 chip via amine coupling. Each antibody was diluted to 200, 50, and 10 nM and injected over the receptors. Campath, CHO-produced WT 2C3, and DEPC-treated Campath were included as positive and negative controls. These data show that the mutant binds to both human and murine FcRn receptor with the same affinity as the wild-type antibody control and that it likely has no alterations in its circulation half-life or other pharmacokinetic properties (see FIG. 12C, FIGS. 13A and B). Accordingly, the S298N/Y300S mutation is applicable to antibodies in general, to reduce or eliminate undesired Fc effector function, for example through engagement of human Fcγ receptors.

Example 6: Circulating Immune Complex Detection in the S298N/Y300S Mutant

Figure 15:
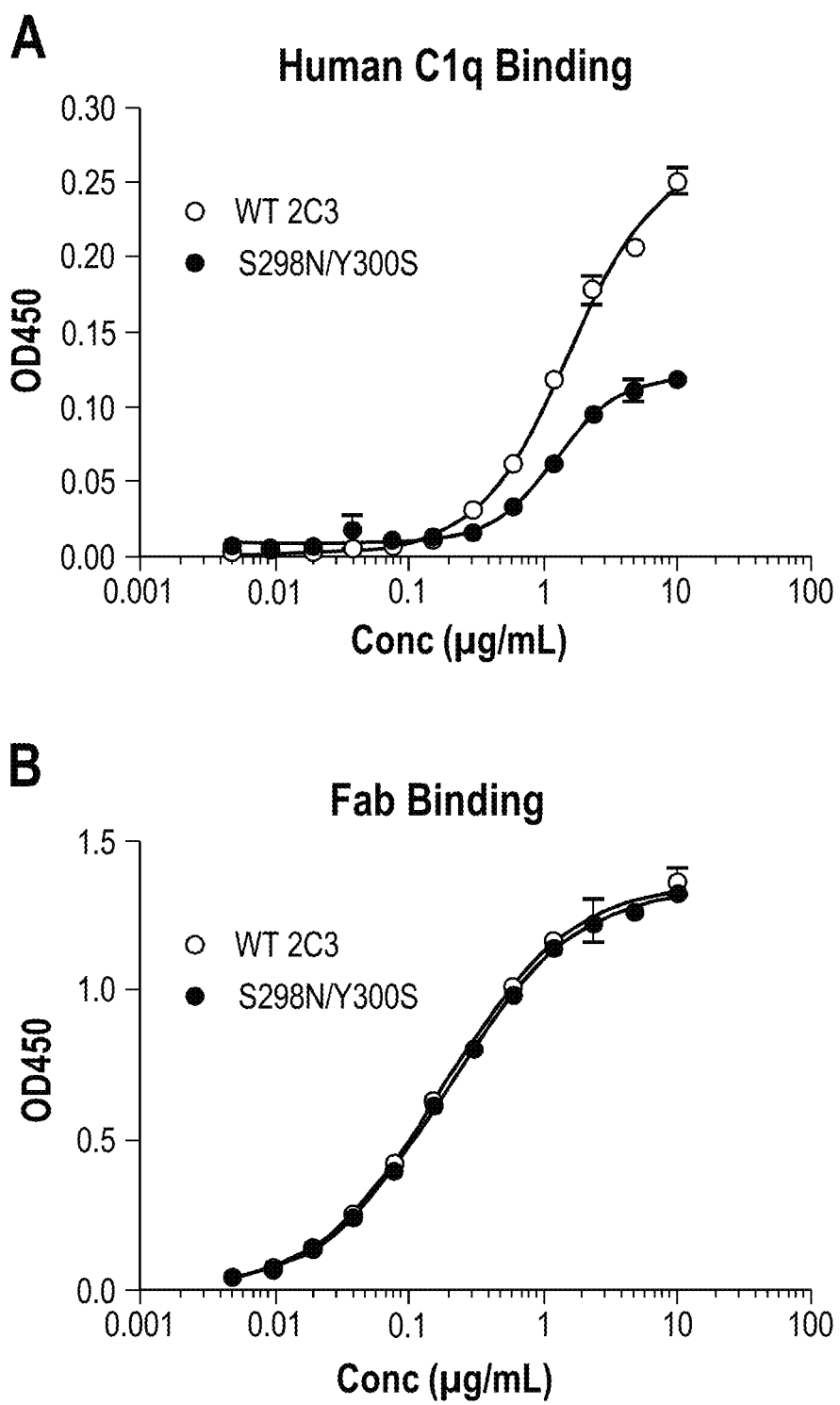
FIG. 15 depicts the analysis of C1q binding in the S298N/Y300S mutant and the WT 2C3 control (A) and the results of an Eliza analysis confirming equivalent coating of the wells.

Circulating immune complex detection was also investigated using a C1q binding assay for the S298N/Y300S mutant and WT control. High binding Costar 96-well plates were coated overnight at 4° C. with 100 µl of 2-fold serially diluted 2C3 Abs at concentrations ranging from 10-0.001 µg/ml in coating buffer (0.1M NaCHO₃ pH 9.2). ELISA analysis showed that C1q binding is reduced for the S298N/Y300S mutant compared to WT (FIG. 15A). The binding of anti-Fab Ab to the coated 2C3 Abs confirmed equivalent coating of the wells (FIG. 15B).

Figure 18:
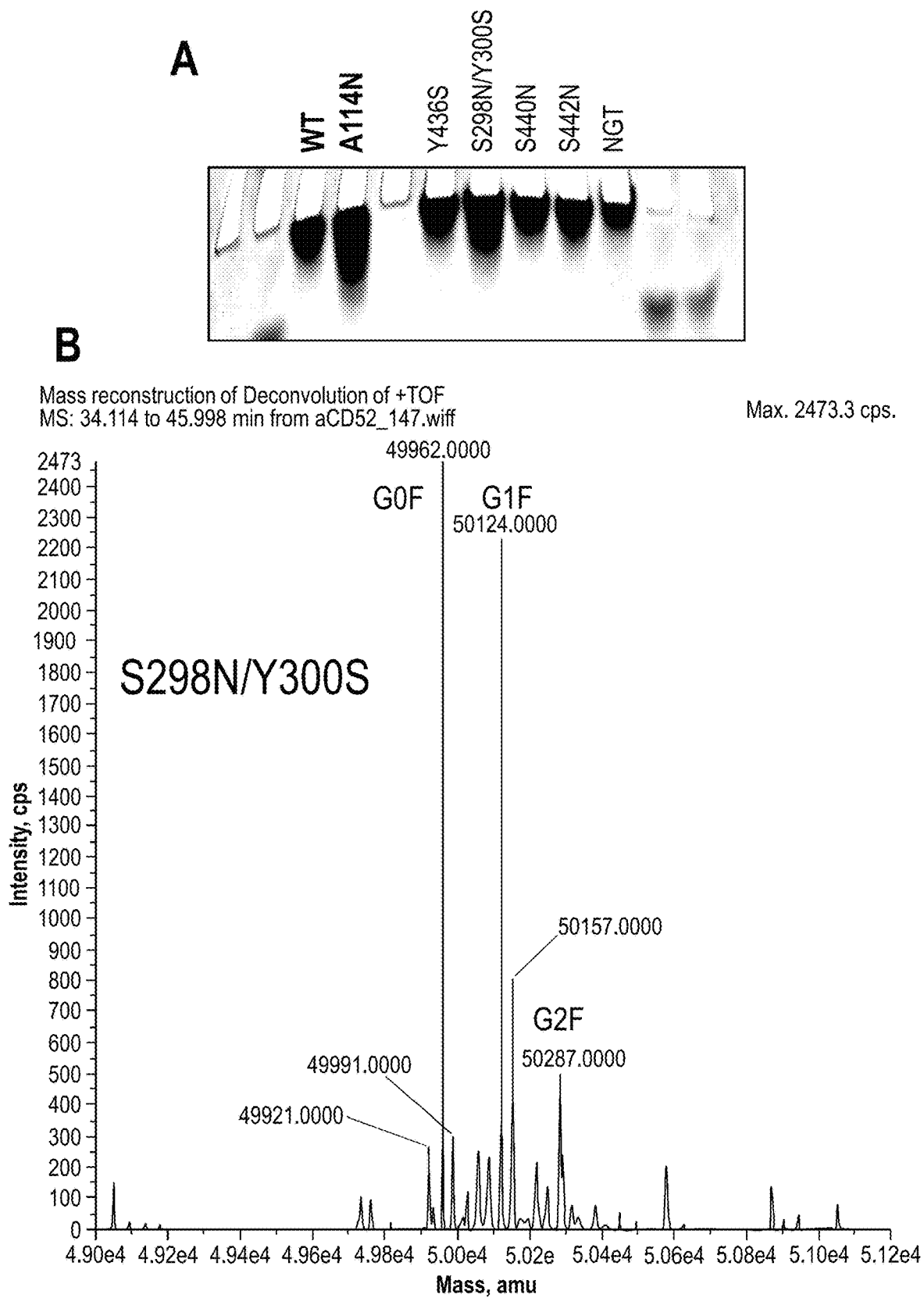
FIG. 18 depicts the results of isoelectric focusing and mass spectrometry charge characterization experiments to determine the glycan content of 2C3 mutants.
Figure 18:
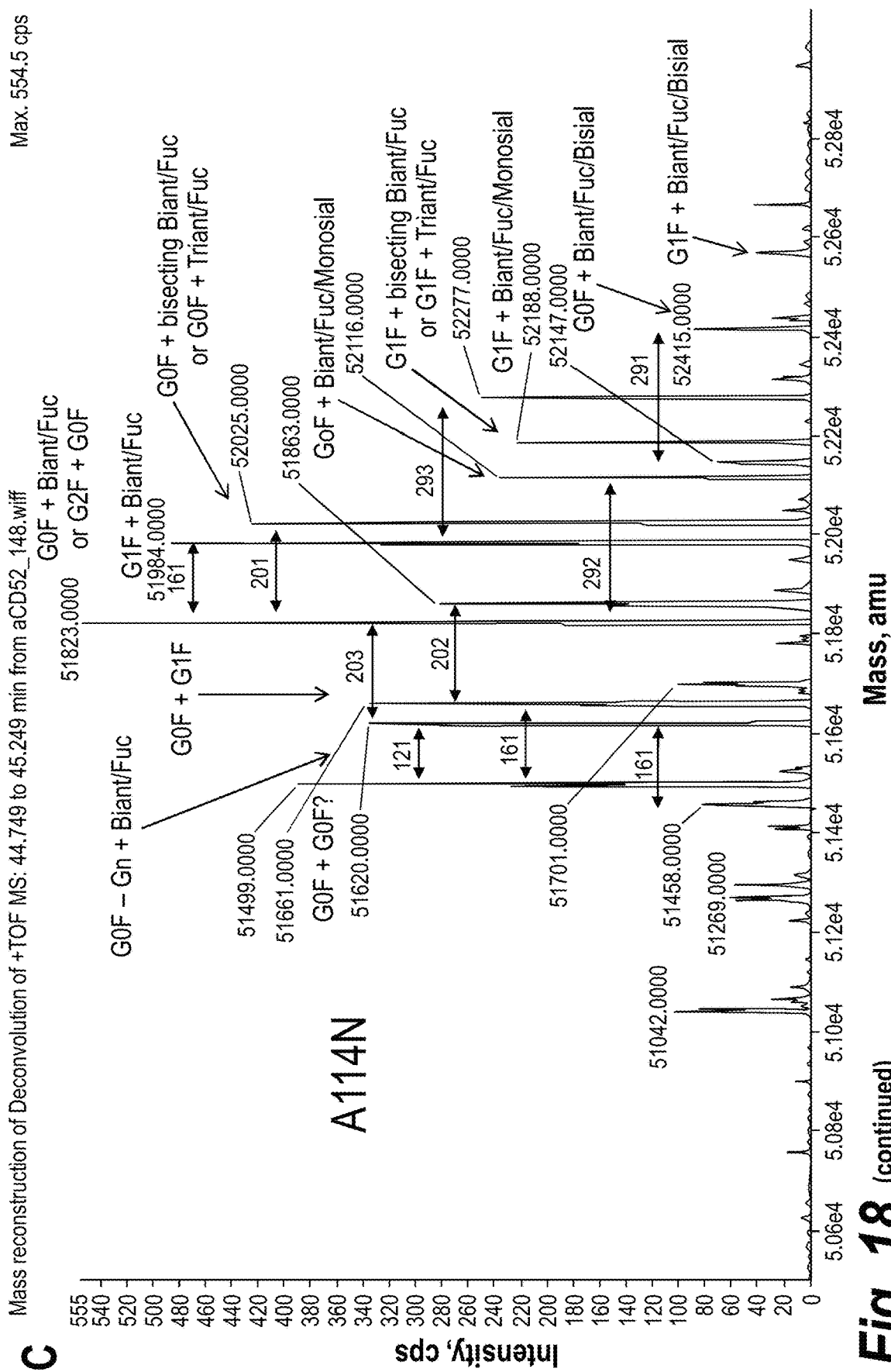
Figure 18:
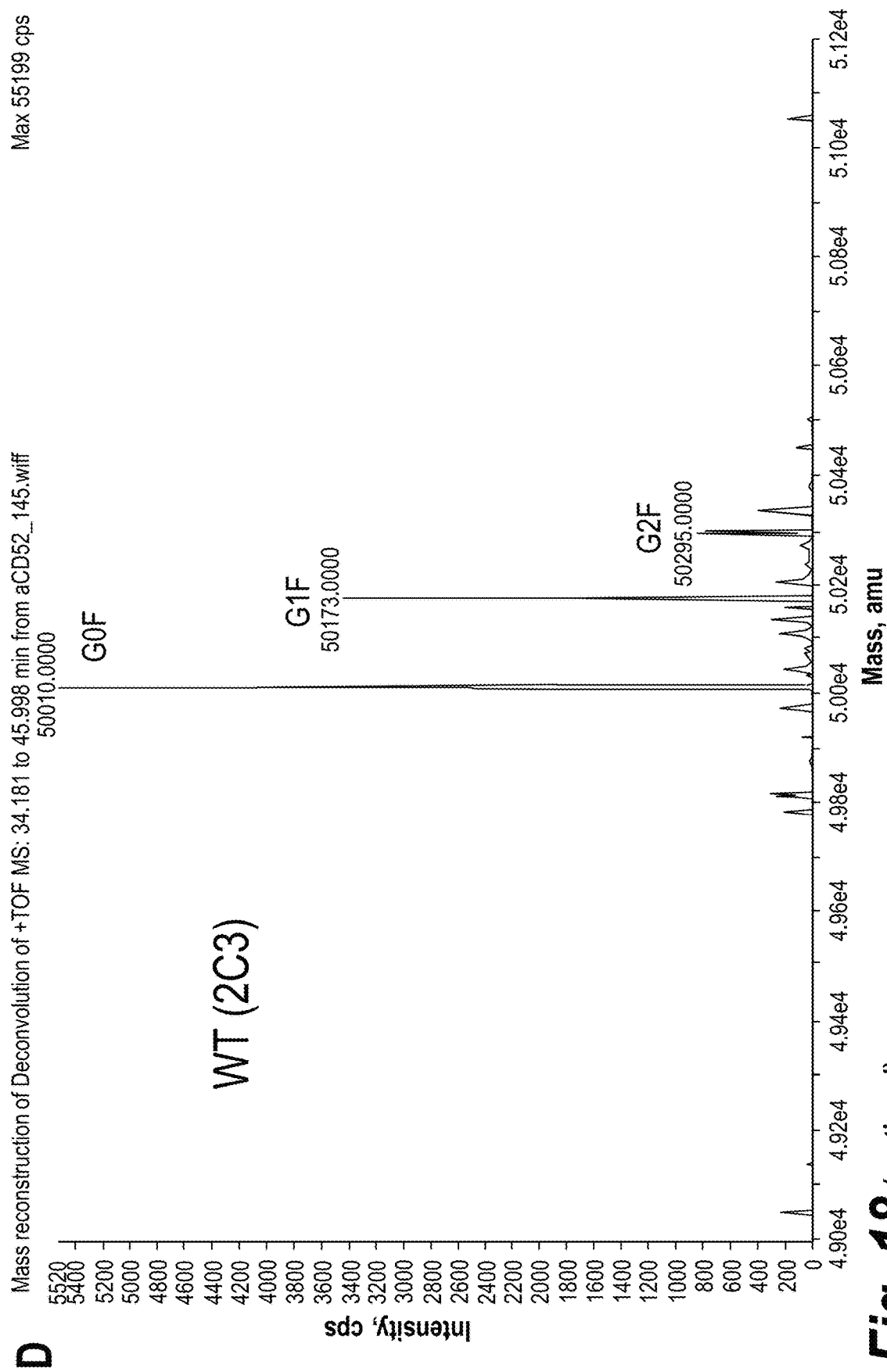

Example 7: Separation and Analysis of S298N/Y300S Mutant Using Isoelectric Focusing A pH 3-10 Isoelectric Focusing (IEF) gel was run to characterize the S298N/Y300S mutants. S298/Y300S was found to have more negative charges, and therefore, likely more sialic acid molecules (FIG. 18A). Both the S298N/Y300S mutant and WT 2C3 were shown by intact MS to have G0F and G1F as the dominant glycosylation species (FIGS. 18 B and D, respectively).

Example 8: Antigen Binding Affinity of S298N/Y300S

Biacore was used to compare the antigen binding affinity of WT anti-CD52 2C3 Ab and the S298N/Y300S mutant that had been prepared and purified from both smaller (FIG. 16) and larger (FIG. 17) scale expressions. CM5 chips immobilized with CD52 peptide 741 and control peptide 777 were obtained. Antibodies were serially diluted 2-fold from 60 to 0.2 nM in HBS-EP and were then injected over the chip surface for 3 min followed by a 5 min dissociation in buffer at a flow rate of 50 µl/min. The surface was then regenerated with a pulse of 40 mM HCl. These analyses were performed in duplicate and demonstrate that the S298N/Y300S mutant and WT 2C3 antibodies show comparable CD52 peptide binding.

Figure 19:
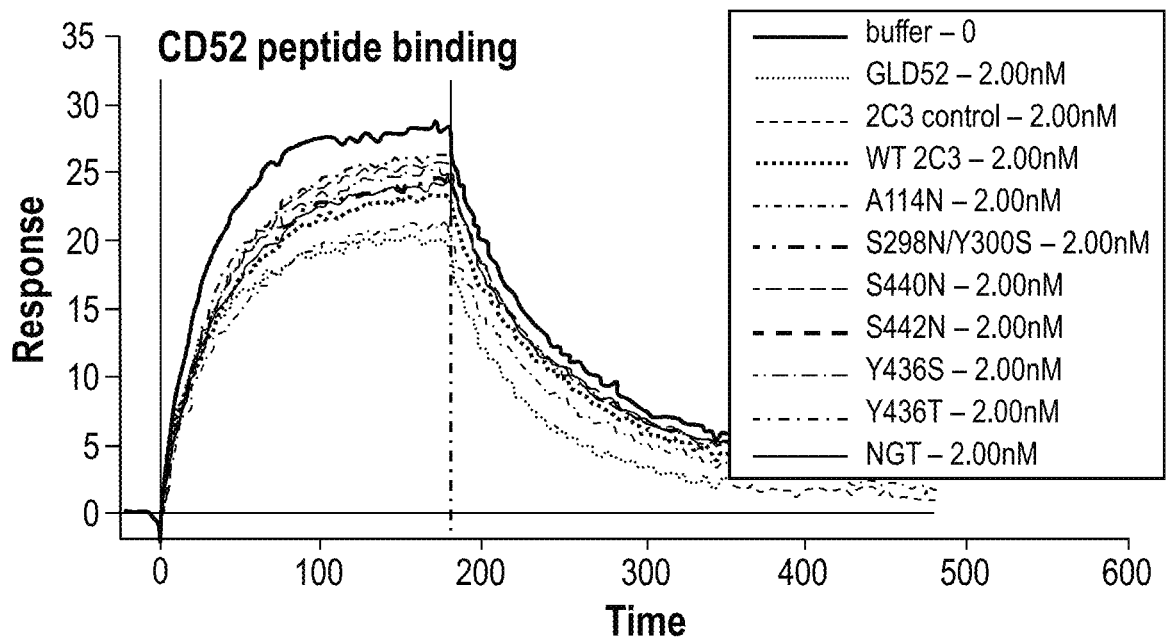
FIG. 19 depicts the results of concentration (Octet) and plamon resonance experiments comparing the antigen binding affinity of WT anti-CD-52 2C3 and mutants.

A media screening platform was designed to test functional binding properties prior to purification in order to screen antibodies created during small scale transfections. These tests were performed using Octet (FIG. 19A) to determine concentration and used Protein A biosensors and a GLD52 standard curve. Samples were diluted to 7.5 and 2 nM in HBS-Ep for a CD52 binding comparison using Biacore (FIG. 19B). The results of the peptide binding assay showed that both the S298N/Y300S mutant and the WT 2C3 antibodies have comparable CD52 peptide binding. Furthermore, these analyses demonstrate that Octet and Biacore work well to predict antigen binding by antibodies from small scale transfections.

Example 9: Preparation of S298N/Y300S, S298N/T299A/Y300S, and

N297Q/S298N/Y300S altered glycosylation mutants in additional antibody backbones. In addition to the anti-αβ-TCR antibody and 2C3 anti-CD-52 antibody, the S298/Y300S, S298N/T299A/Y300S, and N297Q/S298N/Y300S mutations were engineered in other antibody backbones to confirm that the additional tandem glycosylation site could be introduced into unrelated heavy chain variable domain sequences. The alternatively glycosylated anti-CD-52 12G6 and anti-Her2 mutants are set forth in Tables 12 and 13.

TABLE 12

Anti-CD52 clone 12G6 antibody sequences

| SEQ ID NO | Name | Amino Acid Sequence |
|---|---|---|
| 31 | Anti-CD-52 12G6 WT light chain | DIVMTQTPLSLSVTPGQPASISCKSSQSLLYSNGKTYLNWV LQKPGQSPQRLIYLVSKLDSGVPDRFSGSGSGTDFTLKISR VEAEDVGVYYCVQGSHFHTFGQGTKLEIKRTVAAPSVFIFP PSDEQLKSGTASVVCLLNNFYPREAKVQWKVDNALQSGNS QESVTEQDSKDSTYSLSSTLTLSKADYEKHKVYACEVTHQ GLSSPVTKSFNRGEC |
| 32 | Anti-CD-52 12G6 WT heavy chain | EVQLVESGGGLVQPGGSLRLSCAASGFPFSNYWMNWVRQ APGKGLEWVGQIRLKSNNYATHYAESVKGRFTISRDDSKN SLYLQMNSLKTEDTAVYYCTPIDYWGQGTTVTVSSASTKG PSVFPLAPSSKSTSGGTAALGCLVKDYFPEPVTVSWNSGAL TSGVHTFPAVLQSSGLYSLSSVVTVPSSSLGTQTYICNVNH KPSNTKVDKKVEPKSCDKTHTCPPCPAPELLGGPSVFLFPP KPKDTLMISRTPEVTCVVVDVSHEDPEVKFNWYVDGVEV HNAKTKPREEQYNSTYRVVSVLTVLHQDWLNGKEYKCKV SNKALPAPIEKTISKAKGQPREPQVYTLPPSRDELTKNQVS LTCLVKGFYPSDIAVEWESNGQPENNYKTTPPVLDSDGSFF LYSKLTVDKSRWQQGNVFSCSVMHEALHNHYTQKSLSLSP GK* |
| 33 | Anti-CD-52 12G6 S298N/ Y300S heavy chain | EVQLVESGGGLVQPGGSLRLSCAASGFPFSNYWMNWVRQ APGKGLEWVGQIRLKSNNYATHYAESVKGRFTISRDDSKN SLYLQMNSLKTEDTAVYYCTPIDYWGQGTTVTVSSASTKG PSVFPLAPSSKSTSGGTAALGCLVKDYFPEPVTVSWNSGAL TSGVHTFPAVLQSSGLYSLSSVVTVPSSSLGTQTYICNVNH KPSNTKVDKKVEPKSCDKTHTCPPCPAPELLGGPSVFLFPP KPKDTLMISRTPEVTCVVVDVSHEDPEVKFNWYVDGVEV HNAKTKPREEQY<u>NNTS</u>RVVSVLTVLHQDWLNGKEYKCKV SNKALPAPIEKTISKAKGQPREPQVYTLPPSRDELTKNQVS LTCLVKGFYPSDIAVEWESNGQPENNYKTTPPVLDSDGSFF LYSKLTVDKSRWQQGNVFSCSVMHEALHNHYTQKSLSLSP GK* |
| 34 | Anti-CD-52 12G6 | EVQLVESGGGLVQPGGSLRLSCAASGFPFSNYWMNWVRQ APGKGLEWVGQIRLKSNNYATHYAESVKGRFTISRDDSKN SLYLQMNSLKTEDTAVYYCTPIDYWGQGTTVTVSSASTKG |

TABLE 12-continued

Anti-CD52 clone 12G6 antibody sequences

| SEQ ID NO | Name | Amino Acid Sequence |
|---|---|---|
| | S298N/ T299A/ Y300S heavy chain | PSVFPLAPSSKSTSGGTAALGCLVKDYFPEPVTVSWNSGAL TSGVHTFPAVLQSSGLYSLSSVVTVPSSSLGTQTYICNVNH KPSNTKVDKKVEPKSCDKTHTCPPCPAPELLGGPSVFLFPP KPKDTLMISRTPEVTCVVVDVSHEDPEVKFNWYVDGVEV HNAKTKPREEQYN<u>NAS</u>RVVSVLTVLHQDWLNGKEYKCKV SNKALPAPIEKTISKAKGQPREPQVYTLPPSRDELTKNQVS LTCLVKGFYPSDIAVEWESNGQPENNYKTTPPVLDSDGSFF LYSKLTVDKSRWQQGNVFSCSVMHEALHNHYTQKSLSLSP GK* |
| 35 | Anti-CD-52 12G6 N297Q/ S298N/ T299A/ Y300S heavy chain | EVQLVESGGGLVQPGGSLRLSCAASGFPFSNYWMNWVRQ APGKGLEWVGQIRLKSNNYATHYAESVKGRFTISRDDSKN SLYLQMNSLKTEDTAVYYCTPIDYWGQGTTVTVSSASTKG PSVFPLAPSSKSTSGGTAALGCLVKDYFPEPVTVSWNSGAL TSGVHTFPAVLQSSGLYSLSSVVTVPSSSLGTQTYICNVNH KPSNTKVDKKVEPKSCDKTHTCPPCPAPELLGGPSVFLFPP KPKDTLMISRTPEVTCVVVDVSHEDPEVKFNWYVDGVEV HNAKTKPREEQYQ<u>NTS</u>RVVSVLTVLHQDWLNGKEYKCKV SNKALPAPIEKTISKAKGQPREPQVYTLPPSRDELTKNQVS LTCLVKGFYPSDIAVEWESNGQPENNYKTTPPVLDSDGSFF LYSKLTVDKSRWQQGNVFSCSVMHEALHNHYTQKSLSLSP GK* |

TABLE 13

Anti-Her2 antibody sequences

| SEQ ID NO | Name | Amino Acid Sequence |
|---|---|---|
| 36 | Anti-Her2 WT light chain | DIQMTQSPSSLSASVGDRVTITCRASQDVNTAVAWYQQKP GKAPKLLIYSASFLYSGVPSRFSGSRSGTDFTLTISSLQPE DFATYYCQQHYTTPPTFGQGTKVEIKRTVAAPSVFIFPPSD EQLKSGTASVVCLLNNFYPREAKVQWKVDNALQSGNSQESV TEQDSKDSTYSLSSTLTLSKADYEKHKVYACEVTHQGLSSP VTKSFNRGEC* |
| 37 | Anti-Her2 WT heavy chain | EVQLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVTV SSASTKGPSVFPLAPSSKSTSGGTAALGCLVKDYFPEPVTV SWNSGALTSGVHTFPAVLQSSGLYSLSSVVTVPSSSLGTQT YICNVNHKPSNTKVDKKVEPKSCDKTHTCPPCPAPELLGGP SVFLFPPKPKDTLMISRTPEVTCVVVDVSHEDPEVKFNWYV DGVEVHNAKTKPREEQYNSTYRVVSVLTVLHQDWLNGKE YKCKVSNKALPAPIEKTISKAKGQPREPQVYTLPPSRDELT KNQVSLTCLVKGFYPSDIAVEWESNGQPENNYKTTPPVLD SDGSFFLYSKLTVDKSRWQQGNVFSCSVMHEALHNHYTQ KSLSLSPGK* |
| 38 | Anti-Her2 S298N/ T299A/ Y300S heavy chain | EVQLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVTV SSASTKGPSVFPLAPSSKSTSGGTAALGCLVKDYFPEPVTV SWNSGALTSGVHTFPAVLQSSGLYSLSSVVTVPSSSLGTQT YICNVNHKPSNTKVDKKVEPKSCDKTHTCPPCPAPELLGGP SVFLFPPKPKDTLMISRTPEVTCVVVDVSHEDPEVKFNWYV DGVEVHNAKTKPREEQYN<u>NAS</u>RVVSVLTVLHQDWLNGKE YKCKVSNKALPAPIEKTISKAKGQPREPQVYTLPPSRDELT KNQVSLTCLVKGFYPSDIAVEWESNGQPENNYKTTPPVLD SDGSFFLYSKLTVDKSRWQQGNVFSCSVMHEALHNHYTQ KSLSLSPGK* |

Example 10. Generation of Altered Antibodies Containing Reactive Glycan Moieties In order to generate antibodies containing glycan moieties capable of reacting with derivatized effector moieties, an anti-HER antibody was first glycosylated in vitro using glycosyltransferase and relevant UDP sugar donors. For example, to introduce the sialic acid residues, donor antibodies were first galactosylated with β-galactosyltransferase, followed with sialylation with α2,6-sialyltransferase according to the methods of Kaneko et al. (Kaneko, Y., Nimmerjahn, F., and Ravetch, J. V. (2006) Anti-inflammatory activity of immunoglobulin G resulting from Fc sialylation. Science 313, 670-3). The reaction was performed in a one-pot synthesis step using β-galactosyltransferase (50 mU/mg, Sigma) and α2,6-sialyltranafrease (5 ug/mg, R&D system) with donor sugar nucleotide substrates, UDP-galactose (10 mM) and CMP-sialic acid (10 mM) in 50 mM MES buffer (pH 6.5) containing 5 mM $MnCl_2$. The reaction mixture containing 5 mg/ml anti-HER2 antibody was incubated for 48 hours at 37° C. The sialylation was verified using MALDI-TOF MS analysis of permethylated glycans released from the antibody with PNGase F, sialic acid content analysis using Dionex HPLC and lectin blotting with SNA, a lectin specific for a2,6-sialic acid.

Figure 27:
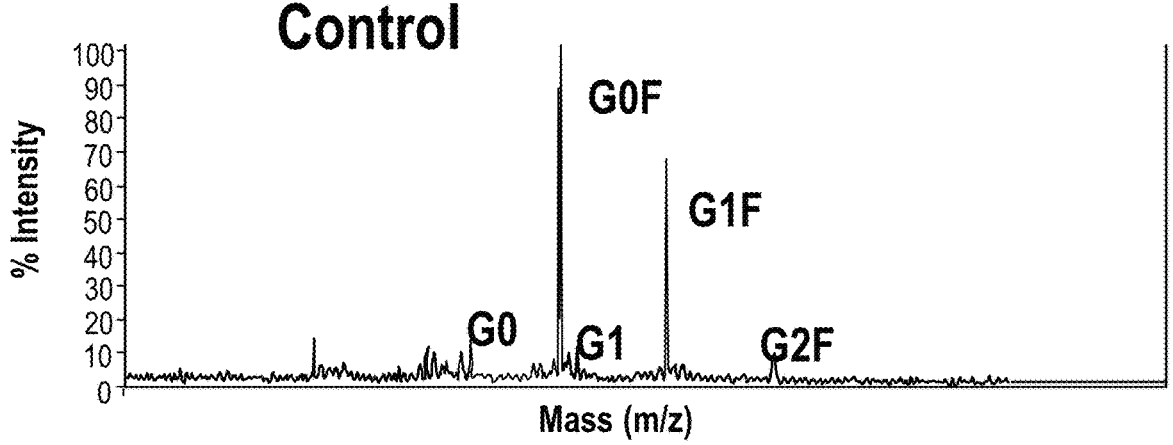
FIG. 27 depicts characterization information for a sialylated HER2 antibody.
Figure 27:
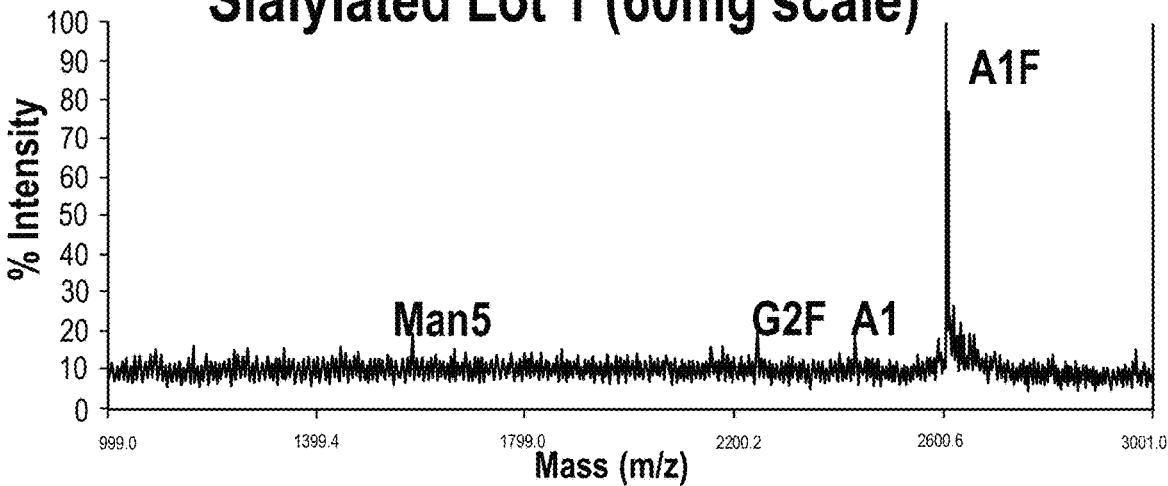
Figure 27:
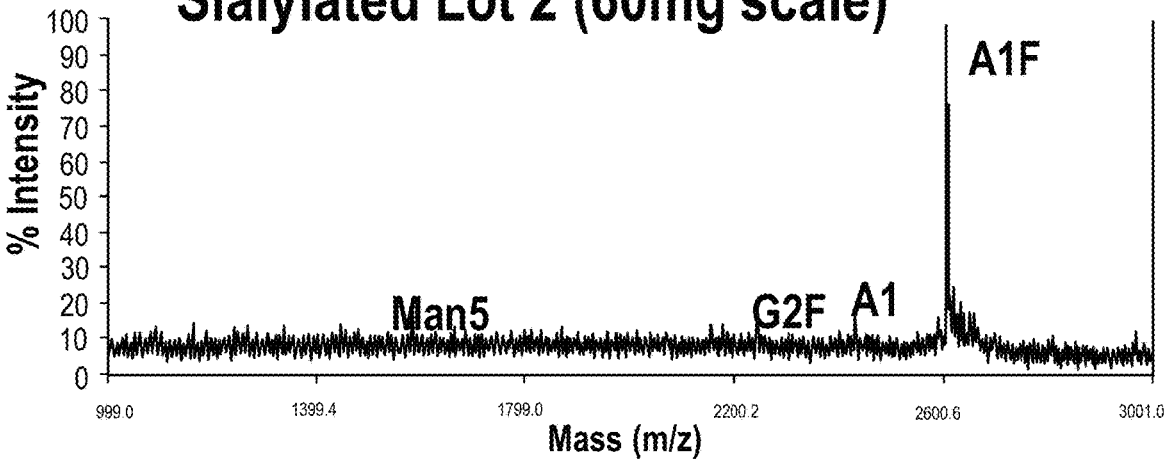
Figure 27:
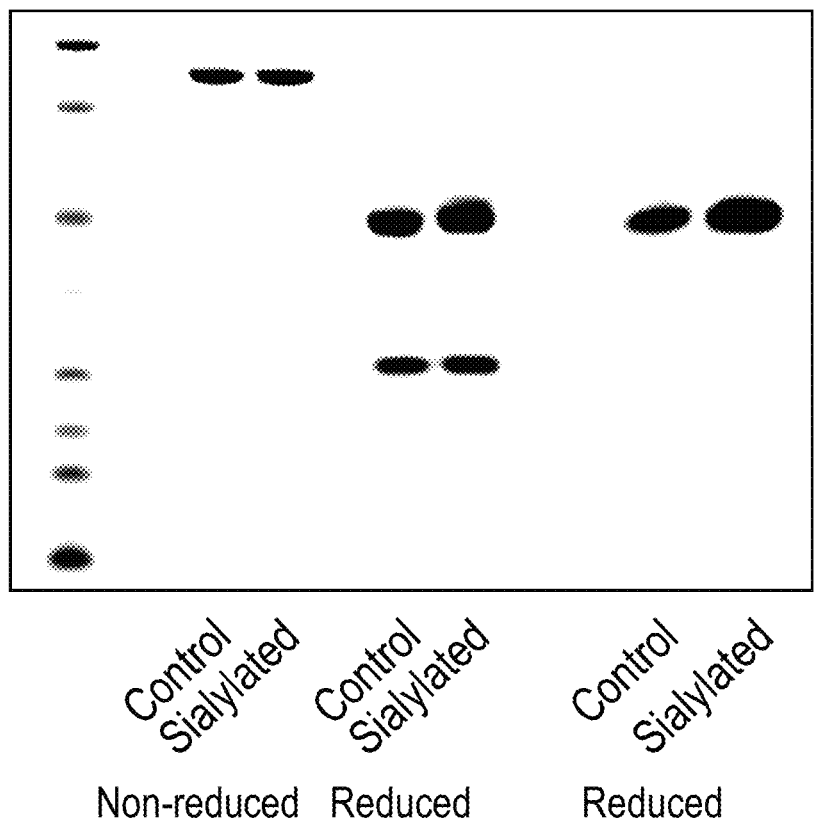

MALDI-TOF analysis of glycans released by PNGase F treatment of the sialylated anti-HER2 antibody indicated that native glycans had been completely remodeled with a mainly monosialylated biantennary structure, A1F (FIG. 27A) together with small amount of disialylated species. Treatment of the antibody with higher amounts of a2,6-sialyltransferase produced more homogenous populations of the A1F glycoform, suggesting that either the enzyme activity or glycan localization may prevent full sialylation. Sialic acid content was determined to be ~2 mol per mol of antibody, which is consistent with A1F glycan as the major glycoform species (FIG. 27B). Lectin blotting with a SAN lectin, Sambucus nigra agglutinin specific for a2,6-linked sialic acid, confirmed that the sialic acid was present in an a2,6-linkage configuration (FIG. 27C).

In conclusion, although the native protein glycans are somewhat heterogeneous, remodeling through galactosyl and sialyltransferases yields a nearly homogeneous antibody with monosialylated but fully galactosylated biantennary glycans (A1F). The introduction of only ~1 sialic acid on the two galactose acceptors on each branched glycan may be due to limited accessibility of one of the galactoses from glycans which are often buried in the antibody or non-covalent interactions of the glycans with the protein surface.

Example 11. Oxidation of Altered Antibodies Containing Reactive Glycan Moieties

Figure 28:
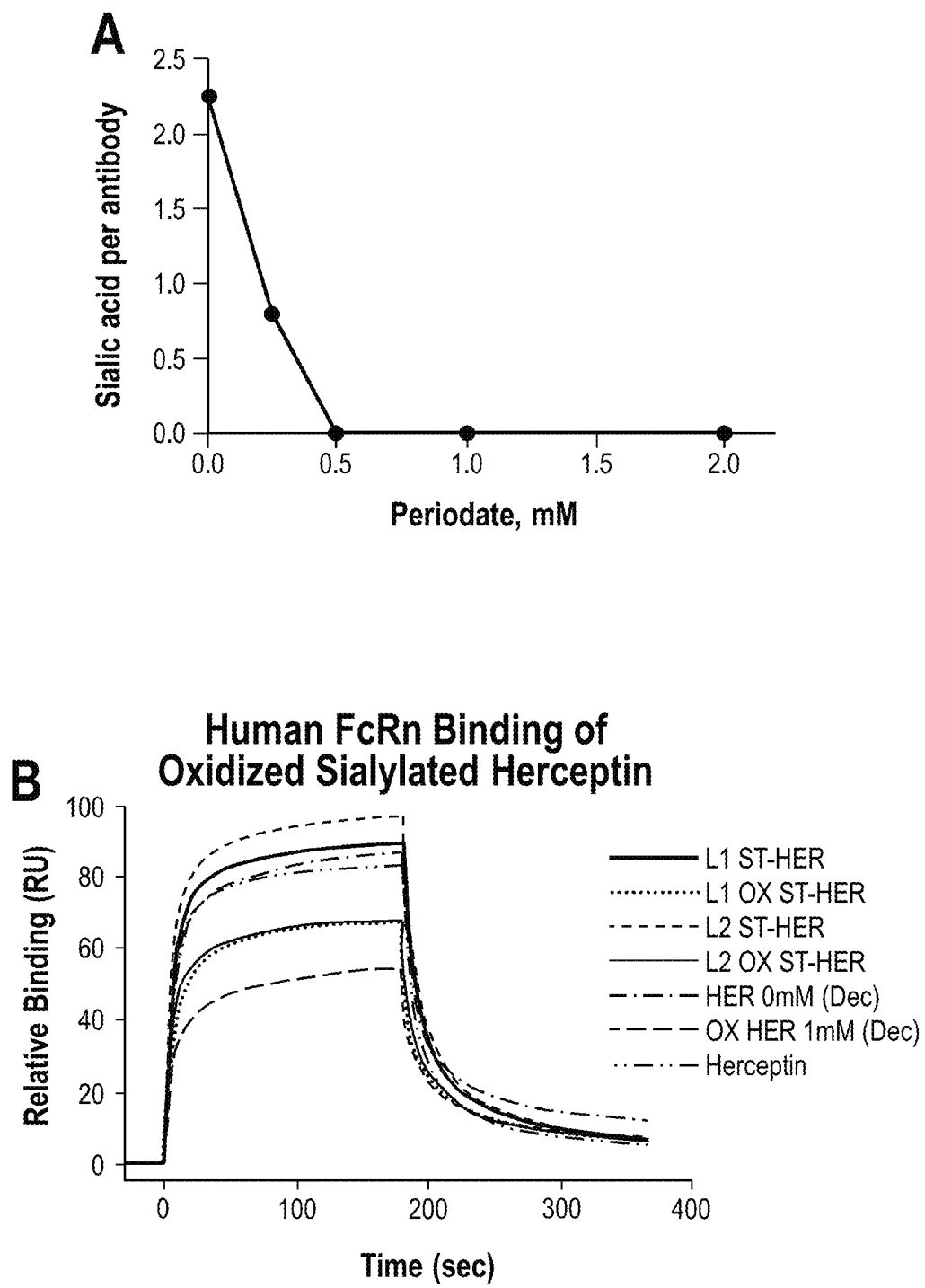
FIG. 28 depicts characterization information for oxidized sialylated anti-HER 2 antibody.
Figure 28:
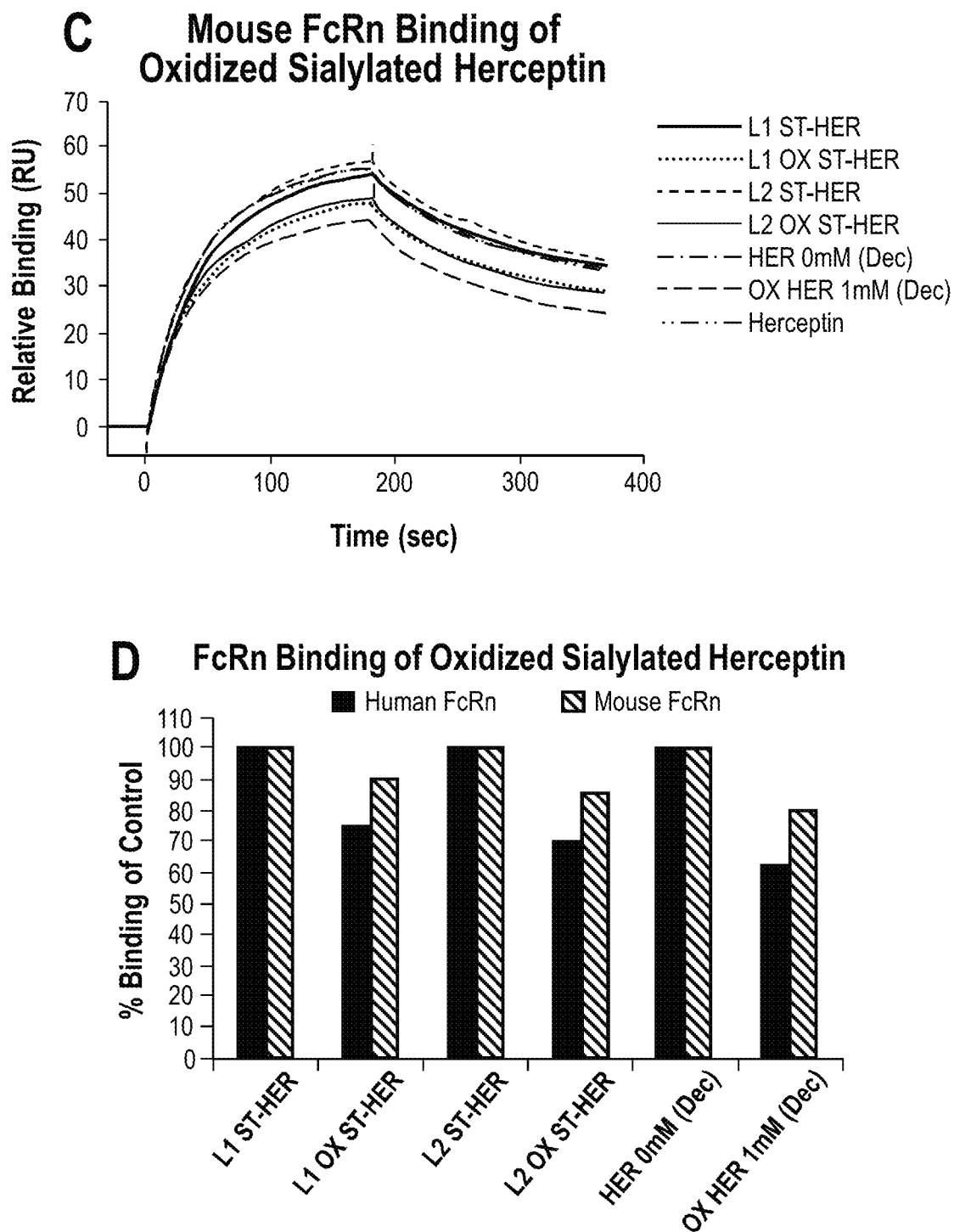

Once the sialylation was verified, the in-process oxidation of sialylated anti-HER2 antibody with various concentrations of periodate (0.25 to 2 mM) was investigated. The sialylated antibody was first buffer-exchanged into 25 mM Tris-HCl (pH 7.5) containing 5 mM EDTA followed by buffer exchange with PBS buffer. The buffered antibody mixture was then applied to protein A Sepharose column pre-equilibrated with PBS buffer. After the column was washed with 15 column volumes of PBS, 15 column volumes of PBS containing 5 mM EDTA, and 30 column volumes of PBS, it was then eluted with 25 mM citrate phosphate buffer (pH 2.9). The eluates were immediately neutralized with dibasic phosphate buffer and the antibody concentrated using Amicon ultra from Millipore. Following purification, the sialylated anti-HER2 antibody then was oxidized with sodium periodate (Sigma) in 100 mM sodium acetate buffer (pH 5.6) on ice in the dark for 30 minutes, and the reaction quenched with 3% glycerol on ice for 15 minutes. The product was desalted and exchanged into 100 mM sodium acetate (pH 5.6) by 5 rounds of ultrafiltration over 50 kDa Amicons. FIG. 28A shows sialic acid content analysis of sialylated antibody titrated with various amounts of periodate. Complete oxidation of the sialic acid residues was achieved at a periodate concentration above 0.5 mM. Indeed, a periodate concentration as low as 0.5 mM was enough to fully oxidize the introduced sialic acid. Accordingly, a 1 mM concentration of periodate was chosen for oxidation of sialylated antibody for drug conjugation.

Oxidation can have adverse effects on the integrity of an antibody. For, the oxidation of methionine residues, including Met-252 and Met-428, located in Fc CH3 region, close to FcRn binding site are known to affect FcRn binding which is critical for prolonging antibody serum half-life (Wang, W., et al. (2011) Impact of methionine oxidation in human IgG1 Fc on serum half-life of monoclonal antibodies. *Mol Immunol* 48, 860-6). Accordingly, to examine the potential side effects of periodate oxidation on methionine residues (e.g., Met-252) critical for FcRn interaction, the oxidation state of the sialylated antibody was determined by LC/MS analysis of a trypsin peptide digest. This analysis revealed ~30% oxidation of Met-252 and <10% oxidation of Met-428 after treatment of the sialylated trastuzumab with 1 mM periodate. To determine the impact of this degree of methionine oxidation on FcRn binding, the FcRn binding kinetics for each antibody was evaluated using surface plasmon resonance (BIACORE). This analysis revealed that oxidation state correlated with a minor loss in FcRn binding (12% and 26% reduction in Ka for mouse and human FcRn, see FIGS. 28B and 28C respectively). Notably, a ~25% reduction in the Ka for human FcRn has been reported to have no effect on the serum half-life in a human FcRn transgenic mouse, since a single intact FcRn site on each antibody is sufficient to provide functionality and the PK advantage (Wang et al., Id).

In summary, these data indicate that the introduction of periodate-sensitive sialic acid residues by sialyltransferase treatment permits the use of much lower concentrations of periodate, resulting in minimal side effects on antibody-FcRn interactions and antibody integrity as assessed by aggregation (≤1%). Thus, the use of sialylated antibodies according to the methods of the invention provides a wider window of oxidation conditions to be employed, allowing the reproducible generation of active glycoconjugates without an effect on serum half-life.

The galactose in a hyperglycosylated antibody mutant can also be oxidized specifically using galactose oxidase to generate an aldehyde group for conjugation. To confirm this approach, an A114N anti-TEM1 antibody was concentrated to 13-20 mg/ml and then treated with 20 mU/mg sialidase in PBS for 6 hours at 37° C. The desialated product was then oxidized with galactose oxidase ("GAO"), first with 5 ug GAO/mg protein overnight at 37° C. followed by addition of 2 ug GAO/mg protein and incubation for an additional 5 hours. Sodium acetate was added to adjust the pH to 5.6 (0.1 v/v, pH5.6), and DMSO was added to achieve a final reaction concentration of 16%, were added prior to conjugation. The hyperglycosylation mutant A114N anti-HER antibody (15 mg/ml) was similarly desialylated with sialidase (20 mU/mg) and oxidized with 5 ug GAO per mg protein in a single reaction overnight at 37° C.

Example 12. Synthesis of Reactive Effector Moieties

In order to facilitate conjugation with the aldehyde-derivatized antibody glycoforms of the invention, candidate drug effector moieties (e.g., Momomethyl Auristatin E (MMAE) and Dolastatin 10 (Dol10)) were derivatized with aminooxy-cystamide to contain functional groups (e.g., aminooxy-cys) specifically reactive with the aldehyde.

Briefly, to generate aminooxy-cystamide as a starting material, S-Trityl-L-cysteinamide (362 mg, 1 mmol) was added to a 3 mL of a DMF solution of t-BOC-aminooxy-acetic acid N-hydroxysuccinimide ester (289 mg, 1 mmol). The reaction was complete after 3 h as evident from HPLC analysis. The reaction mixture was subsequently diluted with 30 ml of dichloromethane and was washed with 0.1 M sodium bicarbonate solution (2×20 mL), water (2×20 mL), and brine (2×20 mL). The solution was dried over anhydrous sodium sulfate, filtered and concentrated to dryness. To this dried residue was added 3 mL of TFA followed by 150 µL of triethylsilane. The resulting solution was precipitated from t-butyl methyl ether and the process repeated three times. After filtration, the residue was dried under reduced pressure yielding 205 mg of an off white solid (67% yield). The compound was used for next step without further purification.

To generate aminooxy-derivatized MMAE (Aminooxy-Cys-MC-VC-PABC-MMAE), 30.1 mg of aminooxy-cystamide (0.098 mmol, 2 eq.) was combined with 64.6 mg of MC-VC-PABC-MMAE (0.049 mmol), and 100 µL of triethylamine in 3 mL of DMF. The resulting reaction mixture was stirred at room temperature for 15 minutes, by which time reaction was complete according to HPLC analysis. The compound was purified by preparative HPLC yielding 45 mg (62%) of the desired product as an off-white solid. Reversed-phase HPLC analysis suggested the purity of the compound to be >96%. ESI calcd for $C_{73}H_{116}N_{14}O_{18}S$ $(MH)^+$ 1509.8501; found, m/z 1509.8469.

To generate aminooxy-derivatized Dol10 (Aminooxy-Cys-MC-VC-PABC-PEG8-Dol10), 7.4 mg (0.024 mmol, 3 eq.) of aminooxy-cystamide, 12 mg (0.008 mmol) of MC-VC-PABC-PEG8-Dol10 and 30 µL triethylamine were combined in 3 mL of DMF. The reaction was complete within 15 minutes according to HPLC analysis. Preparative HPLC purification resulted in 6.2 mg (46%) of the desired product as an offwhite solid. Reversed-phase HPLC analysis suggests the purity of the compound to be >96%. ESI calcd for $C_{80}H_{124}N_{16}O_{19}S_2$ $(MH)^+$1678.0664; found, m/z 1678.0613.

Example 13. Sialic Acid-Mediated (SAM) Conjugation of Reactive Effector Moieties Following desalting, drug-linkers of Example 11 were combined with the oxidized, sialylated antibodies of Example 10 in 75% DMSO at a concentration of 25 mM to achieve a 24:1 molar ratio of drug-linker to antibody and a final antibody concentration at 5 mg/ml. The mixture was incubated overnight at room temperature. The unincorporated drug-linkers and any free drugs were scavenged using BioBeads. The product was buffer-exchanged into Histidine-Tween buffer using PD-10 columns and sterile filtered. The endotoxin levels were determined and less than 0.1 EU/mg ADC was achieved for in vivo study.

Figure 29:
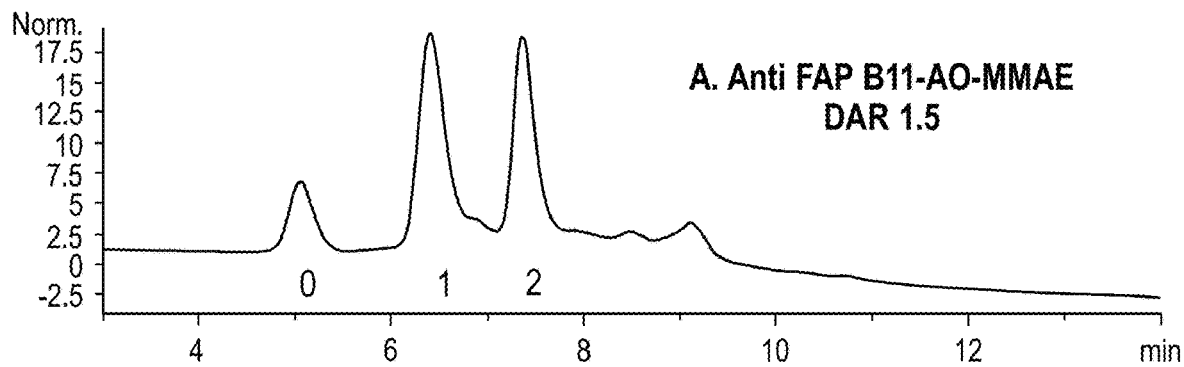
FIG. 29 depicts hydrophobic interaction chromatographs of glycoconjugates prepared with three different sialylated antibodies with two different aminooxy groups.
Figure 29:
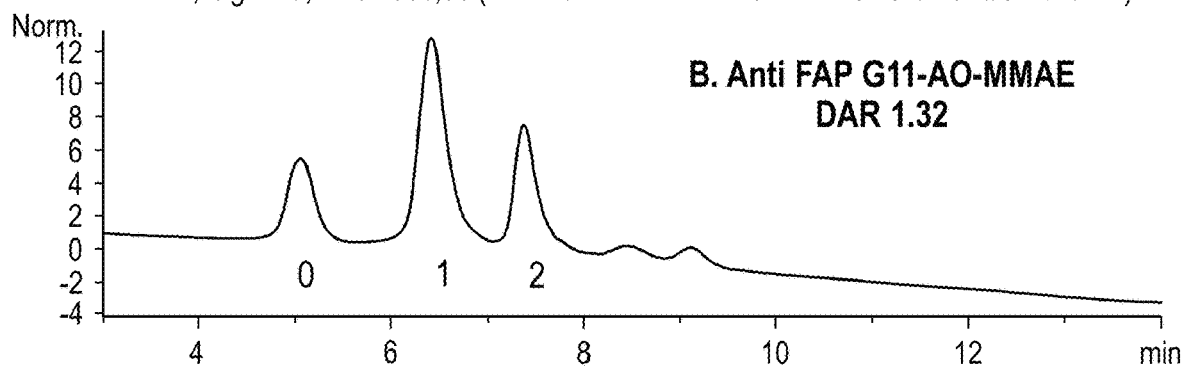
Figure 29:
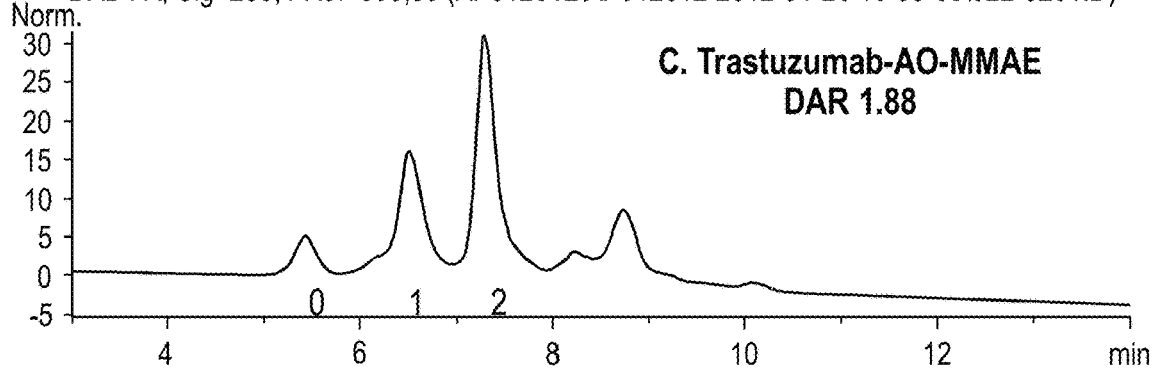
Figure 29:
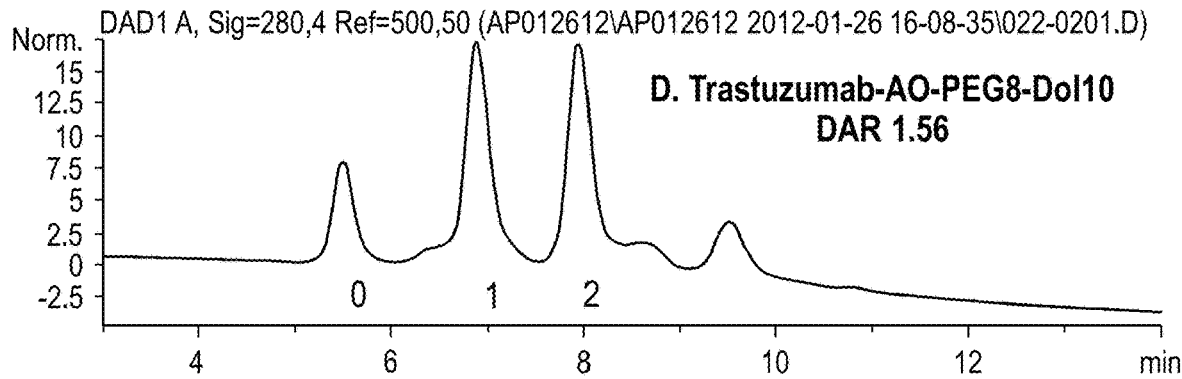

FIG. 29A-C shows a hydrophobic interaction chromatograph (HIC) of different sialylated antibodies (anti FAP B11 and G11 and the anti-HER2 antibody of Example 11) glycoconjugated to AO-MMAE. Sialylated HER2 antibody was also conjugated with the drug-linker, AO-Cys-MC-VC-PABC-PEGS-Dol10 (FIG. 29D). This analysis reveals that there are mainly one or two drug conjugates per antibody with a drug-to-antibody ratio (DAR) ranging from 1.3-1.9. The increased retention time of the Dol10 glycoconjugate (FIG. 29D) as compared to the MMAE glycoconjugate (FIG. 29C) is likely due to the greater hydrophobicity of Dol10.

LC-MS analysis was also conducted with an anti-HER antibody conjugated with two different drug-linkers (AO-MMAE or AO-PEGS-Dol10) at 30 mg scale. This analysis showed similar DAR values of 1.7 and 1.5 following conjugation, which is comparable to HIC analysis. Size-exclusion chromatography (SEC) showed very low levels (1%) of aggregates in these conjugates.

Example 14. Galactose-Mediated (GAM) Conjugation of Reactive Effector Moieties

Figure 30:
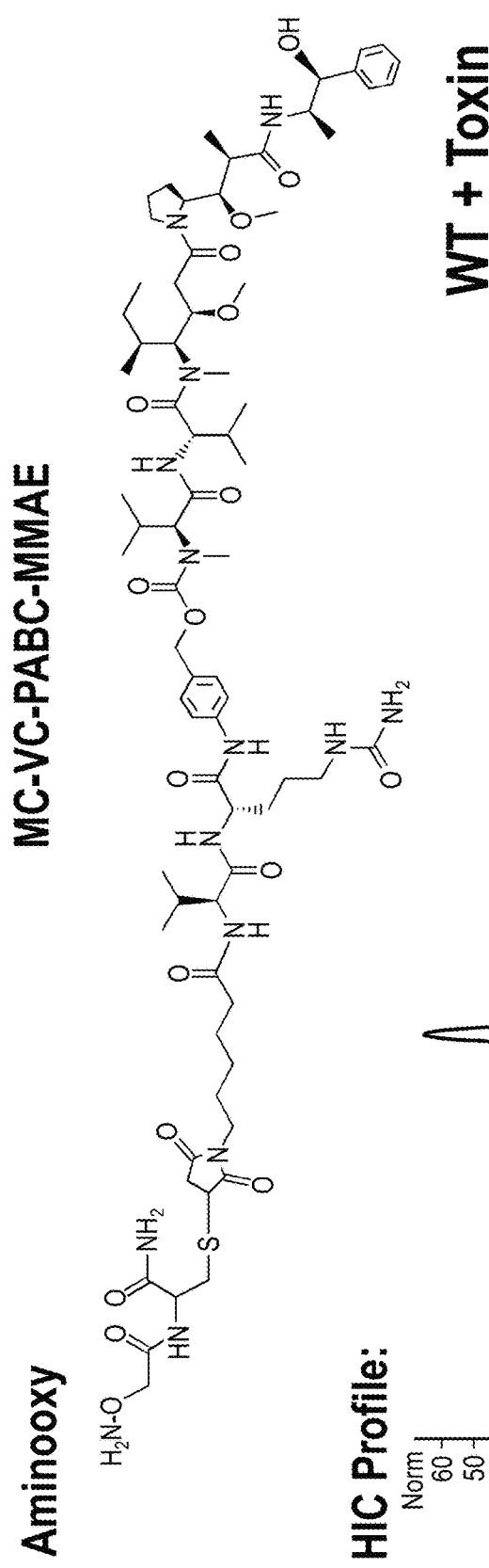
FIG. 30 shows a HIC chromatograph of antiHer2 A114 glycosylation mutant conjugate with AO-MMAE prepared using GAM(+) chemistry.
Figure 30:
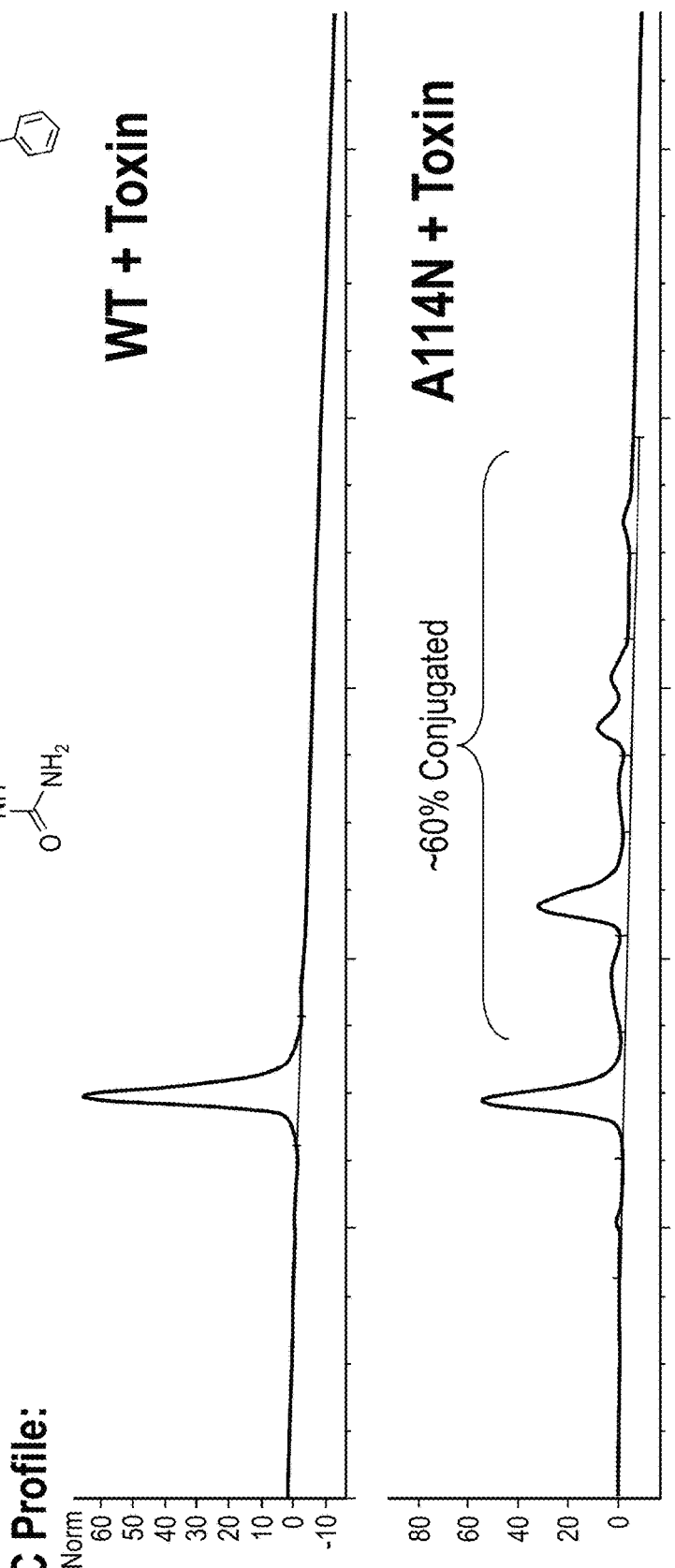

The galactose aldehyde generated with galactose oxidase on the A114N antiTEM1 hyperglycosylation mutant antibody as described in Example 11 was conjugated with 24 molar excess of aminooxy-MC-VC-PABC-MMAE drug-linker over antibody by overnight incubation at 25° C., yielding a ADC conjugate with a DAR of 1.72.
To the galactose oxidase-treated antiHER antibody prepared as described in Example 11, one tenth reaction volume of 1M sodium acetate, pH5.6, was added to adjust the pH to 5.6 and DMSO was added to make the final concentration of 14% before adding 24 eq aminooxy MC-VC-PABC-MMAE drug linker. The reactions were incubated for overnight at room temperature. Free drug and drug-linker were scavenged with Biobeads and the product buffer exchanged by SEC (65% yield). The product conjugate was analyzed by HIC. As shown in FIG. 30, AO-MMAE had been conjugated to ~60% of the molecules.

Example 15. In Vitro ADC Cell Proliferation Assays

The in vitro activity of the anti-HER and anti-FAP glycoconjugate molecules of the invention were also compared with corresponding thiol conjugates containing the same drug moiety linked via thiol linkages to hinge region cysteines of the same donor antibody. The thiol conjugates contained approximately twice the number of drugs per antibody (DAR) than the glycoconjugates. Thiol-based conjugation was performed as described by Stefano et al (Methods in Molecular Biology 2013, in press). Her2+ SK-BR-3 and Her2– MDA-MB-231 cell lines were then employed to evaluate the relative efficacy of each ADC. The results of this analysis are presented in Table 15 below

TABLE 15

$EC_{50}$ comparison of glycoconjugates and thiol conjugates

| | DAR | $EC_{50}$ (ng/ml) |
|---|---|---|
| Anti-HER-MC-VC-PABC-MMAE (Thiol MMAE) | 3.8* | 2.3 |
| AntiHER-AO-Cys-MC-VC-PABC-MMAE (Glyco MMAE) | 1.7* | 4.7 |
| Anti-HER-MC-VC-PABC-PEG8-Dol10 (Thiol Dol10) | 3.9* | 0.45 |
| Anti-HER-AO-Cys-MC-VC-PABC-PEG8-Dol10 (Glyco Dol10) | 1.5* | 0.97 |
| Anti FAP B11-MC-VC-PABC-MMAE (Thiol MMAE), CHO + FAP | 3.3** | 382.4 |
| Anti FAP B11-AO-Cys-MC-VC-PABC-MMAE (Glyco MMAE), CHO + FAP | 1.5** | 682.4 |

Note:
*DAR determined by LC-MS;
**DAR determined by HIC

Figure 31:
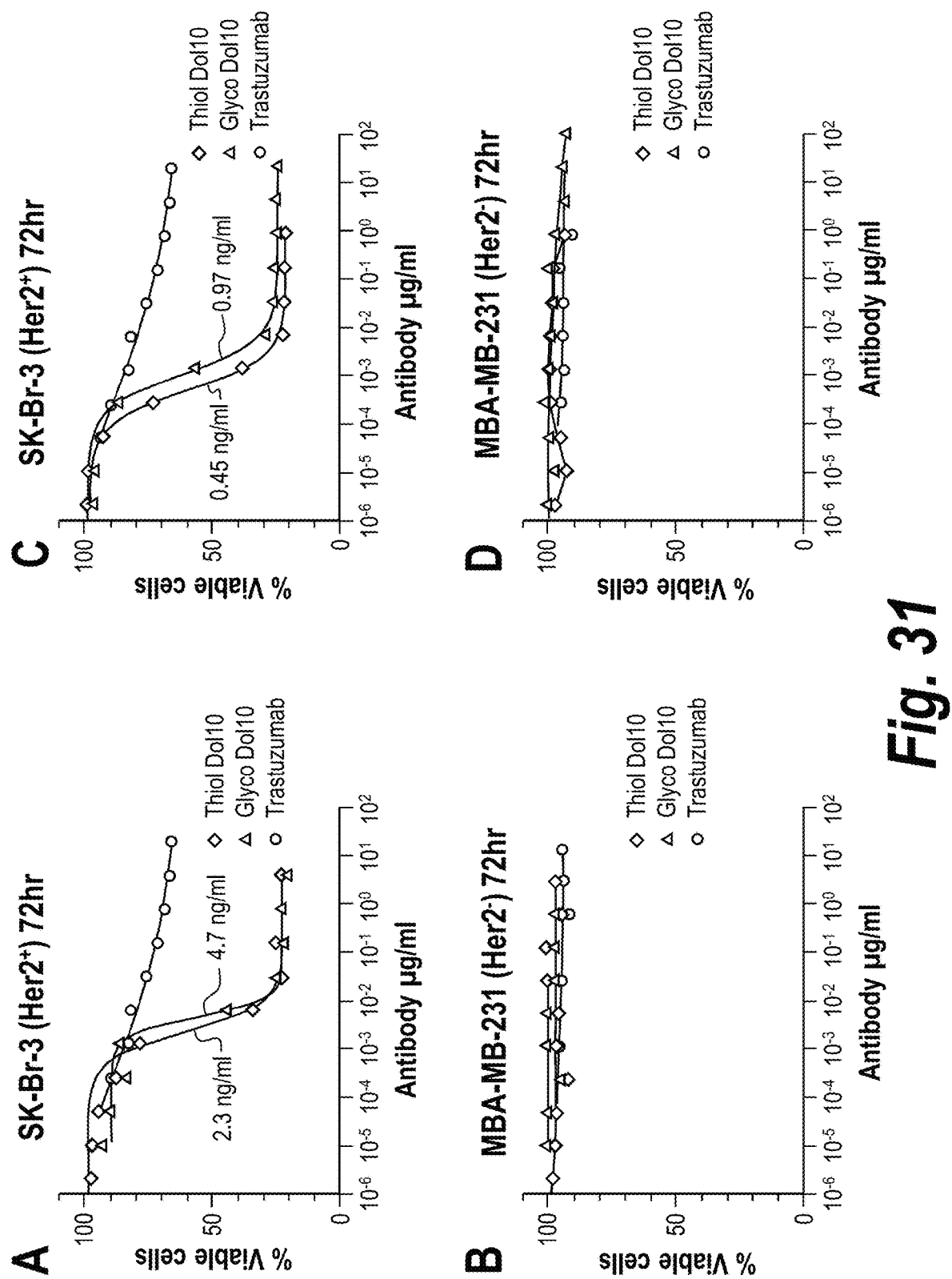
FIG. 31 depicts a comparison of the in vitro potency of an anti-HER2 glycoconjugate and thiol conjugate.

FIG. 31 shows a comparison of in vitro potency of anti-HER glycoconjugate and its counterpart thiol conjugate. Cell viability was determined following 72 hr exposure of the conjugates to Her2 antigen expressing (SK-BR-3) cells (FIGS. 31A and C) or non-expressing (MDA-MB-231) cells (FIGS. 31B and D). The ADCs contained either MMAE or PEGS-Dol10 linked to the glycans ("glyco") or by conventional chemistry to hinge region cysteines ("thiol"). As shown in FIGS. 30A and C, ~2-fold lower $EC_{50}$ was observed for the thiol conjugates compared to the glycoconjugates, which is consistent with 2-fold higher DAR in the former than the latter. No toxicity was observed with the Her2– cell line with any antibody up to 100 ug/ml.

Figure 32:
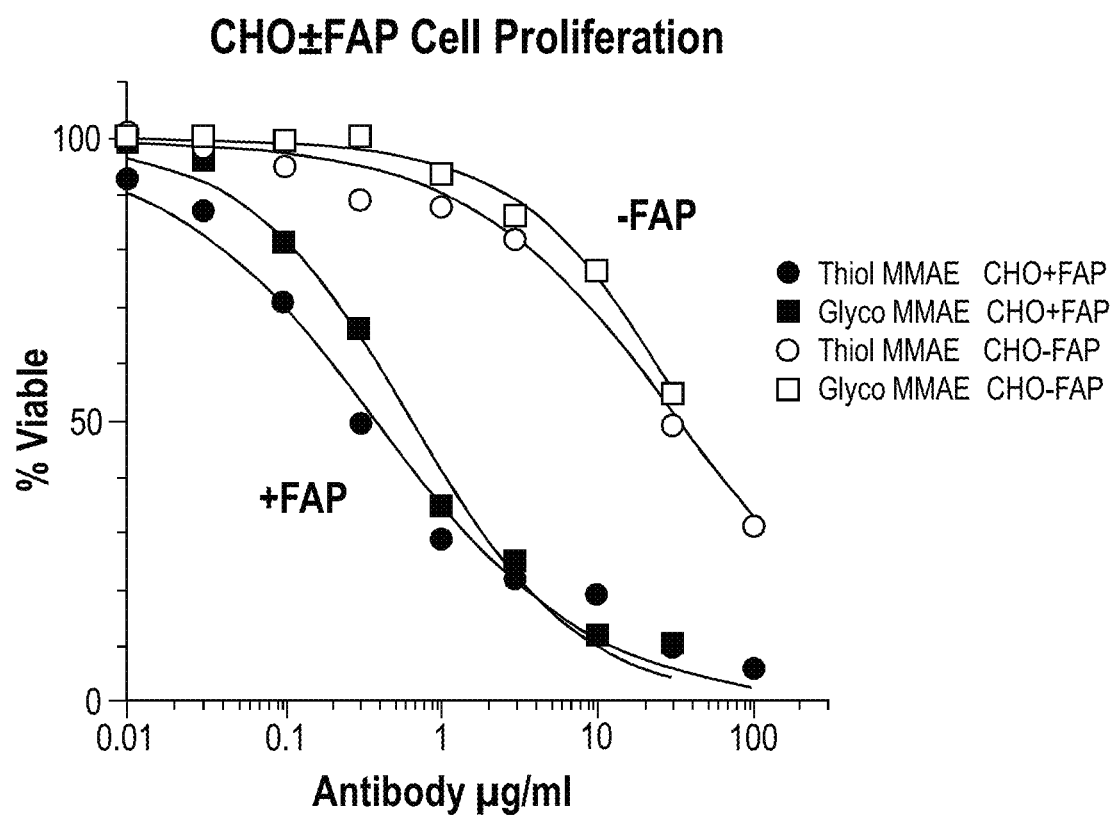
FIG. 32 depicts a comparison of the in vitro potency of an anti FAP B11 glycoconjugate and thiol conjugate.

Similar trends were also observed in the cell proliferation for ADC prepared with antibodies against a tumor antigen (FAP) which is highly expressed by reactive stromal fibroblasts in epithelial cancers including colon, pancreatic and breast cancer (Teicher, B. A. (2009) Antibody-drug conjugate targets. *Curr Cancer Drug Targets* 9, 982-1004). These conjugates were again prepared by conjugating either aminooxy MMAE drug-linker or maleimido MMAE drug-linker to glycans or a thiol group. Cell proliferation assays of these conjugates showed that $EC_{50}$ of the thiol conjugate had ~100-fold higher potency on the CHO cells transfected with human FAP than the same cells lacking FAP expression as depicted in FIG. 32, which shows a comparison of in vitro potency of anti FAP B11 glycoconjugate and thiol conjugate. Cell viability was determined following exposure of the conjugates to CHO cells transfected with or without FAP antigen. The ADCs contained MMAE linked to the glycans ("glyco") or by conventional chemistry to hinge region cysteines ("thiol"). Note that the ~2-fold lower EC50 for the thiol compared to the glycoconjugates is consistent with the relative amounts of drug delivered per antibody assuming similar efficiencies for target binding and internalization in antigen expressing CHO cells. In parallel, a glycoconjugate of anti FAP (B11) ADC with a DAR of 1.5 as described previously was assayed and showed an ~2-fold higher $EC_{50}$ than comparator thiol conjugate (DAR 3.3).

Figure 36:
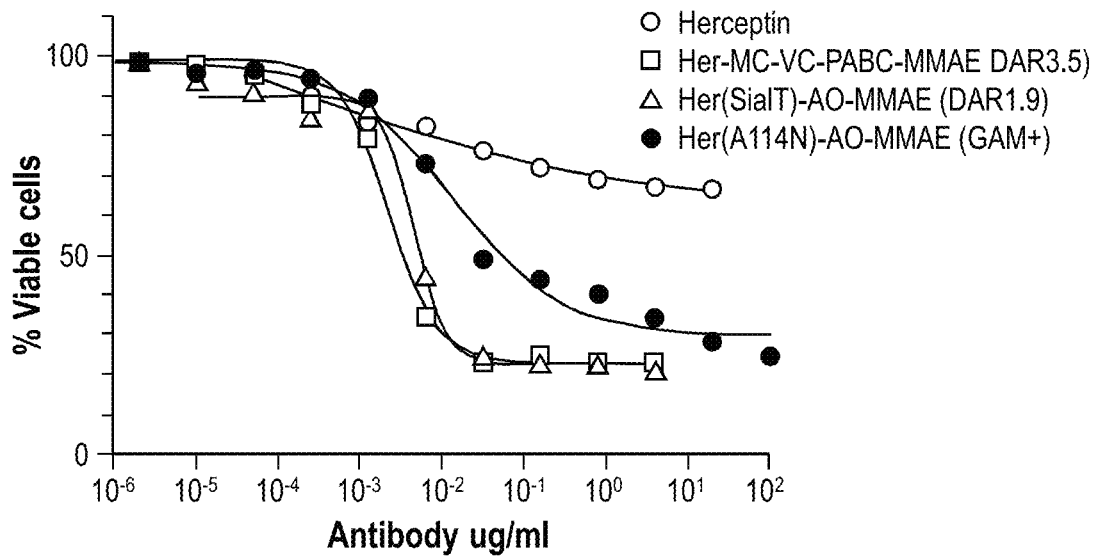
FIG. 36 depicts the results of a cell proliferation assay for ADC prepared with the anti-HER antibody bearing the A114N hyperglycosylation mutation and AO-MMAE.
Figure 36:
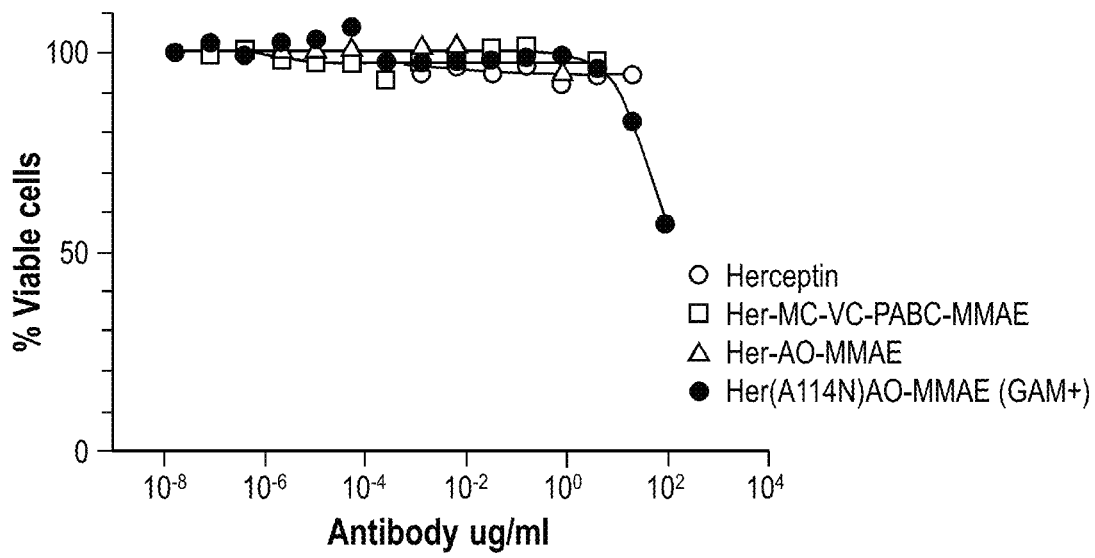

As shown in FIG. 36, similar trends were observed in the cell proliferation assay for ADC prepared with the anti-HER antibody bearing the A114N hyperglycosylation mutation and AO-MMAE as described in Example 14, when assayed on SK-BR-3 expressing cells or MDA-MB-231 cells. The A114N glycoconjugate clearly shows enhanced cell toxicity against the Her2 expressing cell line over the non-expressing line. The relative toxicity compared to the SialT glycoconjugate prepared with the same antibody is consistent with the lower drug loading of this preparation.

A cell proliferation assay was also performed for ADC prepared with the anti-TEM1 antibody bearing the A114N hyperglycosylation mutation and AO-MMAE prepared as described in Example 14. Higher toxicity was observed with the TEM1-expressing cells lines SJSA-1 and A673 compared to the non-expressing MDA-MB-231 line. The level of toxicity compared with a conventional thiol conjugate with the same antibody was in keeping with the drug loading (DAR) of this preparation.

|  | SJSA-1 IC50 | A673-RPMI IC50 | A673-DMEM-RPMI IC50 | MDA-MB-231 IC50 |
|---|---|---|---|---|
| antiTEM1 A114N-AO-MC-VC-PABC-MMAE | 3 µg/ml | 3.2 µg/ml | 2.2 µg/ml | 40 µg/ml |
| antiTEM1-MC-VC-PABC-MMAE | 4 µg/ml | 1 µg/ml | 0.9 µg/ml | 20 µg/ml |

In summary, the site-specific conjugation of the drugs through the glycans with cleavable linkers produces ADCs with toxicities and in vitro efficacy that are equivalent to conventional thiol-based conjugates, as demonstrated using different antibodies and different drug-linkers. Moreover, below 2 mM periodate, the level of drug conjugation correlates with the reduction of sialic acid. Increasing periodate concentration above 2 mM produces little benefit, as expected from the complete conversion of sialic acid to the oxidized form. However, under all conditions, the number of drugs per antibody was slightly lower than the sialic acid content, indicating that some of the oxidized sialic acids may similarly not be available for coupling, either because of being buried or otherwise due to steric hindrance arising from the bulk of the drug-linker.

Example 16. In Vivo Characterization of Antibody Drug Conjugates

Efficacy of anti-HER glycoconjugates were also evaluated in a Her2+ tumor cell xenograft mode and compared with thiol conjugate comparators having ~2-fold higher DAR. Beige/SCID mice were implanted with SK-OV-3 Her2+ tumor cells which were allowed to establish tumors of ~150 mm$^3$ prior to initiation of treatment. ADCs at 3 or 10 mg/kg doses were injected through tail vein on days 38, 45, 52 and 59. There were ~10 mice per group. The tumor volume of mice in different group was measured and their survival was recorded. The survival curve was plotted based on Kaplan-Meier method.

Figure 33:
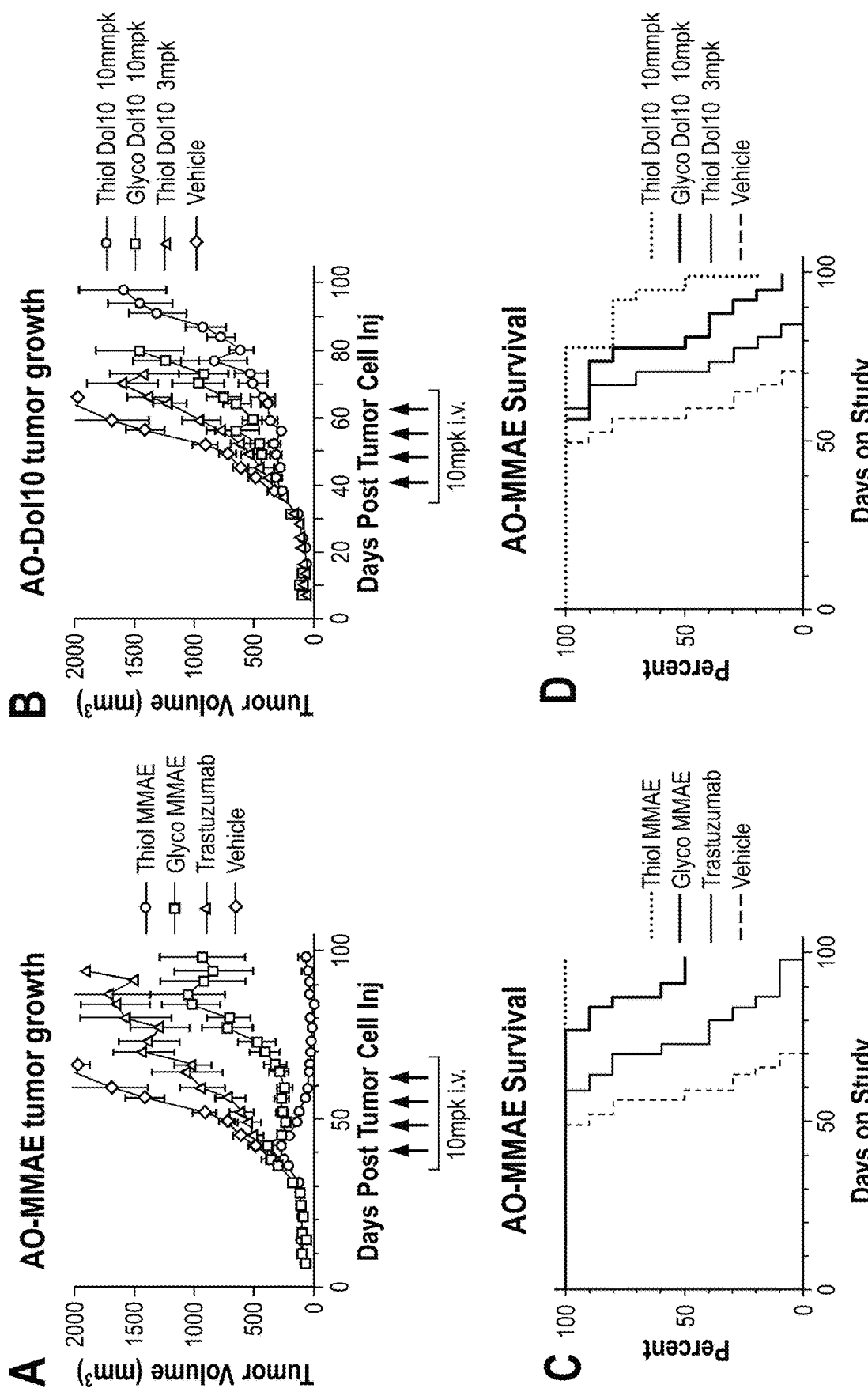
FIG. 33 depicts a comparison of in vivo efficacy of anti-HER2 glycoconjugates and thiol conjugates in a Her2+ tumor cell xenograft model.

FIG. 33 shows a comparison of in vivo efficacy of the anti-HER glycoconjugates and thiol conjugates in a Her2+ tumor cell xenograft model. Beige/SCID mice implanted with SK-OV-3 Her2+ tumor cells were dosed with MMAE (FIGS. 33 A and B) and PEGS-Dol10 (FIGS. 33 C and D) containing glycoconjugates or a thiol conjugate comparators with ~2-fold higher DAR. The tumor growth kinetics of the MMAE conjugates is shown in FIG. 33A. In this case, the glycoconjugate showed a significantly higher efficacy than the naked antibody alone (black) but less than a thiol conjugate comparator having a ~2-fold higher DAR (green). The MMAE glycoconjugate showed significant tumor regression and a ~20 day delay in tumor growth (FIG. 33A) and ~2-fold increase in survival time from first dose (FIG. 33B). The thiol MMAE conjugate showed near-complete tumor suppression at the same dose of ADC (10 mg/kg).

The in vivo efficacy of a PEGS-Dol10 glycoconjugate ("Glyco Dol10") and a thiol conjugate comparator with ~2-fold higher DAR ("Thiol Dol10") was also determined in the same Her2+ tumor cell xenograft model. Both conjugates showed lower efficacy than MMAE conjugates as described previously. However, the aminooxy-PEGS-Dol10 glycoconjugate ("Glyco Dol10") at 10 mg/kg showed a 15-day delay in tumor growth (FIG. 33C) and ~20 day (1.7-fold) increase in survival time following first administration (FIG. 33D). The thiol conjugate was more efficacious at the same dose, showing a 2-fold increase in survival. At a lower dose (3 mg/kg), the thiol conjugate showed a lesser efficacy than the glycoconjugate at 10 mg/kg. This dose corresponds to 80 umol PEGS-Dol10 drug per kg dose, compared to 110 umol PEGS-Dol10 drug per kg dose for the glycoconjugate.

These data demonstrate that site-specific conjugation of drugs onto sialic acid of antibody glycans yields molecules with comparable potency as ADCs generated via thiol-based chemistry. The somewhat lower in vivo efficacy likely stems from the fewer number of drugs which are carried by each antibody into the tumor cells by the internalization of each antibody-bound antigen. Although we have not compared these glycoconjugates with thiol conjugates of the same DAR, the efficacy observed at different doses of the two ADCs representing comparable levels of administered drug shows that the glycoconjugates have comparable intrinsic efficacy as their thiol counterparts, indicating no deleterious effect of conjugation at this site. Moreover, a 10 mg/kg dose of the Dol10 glycoconjugate which introduced only 28% more drug provided a 2-fold increase in survival over the thiol conjugate (at 3 mg/kg), suggesting these conjugates may even provide superior efficacies at the same DAR. Given the apparent limitation in sialic acid incorporation at native glycans, higher drug loading could be achieved by a number of different strategies including the use of branched drug linkers or the introduction of additional glycosylation sites and using the same method.

We claim:

1. An isolated polynucleotide encoding a binding polypeptide comprising an Fc domain, wherein the Fc domain comprises: an asparagine residue at amino acid position 298, according to EU numbering; and a serine or threonine residue at amino acid position 300, according to EU numbering, and wherein the encoded binding polypeptide has a lower affinity for an Fcγ receptor than a binding polypeptide having a native Fc domain.

2. A vector comprising the polynucleotide of claim 1.

3. A host cell comprising the polynucleotide or vector of claim 1.

4. A method of making a binding polypeptide comprising expressing the polynucleotide of claim 1.

5. A method of making a binding polypeptide comprising expressing the vector of claim 2 in a cell.

6. The isolated polynucleotide of claim 1, wherein the encoded binding polypeptide further comprises an alanine residue at amino acid position 299, according to EU numbering.

7. The isolated polynucleotide of claim 1, wherein the encoded binding polypeptide further comprises a glutamine residue at amino acid position 297, according to EU numbering.

8. The isolated polynucleotide of claim 1, wherein the Fc domain of the encoded polypeptide is an IgG1 Fc domain.

9. The isolated polynucleotide of claim 1, wherein the Fc domain of the encoded polypeptide is human.

10. The isolated polynucleotide of claim 1, wherein the Fcγ receptor is FcγRI and/or FcγRIIIa.

11. The isolated polynucleotide of claim 1, wherein the encoded polypeptide has a similar affinity for an FcRn receptor as a binding polypeptide having a native Fc domain.

12. The isolated polynucleotide of claim 1, wherein the encoded polypeptide is an antibody.

13. An isolated polynucleotide encoding a binding polypeptide comprising an Fc domain, wherein the Fc domain comprises: a free asparagine residue at amino acid position 298, according to EU numbering; and a free serine or threonine residue at amino acid position 300, according to EU numbering.

14. An isolated polynucleotide encoding a binding polypeptide comprising an Fc domain, wherein the Fc domain comprises: an N-glycan linked to an asparagine residue at amino acid position 298, according to EU numbering; and a free serine or threonine residue at amino acid position 300, according to EU numbering.

15. The isolated polynucleotide of claim 1, wherein the encoded polypeptide is an immunoadhesin comprising a non-antibody binding region.

16. The isolated polynucleotide of claim 15, wherein the non-antibody binding region of the encoded polypeptide is a receptor.

17. The isolated polynucleotide of claim 15, wherein the non-antibody binding region of the encoded polypeptide is a ligand of a receptor.

18. The isolated polynucleotide of claim 1, wherein the encoded polypeptide comprises at least one binding site which is a receptor binding site of a ligand.

19. An isolated polynucleotide encoding a binding polypeptide comprising a human IgG1 Fc domain, wherein the Fc domain comprises: an asparagine residue at amino acid position 297, according to EU numbering; an asparagine residue at amino acid position 298, according to EU numbering; an amino acid at position 299, according to EU numbering, wherein said amino acid at position 299 is not proline; and a serine or threonine residue at amino acid position 300, according to EU numbering.

20. An isolated polynucleotide encoding a binding polypeptide comprising a human IgG1 Fc domain, wherein the Fc domain comprises: a glutamine residue at amino acid position 297, according to EU numbering; an asparagine residue at amino acid position 298, according to EU numbering; an amino acid at position 299, according to EU numbering, wherein said amino acid at position 299 is not proline; and a serine or threonine residue at amino acid position 300, according to EU numbering.

21. An isolated polynucleotide encoding a binding polypeptide comprising a human IgG1 Fc domain, wherein the Fc domain comprises: an asparagine residue at amino acid position 297, according to EU numbering; an asparagine residue at amino acid position 298, according to EU numbering; an alanine residue at amino acid position 299, according to EU numbering; and a serine or threonine residue at amino acid position 300, according to EU numbering.

22. An isolated polynucleotide encoding a binding polypeptide comprising a human IgG4 Fc domain, wherein the Fc domain comprises: an asparagine residue at amino acid position 298, according to EU numbering; an alanine residue at amino acid position 299, according to EU numbering; and a serine or threonine residue at amino acid position 300, according to EU numbering.

23. The isolated polynucleotide of claim 22, wherein the Fc domain of the encoded polypeptide comprises a hinge region with a Ser228Pro mutation (EU numbering).

* * * * *

SEQUENCE LISTING

<160> NUMBER OF SEQ ID NOS: 45

<210> SEQ ID NO 1
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Leu Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Thr His Leu His Thr Phe Gly Gln Gly Thr Arg Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 2
<211> LENGTH: 443
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Val Gln Leu Val Glu Ser Gly Gly Gly Leu Val Gln Pro Gly Gly Ser
1               5                   10                  15

Leu Arg Leu Ser Cys Ala Ala Ser Gly Phe Thr Phe Asn Thr Tyr Trp
            20                  25                  30

Met Asn Trp Val Arg Gln Ala Pro Gly Lys Gly Leu Glu Trp Val Gly
        35                  40                  45

Gln Ile Arg Leu Lys Ser Asn Asn Tyr Ala Thr His Tyr Ala Glu Ser
    50                  55                  60

Val Lys Gly Arg Phe Thr Ile Ser Arg Asp Asp Ser Lys Asn Ser Leu
65                  70                  75                  80

Tyr Leu Gln Met Asn Ser Leu Lys Thr Glu Asp Thr Ala Val Tyr Tyr
                85                  90                  95

Cys Thr Pro Val Asp Phe Trp Gly Gln Gly Thr Thr Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Asp Lys Thr His Thr Cys Pro Pro
210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Asp
            340                 345                 350

Glu Leu Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 3
<211> LENGTH: 444
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Trp Met Asn Trp Val Arg Gln Ala Pro Gly Lys Gly Leu Glu Trp Val
        35                  40                  45

Gly Gln Ile Arg Leu Lys Ser Asn Asn Tyr Ala Thr His Tyr Ala Glu

```
                50                  55                  60
Ser Val Lys Gly Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                 85                  90                  95

Tyr Cys Thr Pro Val Asp Phe Trp Gly Gln Gly Thr Thr Val Thr Val
                100                 105                 110

Ser Ser Asn Ser Thr Lys Gly Pro Ser Val Phe Pro Leu Ala Pro Ser
                115                 120                 125

Ser Lys Ser Thr Ser Gly Gly Thr Ala Ala Leu Gly Cys Leu Val Lys
130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
                180                 185                 190

Gln Thr Tyr Ile Cys Asn Val Asn His Lys Pro Ser Asn Thr Lys Val
                195                 200                 205

Asp Lys Lys Val Glu Pro Lys Ser Cys Asp Lys Thr His Thr Cys Pro
210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
                260                 265                 270

Asn Trp Tyr Val Asp Gly Val Glu Val His Asn Ala Lys Thr Lys Pro
                275                 280                 285

Arg Glu Glu Gln Tyr Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
                340                 345                 350

Asp Glu Leu Thr Lys Asn Gln Val Ser Leu Thr Cys Leu Val Lys Gly
                355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
                420                 425                 430

Tyr Thr Gln Lys Ser Leu Ser Leu Ser Pro Gly Lys
                435                 440

<210> SEQ ID NO 4
<211> LENGTH: 444
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 4
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Trp Met Asn Trp Val Arg Gln Ala Pro Gly Lys Gly Leu Glu Trp Val
        35                  40                  45

Gly Gln Ile Arg Leu Lys Ser Asn Asn Tyr Ala Thr His Tyr Ala Glu
    50                  55                  60

Ser Val Lys Gly Arg Phe Thr Ile Ser Arg Asp Asp Ser Lys Asn Ser
65              70                  75                  80

Leu Tyr Leu Gln Met Asn Ser Leu Lys Thr Glu Asp Thr Ala Val Tyr
            85                  90                  95

Tyr Cys Thr Pro Val Asp Phe Trp Gly Gln Gly Thr Thr Val Thr Val
            100                 105                 110

Ser Ser Ala Ser Thr Lys Gly Pro Ser Val Phe Pro Leu Ala Pro Ser
            115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145             150                 155                 160

Thr Ser Gly Val His Thr Phe Pro Ala Val Leu Gln Ser Ser Gly Leu
            165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
            195                 200                 205

Asp Lys Lys Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225             230                 235                 240

Pro Pro Lys Pro Lys Asp Thr Leu Met Ile Ser Arg Thr Pro Glu Val
            245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
            275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305             310                 315                 320

Ser Asn Lys Ala Leu Pro Ala Pro Ile Glu Lys Thr Ile Ser Lys Ala
            325                 330                 335

Lys Gly Gln Pro Arg Glu Pro Gln Val Tyr Thr Leu Pro Pro Ser Arg
            340                 345                 350

Asp Glu Leu Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Ser Thr Gln Lys Ser Leu Ser Leu Ser Pro Gly Lys
        435                 440

<210> SEQ ID NO 5
<211> LENGTH: 444
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Trp Met Asn Trp Val Arg Gln Ala Pro Gly Lys Gly Leu Glu Trp Val
        35                  40                  45

Gly Gln Ile Arg Leu Lys Ser Asn Asn Tyr Ala Thr His Tyr Ala Glu
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Thr Pro Val Asp Phe Trp Gly Gln Gly Thr Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr

```
                    290                 295                 300
Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
                340                 345                 350

Asp Glu Leu Thr Lys Asn Gln Val Ser Leu Thr Cys Leu Val Lys Gly
                355                 360                 365

Phe Tyr Pro Ser Asp Ile Ala Val Glu Trp Glu Ser Asn Gly Gln Pro
                370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
                420                 425                 430

Tyr Thr Gln Lys Asn Leu Ser Leu Ser Pro Gly Lys
                435                 440

<210> SEQ ID NO 6
<211> LENGTH: 444
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
                20                  25                  30

Trp Met Asn Trp Val Arg Gln Ala Pro Gly Lys Gly Leu Glu Trp Val
                35                  40                  45

Gly Gln Ile Arg Leu Lys Ser Asn Asn Tyr Ala Thr His Tyr Ala Glu
50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Thr Pro Val Asp Phe Trp Gly Gln Gly Thr Thr Val Thr Val
                100                 105                 110

Ser Ser Ala Ser Thr Lys Gly Pro Ser Val Phe Pro Leu Ala Pro Ser
                115                 120                 125

Ser Lys Ser Thr Ser Gly Gly Thr Ala Ala Leu Gly Cys Leu Val Lys
                130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
                180                 185                 190

Gln Thr Tyr Ile Cys Asn Val Asn His Lys Pro Ser Asn Thr Lys Val
                195                 200                 205
```

Asp Lys Lys Val Glu Pro Lys Ser Cys Asp Lys Thr His Thr Cys Pro
            210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
            275                 280                 285

Arg Glu Glu Gln Tyr Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
            325                 330                 335

Lys Gly Gln Pro Arg Glu Pro Gln Val Tyr Thr Leu Pro Pro Ser Arg
            340                 345                 350

Asp Glu Leu Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
            405                 410                 415

Gly Asn Val Phe Ser Cys Ser Val Met His Glu Ala Leu His Asn His
            420                 425                 430

Tyr Thr Gln Lys Ser Leu Asn Leu Ser Pro Gly Lys
            435                 440

<210> SEQ ID NO 7
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Trp Met Asn Trp Val Arg Gln Ala Pro Gly Lys Gly Leu Glu Trp Val
        35                  40                  45

Gly Gln Ile Arg Leu Lys Ser Asn Asn Tyr Ala Thr His Tyr Ala Glu
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Thr Pro Val Asp Phe Trp Gly Gln Gly Thr Thr Val Thr Val
            100                 105                 110

```
Ser Ser Ala Ser Thr Lys Gly Pro Ser Val Phe Pro Leu Ala Pro Ser
            115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
            195                 200                 205

Asp Lys Lys Val Glu Pro Lys Ser Cys Asp Lys Thr His Thr Cys Pro
210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
            275                 280                 285

Arg Glu Glu Gln Tyr Asn Ser Thr Tyr Arg Val Val Ser Val Leu Thr
            290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Asp Glu Leu Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys Asn Gly Thr
            435                 440                 445

<210> SEQ ID NO 8
<211> LENGTH: 444
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
```

```
            20                  25                  30
Trp Met Asn Trp Val Arg Gln Ala Pro Gly Lys Gly Leu Glu Trp Val
            35                  40                  45

Gly Gln Ile Arg Leu Lys Ser Asn Asn Tyr Ala Thr His Tyr Ala Glu
 50                  55                  60

Ser Val Lys Gly Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                85                  90                  95

Tyr Cys Thr Pro Val Asp Phe Trp Gly Gln Gly Thr Thr Val Thr Val
            100                 105                 110

Ser Ser Ala Ser Thr Lys Gly Pro Ser Val Phe Pro Leu Ala Pro Ser
            115                 120                 125

Ser Lys Ser Thr Ser Gly Gly Thr Ala Ala Leu Gly Cys Leu Val Lys
            130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
            195                 200                 205

Asp Lys Lys Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
            275                 280                 285

Arg Glu Glu Gln Tyr Asn Asn Thr Ser Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Asp Glu Leu Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
            370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
            435                 440
```

```
<210> SEQ ID NO 9
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 10
<211> LENGTH: 454
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Gln Val Gln Leu Gln Glu Ser Ala Pro Gly Leu Val Lys Pro Ser Glu
1               5                   10                  15

Thr Leu Ser Leu Thr Cys Thr Val Ser Gly Gly Ser Ile Arg Ser Tyr
            20                  25                  30

Tyr Trp Ser Trp Ile Arg Gln Pro Pro Gly Lys Gly Leu Glu Tyr Ile
        35                  40                  45

Gly Tyr Ile Tyr Tyr Thr Gly Ser Ala Ile Tyr Asn Pro Ser Leu Gln
    50                  55                  60
```

Ser Arg Val Thr Ile Ser Val Asp Thr Ser Lys Asn Gln Phe Ser Leu
65                  70                  75                  80

Lys Leu Asn Ser Val Thr Ala Ala Asp Thr Ala Val Tyr Tyr Cys Ala
                85                  90                  95

Arg Glu Gly Val Arg Gly Ala Ser Gly Tyr Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 11
<211> LENGTH: 454
<212> TYPE: PRT

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 11

```
Gln Val Gln Leu Gln Glu Ser Ala Pro Gly Leu Val Lys Pro Ser Glu
1               5                   10                  15

Thr Leu Ser Leu Thr Cys Thr Val Ser Gly Gly Ser Ile Arg Ser Tyr
            20                  25                  30

Tyr Trp Ser Trp Ile Arg Gln Pro Pro Gly Lys Gly Leu Glu Tyr Ile
        35                  40                  45

Gly Tyr Ile Tyr Tyr Thr Gly Ser Ala Ile Tyr Asn Pro Ser Leu Gln
    50                  55                  60

Ser Arg Val Thr Ile Ser Val Asp Thr Ser Lys Asn Gln Phe Ser Leu
65                  70                  75                  80

Lys Leu Asn Ser Val Thr Ala Ala Asp Thr Ala Val Tyr Tyr Cys Ala
                85                  90                  95

Arg Glu Gly Val Arg Gly Ala Ser Gly Tyr Tyr Tyr Gly Met Asp
                100                 105                 110

Val Trp Gly Gln Gly Thr Thr Val Thr Val Ser Ser Asn Ser Thr Lys
            115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380
```

```
Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450
```

<210> SEQ ID NO 12
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 13
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
```

```
                       405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 14
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Asn Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300
```

```
Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
                435                 440                 445

Gly Lys
    450

<210> SEQ ID NO 15
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

```
Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Asn Ala Ser Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 16
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
```

85                  90                  95
Ser Arg Trp Gly Gly Asp Gly Phe Tyr Ala Met Asp Tyr Trp Gly Gln
            100                 105                 110
Gly Thr Leu Val Thr Val Ser Ser Asn Ser Thr Lys Gly Pro Ser Val
            115                 120                 125
Phe Pro Leu Ala Pro Ser Ser Lys Ser Thr Ser Gly Gly Thr Ala Ala
            130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
            165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
            195                 200                 205
Pro Ser Asn Thr Lys Val Asp Lys Lys Val Glu Pro Lys Ser Cys Asp
            210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
            245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ala Ser Arg
            290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
            325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
            355                 360                 365
Thr Cys Leu Val Lys Gly Phe Tyr Pro Ser Asp Ile Ala Val Glu Trp
            370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
            405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
            435                 440                 445
Gly Lys
450

<210> SEQ ID NO 17

<400> SEQUENCE: 17

000

```
<210> SEQ ID NO 18
<400> SEQUENCE: 18

000

<210> SEQ ID NO 19
<400> SEQUENCE: 19

000

<210> SEQ ID NO 20
<400> SEQUENCE: 20

000

<210> SEQ ID NO 21
<400> SEQUENCE: 21

000

<210> SEQ ID NO 22
<400> SEQUENCE: 22

000

<210> SEQ ID NO 23
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Tyr Gln Gln Lys Pro Gly Gln Ala Pro Arg Arg Leu Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Thr Leu Thr Ile Ser Ser Leu Glu Pro Glu
65                  70                  75                  80

Asp Phe Ala Val Tyr Tyr Cys Gln Gln Trp Ser Ser Asn Pro Leu Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175
```

```
Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 24
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

```
Glu Val Gln Leu Leu Gln Ser Gly Gly Gly Leu Val Gln Pro Gly Gly
1               5                   10                  15

Ser Leu Arg Leu Ser Cys Ala Ala Ser Gly Tyr Lys Phe Thr Ser Tyr
            20                  25                  30

Val Met His Trp Val Arg Gln Ala Pro Gly Lys Gly Leu Glu Trp Val
        35                  40                  45

Gly Tyr Ile Asn Pro Tyr Asn Asp Val Thr Lys Tyr Asn Glu Lys Phe
    50                  55                  60

Lys Gly Arg Phe Thr Leu Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Tyr Tyr Asp Tyr Asp Gly Phe Val Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
```

```
                    305                 310                 315                 320
Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 25
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Glu Val Gln Leu Leu Gln Ser Gly Gly Gly Leu Val Gln Pro Gly Gly
1               5                   10                  15

Ser Leu Arg Leu Ser Cys Ala Ala Ser Gly Tyr Lys Phe Thr Ser Tyr
            20                  25                  30

Val Met His Trp Val Arg Gln Ala Pro Gly Lys Gly Leu Glu Trp Val
        35                  40                  45

Gly Tyr Ile Asn Pro Tyr Asn Asp Val Thr Lys Tyr Asn Glu Lys Phe
    50                  55                  60

Lys Gly Arg Phe Thr Leu Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Tyr Tyr Asp Tyr Asp Gly Phe Val Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205
```

```
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Asn Thr Ser Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450

<210> SEQ ID NO 26
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Glu Val Gln Leu Leu Gln Ser Gly Gly Gly Leu Val Gln Pro Gly Gly
1               5                   10                  15
Ser Leu Arg Leu Ser Cys Ala Ala Ser Gly Tyr Lys Phe Thr Ser Tyr
            20                  25                  30
Val Met His Trp Val Arg Gln Ala Pro Gly Lys Gly Leu Glu Trp Val
        35                  40                  45
Gly Tyr Ile Asn Pro Tyr Asn Asp Val Thr Lys Tyr Asn Glu Lys Phe
    50                  55                  60
Lys Gly Arg Phe Thr Leu Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
```

Ala Arg Gly Ser Tyr Tyr Asp Tyr Asp Gly Phe Val Tyr Trp Gly Gln
                100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ala Ser Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 27
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

-continued

```
<400> SEQUENCE: 27

Glu Val Gln Leu Leu Gln Ser Gly Gly Gly Leu Val Gln Pro Gly Gly
1               5                   10                  15

Ser Leu Arg Leu Ser Cys Ala Ala Ser Gly Tyr Lys Phe Thr Ser Tyr
            20                  25                  30

Val Met His Trp Val Arg Gln Ala Pro Gly Lys Gly Leu Glu Trp Val
        35                  40                  45

Gly Tyr Ile Asn Pro Tyr Asn Asp Val Thr Lys Tyr Asn Glu Lys Phe
    50                  55                  60

Lys Gly Arg Phe Thr Leu Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Tyr Tyr Asp Tyr Asp Gly Phe Val Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Gln Asn Thr Ser Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415
```

```
Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 28
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Leu Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Thr His Leu His Thr Phe Gly Gln Gly Thr Arg Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 29
<211> LENGTH: 444
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Glu Val Gln Leu Val Glu Ser Gly Gly Gly Leu Val Gln Pro Gly Gly
1               5                   10                  15
```

-continued

Ser Leu Arg Leu Ser Cys Ala Ala Ser Gly Phe Thr Phe Asn Thr Tyr
            20                  25                  30

Trp Met Asn Trp Val Arg Gln Ala Pro Gly Lys Gly Leu Glu Trp Val
        35                  40                  45

Gly Gln Ile Arg Leu Lys Ser Asn Asn Tyr Ala Thr His Tyr Ala Glu
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Thr Pro Val Asp Phe Trp Gly Gln Gly Thr Thr Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Asp Glu Leu Thr Lys Asn Gln Val Ser Leu Thr Cys Leu Val Lys Gly
        355                 360                 365

Phe Tyr Pro Ser Asp Ile Ala Val Glu Trp Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys

<210> SEQ ID NO 30
<211> LENGTH: 444
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 30

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Trp Met Asn Trp Val Arg Gln Ala Pro Gly Lys Gly Leu Glu Trp Val
        35                  40                  45

Gly Gln Ile Arg Leu Lys Ser Asn Asn Tyr Ala Thr His Tyr Ala Glu
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Thr Pro Val Asp Phe Trp Gly Gln Gly Thr Thr Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Asn Thr Ser Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350
```

Asp Glu Leu Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
        370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 31
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Val Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Ser His Phe His Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 32
<211> LENGTH: 444
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic polypeptide"

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Pro Phe Ser Asn Tyr
            20                  25                  30

Trp Met Asn Trp Val Arg Gln Ala Pro Gly Lys Gly Leu Glu Trp Val
        35                  40                  45

Gly Gln Ile Arg Leu Lys Ser Asn Asn Tyr Ala Thr His Tyr Ala Glu
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Thr Pro Ile Asp Tyr Trp Gly Gln Gly Thr Thr Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Asp Glu Leu Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
```

```
385                 390                 395                 400
Phe Phe Leu Tyr Ser Lys Leu Thr Val Asp Lys Ser Arg Trp Gln Gln
                405                 410                 415
Gly Asn Val Phe Ser Cys Ser Val Met His Glu Ala Leu His Asn His
                420                 425                 430
Tyr Thr Gln Lys Ser Leu Ser Leu Ser Pro Gly Lys
                435                 440

<210> SEQ ID NO 33
<211> LENGTH: 444
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Pro Phe Ser Asn Tyr
                20                  25                  30
Trp Met Asn Trp Val Arg Gln Ala Pro Gly Lys Gly Leu Glu Trp Val
                35                  40                  45
Gly Gln Ile Arg Leu Lys Ser Asn Asn Tyr Ala Thr His Tyr Ala Glu
        50                  55                  60
Ser Val Lys Gly Arg Phe Thr Ile Ser Arg Asp Asp Ser Lys Asn Ser
65              70                  75                  80
Leu Tyr Leu Gln Met Asn Ser Leu Lys Thr Glu Asp Thr Ala Val Tyr
                85                  90                  95
Tyr Cys Thr Pro Ile Asp Tyr Trp Gly Gln Gly Thr Thr Val Thr Val
                100                 105                 110
Ser Ser Ala Ser Thr Lys Gly Pro Ser Val Phe Pro Leu Ala Pro Ser
                115                 120                 125
Ser Lys Ser Thr Ser Gly Gly Thr Ala Ala Leu Gly Cys Leu Val Lys
                130                 135                 140
Asp Tyr Phe Pro Glu Pro Val Thr Val Ser Trp Asn Ser Gly Ala Leu
145                 150                 155                 160
Thr Ser Gly Val His Thr Phe Pro Ala Val Leu Gln Ser Ser Gly Leu
                165                 170                 175
Tyr Ser Leu Ser Ser Val Val Thr Val Pro Ser Ser Ser Leu Gly Thr
                180                 185                 190
Gln Thr Tyr Ile Cys Asn Val Asn His Lys Pro Ser Asn Thr Lys Val
                195                 200                 205
Asp Lys Lys Val Glu Pro Lys Ser Cys Asp Lys Thr His Thr Cys Pro
                210                 215                 220
Pro Cys Pro Ala Pro Glu Leu Leu Gly Gly Pro Ser Val Phe Leu Phe
225                 230                 235                 240
Pro Pro Lys Pro Lys Asp Thr Leu Met Ile Ser Arg Thr Pro Glu Val
                245                 250                 255
Thr Cys Val Val Val Asp Val Ser His Glu Asp Pro Glu Val Lys Phe
                260                 265                 270
Asn Trp Tyr Val Asp Gly Val Glu Val His Asn Ala Lys Thr Lys Pro
                275                 280                 285
Arg Glu Glu Gln Tyr Asn Asn Thr Ser Arg Val Val Ser Val Leu Thr
                290                 295                 300
```

```
Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
                340                 345                 350

Asp Glu Leu Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
        370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
                420                 425                 430

Tyr Thr Gln Lys Ser Leu Ser Leu Ser Pro Gly Lys
            435                 440

<210> SEQ ID NO 34
<211> LENGTH: 444
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Pro Phe Ser Asn Tyr
                20                  25                  30

Trp Met Asn Trp Val Arg Gln Ala Pro Gly Lys Gly Leu Glu Trp Val
            35                  40                  45

Gly Gln Ile Arg Leu Lys Ser Asn Asn Tyr Ala Thr His Tyr Ala Glu
        50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Thr Pro Ile Asp Tyr Trp Gly Gln Gly Thr Thr Val Thr Val
                100                 105                 110

Ser Ser Ala Ser Thr Lys Gly Pro Ser Val Phe Pro Leu Ala Pro Ser
            115                 120                 125

Ser Lys Ser Thr Ser Gly Gly Thr Ala Ala Leu Gly Cys Leu Val Lys
        130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205
```

```
Asp Lys Lys Val Glu Pro Lys Ser Cys Asp Lys Thr His Thr Cys Pro
    210                 215                 220
Pro Cys Pro Ala Pro Glu Leu Leu Gly Gly Pro Ser Val Phe Leu Phe
225                 230                 235                 240
Pro Pro Lys Pro Lys Asp Thr Leu Met Ile Ser Arg Thr Pro Glu Val
                245                 250                 255
Thr Cys Val Val Val Asp Val Ser His Glu Asp Pro Glu Val Lys Phe
                260                 265                 270
Asn Trp Tyr Val Asp Gly Val Glu Val His Asn Ala Lys Thr Lys Pro
            275                 280                 285
Arg Glu Glu Gln Tyr Asn Asn Ala Ser Arg Val Val Ser Val Leu Thr
290                 295                 300
Val Leu His Gln Asp Trp Leu Asn Gly Lys Glu Tyr Lys Cys Lys Val
305                 310                 315                 320
Ser Asn Lys Ala Leu Pro Ala Pro Ile Glu Lys Thr Ile Ser Lys Ala
                325                 330                 335
Lys Gly Gln Pro Arg Glu Pro Gln Val Tyr Thr Leu Pro Pro Ser Arg
                340                 345                 350
Asp Glu Leu Thr Lys Asn Gln Val Ser Leu Thr Cys Leu Val Lys Gly
                355                 360                 365
Phe Tyr Pro Ser Asp Ile Ala Val Glu Trp Glu Ser Asn Gly Gln Pro
            370                 375                 380
Glu Asn Asn Tyr Lys Thr Thr Pro Pro Val Leu Asp Ser Asp Gly Ser
385                 390                 395                 400
Phe Phe Leu Tyr Ser Lys Leu Thr Val Asp Lys Ser Arg Trp Gln Gln
                405                 410                 415
Gly Asn Val Phe Ser Cys Ser Val Met His Glu Ala Leu His Asn His
                420                 425                 430
Tyr Thr Gln Lys Ser Leu Ser Leu Ser Pro Gly Lys
                435                 440

<210> SEQ ID NO 35
<211> LENGTH: 444
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Pro Phe Ser Asn Tyr
            20                  25                  30
Trp Met Asn Trp Val Arg Gln Ala Pro Gly Lys Gly Leu Glu Trp Val
        35                  40                  45
Gly Gln Ile Arg Leu Lys Ser Asn Asn Tyr Ala Thr His Tyr Ala Glu
    50                  55                  60
Ser Val Lys Gly Arg Phe Thr Ile Ser Arg Asp Asp Ser Lys Asn Ser
65                  70                  75                  80
Leu Tyr Leu Gln Met Asn Ser Leu Lys Thr Glu Asp Thr Ala Val Tyr
                85                  90                  95
Tyr Cys Thr Pro Ile Asp Tyr Trp Gly Gln Gly Thr Thr Val Thr Val
                100                 105                 110
Ser Ser Ala Ser Thr Lys Gly Pro Ser Val Phe Pro Leu Ala Pro Ser
```

```
            115                 120                 125
Ser Lys Ser Thr Ser Gly Gly Thr Ala Ala Leu Gly Cys Leu Val Lys
        130                 135                 140
Asp Tyr Phe Pro Glu Pro Val Thr Val Ser Trp Asn Ser Gly Ala Leu
145                 150                 155                 160
Thr Ser Gly Val His Thr Phe Pro Ala Val Leu Gln Ser Ser Gly Leu
                165                 170                 175
Tyr Ser Leu Ser Ser Val Val Thr Val Pro Ser Ser Ser Leu Gly Thr
            180                 185                 190
Gln Thr Tyr Ile Cys Asn Val Asn His Lys Pro Ser Asn Thr Lys Val
        195                 200                 205
Asp Lys Lys Val Glu Pro Lys Ser Cys Asp Lys Thr His Thr Cys Pro
210                 215                 220
Pro Cys Pro Ala Pro Glu Leu Leu Gly Gly Pro Ser Val Phe Leu Phe
225                 230                 235                 240
Pro Pro Lys Pro Lys Asp Thr Leu Met Ile Ser Arg Thr Pro Glu Val
                245                 250                 255
Thr Cys Val Val Val Asp Val Ser His Glu Asp Pro Glu Val Lys Phe
            260                 265                 270
Asn Trp Tyr Val Asp Gly Val Glu Val His Asn Ala Lys Thr Lys Pro
        275                 280                 285
Arg Glu Glu Gln Tyr Gln Asn Thr Ser Arg Val Val Ser Val Leu Thr
290                 295                 300
Val Leu His Gln Asp Trp Leu Asn Gly Lys Glu Tyr Lys Cys Lys Val
305                 310                 315                 320
Ser Asn Lys Ala Leu Pro Ala Pro Ile Glu Lys Thr Ile Ser Lys Ala
                325                 330                 335
Lys Gly Gln Pro Arg Glu Pro Gln Val Tyr Thr Leu Pro Pro Ser Arg
            340                 345                 350
Asp Glu Leu Thr Lys Asn Gln Val Ser Leu Thr Cys Leu Val Lys Gly
        355                 360                 365
Phe Tyr Pro Ser Asp Ile Ala Val Glu Trp Glu Ser Asn Gly Gln Pro
370                 375                 380
Glu Asn Asn Tyr Lys Thr Thr Pro Pro Val Leu Asp Ser Asp Gly Ser
385                 390                 395                 400
Phe Phe Leu Tyr Ser Lys Leu Thr Val Asp Lys Ser Arg Trp Gln Gln
                405                 410                 415
Gly Asn Val Phe Ser Cys Ser Val Met His Glu Ala Leu His Asn His
            420                 425                 430
Tyr Thr Gln Lys Ser Leu Ser Leu Ser Pro Gly Lys
        435                 440

<210> SEQ ID NO 36
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Val Asn Thr Ala
            20                  25                  30
```

```
Val Ala Trp Tyr Gln Gln Lys Pro Gly Lys Ala Pro Lys Leu Leu Ile
             35                  40                  45

Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
                210

<210> SEQ ID NO 37
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys Asp Thr
                 20                  25                  30

Tyr Ile His Trp Val Arg Gln Ala Pro Gly Lys Gly Leu Glu Trp Val
             35                  40                  45

Ala Arg Ile Tyr Pro Thr Asn Gly Tyr Thr Arg Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
                100                 105                 110

Gly Thr Leu Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160
```

```
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450

<210> SEQ ID NO 38
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Asn Ile Lys Asp Thr
            20                  25                  30
Tyr Ile His Trp Val Arg Gln Ala Pro Gly Lys Gly Leu Glu Trp Val
        35                  40                  45
Ala Arg Ile Tyr Pro Thr Asn Gly Tyr Thr Arg Tyr Ala Asp Ser Val
```

```
                50                  55                  60
Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
            100                 105                 110

Gly Thr Leu Val Thr Val Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Asn Ala Ser Arg
                290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
450

<210> SEQ ID NO 39
```

```
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Gly Gly Gly Gly
1

<210> SEQ ID NO 40
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Gly Gly Gly Gly Gly
1               5

<210> SEQ ID NO 41
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Gly Gly Gly Gly Gly Gly
1               5

<210> SEQ ID NO 42
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Gly Gly Gly Gly Gly Gly Gly
1               5

<210> SEQ ID NO 43
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Gly Gly Gly Gly Gly Gly Gly Gly
1               5

<210> SEQ ID NO 44
<211> LENGTH: 5
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 44

Gly Gly Gly Gly Ser
1               5

<210> SEQ ID NO 45
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Gly Gly Gly Gly Ser Gly Gly Gly Gly Ser
1               5                   10
```